(12) United States Patent
Gaillard et al.

(10) Patent No.: US 8,071,597 B2
(45) Date of Patent: Dec. 6, 2011

(54) PYRAZINE COMPOUNDS AND USES AS PI3K INHIBITORS

(75) Inventors: Pascale Gaillard, Collonges Sous Salve (FR); Anna Quattropani, Geneva (CH); Vincent Pomel, Groisy (FR); Thomas Rueckle, Geneva (CH); Jasna Klicic, Geneva (CH); Dennis Church, Commugny (CH)

(73) Assignee: Merck Serono SA, Coinsins, Vaud (CH)

( * ) Notice: Subject to any disclaimer, the term of this patent is extended or adjusted under 35 U.S.C. 154(b) by 671 days.

(21) Appl. No.: 12/064,284

(22) PCT Filed: Aug. 25, 2006

(86) PCT No.: PCT/EP2006/065688
§ 371 (c)(1),
(2), (4) Date: Feb. 20, 2008

(87) PCT Pub. No.: WO2007/023186
PCT Pub. Date: Mar. 1, 2007

(65) Prior Publication Data
US 2009/0082356 A1    Mar. 26, 2009

Related U.S. Application Data

(60) Provisional application No. 60/711,873, filed on Aug. 26, 2005.

(30) Foreign Application Priority Data

Aug. 26, 2005  (EP) .................................... 05107838

(51) Int. Cl.
*A61K 31/50*   (2006.01)
*A61K 31/495*  (2006.01)
*A01N 43/58*   (2006.01)
*A01N 43/60*   (2006.01)
*C07D 241/36*  (2006.01)

(52) U.S. Cl. ....................................... 514/249; 544/353

(58) Field of Classification Search ....................... None
See application file for complete search history.

(56) References Cited

FOREIGN PATENT DOCUMENTS
WO    WO 03/035075    5/2003

OTHER PUBLICATIONS

Litvinenkov, et. al., Chemistry of Heterocyclic Compounds (1994), 30(3), 340-44.*
Accession No. 2005:3916002 CHEMCATS, Catalog Name, Ambinter Stock Screening Collection, Jul. 3, 2005, XP-002360554, pp. 1-3.
Hui, A. et al. "Substituent effect of camphor sulfonamide ligand on the asymmetric addition of diethylzinc to aldehyde" *ARKIVOC*, 2006, pp. 41-56, vol. XIII.

* cited by examiner

*Primary Examiner* — Jeffrey Murray
(74) *Attorney, Agent, or Firm* — Saliwanchik, Lloyd & Eisenschenk

(57) ABSTRACT

The present invention is related to pyrazine derivatives of Formula (I) in particular for the treatment and/or prophylaxis of autoimmune disorders and/or inflammatory diseases, cardiovascular diseases, neurodegenerative diseases, bacterial or viral infections, kidney diseases, platelet aggregation, cancer, transplantation, graft rejection or lung injuries.

16 Claims, No Drawings

PYRAZINE COMPOUNDS AND USES AS PI3K INHIBITORS

CROSS-REFERENCE TO RELATED APPLICATION

This application is the U.S. national stage application of International Patent Application No. PCT/EP2006/065688, filed Aug. 25, 2006, which claims the benefit of U.S. Provisional Patent Application No. 60/711,873, filed Aug. 26, 2005, the disclosures of which are hereby incorporated by reference in their entireties, including all figures, tables and amino acid or nucleic acid sequences.

FIELD OF THE INVENTION

This present invention is related to the use of pyrazine derivatives of Formula (I) for the treatment and/or prophylaxis of autoimmune disorders and/or inflammatory diseases, cardiovascular diseases, neurodegenerative diseases, bacterial or viral infections, allergy, asthma, pancreatitis, multi-organ failure, kidney diseases, platelet aggregation, cancer, transplantation, sperm motility, erythrocyte deficiency, graft rejection or lung injuries. Specifically, the present invention is related to pyrazine derivatives for the modulation, notably the inhibition of the activity or function of the phosphoinositide-3-kinases, PI3Ks.

BACKGROUND OF THE INVENTION

Phosphoinositide 3-kinases (PI3Ks) have a critical signalling role in cell proliferation, cell survival, vascularization, membrane trafficking, glucose transport, neurite outgrowth, membrane ruffling, superoxide production, actin reorganization and chemotaxis (Cantley, 2000, *Science*, 296, 1655-1657).

The term PI3K is given to a family of lipid kinases which, in mammals, consists in eight identified PI3Ks that are divided into three sub-families according to their structure and their substrate specificity.

Class I group of PI3Ks consists in two sub-groups, Class IA and Class IB.

Class IA are a family of heterodimeric lipid kinases consisting in a 85 kDa regulatory unit (responsible for protein-protein interactions via the interaction of Src homology 2 (SH2) domain with phosphotyrosine residues of other proteins) and a catalytic sub-unit of 110 kDa that generate second messenger signals downstream of tyrosine kinases, thereby controlling cell metabolism, growth, proliferation, differentiation, motility and survival. Three catalytic forms (p110α, p110β and p110δ) and five regulatory isoforms (p85α, p85β, p55γ, p55α and p50α) exist for this class.

Class IB are stimulated by G protein βγ sub-units of heterodimeric G proteins. The only characterized member of Class IB is PI3Kγ (p110γ catalytic sub-unit complex with a 101-kDa regulatory protein, p 101).

Class II PI3Ks comprises α, β and γ isoforms, which are approximately of 170 kDa and characterized by the presence of a C-terminal C2 domain.

Class III PI3Ks includes the phosphatidylinositol specific 3-kinases.

The evolutionary conserved isoforms p110α and β are ubiquitously expressed, while δ and γ are more specifically expressed in the haematopoetic cell system, smooth muscle cells, myocytes and endothelial cells (Vanhaesebroeck et al., 2001, *Annu. Rev. Biochem.*, 70, 535-602). Their expression might also be regulated in an inducible manner depending on the cellular-, tissue type and stimuli as well as disease context.

PI3Ks are enzymes involved in phospholipid signalling and are activated in response to a variety of extra-cellular signals such as growth factors, mitogens, integrins (cell-cell interactions) hormones, cytokines, viruses and neurotransmitters and also by intra-cellular cross regulation by other signalling molecules (cross-talk, where the original signal can activate some parallel pathways that in a second step transmit signals to PI3Ks by intra-cellular signalling events), such as small GTPases, kinases or phosphatases for example.

Phosphatidylinositol (PtdIns) is the basic building block for the intracellular inositol lipids in eukaryotic cells, consisting of D-myo-inositol-1-phosphate (Ins1P) linked via its phosphate group to diacylglycerol. The inositol head group of PtdIns has five free hydroxy groups and three of these are found to be phosphorylated in cells in different combinations. PtdIns and its phosphorylated derivatives are collectively referred as inositol phospholipids or phosphoinositides (PIs). Eight PI species have been documented in eukaryotic cells (Vanhaesebroeck et al., 2001, above). PIs all reside in membranes and are substrates for kinases, phosphatases and lipases.

In vitro, PI3Ks phosphorylate the 3-hydroxyl group of the inositol ring in three different substrates: phosphatidylinositol (PtdIns), phosphatidylinositol-4-phosphate (PI(4)P) and phosphatidylinositol-4,5-biphosphate (PI(4,5)$P_2$), respectively generating three lipid products, namely phosphatidylinositol 3-monophosphate (PI(3)P), phosphatidylinositol 3,4-bisphosphate (PI(3,4)$P_2$) and phosphatidylinositol 3,4,5-trisphosphate (PI(3,4,5)$P_3$ (see Scheme A below).

Scheme A

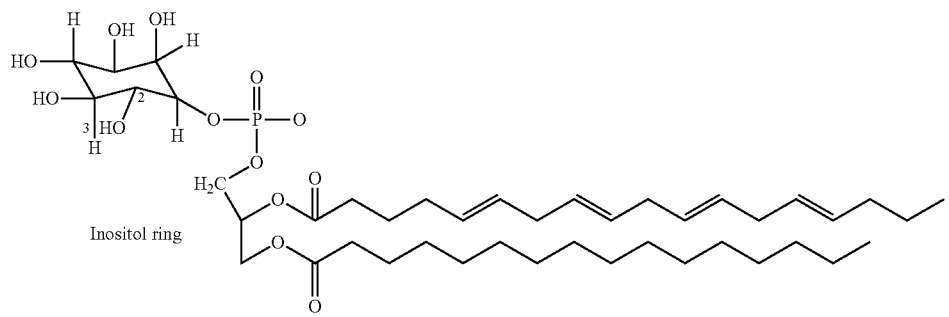

PtdIns (Phosphatidylinositol)

↓ PI3K

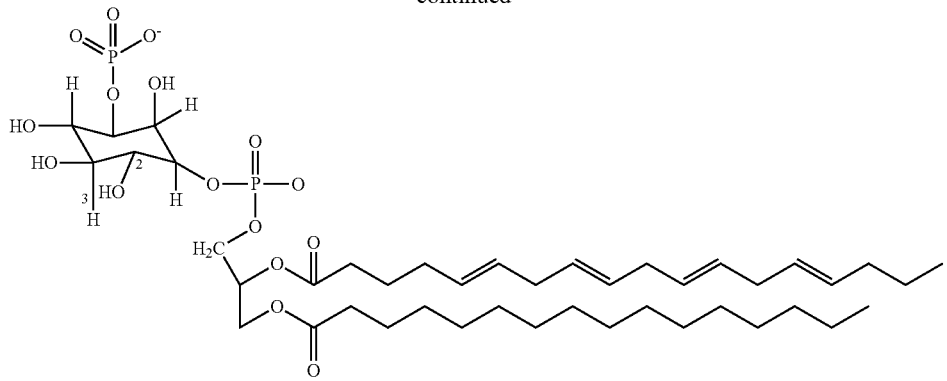

PI(3)P (Phosphatidylinositol 3-monophosphate)

The preferred substrate for Class I PI3Ks is PI(4,5)P$_2$. Class II PIKs have a strong preference for PtdIns as substrate over PI(4)P and PI(4,5)P$_2$. Class III PI3Ks can only use PtdIns as substrate in vivo and are likely to be responsible for the generation of most PI(3)P in cells (Vanhaesebroeck et al., 2001, above).

The phosphoinositides intracellular signalling pathway begins with the binding of a signalling molecule (extracellular ligands, stimuli, receptor dimidiation, transactivation by heterologous receptor (e.g. receptor tyrosine kinase)) to a G-protein linked transmembrane receptor integrated into the plasma membrane resulting in the activation of PI3Ks.

Once activated, PI3Ks convert the membrane phospholipid PI(4,5)P$_2$ into PI(3,4,5)P$_3$ which in turn can be further converted into another 3' phosphorylated form of phosphoinositides by 5'-specific phosphoinositide phosphatases, thus PI3K enzymatic activity results either directly or indirectly in the generation of two 3'-phosphoinositide sub-types that function as second messengers in intra-cellular signal transduction (Toker et al., 2002, Cell Mol. Life Sci. 59(5) 761-79).

The role as second messengers of phosphorylated products of PtdIns act is involved in a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Stein, 2000, Mol Med. Today 6(9) 347-57). Chemotaxis—the directed movement of cells toward a concentration gradient of chemical attractants, also called chemokines is involved in many important diseases such as inflammation/auto-immunity, neurodegeneration, angiogenesis, invasion/metastasis and wound healing (Wyman et al., 2000, Immunol Today 21(6) 260-4 and Gerard et al., 2001, Nat Immunol. 2(2) 108-15).

PI3-kinase activation, is therefore believed to be involved in a range of cellular responses including cell growth, differentiation, migration and apoptosis (Parker et al., 1995, Current Biology, 5, 577-99; Yao et al., 1995, Science, 267, 2003-05).

Recent biochemical studies revealed that, Class I PI3Ks (e.g. Class IB isoform PI3Kγ) are dual-specific kinase enzymes, i.e. they display both lipid kinase activity (phosphorylation of phosphoinositides) as well as protein kinase activity, as they are able to induce the phosphorylation of other protein as substrates, including auto-phosphorylation as intra-molecular regulatory mechanism.

PI3Ks appear to be involved in a number of aspects of leukocyte activation. A p85-associated PI3-kinase activity has been shown to physically associate with the cytoplasmic domain of CD28, which is an important co-stimulatory molecule for the activation of T-cells in response to antigen. These effects are linked to increases in the transcription of a number of genes including interleukin-2 (IL-2), an important T cell growth factor (Fraser et al., 1991, Science, 251, 313-16). Mutation of CD28 such that it can longer interact with PI3-kinase leads to a failure to initiate IL-2 production, suggesting a critical role for PI3-kinase in T cell activation.

Cellular processes in which PI33Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

Recently, it has been described that PI3Kγ relays inflammatory signals through various G(i)-coupled receptors (Laffargue et al., 2002, Immunity 16(3) 441-51) and its central to mast cell function, stimuli in context of leukocytes, immunology includes cytokines, chemokines, adenosines, antibodies, integrins, aggregation factors, growth factors, viruses or hormones for example (Lawlor et al., 2001, J. Cell Sci., 114 (Pt 16) 2903-1).

Two compounds, LY294002 and Wortmannin (cf.hereinafter), have been widely used as PI3-kinase inhibitors. These compounds are non-specific PI3K inhibitors, as they do not distinguish among the four members of Class I PI3-kinases.

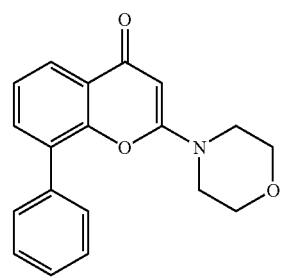

LY 294002

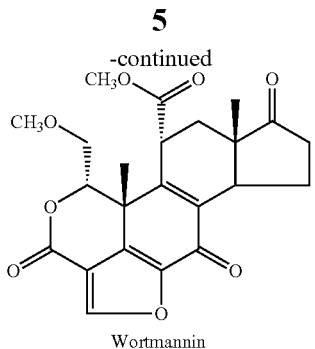
Wortmannin

IC$_{50}$ values of Wortmannin against each of the various Class I PI3-kinases are in the range of 1-10 nM and IC$_{50}$ values for LY294002 against each of these PI3-kinases are about 15-20 μM (Fruman et al., 1998, *Ann. Rev. Biochem.*, 67, 481-507), also 5-10 mM on CK2 protein kinase and some inhibitory activity on phospholipases.

Wortmannin is a fungal metabolite which irreversibly inhibits PI3K activity by binding covalently to the catalytic domain of this enzyme. Inhibition of PI3K activity by wortmannin eliminates the subsequent cellular response to the extracellular factor (Thelen et al, 1994, *Proc. Natl. Acad. Sci. USA*, 91, 4960-64). Experiments with wortmannin, show that PI3K activity in cells of hematopoietic lineage, particularly neutrophils, monocytes, and other types of leukocytes, is involved in many of the non-memory immune response associated with acute and chronic inflammation.

Based on studies using Wortmannin, there is evidence that PI3-kinase function is also required for some aspects of leukocyte signalling through G-protein coupled receptors (Thelen et al., 1994, above). Moreover, it has been shown that Wortmannin and LY294002 block neutrophil migration and superoxide release.

Some results have indicated that PI3K inhibitors, for example, LY294002, can increase the in vivo antitumor activity of certain cytotoxic agents (e.g. paclitaxel) (Grant, 2003, *Current Drugs*, 6(10), 946-948).

However, in as much as these compounds do not distinguish among the various isoforms of PI3K, it remains unclear which particular PI3K isoform or isoforms are involved in these phenomena. Specific inhibitors against individual members of a family of enzymes provide valuable tools for deciphering functions of each enzyme as depending on the disease application, varying the degree of selectivity for PI3K isoforms can be of interest.

p110δ is expressed predominantly in cells of hemopoeitic origin such as leukocytes.

To assess the role of the δ isoform of the p110 catalytic subunit of PI3Ks, PI3Kδ-null mice have been recently developed (Jou et al., 2002, *Molecular and Cellular biology*, 22(4), 8580-8591) and their specific immunological phenotype has been well characterized (Vanhaesebroeck et al., 2005, *Trends in Biochemical Sciences*, 30(4), 194-204). These experiments show that the PI3Kδ-null animals are viable and that a deficiency in PI3Kδ results in a very specific loss of the function of the B-cell antigen specific receptor complex, while signalling through the cytokine receptor complexes is unaffected (Jou et al., 2002, above).

It has been also shown that the inactivation of the p110δ isoform of PI3K in mast cells leads to defective stem cell factor-mediated in vitro proliferation, adhesion and migration and to impaired allergen-IgE-induced degranualtion and cytokine release. Inactivation of p110δ protects mice against anaphylactic allergic responses, suggesting p110δ as a target for therapeutic intervention in allergy and mast-cell-related pathologies (Ali. et al., 2004, *Nature*, 431, 1007-1010).

Mast cells have emerged as a unique immune cell that could participate in a variety of inflammatory diseases in the nervous system (e.g. multiple sclerosis), skin, joints as well as cardiopulmonary, intestinal and urinary systems (Theoharides et al, 2004, *J. of Neuroimmunology*, 146, 1-12).

The high relevance of the PI3K pathway in some widely spread diseases stresses the need to develop inhibitors, including selective inhibitors, of PIK isozymes, in order that the functions of each isozyme can be better characterized.

Recently, PI3K inhibitors have been developed: thiazole derivatives (WO 2005/021519; and WO 04/078754), thiazolidine derivatives (WO 2004/007491 and WO 2004/056820) and Quinazolinones derivatives (WO 03/035075).

SUMMARY OF THE INVENTION

According to one aspect of the invention, are provided substances which are suitable for the treatment and/or prevention of disorders related to phosphoinositide-3-kinases, PI3Ks, such as PI3K alpha or PI3K gamma or PI3K delta.

According to another aspect of the invention, are provided substances which are suitable for the treatment and/or prevention of auto-immune and/or inflammatory disorders.

According to another aspect of the invention, are provided substances which are suitable for the treatment and/or prevention of cardiovascular diseases.

According to another aspect of the invention, are provided substances which are suitable for the treatment and/or prevention of neurodegenerative disorders.

According to another aspect of the invention, are provided substances which are suitable for the treatment and/or prevention of cancers.

According to another aspect of the invention, are provided substances which are suitable for the treatment and/or prevention of a disorder selected from bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

According to another aspect of the invention, are provided chemical compounds which are able to modulate, especially inhibit the activity or function of phosphoinositide-3-kinases, PI3Ks in disease states in mammals, especially in humans.

According to another aspect of the invention, are provided a new category of pharmaceutical formulations for the treatment of and/or diseases mediated selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

According to another aspect of the invention, are provided a method for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

In a first aspect, the invention provides pyrazine derivatives of Formula (I):

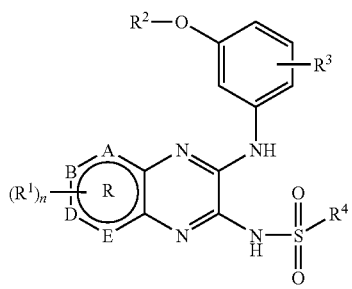

wherein n, A, B, D, E, R, $R^1$, $R^2$, $R^3$ and $R^4$ are defined in the detailed description below.

In a second aspect, the invention provides a compound according to Formula (I) for use as a medicament.

In a third aspect, the invention provides a use of a compound according to Formula (I) for the preparation of a pharmaceutical composition for the treatment of a disorder selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions and other diseases and disorders associated with the phosphoinositide-3-kinases, PI3Ks, comprising PI3K α, γ or δ.

In a fourth aspect, the invention provides a pharmaceutical composition comprising at least one a compound according to Formula (I) and a pharmaceutically acceptable carrier, diluent or excipient thereof.

In a fifth aspect, the invention provides a method for treating a patient suffering from a disorder selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions and other diseases and disorders associated with the phosphoinositide-3-kinases, PI3Ks. The method comprises administering a compound according to Formula (I).

In a sixth aspect, the invention provides methods of synthesis of a compound according to Formula (I).

In a seventh aspect, the invention provides compounds according to Formula (II).

In an eighth aspect, the invention provides compounds according to Formula (XI).

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups and "$C_1$-$C_{10}$-alkyl" refers to monovalent alkyl groups having 1 to 10 carbon atoms, "$C_1$-$C_8$-alkyl" refers to monovalent alkyl groups having 1 to 8 carbon atoms and "$C_1$-$C_5$-alkyl" refers to monovalent alkyl groups having 1 to 5 carbon atoms.

"Heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to aryl groups having a $C_1$-$C_6$-alkyl substituent, including methyl phenyl, ethyl phenyl and the like.

"Aryl $C_1$-$C_6$-alkyl" refers to $C_1$-$C_6$-alkyl groups having an aryl substituent, including 3-phenylpropanoyl, benzyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to heteroaryl groups having a $C_1$-$C_6$-alkyl substituent, including methyl furyl and the like.

"Heteroaryl $C_1$-$C_6$-alkyl" refers to $C_1$-$C_6$-alkyl groups having a heteroaryl substituent, including furyl methyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkenyl aryl" refers to an aryl groups having a $C_2$-$C_6$-alkenyl substituent, including vinyl phenyl and the like.

"Aryl $C_2$-$C_6$-alkenyl" refers to a $C_2$-$C_6$-alkenyl groups having an aryl substituent, including phenyl vinyl and the like.

"$C_2$-$C_6$-alkenyl heteroaryl" refers to heteroaryl groups having a $C_2$-$C_6$-alkenyl substituent, including vinyl pyridinyl and the like.

"Heteroaryl $C_2$-$C_6$-alkenyl" refers to $C_2$-$C_6$-alkenyl groups having a Heteroaryl substituent, including pyridinyl vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, morpholine, tetrahydrofurane and the like.

"$C_1$-$C_6$-alkyl cycloalkyl" refers to $C_3$-$C_8$-cycloalkyl groups having a $C_1$-$C_6$-alkyl substituent, including methyl cyclopentyl and the like.

"Cycloalkyl $C_1$-$C_6$-alkyl" refers to $C_1$-$C_6$-alkyl groups having a $C_3$-$C_8$-cycloalkyl substituent, including 3-cyclopentyl propyl and the like.

"$C_1$-$C_6$-alkyl heterocycloalkyl" refers to heterocycloalkyl groups having a $C_1$-$C_6$-alkyl substituent, including 1-methylpiperazine and the like.

"Heterocycloalkyl $C_1$-$C_6$-alkyl" refers to $C_1$-$C_6$-alkyl groups having a heterocycloalkyl substituent, including 4-methyl piperidyl and the like.

"Carboxy" refers to the group —C(O)OH.

"Carboxy $C_1$-$C_6$-alkyl" refers to $C_1$-$C_6$-alkyl groups having a carboxy substituent, including 2-carboxyethyl and the like.

"Acyl" refers to the group —C(O)R where R includes H, "$C_1$-$C_{12}$-alkyl", preferably "$C_1$-$C_6$-alkyl", "aryl", "heteroaryl", "$C_3$-$C_8$-cycloalkyl", "heterocycloalkyl", "aryl $C_1$-$C_6$-alkyl", "heteroaryl $C_1$-$C_6$-alkyl", "$C_3$-$C_8$-cycloalkyl $C_1$-$C_6$-alkyl" or "heterocycloalkyl $C_1$-$C_6$-alkyl".

"Acyl $C_1$-$C_6$-alkyl" to $C_1$-$C_6$-alkyl groups having an acyl substituent, including acetyl, 2-acetylethyl and the like.

"Acyl aryl" refers to aryl groups having an acyl substituent, including 2-acetylphenyl and the like.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acyloxy $C_1$-$C_6$-alkyl" refers to $C_1$-$C_6$-alkyl groups having an acyloxy substituent, including propionic acid ethyl ester and the like.

"Alkoxy" refers to the group —O—R where R includes "$C_1$-$C_6$-alkyl" or "aryl" or "hetero-aryl" or "aryl $C_1$-$C_6$-alkyl" or "heteroaryl $C_1$-$C_6$-alkyl". Preferred alkoxy groups include for example, methoxy, ethoxy, phenoxy and the like.

"Alkoxy $C_1$-$C_6$-alkyl" refers to alkoxy groups having a $C_1$-$C_6$-alkyl substituent, including methoxy, methoxyethyl and the like.

"Alkoxycarbonyl" refers to the group —C(O)OR where R includes H, "$C_1$-$C_6$-alkyl" or "aryl" or "heteroaryl" or "aryl $C_1$-$C_6$-alkyl" or "heteroaryl $C_1$-$C_6$-alkyl" or "heteroalkyl".

"Alkoxycarbonyl $C_1$-$C_6$-alkyl" refers to $C_1$-$C_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "aryl $C_1$-$C_6$-alkyl" or "heteroaryl $C_1$-$C_6$-alkyl", including N-phenyl formamide.

"Aminocarbonyl $C_1$-$C_6$-alkyl" refers to $C_1$-C6-alkyl groups having an aminocarbonyl substituent, including 2-(dimethylaminocarbonyl)ethyl, N-ethyl acetamide, N,N-Diethyl-acetamide and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acylamino $C_1$-$C_6$-alkyl" refers to $C_1$-C6-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl", and where R' and R", together with the nitrogen atom to which they are attached, can optionally form a 3-8-membered heterocycloalkyl ring.

"Ureido $C_1$-$C_6$-alkyl" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Amino" refers to the group —NRR' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Amino $C_1$-$C_6$-alkyl" refers to $C_1$-$C_5$-alkyl groups having an amino substituent, including 2-(1-pyrrolidinyl)ethyl and the like.

"Ammonium" refers to a positively charged group —N$^+$RR'R", where each R, R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Ammonium $C_1$-$C_6$-alkyl" refers to $C_1$-$C_6$-alkyl groups having an ammonium substituent, including 1-ethylpyrrolidinium and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyloxy $C_1$-$C_6$-alkyl" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-C6-alkyl", "heterocycloalkyl $C_1$-$C_6$-alkyl".

"Sulfonyl $C_1$-$C_6$-alkyl" refers to $C_1$-C5-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., a —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfinyl $C_1$-$C_6$-alkyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., a —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "alkynylheteroaryl $C_2$-$C_6$", "cycloalkyl $C_1$-$C_6$-alkyl", "heterocycloalkyl $C_1$-$C_6$-alkyl". Preferred sulfanyl groups include methylsulfanyl, ethylsulfanyl, and the like.

"Sulfanyl $C_1$-$C_6$-alkyl" refers to $C_1$-$C_5$-alkyl groups having a sulfanyl substituent, including 2-(ethylsulfanyl)ethyl and the like.

"Sulfonylamino" refers to a group —$NRSO_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonylamino $C_1$-$C_6$-alkyl" refers to $C_1$-$C_6$-alkyl groups having a sulfonylamino substituent, including 2-(ethylsulfonylamino)ethyl and the like.

"Aminosulfonyl" refers to a group —$SO_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Aminosulfonyl $C_1$-$C_6$-alkyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkenyl", "alkynyl", "aryl", "heteroaryl", "cycloalkyl", "heterocycloalkyl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Substituted" refers to groups substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "aminosulfonyl", "ammonium", "acyl amino", "amino carbonyl", "aryl", "heteroaryl", "sulfinyl", "sulfonyl", "alkoxy", "alkoxy carbonyl", "carbamate", "sulfanyl", "halogen", trihalomethyl, cyano, hydroxy, mercapto, nitro, and the like.

"Pharmaceutically acceptable salts or complexes" refers to salts or complexes of the below-identified compounds of Formula (I) that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR, R',R"+Z−, wherein R, R', R" is independently hydrogen, alkyl, or benzyl, $C_1$-$C_6$-alkyl, $C_2$-$C_6$-alkenyl, $C_2$-$C_6$-alkynyl, $C_1$-$C_6$-alkyl aryl, $C_1$-$C_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

Also comprised are salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methyl amine, dimethylamine, trimethylamine, ethylamine, diethylamine, triethylamine, morpholine, ammonium, N-methyl-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism.

It has now been found that compounds of the present invention are modulators of the Phosphatoinositides 3-kinases (PI33Ks), comprising PI3K α, γ or δ. When the phosphatoinositides 3-kinase (PI33K) enzyme is inhibited by the compounds of the present invention, PI3K is unable to exert its enzymatic, biological and/or pharmacological effects.

The compounds of the present invention are therefore useful in the treatment and prevention of autoimmune disorders and/or inflammatory diseases, cardiovascular diseases, neurodegenerative diseases, bacterial or viral infections, allergy, asthma, pancreatitis, multi-organ failure, kidney diseases, platelet aggregation, cancer, transplantation, sperm motility, erythrocyte deficiency, graft rejection or lung injuries.

General Formula (I) according to the present invention also comprises its tautomers, its geometrical isomers, its optically active forms as enantiomers, diastereomers and its racemate forms, as well as pharmaceutically acceptable salts thereof. Preferred pharmaceutically acceptable salts of the Formula (I) are base addition salts formed by reaction of compounds of formula (I) with pharmaceutically acceptable bases like sodium, potassium or calcium of hydroxides, ammonium or N-methyl-D-glucamine.

The compounds according to Formula (I) are suitable for the modulation, notably the inhibition of the activity of phosphatoinositides 3-kinases (PI3K). It is therefore believed that the compounds of the present invention are also particularly useful for the treatment and/or prevention of disorders, which are mediated by PI3Ks, particularly PI3K α and/or PI3K γ and/or PI3K δ. Said treatment involves the modulation— notably the inhibition or the down regulation—of the phosphatoinositides 3-kinases.

The compounds according to Formula (I) are suitable for use as a medicament.

In one embodiment, the invention provides pyrazine derivatives of Formula (I):

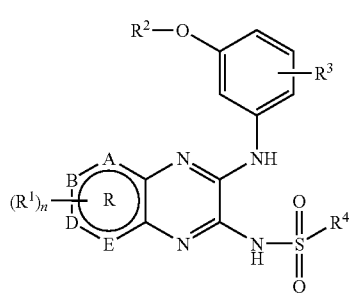

wherein:
A, B, D and E are independently selected from C and N, such that the ring R is a stable aromatic ring, including optionally substituted phenyl and optionally substituted pyridinyl;
$R^1$ is selected from H; halogen, including chloro; nitro; optionally substituted $C_1$-$C_6$-alkyl, including methyl; optionally substituted $C_2$-$C_6$-alkenyl and optionally substituted $C_2$-$C_6$-alkynyl;
$R^2$ is selected from H; optionally substituted $C_1$-$C_6$-alkyl, including methyl; optionally substituted $C_2$-$C_6$-alkenyl and optionally substituted $C_2$-$C_6$-alkynyl;
$R^3$ is selected from H; halo, including chloro; optionally substituted $C_1$-$C_6$-alkyl; optionally substituted $C_2$-$C_6$-alkenyl; optionally substituted $C_2$-$C_6$-alkynyl, optionally substituted alkoxy, including methoxy; optionally substituted aryl; optionally substituted heteroaryl, including pyrrolyl;
$R^4$ is selected from optionally substituted $C_1$-$C_6$-alkyl, including methyl, ethyl, butyl, propyl, carboxy $C_1$-$C_6$-alkyl (e.g. butanoic acid), alkoxycarbonyl $C_1$-$C_6$-alkyl (e.g. methyl-4-butanoate); optionally substituted $C_2$-$C_6$-alkenyl; optionally substituted $C_2$-$C_6$-alkynyl; optionally substituted aryl, including optionally substituted phenyl such as cyano phenyl (e.g. 4-cyano phenyl, 2-cyano phenyl, 3-cyano phenyl), phenyl, halo phenyl such as fluoro phenyl (e.g. 3-fluorophenyl, 4-fluorophenyl, 2-fluorophenyl), chloro phenyl (e.g. 2-chloro phenyl, 3-chloro phenyl), 4-chloro phenyl), iodo phenyl (e.g. 4-iodo phenyl) and bromo phenyl (e.g. 4-bromo phenyl), sulfonyl phenyl (e.g. 4-methyl sulfonyl phenyl, 3-methyl sulfonyl phenyl), optionally substituted $C_1$-$C_6$-alkyl phenyl (e.g. 4-methyl phenyl, 3-methyl phenyl, 4-trifluoromethyl phenyl), carboxy phenyl (e.g. 3-benzoic acid, 4-benzoic acid, 3-propanoic acid phenyl), optionally substituted acyl amino phenyl (3-methyl acetamide phenyl), optionally substituted alkoxy phenyl (e.g. 4-methoxy phenyl, 3-methoxy phenyl), optionally substituted acyl phenyl (eg. 4-acetyl phenyl), alkoxycarbonyl $C_1$-$C_6$-alkyl phenyl (e.g. methyl 3-propanoate phenyl, methyl-4-benzoate, methyl-3-benzoate, optionally substituted heteroaryl, including optionally substituted imidazolyl (e.g. 1-methyl imidazolyl, 1,2-dimethyl-imidazol-5-yl), optionally substituted thiophenyl such as halo thiophenyl (e.g. 5-bromo-thiophenyl, 4,5-dichloro thiophenyl), thiophen-3-yl, carboxy thiophenyl (e.g. thiophene-2-carboxylic acid), alkoxycarbonyl $C_1$-$C_6$-alkyl thiophenyl (e.g. methyl-3-thiophene-2-carboxylate) and alkoxycarbonyl thiophenyl (e.g. methyl 3-thiophen-2-yl), optionally substituted pyridinyl (e.g. 6-morpholin-4-yl-pyridin-3-yl), optionally substituted pyrazolyl such as halo pyrazolyl (e.g. 5-chloro-1,3 dimethyl-pyrazol-4-yl), optionally fused heteroaryl ring such as optionally substituted dihydrobenzodioxinyl (e.g. 2,3-dihydro-1,4-benzodioxinyl), optionally substituted oxo dihydro-benzothiazolyl (e.g. 3-methyl-2-oxo-2,3-dihydro-1,3-benzothiazolyl), optionally substituted dihydro-benzothiadiazolyl (e.g. 2,1,3-benzothiadiazolyl), optionally substituted benzoxadiazolyl (e.g. 2,1,3-benzoxadiazol-4-yl); optionally substituted $C_3$-$C_8$ cycloalkyl; optionally substituted heterocycloalkyl, including optionally substituted pyrrolidinyl; optionally substituted aryl $C_1$-$C_6$-alkyl; optionally substituted heteroaryl $C_1$-$C_6$-alkyl, including optionally substituted $C_1$-$C_6$-alkyl pyridinyl such as pyridinyl methyl (e.g. pyridinyl-3-methyl, pyridinyl-2-methyl); optionally substituted $C_3$-$C_8$ cycloalkyl $C_1$-$C_6$-alkyl; optionally substituted heterocycloalkyl $C_1$-$C_6$-alkyl; optionally substituted aryl $C_2$-$C_6$-alkenyl, including phenyl ethylenyl; optionally substituted heteroaryl $C_2$-$C_6$-alkenyl;
n is an integer selected from 0, 1, 2, 3 and 4;
as well as its geometrical isomers, its optically active forms as enantiomers, diastereomers, tautomers and its racemate forms, as well as pharmaceutically acceptable salts thereof for use as a medicament.

In another embodiment, the invention provides pyrazine derivatives of Formula (I):

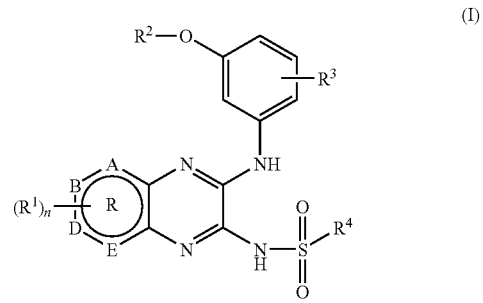

wherein:
A, B, D and E are independently selected from C and N, such that the ring R is a stable aromatic ring, including optionally substituted phenyl and optionally substituted pyridinyl;
$R^1$ is selected from H; halogen, including chloro; nitro; optionally substituted $C_1$-$C_6$-alkyl, including methyl; optionally substituted $C_2$-$C_6$-alkenyl and optionally substituted $C_2$-$C_6$-alkynyl;
$R^2$ is selected from H; optionally substituted $C_1$-$C_6$-alkyl, including methyl; optionally substituted $C_2$-$C_6$-alkenyl and optionally substituted $C_2$-$C_6$-alkynyl;

$R^3$ is selected from H; halo, including chloro; optionally substituted $C_1$-$C_6$-alkyl; optionally substituted $C_2$-$C_6$-alkenyl; optionally substituted $C_2$-$C_6$-alkynyl, optionally substituted alkoxy, including methoxy; optionally substituted aryl; optionally substituted heteroaryl, including pyrrolyl;

$R^4$ is selected from optionally substituted $C_1$-$C_6$-alkyl, including methyl, ethyl, butyl, propyl, carboxy $C_1$-$C_6$-alkyl (e.g. butanoic acid), alkoxycarbonyl $C_1$-$C_6$-alkyl (e.g. methyl-4-butanoate); optionally substituted $C_2$-$C_6$-alkenyl; optionally substituted $C_2$-$C_6$-alkynyl; optionally substituted aryl, including optionally substituted phenyl such as cyano phenyl (e.g. 4-cyano phenyl, 2-cyano phenyl, 3-cyano phenyl), phenyl, halo phenyl such as fluoro phenyl (e.g. 3-fluorophenyl, 4-fluorophenyl, 2-fluorophenyl), chloro phenyl (e.g. 2-chloro phenyl, 3-chloro phenyl), 4-chloro phenyl), iodo phenyl (e.g. 4-iodo phenyl) and bromo phenyl (e.g. 4-bromo phenyl), sulfonyl phenyl (e.g. 4-methyl sulfonyl phenyl, 3-methyl sulfonyl phenyl), optionally substituted $C_1$-$C_6$-alkyl phenyl (e.g. 4-methyl phenyl, 3-methyl phenyl, 4-trifluoromethyl phenyl), carboxy phenyl (e.g. 3-benzoic acid, 4-benzoic acid, 3-propanoic acid phenyl), optionally substituted acyl amino phenyl (3-methyl acetamide phenyl), optionally substituted alkoxy phenyl (e.g. 4-methoxy phenyl, 3-methoxy phenyl), optionally substituted acyl phenyl (eg. 4-acetyl phenyl), alkoxycarbonyl $C_1$-$C_6$-alkyl phenyl (e.g. methyl 3-propanoate phenyl, methyl-4-benzoate, methyl-3-benzoate); optionally substituted heteroaryl, including optionally substituted imidazolyl (e.g. 1-methyl imidazolyl, 1,2-dimethyl-imidazol-5-yl), optionally substituted thiophenyl such as halo thiophenyl (e.g. 5-bromo-thiophenyl, 4,5-dichloro thiophenyl), thiophen-3-yl, carboxy thiophenyl (e.g. thiophene-2-carboxylic acid), alkoxycarbonyl $C_1$-$C_6$-alkyl thiophenyl (e.g. methyl-3-thiophene-2-carboxylate) and alkoxycarbonyl thiophenyl (e.g. methyl 3-thiophen-2-yl), optionally substituted pyridinyl (e.g. 6-morpholin-4-yl-pyridin-3-yl), optionally substituted pyrazolyl such as halo pyrazolyl (e.g. 5-chloro-1,3 dimethyl-pyrazol-4-yl), optionally fused heteroaryl ring such as optionally substituted dihydrobenzodioxinyl (e.g. 2,3-dihydro-1,4-benzodioxinyl), optionally substituted dihydro-benzothiazolyl (e.g. 3-methyl-2,3-dihydro-1,3 benzothiazolyl), optionally substituted dihydrobenzothiadiazolyl (e.g. 2,1,3-benzothiadiazolyl), optionally substituted benzoxadiazolyl (e.g. 2,1,3-benzoxadiazol-4-yl); optionally substituted $C_3$-$C_8$ cycloalkyl; optionally substituted heterocycloalkyl, including optionally substituted pyrrolidinyl; optionally substituted aryl $C_1$-$C_6$-alkyl; optionally substituted heteroaryl $C_1$-$C_6$-alkyl, including optionally substituted $C_1$-$C_6$-alkyl pyridinyl such as pyridinyl methyl (e.g. pyridinyl-3-methyl, pyridinyl-2-methyl); optionally substituted $C_3$-$C_8$ cycloalkyl $C_1$-$C_6$-alkyl; optionally substituted heterocycloalkyl $C_1$-$C_6$-alkyl; optionally substituted aryl $C_2$-$C_6$-alkenyl, including phenyl ethylenyl; optionally substituted heteroaryl $C_2$-$C_6$-alkenyl;

n is an integer selected from 0, 1, 2, 3 and 4;

with the first proviso that when $R^4$ is thiophenyl, it is not a group selected from unsubstituted thiophenyl, unsubstituted chloro-5-thiophenyl or unsubstituted bromo-5-thiophenyl;

with the second proviso that when $R^4$ is a phenyl, it is a mono-substituted phenyl that is not selected from the group consisting of: p-bromo phenyl, p-methoxy phenyl, p-ethoxy phenyl, o-, m- or p-chloro phenyl; m- or p-methyl phenyl; o- or p-fluoro phenyl; o-CF3-phenyl; p- or m-nitro phenyl; p-NHAc-phenyl and p-amino phenyl; or it is a multi-substituted phenyl, that is not an unsubstituted bi-substituted phenyl selected from the group consisting of: m-,p-dimethyl phenyl; m-,m-dimethyl phenyl; o-,p-dimethyl phenyl; o-,m-dimethyl phenyl; o-methyl p-fluoro phenyl; m-,m-dichloro phenyl; o-,m-dichloro phenyl; p-chloro m-nitro phenyl; o-ethoxy m-bromo-phenyl;

with the final proviso that wherein $R^4$ is a 1,4 benzodioxin it is a substituted benzodioxin;

as well as its geometrical isomers, its optically active forms as enantiomers, diastereomers, tautomers and its racemate forms, as well as pharmaceutically acceptable salts thereof;

In a specific embodiment, the invention provides pyrazine derivatives of Formula (I) wherein $R^1$ selected from H and halogen, including chloro.

In another specific embodiment, the invention provides pyrazine derivatives of Formula (I) wherein $R^2$ is methyl.

In another specific embodiment, the invention provides pyrazine derivatives of Formula (I) wherein $R^3$ is selected from H and optionally substituted alkoxy, including methoxy.

In another specific embodiment, the invention provides pyrazine derivatives of Formula (I) wherein $R^3$ is selected from halo, including chloro, optionally substituted aryl and optionally substituted heteroaryl, including pyrrolyl.

In another specific embodiment, the invention provides pyrazine derivatives of Formula (I) wherein $R^4$ is selected from optionally substituted $C_1$-$C_6$-alkyl, optionally substituted $C_2$-$C_6$-alkenyl, optionally substituted $C_2$-$C_6$-alkynyl, optionally substituted aryl $C_1$-$C_6$-alkyl and optionally substituted heteroaryl $C_1$-$C_6$-alkyl.

In another specific embodiment, the invention provides pyrazine derivatives of Formula (I) wherein $R^4$ is selected from optionally substituted aryl and optionally substituted heteroaryl.

In another specific embodiment, the invention provides pyrazine derivatives of Formula (I) wherein A, B, D and E are C.

In another further specific embodiment, the invention provides pyrazine derivatives of Formula (I) wherein A is N; B, D and E are C.

In another further specific embodiment, the invention provides pyrazine derivatives of Formula (I) wherein A, B and E are C; D is N.

In another specific embodiment, the invention provides pyrazine derivatives of Formula (I) wherein $R^1$ selected from H and halogen; $R^2$ is methyl; $R^3$ is selected from H and optionally substituted alkoxy; R, n, $R^4$, A, B, D and E are as defined above.

In another specific embodiment, the invention provides pyrazine derivatives of Formula (I) wherein $R^1$ selected from H and halogen; $R^2$ is methyl; $R^3$ is selected from H and optionally substituted alkoxy; A, B, D and E are C; R, n and $R^4$ are as defined above.

In another specific embodiment, the invention provides pyrazine derivatives of Formula (I) Wherein $R^1$ is H; $R^2$ is methyl; $R^3$ is selected from H and alkoxy; n is 3; A, B, D and E are independently selected from C and N, such that the ring R is optionally substituted pyridinyl; $R^4$ is as defined above.

Compounds of the present invention include in particular those of the group consisting of:

| Example N° | Name |
|---|---|
| 1 | 4-cyano-N-{3-[(2,5-dimethoxyphenyl)amino]quinoxalin-2-yl}benzenesulfonamide; |
| 2 | 4-cyano-N-{3-[(3,5-dimethoxyphenyl)amino]quinoxalin-2-yl}benzenesulfonamide; |

-continued

| Example N° | Name |
|---|---|
| 3 | N-{3-[(3,5-dimethoxyphenyl)amino]quinoxalin-2-yl}benzenesulfonamide; |
| 4 | 3-[({3-[(3,5-dimethoxyphenyl)amino]quinoxalin-2-yl}amino)sulfonyl]benzoic acid; |
| 5 | N-{3-[(2,5-dimethoxyphenyl)amino]quinoxalin-2-yl}-1-methyl-1H-imidazole-4-sulfonamide; |
| 6 | N-{3-[(2,5-dimethoxyphenyl)amino]quinoxalin-2-yl}-4-methylbenzene sulfonamide; |
| 7 | N-{3-[(3,5-dimethoxyphenyl)amino]quinoxalin-2-yl}-3-methylbenzene sulfonamide; |
| 8 | N-{3-[(2,5-dimethoxyphenyl)amino]quinoxalin-2-yl}-3-methylbenzene sulfonamide; |
| 9 | N-{3-[(3,5-dimethoxyphenyl)amino]quinoxalin-2-yl}-4-methylbenzene sulfonamide |
| 10 | 5-bromo-N-{3-[(3,5-dimethoxyphenyl)amino]quinoxalin-2-yl}thiophene-2-sulfonamide; |
| 11 | N-{3-[(2,5-dimethoxyphenyl)amino]quinoxalin-2-yl}-1-pyridin-3-ylmethane sulfonamide; |
| 12 | methyl 3-{4-[({3-[(3,5-dimethoxyphenyl)amino]quinoxalin-2-yl}amino)sulfonyl]phenyl}propanoate; |
| 13 | methyl 4-[({3-[(3,5-dimethoxyphenyl)amino]quinoxalin-2-yl}amino)sulfonyl]benzoate; |
| 14 | N-{3-[(2,5-dimethoxyphenyl)amino]quinoxalin-2-yl}-3-fluorobenzene sulfonamide; |
| 15 | N-{3-[(3,5-dimethoxyphenyl)amino]quinoxalin-2-yl}-4-(methylsulfonyl)benzenesulfonamide; |
| 16 | N-{3-[(2,5-dimethoxyphenyl)amino]quinoxalin-2-yl}-2,3-dihydro-1,4-benzodioxine-6-sulfonamide; |
| 17 | N-{3-[(2,5-dimethoxyphenyl)amino]quinoxalin-2-yl}-4-(pyrrolidin-1-ylsulfonyl)benzenesulfonamide; |
| 18 | N-{3-[(2,5-dimethoxyphenyl)amino]quinoxalin-2-yl}-3-(methylsulfonyl)benzenesulfonamide; |
| 19 | N-{3-[(3,5-dimethoxyphenyl)amino]quinoxalin-2-yl}-3-(methylsulfonyl)benzenesulfonamide; |
| 20 | 2-cyano-N-{3-[(3,5-dimethoxyphenyl)amino]quinoxalin-2-yl}benzene sulfonamide; |
| 21 | 2-cyano-N-{3-[(2,5-dimethoxyphenyl)amino]quinoxalin-2-yl}benzene sulfonamide; |
| 22 | 2-chloro-N-{3-[(3,5-dimethoxyphenyl)amino]quinoxalin-2-yl}benzene sulfonamide; |
| 23 | N-{3-[(2,5-dimethoxyphenyl)amino]quinoxalin-2-yl}pyridine-3-sulfonamide; |
| 24 | N-{3-[(3,5-dimethoxyphenyl)amino]quinoxalin-2-yl}-1-methyl-1H-imidazole-4-sulfonamide; |
| 25 | N-{3-[(2,5-dimethoxyphenyl)amino]quinoxalin-2-yl}-4-fluorobenzene sulfonamide; |
| 26 | N-{3-[(2,5-dimethoxyphenyl)amino]pyrido[2,3-b]pyrazin-2-yl}benzene sulfonamide; |
| 27 | N-{3-[(3,5-dimethoxyphenyl)amino]quinoxalin-2-yl}-4-fluorobenzene sulfonamide; |
| 28 | N-{3-[(2,5-dimethoxyphenyl)amino]quinoxalin-2-yl}benzenesulfonamide; |
| 29 | N-{3-[(2,5-dimethoxyphenyl)amino]quinoxalin-2-yl}methanesulfonamide; |
| 30 | N-{3-[(3,5-dimethoxyphenyl)amino]quinoxalin-2-yl}thiophene-3-sulfonamide; |
| 31 | N-{3-[(3,5-dimethoxyphenyl)amino]quinoxalin-2-yl}methanesulfonamide; |
| 32 | 3-[({3-[(2,5-dimethoxyphenyl)amino]quinoxalin-2-yl}amino)sulfonyl]benzoic acid; |
| 33 | methyl 4-[({3-[(2,5-dimethoxyphenyl)amino]quinoxalin-2-yl}amino)sulfonyl]benzoate; |
| 34 | methyl 3-[({3-[(3,5-dimethoxyphenyl)amino]quinoxalin-2-yl}amino)sulfonyl]thiophene-2-carboxylate; |
| 35 | 5-chloro-N-{3-[(2,5-dimethoxyphenyl)amino]quinoxalin-2-yl}-1,3-dimethyl-1H-pyrazole-4-sulfonamide; |
| 36 | 4-chloro-N-{3-[(2,5-dimethoxyphenyl)amino]quinoxalin-2-yl}benzene sulfonamide; |
| 37 | 3-[({3-[(2,5-dimethoxyphenyl)amino]quinoxalin-2-yl}amino)sulfonyl]thiophene-2-carboxylic acid; |
| 38 | 3-{4-[({3-[(3,5-dimethoxyphenyl)amino]quinoxalin-2-yl}amino)sulfonyl]phenyl}propanoic acid; |
| 39 | N-{3-[(3,5-dimethoxyphenyl)amino]quinoxalin-2-yl}-3-methyl-2-oxo-2,3-dihydro-1,3-benzothiazole-6-sulfonamide; |
| 40 | N-{3-[(2,5-dimethoxyphenyl)amino]quinoxalin-2-yl}-2,1,3-benzothiadiazole-4-sulfonamide; |
| 41 | 4-chloro-N-{3-[(3,5-dimethoxyphenyl)amino]quinoxalin-2-yl}benzene sulfonamide; |
| 42 | N-{3-[(2,5-dimethoxyphenyl)amino]quinoxalin-2-yl}-3-methyl-2-oxo-2,3-dihydro-1,3-benzothiazole-6-sulfonamide; |
| 43 | 4-bromo-N-{3-[(2,5-dimethoxyphenyl)amino]quinoxalin-2-yl}benzene sulfonamide; |

-continued

| Example N° | Name |
|---|---|
| 44 | N-{3-[(3,5-dimethoxyphenyl)amino]pyrido[2,3-b]pyrazin-2-yl}benzene sulfonamide; |
| 45 | 4-bromo-N-{3-[(3,5-dimethoxyphenyl)amino]quinoxalin-2-yl}benzene sulfonamide; |
| 46 | 4-acetyl-N-{3-[(3,5-dimethoxyphenyl)amino]quinoxalin-2-yl}benzene sulfonamide; |
| 47 | N-{3-[(3,5-dimethoxyphenyl)amino]quinoxalin-2-yl}propane-1-sulfonamide; |
| 48 | N-{3-[(2,5-dimethoxyphenyl)amino]quinoxalin-2-yl}thiophene-3-sulfonamide; |
| 49 | 4-acetyl-N-{3-[(2,5-dimethoxyphenyl)amino]quinoxalin-2-yl}benzene sulfonamide; |
| 50 | 2-chloro-N-{3-[(2,5-dimethoxyphenyl)amino]quinoxalin-2-yl}benzene sulfonamide; |
| 51 | N-{3-[(2,5-dimethoxyphenyl)amino]quinoxalin-2-yl}-1,2-dimethyl-1H-imidazole-5-sulfonamide; |
| 52 | N-{3-[(3,5-dimethoxyphenyl)amino]quinoxalin-2-yl}-2,1,3-benzoxadiazole-4-sulfonamide; |
| 53 | 3-chloro-N-{3-[(3,5-dimethoxyphenyl)amino]quinoxalin-2-yl}benzene sulfonamide; |
| 54 | 5-chloro-N-{3-[(3,5-dimethoxyphenyl)amino]quinoxalin-2-yl}-1,3-dimethyl-1H-pyrazole-4-sulfonamide; |
| 55 | 3-cyano-N-{3-[(2,5-dimethoxyphenyl)amino]quinoxalin-2-yl}benzene sulfonamide; |
| 56 | N-{3-[({3-[(3,5-dimethoxyphenyl)amino]quinoxalin-2-yl}amino)sulfonyl]phenyl}acetamide; |
| 57 | 3-cyano-N-{3-[(3,5-dimethoxyphenyl)amino]quinoxalin-2-yl}benzene sulfonamide; |
| 58 | N-{3-[(2,5-dimethoxyphenyl)amino]quinoxalin-2-yl}propane-1-sulfonamide; |
| 59 | N-{3-[(2,5-dimethoxyphenyl)amino]quinoxalin-2-yl}-4-(trifluoromethyl)benzenesulfonamide; |
| 60 | 4-[({3-[(3,5-dimethoxyphenyl)amino]quinoxalin-2-yl}amino)sulfonyl]butanoic acid; |
| 61 | 3-chloro-N-{3-[(2,5-dimethoxyphenyl)amino]quinoxalin-2-yl}benzene sulfonamide; |
| 62 | 4-fluoro-N-{3-[(3-methoxyphenyl)amino]quinoxalin-2-yl}benzenesulfonamide; |
| 63 | N-{6-chloro-3-[(3,5-dimethoxyphenyl)amino]quinoxalin-2-yl}benzene sulfonamide; |
| 64 | N-{3-[(2,5-dimethoxyphenyl)amino]quinoxalin-2-yl}-1-pyridin-2-ylmethane sulfonamide; |
| 65 | N-{3-[(2,5-dimethoxyphenyl)amino]quinoxalin-2-yl}-4-methoxybenzene sulfonamide; |
| 66 | N-{3-[(3,5-dimethoxyphenyl)amino]pyrido[2,3-b]pyrazin-2-yl}ethane sulfonamide; |
| 67 | N-{3-[(3,5-dimethoxyphenyl)amino]quinoxalin-2-yl}-3-methoxybenzene sulfonamide; |
| 68 | N-{3-[(3,5-dimethoxyphenyl)amino]quinoxalin-2-yl}-1-pyridin-2-ylmethane sulfonamide; |
| 69 | N-{3-[(3,5-dimethoxyphenyl)amino]quinoxalin-2-yl}-1-pyridin-3-ylmethane sulfonamide; |
| 70 | methyl 3-[({3-[(2,5-dimethoxyphenyl)amino]quinoxalin-2-yl}amino)sulfonyl]thiophene-2-carboxylate; |
| 71 | N-{2-[(2,5-dimethoxyphenyl)amino]pyrido[3,4-b]pyrazin-3-yl}benzene sulfonamide; |
| 72 | N-{3-[(3-methoxyphenyl)amino]quinoxalin-2-yl}benzenesulfonamide; |
| 73 | 4-chloro-N-{3-[(3-methoxyphenyl)amino]quinoxalin-2-yl}benzenesulfonamide; |
| 74 | N-{3-[(2,5-dimethoxyphenyl)amino]quinoxalin-2-yl}-3-methoxybenzene sulfonamide; |
| 75 | 4-[({3-[(2,5-dimethoxyphenyl)amino]quinoxalin-2-yl}amino)sulfonyl]butanoic acid; |
| 76 | N-{3-[(3-methoxyphenyl)amino]quinoxalin-2-yl}methanesulfonamide; |
| 77 | N-{3-[(2,5-dimethoxyphenyl)amino]quinoxalin-2-yl}-4-iodobenzene sulfonamide; |
| 78 | 4-bromo-N-{3-[(3-methoxyphenyl)amino]quinoxalin-2-yl}benzene sulfonamide; |
| 79 | N-{3-[(3,5-dimethoxyphenyl)amino]quinoxalin-2-yl}-4-iodobenzene sulfonamide; |
| 80 | 4-[({3-[(2,5-dimethoxyphenyl)amino]quinoxalin-2-yl}amino)sulfonyl]benzoic acid; |
| 81 | methyl 4-[({3-[(2,5-dimethoxyphenyl)amino]quinoxalin-2-yl}amino)sulfonyl]butanoate; |
| 82 | 4-[({3-[(3,5-dimethoxyphenyl)amino]quinoxalin-2-yl}amino)sulfonyl]benzoic acid; |
| 83 | N-{3-[(3,5-dimethoxyphenyl)amino]quinoxalin-2-yl}-2-fluorobenzene sulfonamide; |
| 84 | N-(3-{[5-methoxy-2-(1H-pyrrol-1-yl)phenyl]amino}quinoxalin-2-yl)benzene sulfonamide; |
| 85 | methyl 3-[({3-[(2,5-dimethoxyphenyl)amino]quinoxalin-2-yl}amino)sulfonyl]benzoate; |

| Example N° | Name |
|---|---|
| 86 | N-{3-[(2,5-dimethoxyphenyl)amino]quinoxalin-2-yl}-6-morpholin-4-yl pyridine-3-sulfonamide; |
| 87 | 4-methoxy-N-{3-[(3-methoxyphenyl)amino]quinoxalin-2-yl}benzene sulfonamide; |
| 88 | methyl 3-[({3-[(3,5-dimethoxyphenyl)amino]quinoxalin-2-yl}amino)sulfonyl] benzoate; |
| 89 | 3-[({3-[(3,5-dimethoxyphenyl)amino]quinoxalin-2-yl}amino)sulfonyl]thiophene-2-carboxylic acid; |
| 90 | N-{3-[(2-chloro-5-methoxyphenyl)amino]quinoxalin-2-yl}benzenesulfonamide; |
| 91 | N-{3-[(3,5-dimethoxyphenyl)amino]quinoxalin-2-yl}-2-(methylsulfonyl) benzenesulfonamide; |
| 92 | N-{3-[(2,5-dimethoxyphenyl)amino]quinoxalin-2-yl}-2-fluorobenzene sulfonamide; |
| 93 | 4,5-dichloro-N-{3-[(2,5-dimethoxyphenyl)amino]quinoxalin-2-yl}thiophene-2-sulfonamide; |
| 94 | N-{3-[(5-methoxy-2-methylphenyl)amino]quinoxalin-2-yl}benzene sulfonamide; |
| 95 | N-{3-[(3,5-dimethoxyphenyl)amino]quinoxalin-2-yl}-3-fluorobenzene sulfonamide; |
| 96 | N-{3-[(2,5-dimethoxyphenyl)amino]quinoxalin-2-yl}-2-(methylsulfonyl) benzenesulfonamide; |
| 97 | N-{3-[(2,3-dihydro-1,4-benzodioxin-5-ylmethyl)amino]quinoxalin-2-yl} benzenesulfonamide; |
| 98 | N-{3-[(3,5-dimethoxyphenyl)amino]-6-nitroquinoxalin-2-yl}benzene sulfonamide; |
| 99 | N-{3-[(3,5-dimethoxyphenyl)amino]quinoxalin-2-yl}-4-(pyrrolidin-1-ylsulfonyl)benzenesulfonamide; |
| 100 | methyl 4-[({3-[(3,5-dimethoxyphenyl)amino]quinoxalin-2-yl}amino) sulfonyl]butanoate; |
| 101 | methyl 5-[({3-[(2,5-dimethoxyphenyl)amino]quinoxalin-2-yl}amino)sulfonyl]-4-methylthiophene-2-carboxylate; |
| 102 | methyl 5-[({3-[(2,5-dimethoxyphenyl)amino]quinoxalin-2-yl}amino)sulfonyl]-1-methyl-1H-pyrrole-2-carboxylate; |
| 103 | methyl 5-[({3-[(3,5-dimethoxyphenyl)amino]quinoxalin-2-yl}amino)sulfonyl]-1-methyl-1H-pyrrole-2-carboxylate; |
| 104 | N-{3-[(2,5-dimethoxyphenyl)amino]quinoxalin-2-yl}thiophene-2-sulfonamide; |
| 105 | 2-chloro-N-{3-[(2,5-dimethoxyphenyl)amino]quinoxalin-2-yl}-4-fluorobenzene sulfonamide; |
| 106 | 2-chloro-N-{3-[(3,5-dimethoxyphenyl)amino]quinoxalin-2-yl}-4-fluorobenzene sulfonamide; |
| 107 | N-{3-[(3,5-dimethoxyphenyl)amino]quinoxalin-2-yl}pyridine-3-sulfonamide; |
| 108 | 3-cyano-N-{3-[(3,5-dimethoxyphenyl)amino]quinoxalin-2-yl}-4-fluorobenzene sulfonamide; |
| 109 | 3-cyano-N-{3-[(2,5-dimethoxyphenyl)amino]quinoxalin-2-yl}-4-fluorobenzene sulfonamide; |
| 110 | 6-chloro-N-{3-[(3,5-dimethoxyphenyl)amino]quinoxalin-2-yl}pyridine-3-sulfonamide; |
| 111 | N-{3-[(3,5-dimethoxyphenyl)amino]quinoxalin-2-yl}-6-(dimethylamino) pyridine-3-sulfonamide; |
| 112 | N-{3-[(3,5-dimethoxyphenyl)amino]quinoxalin-2-yl}-6-[(3-methoxypropyl) amino]pyridine-3-sulfonamide; |
| 113 | N-{3-[(5-methoxy-2-methylphenyl)amino]quinoxalin-2-yl}pyridine-3-sulfonamide; |
| 114 | N-{3-[(2-chloro-5-methoxyphenyl)amino]quinoxalin-2-yl}-4-cyanobenzenesulfonamide; |
| 115 | N-{3-[(2-chloro-5-methoxyphenyl)amino]quinoxalin-2-yl}pyridine-3-sulfonamide; |
| 116 | N-{3-[(3,5-dimethoxyphenyl)amino]quinoxalin-2-yl}-6-methoxypyridine-3-sulfonamide; |
| 117 | N-{3-[(3,5-dimethoxyphenyl)amino]quinoxalin-2-yl}-6-oxo-1,6-dihydropyridine-3-sulfonamide; |
| 118 | N-{3-[(3,5-dimethoxyphenyl)amino]quinoxalin-2-yl}-6-methylpyridine-3-sulfonamide; |
| 119 | N-{3-[(3,5-dimethoxyphenyl)amino]quinoxalin-2-yl}-4-fluoro-2-methyl benzenesulfonamide; |
| 120 | N-{3-[(2,5-dimethoxyphenyl)amino]quinoxalin-2-yl}-6-methylpyridine-3-sulfonamide; |
| 121 | 4-cyano-N-{3-[(5-methoxy-2-methylphenyl)amino]quinoxalin-2-yl} benzene sulfonamide; |
| 122 | N-{3-[(5-methoxy-2-methylphenyl)amino]quinoxalin-2-yl}-6-methylpyridine-3-sulfonamide; |
| 123 | N-{3-[(2-chloro-5-methoxyphenyl)amino]quinoxalin-2-yl}-6-methylpyridine-3-sulfonamide; |
| 124 | methyl 5-[({3-[(3,5-dimethoxyphenyl)amino]quinoxalin-2-yl}amino)sulfonyl] pyridine-2-carboxylate; |
| 125 | N-{3-[(2-bromo-5-methoxyphenyl)amino]quinoxalin-2-yl}-1-methyl-1H-imidazole-4-sulfonamide; |

| Example N° | Name |
|---|---|
| 126 | N-{3-[(3,5-dimethoxyphenyl)amino]quinoxalin-2-yl}-3-(morpholin-4-ylcarbonyl)benzenesulfonamide; |
| 127 | 5-[({3-[(2,5-dimethoxyphenyl)amino]quinoxalin-2-yl}amino)sulfonyl]-4-methylthiophene-2-carboxylic acid; |
| 128 | 5-[({3-[(3,5-dimethoxyphenyl)amino]quinoxalin-2-yl}amino)sulfonyl]-4-methylthiophene-2-carboxylic acid; |
| 129 | 5-[({3-[(2,5-dimethoxyphenyl)amino]quinoxalin-2-yl}amino)sulfonyl]-1-methyl-1H-pyrrole-2-carboxylic acid; |
| 130 | 5-[({3-[(3,5-dimethoxyphenyl)amino]quinoxalin-2-yl}amino)sulfonyl]-1-methyl-1H-pyrrole-2-carboxylic acid; |
| 131 | 5-[({3-[(3,5-dimethoxyphenyl)amino]quinoxalin-2-yl}amino)sulfonyl]pyridine-2-carboxylic acid; |
| 132 | N-{3-[(3,5-dimethoxyphenyl)amino]quinoxalin-2-yl}-3-(morpholin-4-ylmethyl)benzene sulfonamide; |
| 133 | N-{3-[(3,5-dimethoxyphenyl)amino]quinoxalin-2-yl}-4-[(4-methylpiperazin-1-yl) methyl]benzenesulfonamide; |
| 134 | 4-(aminomethyl)-N-{3-[(2,5-dimethoxyphenyl)amino]quinoxalin-2-yl} benzene sulfonamide; |
| 135 | N-{3-[(3,5-dimethoxyphenyl)amino]quinoxalin-2-yl}-3-(hydroxymethyl)benzenesulfonamide; |
| 136 | 3-(aminomethyl)-N-{3-[(3,5-dimethoxyphenyl)amino]quinoxalin-2-yl} benzenesulfonamide; |
| 137 | N-{3-[(3,5-dimethoxyphenyl)amino]quinoxalin-2-yl}-4-(hydroxymethyl)benzenesulfonamide; |
| 138 | N-{3-[(3,5-dimethoxyphenyl)amino]quinoxalin-2-yl}-6-(hydroxymethyl)pyridine-3-sulfonamide; |
| 139 | N-{3-[(3,5-dimethoxyphenyl)amino]quinoxalin-2-yl}-4-(morpholin-4-ylmethyl)benzenesulfonamide; |
| 140 | N-{3-[(3,5-dimethoxyphenyl)amino]quinoxalin-2-yl}-3-[(4-methylpiperazin-1-yl)methyl]benzenesulfonamide; |
| 141 | N-{3-[(3,5-dimethoxyphenyl)amino]quinoxalin-2-yl}-4-[(dimethylamino)methyl]benzenesulfonamide; |
| 142 | N-{3-[(3,5-dimethoxyphenyl)amino]quinoxalin-2-yl}-3-[(dimethylamino)methyl]benzenesulfonamide; |
| 143 | 4-[({3-[(3,5-dimethoxyphenyl)amino]quinoxalin-2-yl}amino) sulfonyl]benzamide; |
| 144 | 4-[({3-[(5-methoxy-2-methylphenyl)amino]quinoxalin-2-yl}amino)sulfonyl]benzamide; |
| 145 | 4-[({3-[(3,5-dimethoxyphenyl)amino]quinoxalin-2-yl}amino)sulfonyl]-N-(3-methoxypropyl)benzamide; |
| 146 | 4-[({3-[(3,5-dimethoxyphenyl)amino]quinoxalin-2-yl}amino)sulfonyl]-N-[3-(dimethylamino)propyl]benzamide; |
| 147 | 3-[({3-[(3,5-dimethoxyphenyl)amino]quinoxalin-2-yl}amino)sulfonyl]-N-[3-(dimethylamino)propyl]benzamide; |
| 148 | 5-[({3-[(3,5-dimethoxyphenyl)amino]quinoxalin-2-yl}amino)sulfonyl]-N,N-dimethylpyridine-2-carboxamide; |
| 149 | N-{3-[(3,5-dimethoxyphenyl)amino]quinoxalin-2-yl}-3-[(4-methylpiperazin-1-yl)carbonyl]benzenesulfonamide; |
| 150 | N-{3-[(3,5-dimethoxyphenyl)amino]quinoxalin-2-yl}-6-(morpholin-4-yl carbonyl)pyridine-3-sulfonamide; |
| 151 | N-{3-[(3,5-dimethoxyphenyl)amino]quinoxalin-2-yl}-6-[(4-methylpiperazin-1-yl)methyl]pyridine-3-sulfonamide; |
| 152 | 5-(aminomethyl)-N-{3-[(3,5-dimethoxyphenyl)amino]quinoxalin-2-yl}thiophene-2-sulfonamide. |

The compounds of the present invention are useful as medicaments. They may be used for the preparation of a medicament for the prophylaxis and/or treatment of autoimmune disorders and/or inflammatory diseases, cardiovascular diseases, neurodegenerative diseases, bacterial or viral infections, kidney diseases, platelet aggregation, cancer, transplantation, erythrocyte deficiency, graft rejection or lung injuries.

In one embodiment, the compounds of Formula (I) are useful for the treatment and/or prophylaxis of autoimmune diseases or inflammatory diseases such as multiple sclerosis, psoriasis, rheumatoid arthritis, systemic lupus erythematosis, inflammatory bowel disease, lung inflammation, thrombosis or brain infection/inflammation such as meningitis or encephalitis.

In another embodiment, the compounds of Formula (I) are useful for the treatment and/or prophylaxis of neurodegenerative diseases including Alzheimer's disease, Huntington's disease, CNS trauma, stroke or ischemic conditions.

In still a further embodiment according to the invention, the compounds of Formula (I) are useful for the treatment and/or prophylaxis of cardiovascular diseases such as athero-sclerosis, heart hypertrophy, cardiac myocyte dysfunction, elevated blood pressure or vasoconstriction.

In still a further embodiment according to the invention, the compounds of Formula (I) are useful for the treatment and/or prophylaxis of erythrocyte deficiency such as an anaemia, including haemolytic anaemia, aplastic anaemia and pure red cell anaemia.

In still a further embodiment according to the invention, the compounds of Formula (I) are useful for the treatment and/or prophylaxis of cancers including non-small cell lung (NSCL) cancer, pancreatic cancer, endometrial cancer, ovarian cancer, bladder cancer, seminomas, thyroid cancer, breast cancer, glioblastoma multiforme, mammary carcinoma, gastric cancers, and lymphomas, cancers of the lung, prostate, liver, colon, breast, kidney, brain, skin including malignant melanoma, testes or ovaries, or leukemias, including myeloid and lymphocytic leukemias, acute myeloid leukemia (AML), multiple myeloma-related bone disorder, mestatic melanoma and malignant melanoma and Kaposi's sarcoma.

In still another embodiment according to the invention, the compounds of Formula (I) are useful for the treatment and/or prophylaxis of chronic obstructive pulmonary disease, anaphylactic shock fibrosis, psoriasis, allergic diseases, asthma, stroke or ischemic conditions, ischemia-reperfusion, platelets aggregation/activation, skeletal muscle atrophy/hypertrophy, leukocyte recruitment in cancer tissue, angiogenesis, invasion metastasis, in particular melanoma, Karposi's sarcoma, acute and chronic bacterial and viral infections, sepsis, transplantation, graft rejection, glomerulo sclerosis, glomerulo nephritis, progressive renal fibrosis, endothelial and epithelial injuries in the lung or in general lung airways inflammation.

In another embodiment according to the invention, is provided a process for the preparation of pyrazine derivative according to Formula (I), comprising the step of reacting a chloro derivative of Formula (II) with an aniline of Formula (III) in an appropriate solvent such as EtOH or MeOH in absence of base, either by traditional thermic methods or using microwave technology such as those described hereinafter in the Examples:

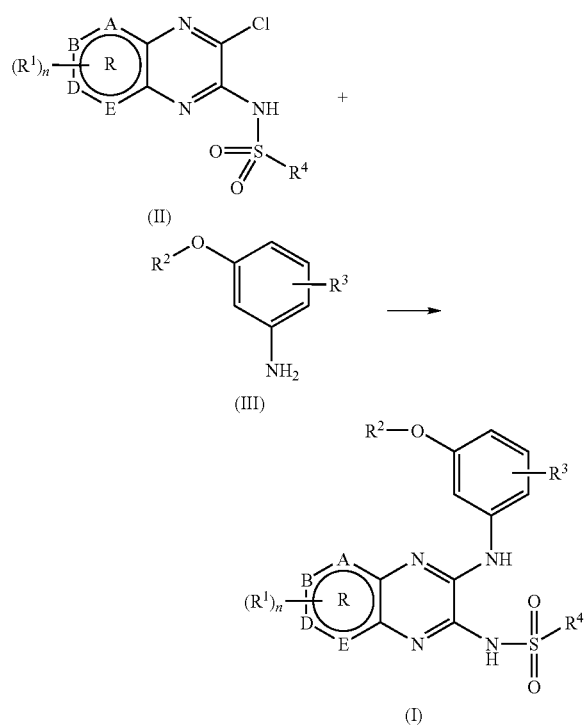

optional presence of a co-solvent such as 1,2-dichlorobenzene. A preferred base is pyridine.

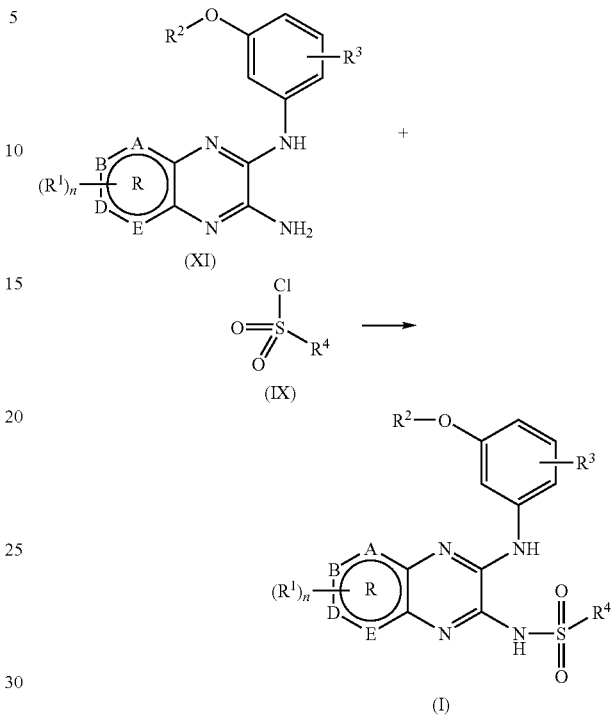

erein n, A, B, D, E, R, $R^1$, $R^2$, $R^3$, $R^4$ are as above defined.

In another embodiment according to the invention, is provided a compound of Formula (II)

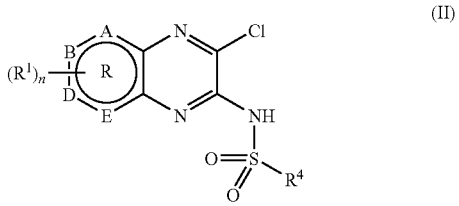

wherein n, A, B, D, E, R, $R^1$, $R^4$ are as defined above and wherein the compounds of Formula (II) are selected from the list below:

4,5-dichloro-N-(3-chloroquinoxalin-2-yl)thiophene-2-sulfonamide;
4-acetyl-N-(3-chloroquinoxalin-2-yl)benzenesulfonamide;
4-cyano-N-(3-chloroquinoxalin-2-yl)benzenesulfonamide;
5-bromo-N-(3-chloroquinoxalin-2-yl)thiophene-2-sulfonamide;
5-chloro-N-(3-chloroquinoxalin-2-yl)-1,3-dimethyl-1H-pyrazole-4-sulfonamide;
methyl 3-(4-{[(3-chloroquinoxalin-2-yl)amino]sulfonyl}phenyl)propanoate;
methyl 4-{[(3-chloroquinoxalin-2-yl)amino]sulfonyl}butanoate;
N-(2-chloropyrido[3,4-b]pyrazin-3-yl)benzenesulfonamide;
N-(3,6-dichloroquinoxalin-2-yl)benzenesulfonamide;
N-(3-chloro-6-nitroquinoxalin-2-yl)benzenesulfonamide;
N-(3-chloro-7-methoxyquinoxalin-2-yl)benzenesulfonamide;

wherein n, A, B, D, E, R, $R^1$, $R^2$, $R^3$, $R^4$ are as above defined.

In another embodiment according to the invention, is provided a process for the preparation of pyrazine derivative according to Formula (I) comprising the step of reacting an amino derivative of Formula (XI) and a sulfonylchloride of Formula (IX) in the presence of base such as triethylamine, isopropylamine, DIEA(diisopropylethylamine), with the N-(3-chloropyrido[2,3-b]pyrazin-2-yl)benzenesulfonamide;
N-(3-chloroquinoxalin-2-yl)-2,2-dimethylchromane-7-sulfonamide;
N-(3-chloroquinoxalin-2-yl)-3-fluorobenzenesulfonamide;
N-(3-chloroquinoxalin-2-yl)-3-methylbenzenesulfonamide;
N-(3-chloroquinoxalin-2-yl)-4-(trifluoromethyl)benzenesulfonamide;
N-(3-chloroquinoxalin-2-yl)-4-cyanobenzenesulfonamide;
N-(3-chloroquinoxalin-2-yl)-4-iodobenzenesulfonamide;
N-(3-chloroquinoxalin-2-yl)-4-methoxybenzenesulfonamide;
N-(3-chloroquinoxalin-2-yl)biphenyl-4-sulfonamide;
N-(3-chloroquinoxalin-2-yl)methanesulfonamide;
N-(3-chloroquinoxalin-2-yl)propane-1-sulfonamide; and
N-(3-chloroquinoxalin-2-yl)pyridine-3-sulfonamide;
methyl 5-{[(3-chloroquinoxalin-2-yl)amino]sulfonyl}-4-methylthiophene-2-carboxylate;
methyl 5-{[(3-chloroquinoxalin-2-yl)amino]sulfonyl}-1-methyl-1H-pyrrole-2-carboxylate;
N-(3-chloroquinoxalin-2-yl)thiophene-2-sulfonamide;
2-chloro-N-(3-chloroquinoxalin-2-yl)-4-fluorobenzenesulfonamide;
N-(3-chloroquinoxalin-2-yl)-5-[(1,3-dioxo-1,3-dihydro-2H-isoindol-2-yl)methyl]thiophene-2-sulfonamide;
N-(3-chloroquinoxalin-2-yl)-3-cyano-4-fluorobenzenesulfonamide;
6-chloro-N-(3-chloroquinoxalin-2-yl)pyridine-3-sulfonamide;
N-(3-chloroquinoxalin-2-yl)-6-(dimethylamino)pyridine-3-sulfonamide;
N-(3-chloroquinoxalin-2-yl)-6-[(3-methoxypropyl)amino]pyridine-3-sulfonamide;
N-(3-chloroquinoxalin-2-yl)-6-methoxypyridine-3-sulfonamide;
N-(3-chloroquinoxalin-2-yl)-6-methylpyridine-3-sulfonamide;
methyl 5-{[(3-chloroquinoxalin-2-yl)amino]sulfonyl}pyridine-2-carboxylate;
N-(3-chloroquinoxalin-2-yl)-3-(morpholin-4-ylcarbonyl)benzenesulfonamide;
N-(3-chloroquinoxalin-2-yl)-1-methyl-1H-imidazole-4-sulfonamide.

In another embodiment according to the invention, is provided a compound of Formula (XI):

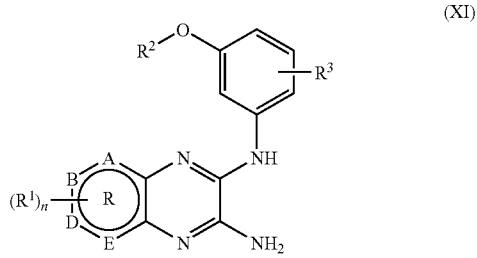

(XI)

wherein n, A, B, D, E, R, R$^1$, R$^2$, R$^3$, R$^4$ are as defined above with the proviso that the compound of Formula (XI) is not N-(3-methoxyphenyl)-2,3-Quinoxalinediamine (RN 165058-49-1) nor 3-[(3-amino-2-quinoxalinyl)amino]-Phenol (165058-51-5).

In a further embodiment according to the invention, is provided a compound of Formula (XI) selected from the following group:
N-(2,5-dimethoxyphenyl)quinoxaline-2,3-diamine;
N-(5-methoxy-2-methyl-phenyl)quinoxaline-2,3-diamine;
N-(5-methoxy2-pyrrol-1-yl-phenyl)quinoxaline-2,3-diamine;
N-(5-methoxy-2-chloro-phenyl)quinoxaline-2,3-diamine;
N-(3-methoxy-phenyl)quinoxaline-2,3-diamine;
N-(5-methoxy-2-bromo-phenyl)quinoxaline-2,3-diamine;
N-(3,5-dimethoxyphenyl)quinoxaline-2,3-diamine.

The pyrazine derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

When employed as pharmaceuticals, the compounds of the present invention are typically administered in the form of a pharmaceutical composition. Hence, pharmaceutical compositions comprising a compound of Formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing pyrazine derivatives of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the pyrazine derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the pyrazine derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharma-ceutical Sciences*.

Synthesis of Compounds of the Invention

The pyrazine derivatives according to Formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The following abbreviations refer respectively to the definitions below:
min (min-ute), hr (hour), g (gram), mmol (millimole), m.p. (melting point), eq. (equivalents), mL (milliliter), μL (microliters), ACN (Acetonitrile), AcOH, (acetic acid), CDCl$_3$ (deuterated chloroform), CsCO$_3$ (Cesium carbonate), CuI (Copper iodide), DCM (Dichloromethane), DMA (Dimethylacetamide), DMF (Dimethylformamide), DMSO (Dimethyl-sulfoxide), DMSO-d$_6$ (deuterated dimethylsulfoxide), Et$_3$N (Triethylamine), EtOAc (ethyl acetate), EtOH (Ethanol), Et$_2$O (Diethyl ether), HPLC (High Performance Liquid Chromatography), K$_2$CO$_3$ (Potassium carbonate), MS (mass spectrometry), MgSO$_4$ (Magnesium sulfate), NMP (N-methylpyrrolidone), NMR (Nuclear Magnetic Resonance), MeOH (methanol), NaI (Sodium iodide), NaHCO$_3$ (Sodium bicarbonate), NH$_4$Cl (Ammonium chloride), (NH$_4$)$_2$CO$_3$ (Ammonium carbonate), PIs (Phosphoinositides), PI3Ks (Phosphoinositide 3-kinases), PI(3)P (Phosphatidylinositol 3-monophosphate), PI(3,4)P$_2$ (Phosphatidylinositol 3,4-bisphosphate), PI(3,4,5)P$_3$ (Phosphatidylinositol 3,4,5-trisphosphate), PI(4)P (Phosphatidylinositol-4-phosphate), PI(4,5)P$_2$) (Phosphatidyl inositol-4,5-biphosphate), POCl$_3$ (phosphorus oxychloride), PtdIns (Phosphatidylinositol), TDB pol (7-methyl-1,5,7-triazabicyclo[4.4.0]dec-5-ene on polystyrene), THF (Tetrahydrofuran), TLC (Thin Layer Chromatography), rt (room temperature), Rt (retention time).

Depending on the nature of A, B, D, E, R, R$^1$, R$^2$, R$^3$, R$^4$, R$^5$ and R$^6$ different synthetic strategies may be selected for the synthesis of compounds of Formula (I). In the process illustrated in the following schemes A, B, D, E, R$^1$, R$^2$, R$^3$, R$^4$ and R$^5$ as above-defined in the description.

Generally, the quinoxaline sulfonamide and the azaquinoxaline sulfonamide derivatives according to the general Formula (I) may be obtained by several processes using solution-phase chemistry protocols.

According to one process, quinoxaline sulfonamide and azaquinoxaline sulfonamide derivatives according to the general Formula (I), whereby the substituents A, B, D, E and R$^1$, R$^2$, R$^3$ and R$^4$ are as above defined, are prepared from the chloro derivatives of Formula (II) and anilines of Formula (III), by well known solution-phase chemistry protocols, such as those shown in Scheme 1 below. In a typical procedure, the nucleophilic substitution is performed in an appropriate solvent such as EtOH or MeOH in absence of base or presence of acid such as AcOH, either by traditional thermic methods or using microwave technology such as those described hereinafter in the Examples.

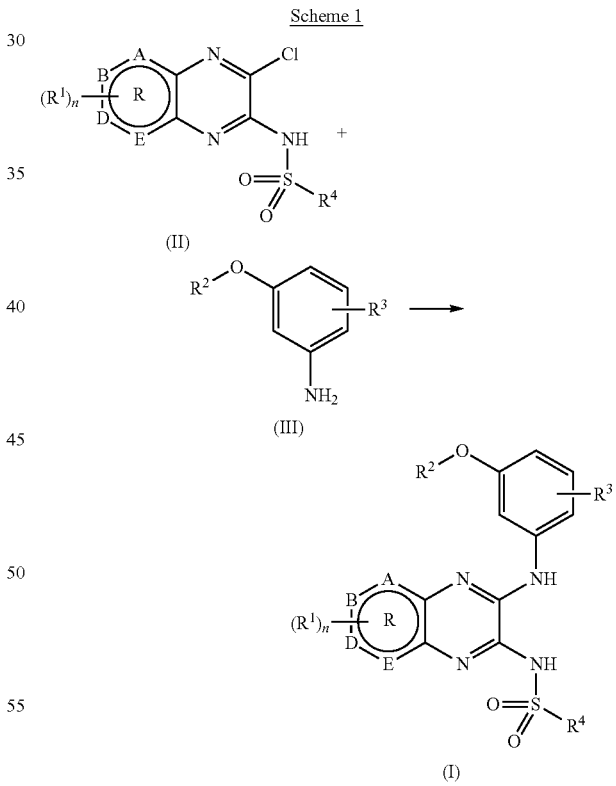

Scheme 1

The aniline derivatives of Formula (III) may be obtained either from commercial sources or they may be prepared from known compounds using procedures such as those described hereinafter in the examples, or conventional procedures, known by one skilled in the art.

The chloro derivatives of Formula (II), whereby the substituents A, B, D, E and R$^1$, R$^2$, R$^3$, R$^4$ are as above defined, are prepared from the dichloro derivatives of Formula (IV)

and sulfonamides of Formula (V), by well known solution-phase chemistry protocols such as shown in Scheme 2 below (Litvinenko et al., 1994, *Chemistry of heterocyclic compounds*, 30 (3), 340-344). In a typical procedure, the nucleophilic substitution is performed in an appropriate solvent such as DMF or DMA in presence of a base such as $K_2CO_3$, $Cs_2CO_3$ or TDB pol. Depending on the intrinsic reactivity of dichloro derivatives of Formula (IV) and sulphonamide derivatives of Formula (V), the reaction can be performed at various temperatures in the presence or absence of NaI or CuI, either by traditional thermic methods or using microwave technology such as those described hereinafter in the Examples.

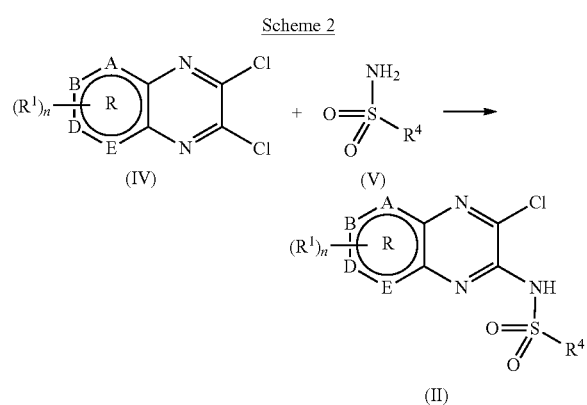

The dichloro derivatives of Formula (IV) may be obtained either from commercial sources or they may be prepared from the corresponding bis amino derivatives of Formula (VI) using conventional procedures, known by one skilled in the art as shown in the Scheme 3 below. In a typical procedure, the first step is performed in aqueous HCl under reflux. In a subsequent step, a dione of Formula (VIII) is treated with $POCl_3$ in the presence of an organic base such as $Et_3N$ to give the expected dichloro derivatives of Formula (IV), such as those described hereinafter in the Examples.

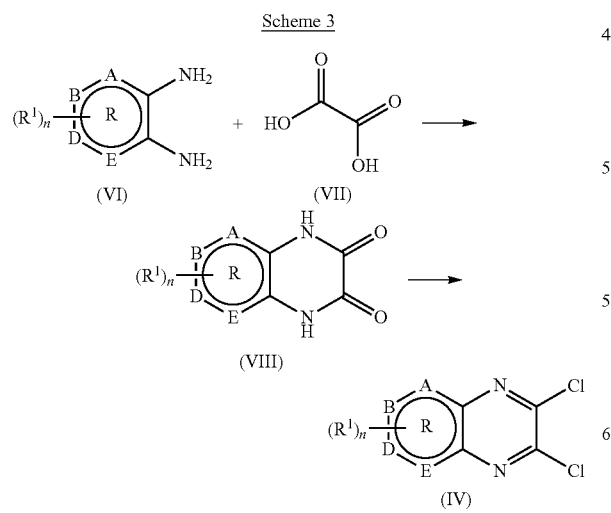

Sulfonamides of Formula (V) may be obtained either from commercial sources or they may be prepared from the corresponding sulfonylchlorides of Formula (IX) using conventional procedures known by one skilled in the art, as shown in the Scheme 4 below. In a typical procedure, the reaction is performed in the presence of ammonia of Formula (X), in a solvent such as EtOH, MeOH, dioxane or water, such as those described hereinafter in the Examples.

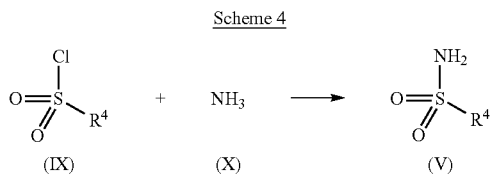

According to another process, quinoxaline sulfonamide and the azaquinoxaline sulfonamide derivatives according to the general Formula (I), whereby the substituents A, B, D, E and $R^1$, $R^2$, $R^3$, $R^4$ are as above defined, are prepared from the amino derivatives of Formula (XI) and sulfonylchlorides of Formula (IX), by well known solution-phase chemistry protocols, as shown in Scheme 5, below. In a typical procedure, the sulfonylation is performed in the presence of pyridine, with or without a co-solvent such as 1,2-dichlorobenzene. Depending on the intrinsic reactivity of the sulfonylchlorides of Formula (IX), the reaction can be performed at various temperatures, either by traditional thermic methods or using microwave technology such as those described hereinafter in the Examples.

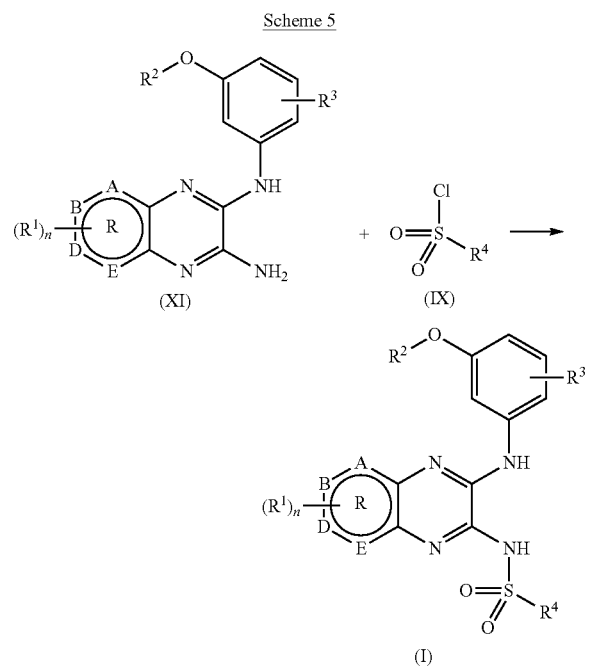

Amino derivatives of Formula (XI) are prepared from the 2-amino 3-chloro derivatives of Formula (XII) and anilines of Formula (III), by well-known solution-phase chemistry protocols, as shown in Scheme 6 below. In a typical procedure, the nucleophilic substitution is performed in absence of base using an appropriate solvent such as NMP, DMF or DMA, such as those described hereinafter in the Examples.

Scheme 6

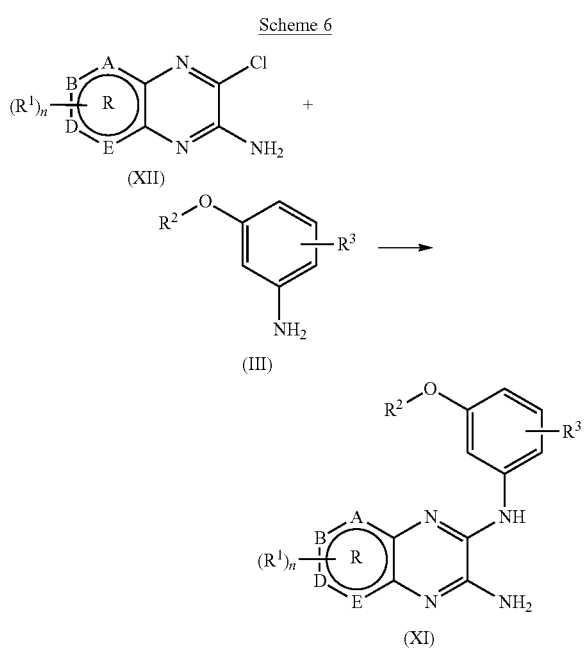

2-Amino 3-chloro derivatives of Formula (XII) are prepared from the dichloro derivatives of Formula (IV), by well-known solution-phase chemistry protocols, as shown in Scheme 7 below. In a typical procedure, the reaction is performed using $(NH_4)_2CO_3$ (XIII) or aqueous ammonia in an appropriate solvent such as DMF, DMA or dioxane, such as those described hereinafter in the Examples.

Scheme 7

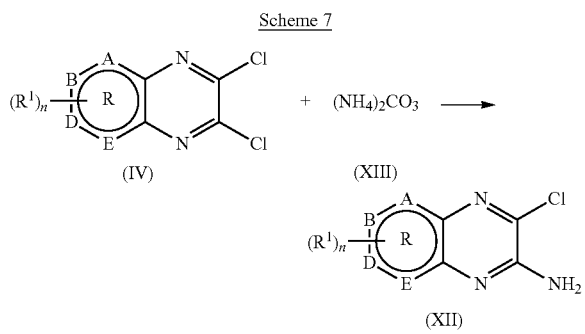

If the above set out general synthetic methods are not applicable for the obtention of compounds of Formula (I), suitable methods of preparation known by a person skilled in the art should be used.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

According to a further general process, compounds of Formula (I) can be converted to alternative compounds of Formula (I), employing suitable interconversion techniques well known by a person skilled in the art.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substitutents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, N.Y., 1994 and, Theodora W. Greene and Peter G. M. Wuts in "*Protective Groups in Organic Synthesis*", Wiley Interscience, $3^{rd}$ Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

EXAMPLES

The commercially starting materials used in the following experimental description were purchased from Aldrich or Fluka unless otherwise reported.

The HPLC, NMR and MS data provided in the examples described below are obtained as followed: HPLC: column Waters Symmetry C8 50×4.6 mm, Conditions: MeCN/$H_2O$, 5 to 100% (8 min), max plot 230-400 nm; LC/MS spectra: Waters ZMD (ES); $^1$H-NMR: Bruker DPX-300 MHz.

The preparative HPLC purifications are performed with HPLC Waters Prep LC 4000 System equipped with columns XTERRAPrepMS C18 10 μm, 50×300 mm. All the purifications were performed with a gradient of ACN/$H_2O$ 0.1% TFA.

The microwave chemistry is performed on a single mode microwave reactor EMRYS Optimiser from Personal Chemistry.

Intermediate 1: 3-chloroquinoxalin-2-amine
(Formula XII)

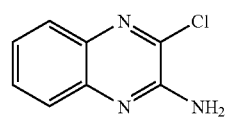

2,3-dichloroquinoxaline (4 g, 20 mmol, commercially available from Aldrich) is dissolved in dry DMF (20 ml) and treated with solid $(NH_4)_2CO_3$ (9.7 g, 101 mmol). The resulting mixture is stirred at 60° C. for 3 days (reaction showed 60% completion). The reaction mixture is diluted with water and the product is extracted with EtOAc. The organic layer is dried and the solvent was removed under reduced pressure. The crude residue obtained is purified via column chromatography by eluting with petroleum ether: EtOAc to afford 1.9 g (53%) of the title compound as a pale yellow solid. LC/MS: (ES+): 180.1.

Intermediate 2:
N-(3,5-dimethoxyphenyl)quinoxaline-2,3-diamine
(Formula XI)

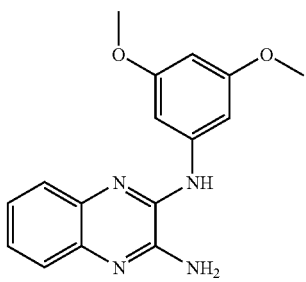

3-chloroquinoxalin-2-amine (1.8 g, 10 mmol) and 3,5-dimethoxyaniline (4.6 g, 30 mmol, commercially available from Aldrich) are taken up in NMP (4.5 ml) and heated to 145° C. in the sealed tube for 3 h under $N_2$. When TLC confirms the total consumption of the starting material, the reaction is cooled to rt and treated with EtOAc (4 ml). The first crop of solid is filtered followed by the $2^{nd}$ crop. The first is recrystallised from $CHCl_3$: EtOAc and the $2^{nd}$ crop is washed with EtOAc, to afford 1.8 g (60%) of pure title compound. LC/MS: (ES+): 297.1, (ES−): 295.1.

Intermediate 3:
N-(2,5-dimethoxyphenyl)quinoxaline-2,3-diamine
(Formula XI)

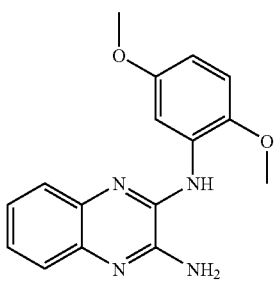

Following the procedure outlined for the synthesis of 2, N-(2,5-dimethoxyphenyl)quinoxaline-2,3-diamine is obtained from 3-chloroquinoxalin-2-amine (1.6 g, 8.9 mmol) and 2,5-dimethoxyaniline (4.1 g, 26.8 mmol, commercially available from Aldrich). The title compound is extracted with EtOAc and the organic layer is consequently washed with water (4×20 ml) and brine (25 ml) then dried. The solvent is removed under reduced pressure and the residue obtained is purified via column chromatography by eluting with DCM: MeOH to afford 1.1 g (42%) of the title compound as a yellow solid. 1H NMR (DMSO-d6) δ 9.40-8.50 (brs, 2H), 7.95-7.20 (m, 5H), 7.15-6.95 (m, 1H), 6.85-6.55 (m, 1H), 3.77 (s, 3H), 3.73 (s, 3H). HPLC (max plot) 98%; Rt 2.56 min. LC/MS: (ES+): 297.1, (ES−): 295.1.

Procedure A

Intermediate 4: Benzene sulfonamide (Formula V)

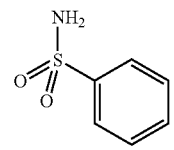

200 ml of aq. $NH_3$ is cooled to −10° C. and treated with benzenesulfonylchloride (13 g, 73 mmol). The resulting mixture is stirred at this temperature for 3 h. When TLC confirmed the completion of the reaction, the reaction mixture is warmed to rt, and the resulting solid is filtered, washed with water and dried under vacuum to afford the title compound (11.1 g, 96%). LC/MS: (ES+): 158.2, (ES−): 156.2.

Intermediate 5: Propane-1-sulfonamide (Formula V)

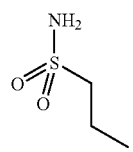

Following the protocol outlined in procedure A, propane-1-sulfonamide is obtained from propane-1-sulfonyl chloride (0.3 g, 2.1 mmol) and aqueous $NH_3$ to afford 230 mg (88%) of the title compound. LC/MS: (ES+): 124.2, (ES−): 122.2.

Procedure B

Intermediate 6: Methyl
3-[4-(aminosulfonyl)phenyl]propanoate methyl
(Formula V)

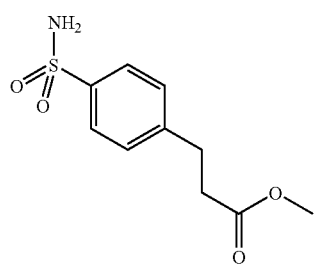

To a solution of methyl 3-(4-chlorosulphonyl)phenypropionate (1000 mg; 3.81 mmol; 1 eq., commercially available from Lancaster) in THF (5 ml) is added ammonia 0.5 M in dioxane (38.1 ml, 0.5 M, 19 mmol, 5 eq.). The resulting suspension was stirred at r.t for 1 h. The solvent is removed and the residue is taken up in DCM. The organic phase was washed with a saturated aqueous solution of NH₄Cl then brine and the DCM was removed under reduced pressure to afford, after drying under vacuum at 40° C., 831.4 mg (90%) of the title compound as a off white powder. 1H NMR (DMSO-d6) δ 7.72 (d, J=8.3 Hz, 2H), 7.40 (d, J=8.3 Hz, 2H), 7.31 (s, 2H), 3.56 (s, 3H), 2.90 (t, J=7.6 Hz, 2H), 2.66 (t, J=7.6 Hz, 2H). HPLC (max plot) 98%; Rt 1.80 min.

Intermediate 7: 3-Methylbenzenesulfonamide (Formula V)

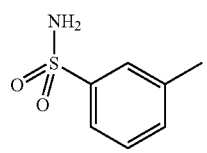

Following the protocol outlined in procedure B, intermediate 7 is obtained from m-toluene sulfonyl chloride (761 μl, 5.25 mmol, 1 eq.) and ammonia 2M in EtOH (13.1 ml, 2 M, 26.2 mmol, 5 eq.) in THF (5 ml) under stirring at r.t. for 2 h to afford 898 mg (100%) of the title compound. 1H NMR (DMSO-d6) δ 7.67-7.59 (m, 2H), 7.50-7.38 (m, 2H), 7.29 (s, 2H), 2.39 (s, 3H). HPLC (max plot) 99%; Rt 1.29 min. LC/MS: (ES−): 170.2.

Intermediate 8: 4-Acetylbenzenesulfonamide (Formula V)

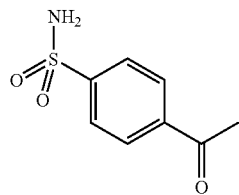

Following the protocol outlined in procedure B, intermediate 8 is obtained from 4-acetylbenzensulphonyl chloride (1000 mg, 4.57 mmol, 1 eq.) and ammonia 0.5 M in dioxane (45.7 ml, 0.5 M, 22.9 mmol, 5 eq.) in THF (5 ml) under stirring at r.t. for 1 h, to afford 715 mg (78%) of the title compound. 1H NMR (DMSO-d6) δ 8.13-8.10 (m, 2H), 7.95-7.92 (m, 2H), 7.53 (br s, 2H), 2.62 (s, 3H). HPLC (max plot 99%; Rt 1.04 min. LC/MS: (ES−): 198.2.

Intermediate 9: 4,5-Dichlorothiophene-2-sulfonamide (Formula V)

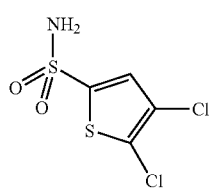

Following the protocol outlined in procedure B, intermediate 9 is obtained from 2,3-dichlorothiophene-5-sulphonyl chloride (1000 mg, 3.98 mmol, 1 eq., commercially available from Lancaster) and ammonia 0.5 M in dioxane (39.7 ml, 0.5 M, 19.9 mmol, 5 eq). in THF (5 ml) under stirring at rt for 1 h, to afford 802 mg (87%) of the title compound. 1H NMR (DMSO-d6) δ 7.80 (br s, 2H), 7.44 (s, 1H). HPLC (max plot) 98%; Rt 2.50 min. LC/MS: (ES−): 230.0.

Intermediate 10: 4-Iodobenzenesulfonamide (Formula V)

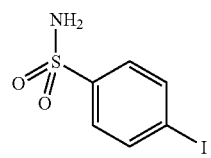

Following the protocol outlined in procedure B, intermediate 10 is obtained from pipsyl chloride (2000 mg, 6.61 mmol, 1 eq.) and ammonia 2M in EtOH (66.1 ml, 0.5 M, 33.1 mmol, 5 eq.) in THF (8 ml) under stirring at rt for 3 h, to afford 1336.3 mg (71%) of the title compound. 1H NMR (DMSO-d6) δ 7.97 (d, J=8.3 Hz, 2H), 7.59 (d, J=8.3 Hz, 2H), 7.43 (s, 2H). HPLC (max plot) 100%; Rt 2.19 min. LC/MS: (ES+): 116.2, (ES−): 282.0.

Intermediate. 11: Pyridine-3-sulfonamide (Formula V)

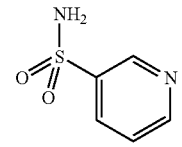

Following the protocol outlined in procedure B, intermediate 11 is obtained from pyridine-3-sulphonyl chloride (1000 mg, 5.6 mmol, 1 eq., commercially available from Davos) and ammonia 0.5 M in dioxane (23.9 ml, 2 M, 47.9 mmol, 8.5 eq.) in THF (5 ml) under stirring at rt for 1 h, to afford 636.6 mg (71%) of the title compound as a yellowish powder. 1H NMR (DMSO-d6) δ 9.20-8.90 (m, 1H), 8.85-8.75 (m, 1H), 8.40-8.05 (m, 1H), 7.80-7.40 (m, 3H).

Intermediate 12: 5-Chloro-1,3-dimethyl-1H-pyrazole-4-sulfonamide (Formula V)

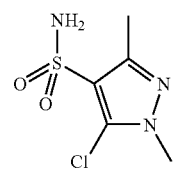

Following the protocol outlined in procedure B, intermediate 12 is obtained from 5-chloro-1.3-dimethypyrazole-4- sulphonyl chloride (1000 mg, 4.4 mmol, 1 eq, commercially available from Maybridge) and ammonia 0.5 M in dioxane (43.6 ml, 0.5 M, 21.8 mmol, 5 eq.) in THF (5 ml) under stirring at rt for 1 h, to afford 345.3 mg (38%) of the title compound as a off white powder. 1H NMR (DMSO-d6) δ 7.39 (s, 2H), 3.74 (s, 3H), 2.28 (s, 3H). HPLC (max plot) 100%; Rt 0.98 min.

Intermediate 13: 5-Bromothiophene-2-sulfonamide (Formula V)

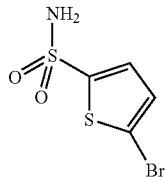

Following the protocol outlined in procedure B, Intermediate 13 is obtained from 5-bromothiophene-2-sulphonyl chloride (1000 mg, 3.82 mmol, 1 eq., commercially available from Maybridge) and ammonia 0.5M in dioxane (38.2 ml, 0.5 M, 19.1 mmol, 5 eq.) in THF (5 ml) under stirring at rt for 1 h, to afford 904 mg (98%) of the title compound. 1H NMR (DMSO-d6) δ 7.73 (br s, 2H), 7.37 (d, J=4.1 Hz, 1H), 7.29 (d, J=4.1 Hz, 1H). HPLC (max plot) 98%; Rt 1.60 min. LC/MS: (ES−): 240.0.

Intermediate 14: methyl 5-(aminosulfonyl)-4-methylthiophene-2-carboxylate (Formula V)

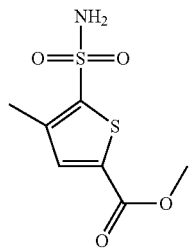

Following the protocol outlined in Procedure B, Intermediate 14 is obtained from methyl 5-(chlorosulfonyl)-4-methyl-2-thiophenecarboxylate (600 mg; 2.36 mmol; 1 eq), commercially available (Acros), and ammonia 2M in MeOH (5.89 ml; 2M; 11.78 mmol; 5 eq) in THF (3 ml) under stirring at r.t. for 3 h, to afford 413.7 mg (75%) of the title compound. 1H NMR (DMSO-d6) δ 7.90 (brs, 2H), 7.68 (s, 1H), 3.84 (s, 3H), 2.41 (s, 3H). HPLC (max plot) 96.66%; Rt 1.79 min. LC/MS: (ES−) 234.1.

Intermediate 15: thiophene-2-sulfonamide (Formula V)

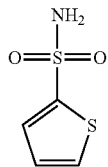

Following the protocol outlined in Procedure B, Intermediate 15 is obtained from 2-thiophenesulfonyl chloride (1000 mg; 5.47 mmol; 1 eq), commercially available (Aldrich), and ammonia 2M in EtOH (13.7 ml; 2M; 27.4 mmol; 5 eq) in THF (10 ml) under stirring at r.t. for 3 h, to afford 540 mg (60%) of the title compound as a grey powder. 1H NMR (DMSO-d6) δ 7.83 (dd, J=1.5, 4.9 Hz, 1H), 7.54 (dd, J=1.5, 3.8 Hz, 1H), 7.13 (dd, J=3.8, 4.9 Hz, 1H). HPLC (max plot) 92%; Rt 1.56 min. LC/MS: (ES−) 162.1

Intermediate 16: 2-chloro-4-fluorobenzenesulfonamide (Formula V)

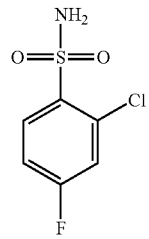

Following the protocol outlined in Procedure B, Intermediate 16 is obtained from 2-chloro-4-fluorobenzenesulfonyl chloride (1000 mg; 4.37 mmol; 1 eq), commercially available (ABCR), and ammonia 2M in MeOH (10.91 ml; 2M; 21.83 mmol; 5 eq) in THF (4 ml) under stirring at r.t. for 3 h, to afford 784 mg (86%) of the title compound. 1H NMR (DMSO-d6) δ 8.03 (dd, J=9.0, 6.0 Hz, 1H), 7.68 (dd, J=9.7, 2.7 Hz, 1H), 7.64 (br s, 2H), 7.40 (dt, J=8.7, 2.7 Hz, 1H). HPLC (max plot) 98%; Rt 1.29 min. LC/MS: (ES−): 208.2.

Intermediate 17: 5-[(1,3-dioxo-1,3-dihydro-2H-isoindol-2-yl)methyl]thiophene-2-sulfonamide (Formula V)

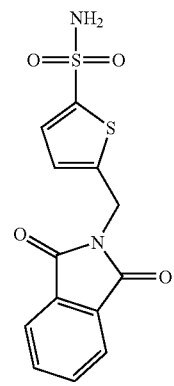

Following the protocol outlined in Procedure B, Intermediate 17 is obtained from 5-(1,3-dioxo-1,3-dihydro-isoindol-2-ylmethyl)-thiophene-2-sulfonyl chloride (2000 mg; 5.85 mmol; 1 eq) and ammonia 2M in EtOH (14.63 ml; 2M; 29.26 mmol; 5 eq) in THF (10 ml) under stirring at r.t. for 2 h, to afford 1428 mg (76%) of the title compound. 1H NMR (DMSO-d6) δ 7.93-7.84 (m, 4H), 7.37 (d, J=3.8 Hz, 1H), 7.30 (s, 2H), 7.09 (d, J=3.8 Hz, 1H), 4.96 (s, 2H). HPLC (max plot) 96%; Rt 2.65 min. LC/MS: (ES−):321.1.

Intermediate 18: 3-cyano-4-fluorobenzenesulfonamide (Formula V)

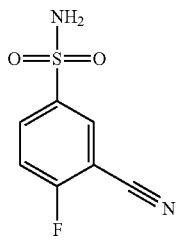

Following the protocol outlined in Procedure B, Intermediate 18 is obtained from 4-fluoro-3-cyanobenzenesulfonyl chloride (2000 mg; 9.11 mmol; 1 eq), commercially available (Aldrich), and ammonia 2M in EtOH (22.77 ml; 2M; 45.53 mmol; 5 eq) in THF (8 ml) under stirring at −10° C. for 30 min, to afford 1625.5 mg (89%) of the title compound as a white solid. 1H NMR (DMSO-d6) δ 8.32 (dd, J=6.0, 2.3 Hz, 1H), 8.22-8.15 (m, 1H), 7.76 (t, J=9.0 Hz, 1H), 7.59 (br s, 2H). HPLC (max plot) 99%; Rt 1.10 min. LC/MS: (ES−): 199.2.

Intermediate 19: 6-methoxypyridine-3-sulfonamide (Formula V)

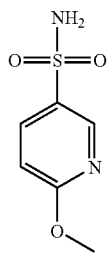

Following the protocol outlined in Procedure B, Intermediate 19 is obtained from 6-methoxy-pyridine-3-sulfonyl chloride (1000 mg; 4.82 mmol; 1 eq), commercially available (Anichem), and ammonia 2M in MeOH (12.04 ml; 2M; 24.08 mmol; 5 eq) in THF (8 ml) under stirring at rt for 3 h, to afford 474.5 mg (52%) of the title compound. 1H NMR (DMSO-d6) δ 8.56 (d, J=2.6 Hz, 1H), 8.05 (dd, J=2.6, 8.7 Hz, 1H), 7.34 (s, 3H), 6.98 (d, J=8.7 Hz, 1H). HPLC (max plot) 100%; Rt 0.88 min. LC/MS: (ES+): 189.1, (ES−): 187.2.

Procedure C

Intermediate 20: 3-(Aminosulfonyl)benzoic acid (Formula V)

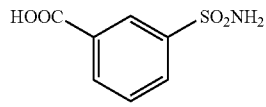

To ice-cold solution of ammonium hydroxide (25%, 250 ml) is added 3-(chlorosulfonyl)benzoic acid (25 g, commercially available, Aldrich) portionwise and the mixture is stirred at room temperature for 15 h. The solvent is removed under vacuum to about 50 ml and the mixture is acidified with conc. HCl. The precipitate is collected by filtration and dried under vacuum to afford 22 g (96%) of the title compound as a white solid. 1H NMR (DMSO-d6) δ 13.44 (br s, 1H), 8.38 (s, 1H), 8.14 (d, J=7.5 Hz, 1H), 8.04 (d, J=7.9 Hz, 1H), 7.72 (t, J=7.9 Hz, 1H), 7.49 (s, 2H), HPLC (max plot) 97%; Rt 0.68 min. LC/MS: (ES−): 199.8.

Intermediate 21: 6-Chloropyridine-3-sulfonamide (Formula V)

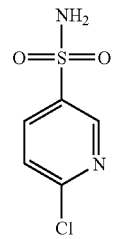

Following the protocol outlined in Procedure C, Intermediate 21 is obtained from ammonium hydroxide (150 ml, 25% w/v) and 6-chloropyridine-3-sulfonyl chloride (19.3 g, commercially available, Aldrich) at rt for 12 h to afford 14.5 g (83%) of the title compound as an off-white solid. mp: 151-154° C., HPLC (max plot) 99%, Rt 4.77 min, LC/MS: (ES−): 190.7, 1H NMR (DMSO-d6:400 MHz) δ 8.80 (1H, s), 8.20-8.23 (1H, d), 7.76-7.78 (1H, d), 7.72 (2H, bs).

Intermediate 22: 6-Methylpyridine-3-sulfonamide (Formula V)

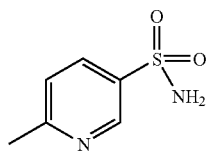

Following the protocol outlined in Procedure C, Intermediate 22 is obtained from ammonium hydroxide (25 ml, 25% w/v) and 6-methylpyridine-3-sulfonyl chloride (2.5 g) at rt for 3 h to afford 1 g (41%) of the title compound as an off-white solid. mp: 151-155° C., LC/MS: (ES+): 172.9, HPLC (max plot) 95%, Rt: 4.05 min, 1H NMR (DMSO-d6: 400 MHz) δ 9.10 (1H, m), 8.04-8.06 (1H, m), 7.53 (2H, bs), 7.45-7.47 (1H, m), 2.54 (3H, s).

Procedure D

Intermediate 23: 6-Cyanopyridine-3-sulfonyl chloride (Formula IX)

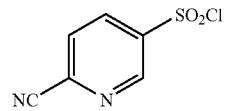

Thionylchloride (34.1 ml, 0.467 mol) is added to water (182 ml) at 0° C. over a period of 1 h maintaining the reaction temperature below 5° C. The reaction mixture is allowed to warm to 18° C. over a period of 20 h. To this mixture is added copper (I) chloride (0.143 g, 0.0014 mol) and the resulting yellow-green solution is cooled to −5° C.

In parallel, 5-amino-2-cyano pyridine (10 g, 0.084 mol) is dissolved in concentrated HCl (98 ml) and the mixture is cooled to −5° C. To this mixture is added dropwise over a period of 1 h a solution of NaNO₂ (8.2 g, 0.118 mol) in water (50 ml), maintaining the reaction temperature between −5° C. and 0° C. This slurry is then added dropwise over a period of 1 h to the above reaction mixture (thionylchloride/water mixture), maintaining the reaction temperature between −5° C. and 0° C. (Note: The diazotized mixture should be also kept at −5° C. through out the addition). As the addition proceeds, a white solid precipitates. When the addition is over, the reaction mixture is stirred for an additional hour. The precipitate is collected by filtration, washed with cold water and dried under vacuum to afford the title compound as light yellow solid (12.5 g, Yield 73.5%). 1H NMR (DMSO-d6:400 MHz) δ 14.49 (1H, s), 8.87 (1H, s), 8.11-8.14 (1H, d), 8.0-8.03 (1H, d); HPLC (max plot) 97% Rt 1.155 min; LCMS: m/z, M+, 202.8.

Intermediate 24: 6-Chloropyridine-3-sulfonyl chloride (Formula IX)

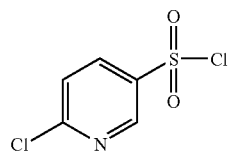

Following the protocol outlined in Procedure D, Intermediate 24 is obtained from thionyl chloride (42 ml, 0.575 mol) and copper (I) chloride (0.151 g, 0.00152 mol) in water (250 ml) at 0° C. to which is added, over a period of 2 h, a slurry obtained from 5-amino-2-chloro pyridine (17.3 g, 0.134 mol) in concentrated HCl (135 ml) and NaNO$_2$ (10 g, 0.1449 mol) in water (40 ml) at −5° C., to afford 19.7 g (70%) of the title compound as a solid. mp: 48.3-49.3° C., LC/MS: (ES−):192 which corresponds to the sulfonic acid, 1H NMR (CDCl$_3$:400 MHz) δ 9.05 (1H, s), 8.26-8.29 (1H, d), 7.62-7.64 (1H, d).

Intermediate 25: 6-Methylpyridine-3-sulfonyl chloride (Formula IX)

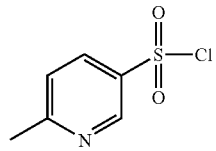

Following the protocol outlined in Procedure D, Intermediate 25 is obtained from thionyl chloride (46.1 ml, 0.39 mol) and copper (I) chloride (0.118 g, 0.0012 mol) in water (160 ml) at 0° C. to which is added, over a period of 2 h, a slurry obtained from 3-amino-6-picoline (10 g, 0.094 mol) in concentrated HCl (80 ml) and NaNO$_2$ (6.8 g, 0.0988 mol) in water (20 ml) at −5° C., to afford 2.5 g (14%) of the title compound as a liquid, which is used in the next step without storage. LC/MS: (ES−):172 which corresponds to the sulfonic acid.

Intermediate 26: methyl 5-(aminosulfonyl)-1-methyl-1H-pyrrole-2-carboxylate (Formula V)

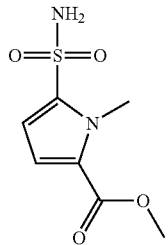

5-(Aminosulfonyl)-1-methyl-1H-pyrrole-2-carboxylic acid (1310 mg; 6.42 mmol; 1 eq.), commercially available (ASDI), is dissolved in MeOH (24 ml), then toluene (8 ml) is added followed by the dropwise addition of (trimethylsilyl)diazomethane (9.62 ml; 2M; 19.25 mmol; 3 eq). The solution is stirred at r.t. for 2 hr and another equivalent of (trimethylsilyl)diazomethane (3.21 ml; 2 M; 6.42 mmol; 1 eq) is added to reaction mixture. After 1 hr stirring, the solvent is concentrated to dryness and the resulting off white solid is recrystallized in MeOH to afford 851.1 mg (61%) of the title compound. 1H NMR (DMSO-d6) δ 7.58 (d, J=1.5 Hz, 1H), 7.13 (s, 2H), 7.06 (d, J=1.9 Hz, 1H), 3.88 (s, 3H), 3.77 (s, 3H). HPLC (max plot) 100%; Rt 1.19 min. LC/MS: (ES−) 217.1.

Intermediate 27: 6-Cyanopyridine-3-sulfonamide (Formula V)

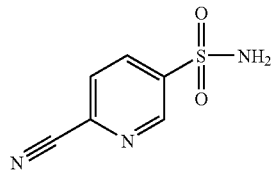

To an ice-cold solution of ammonium hydroxide (75 ml, 25% w/v) is added 6-cyanopyridine-3-sulfonyl chloride (12.5 g) portionwise and the mixture is stirred for 30 minutes at 0-5° C. The reaction mixture is then concentrated to 1/5$^{th}$ of its original volume and cooled. The precipitate is filtered and dried under vacuum to afford the title compound as light brown solid (9 g, Yield 80%). 1H NMR (DMSO-d6:400 MHz) δ 9.10 (1H, s), 8.33-8.35 (1H, m), 8.23-8.25 (1H, d); 7.88-8.03 (2H, bs); HPLC (max plot) 98%, Rt 4.67 min; LCMS: (ES+) 183.8.

Intermediate 28: Methyl 5-(aminosulfonyl)pyridine-2-carboxylate (Formula V)

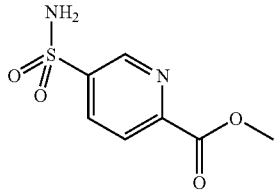

6-Cyanopyridine-3-sulfonamide (10 g, 0.0545 mol) is dissolved in dry HCl in methanol (400 ml) at 25-26° C. under nitrogen atmosphere. Reaction mixture is heated to 50° C. and stirred for 15 h at 50° C. The reaction mixture is concentrated under vacuum and the residue obtained is diluted with water (100 ml) and basified with solid sodium bicarbonate to pH 6-7. The reaction mixture is stirred for 15 minutes and filtered. The resulting solid obtained is washed with water(50 ml) and dried under vacuum to afford the title compound (9 g, 76%) as light yellow solid. 1H NMR (DMSO-d6) δ 9.08 (d, J=3 Hz, 1H), 8.38 (dd, J=9 and 3 Hz, 1H), 8.26 (d, J=9 Hz, 1H), 7.79 (m, 2H), 3.93 (s, 3H). HPLC (max plot) 94%; Rt 3.45 min; LC/MS: (ES+) 216.9.

Intermediate 29: Methyl 4-(aminosulfonyl)benzoate (Formula V)

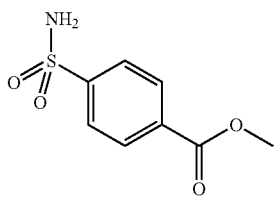

To a suspension of 4-(aminosulfonyl)benzoic acid (500 mg, 2.5 mmol) in MeOH (2 ml) at 0° C. is added thionylchloride (0.2 ml, 7.4 mmol). The reaction mixture is stirred at rt overnight. When TLC confirms the total consumption of the starting acid, the solvent and excess thionyl chloride are removed under reduced pressure to afford 400 mg (75%) of the title compound, which was used in the next step without any further purification. LC/MS: (ES+):215.9, (ES−):214.1.

Intermediate 30: Methyl 3-(chlorosulfonyl)benzoate (Formula IX)

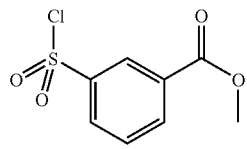

To a suspension of 3-(chlorosulphonyl)benzoic acid (300 mg, 1.4 mmol) in DCM (2 ml) at 0° C. is added thionylchloride (0.3 ml, 4.1 mmol), the reaction mixture is stirred at rt overnight. When TLC confirms the total consumption of the starting acid, the solvent and excess thionyl chloride are removed under reduced pressure to obtain the corresponding acid chloride A suspension of the acid chloride in MeOH (2 ml) at −5° C. is stirred for 2 hr and the solvent is removed under reduced pressure to afford 200 mg (63%) of the title compound, which is used in the next step without any further purification. LC/MS: (ES−): 233.1.

Intermediate 31: Methyl 3-(aminosulfonyl)benzoate (Formula V)

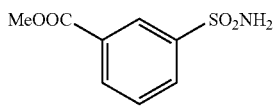

To a solution of 3-(aminosulfonyl)benzoic acid (22 g, 0.109 mol) in MeOH (250 ml) is added thionyl chloride (25 ml, 0.328 mol) and the mixture is refluxed for 16 h. The solvent is removed and the residue is diluted with EtOAc (200 ml), washed with a 10% solution of sodium bicarbonate, water and brine. The solvent was removed under vacuum to afford 17 g (73%) of the title compound as a solid. 1H NMR (DMSO-d6) δ 8.39 (t, J=1.5 Hz, 1H), 8.16-8.13 (m, 1H), 8.09-8.05 (m, 1H), 7.76 (t, J=7.9 Hz, 1H), 7.53 (s, 2H), 3.90 (s, 3H). HPLC (max plot) 99%; Rt 1.49 min. LC/MS: (ES+): 215.9, (ES−):214.1.

Intermediate 32: 3-(Morpholin-4-ylcarbonyl)benzenesulfonamide (Formula V)

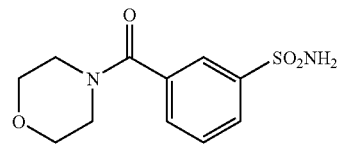

To a solution of 3-(aminosulfonyl)benzoic acid (6 g, 0.029 mol) in THF (100 ml) at 0° C. is added CDI (5.8 g, 0.035 mol) and the mixture is stirred for 4 h. To this mixture morpholine (7.8 ml, 0.089 mol) is added dropwise and the mixture is stirred at room temperature for 15 h. The solvent is removed under vacuum and the residue is diluted with EtOAc (100 ml), washed with a 10% solution of sodium bicarbonate, water and brine. The solvent is removed under vacuum and the residue is taken up with small amount of water (15 ml) and stirred for 15 min. The solid is collected by filtration to afford 4 g (50%) of the title compound as a solid. 1H NMR (DMSO-d6, 400 MHz) δ 7.88-7.90 (1H, m), 7.83 (1H, s), 7.64-7.65 (2H, m), 7.47 (2H, bs), 3.56-3.64 (6H, m), 3.28-3.34 (2H, m); HPLC (Max polt) 98%, Rt, 4.09 min; LCMS: (ES+): 206.2.

Intermediate 33: 6-(Dimethylamino)pyridine-3-sulfonamide (Formula V)

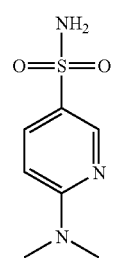

A mixture of 6-chloropyridine-3-sulfonamide (5 g, 0.0259 mol) and aqueous dimethylamine (100 ml, 40%) is stirred at rt for 13 h. The mixture is concentrated to ⅕$^{th}$ of its original volume and cooled. The precipitate is collected by filtration, washed with ice-cold water (10 ml) and dried under vacuum to afford 4.5 g (95%) of the title compound as a solid. mp: 133-138° C., LC/MS: (ES+) 201.9.

Intermediate 34: 6-[(3-Methoxypropyl)amino]pyridine-3-sulfonamide (Formula V)

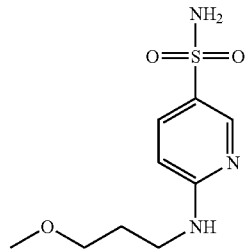

A mixture of 6-chloropyridine-3-sulfonamide (5 g, 0.025 mol) and 3-methoxy propylamine (50 ml) is stirred at 100° C.

for 12 h. The mixture is cooled and excess reagent is removed by distillation. The residue is suspended in DCM (25 ml) and cooled. The precipitate is filtered, washed with cold ammonium hydroxide (2×50 ml) and dried under vacuum to afford 5 g (78%) of the titled compound as a white solid. mp: 129-132° C., LC/MS: (ES+) 246.

Procedure E

Intermediate 35: N-(3-Chloro-quinoxalin-2-yl)-3-fluoro-benzenesulfonamide (Formula II)

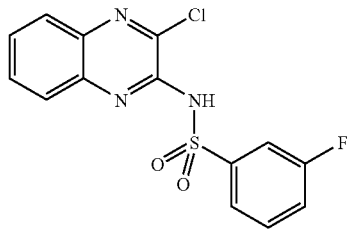

3-fluorobenzenesulfonamide (250 mg, 1.4 mmol), 2,3-dichloroquinoxaline (284.1 mg, 1.4 mmol) and dry $K_2CO_3$ (198.4 mg, 1.4 mmol) are dissolved in dry DMF (0.8 ml) and heated up to 135° C. in a sealed tube for 2.5 h. When TLC confirms the completion of the reaction, the reaction mixture is cooled down to rt and quenched by addition of water (4 ml) and AcOH (0.03 ml). The residue obtained is triturated and the resulting solid is filtered and washed with water until neutral pH then dried under vacuum to afford 400 mg (83%) of the title compound as an off white solid. 1H NMR (DMSO-d6) δ 12.8-10.9 (br s, 1H), 8.05-7.62 (m, 7H), 7.54 (td, J=2.0, 8.5 Hz, 1H). HPLC (max plot) 94%; Rt 3.79 min. LC/MS: (ES+): 338.1, (ES−): 336.1.

Intermediate 36:
N-(3-chloro-2-quinoxalinyl)benzenesulfonamide (Formula II)

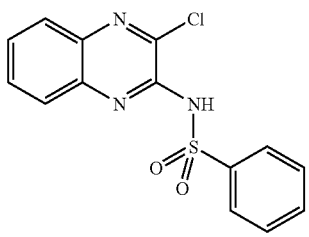

Following the protocol outlined in Procedure E, Intermediate 36 is obtained from 2,3-dichloroquinoxaline (1000 mg, 5.0 mmol, 1 eq.) and benzenesulfonamide (789.8 mg, 5.0 mmol; 1 eq.) in the presence of $K_2CO_3$ (694.4 mg, 5.0 mmol; 1 eq.) in DMA (10 ml), to afford 1291 mg (80%) of the title compound as a yellow powder. 1H NMR (DMSO-d6) δ 12.5-10-5 (br s, 1H), 8.25-8.08 (m, 2H), 7.95-7.50 (m, 7H). HPLC (max plot) 90%; Rt 3.54 min. LC/MS: (ES+): 320.03, (ES−): 318.02.

Intermediate 37:
N-(3-chloroquinoxalin-2-yl)propane-1-sulfonamide (Formula II)

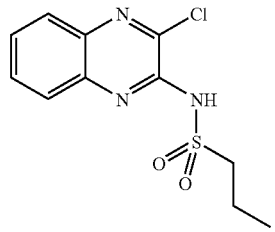

Following the protocol outlined in Procedure E, Intermediate 37 is obtained from 2,3-dichloroquinoxaline (0.2 g, 1 mmol, 1 eq.) and propane-1-sulfonamide (123.8 mg, 1 mmol, 1 eq.) in the presence of $K_2CO_3$ (138.8 mg, 1 mmol, 1 eq.) in DMF (2 ml), to afford 187 mg (65%) of the title compound as a yellow powder. LC/MS: (ES+): 286.7.

Intermediate 38: Methyl 4-{[(3-chloroquinoxalin-2-yl)amino]sulfonyl}butanoate (Formula II)

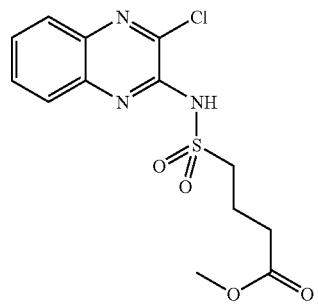

Following the protocol outlined in Procedure E, Intermediate 38 is obtained from 2,3-dichloroquinoxaline (0.2 g, 1 mmol, 1 eq.) and methyl 4-sulfamido butanoate (181.2 mg, 1 mmol, 1 eq.) in the presence of $K_2CO_3$ (138.8 mg, 1 mmol, 1 eq.) in DMF (2 ml), to afford 307 mg (87%) of the title compound as a yellow powder. LC/MS: (ES+): 344.6.

Intermediate 39: Methyl 4-{[(3-chloroquinoxalin-2-yl)amino]sulfonyl}benzoate (Formula II)

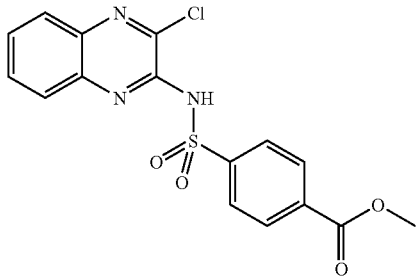

Following the protocol outlined in Procedure E, Intermediate 39 is obtained from 2,3-dichloroquinoxaline (500 mg, 2.5 mmol, 1 eq.) and methyl 4-(aminosulfonyl)benzoate (538.1 mg, 2.5 mmol, 1 eq.) in the presence of $K_2CO_3$ (347.2 mg, 2.5 mmol, 1 eq.) in DMF (5 ml), to afford 757 mg (80%) of the title compound as a yellow powder. LC/MS: (ES+): 378.8.

Procedure F

Intermediate 40: N-(3-chloroquinoxalin-2-yl)-3-methylbenzenesulfonamide (Formula II)

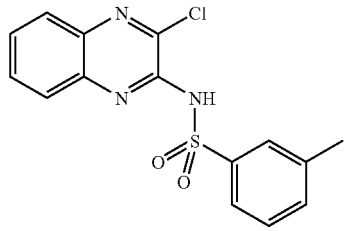

A suspension of 2,3-dichloroquinoxaline (500 mg; 2.5 mmol; 1 eq), 3-methylbenzene sulfonamide (430.1 mg, 2.5 mmol, 1 eq.), dry $K_2CO_3$ (347.2 mg, 2.5 mmol, 1 eq.) in DMA (5 ml) is heated up at 170° C. in the microwave for 30 min under normal absorption. The solvent is evaporated to dryness. Water (20 ml) is added then AcOH until acidic pH. The residual suspension is left at 4° C. for 1 h and the precipitate formed is filtered off, washed with water until neutral, then ACN and dried under vacuum at 40° C. overnight, to afford 548.3 mg (65%) of the title compound. 1H NMR (DMSO-d6) δ 11.53 (brs, 1H), 7.99 (m, 2H), 7.87 (t, J=8.6 Hz, 2H), 7.77 (dt, J=1.5, 7.5 Hz, 1H), 7.67 (t, J=8.0 Hz, 1H), 7.56-7.43 (m, 2H), 2.42 (s, 3H). HPLC (max plot) 99%; Rt 3.70 min. LC/MS: (ES+): 334.2, (ES−): 332.2.

Intermediate 41: 4-Chloro-N-(3-chloroquinoxalin-2-yl)benzenesulfonamide (Formula II)

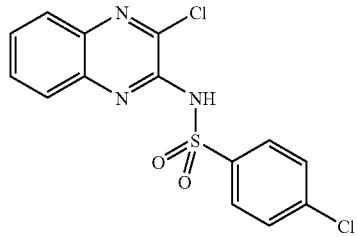

Following the protocol outlined in procedure F, intermediate 41 is obtained from 2,3-dichloroquinoxaline (1000 mg, 5.0 mmol, 1 eq.) and 4-chlorobenzenesulfonamide (962.8 mg, 5.0 mmol, 1 eq.) in the presence of $K_2CO_3$ (694.3 mg, 5.0 mmol, 1 eq.) in DMA (10 ml), to afford 1.69 g (95%) of the title compound as a yellow solid. 1H NMR (DMSO-d6) δ 8.16 (d, J=8.7 Hz, 2H), 7.89-7.88 (m, 2H), 7.78-7.63 (m, 2H), 7.69 (d, J=8.7 Hz, 2H). HPLC (max plot) 90%; Rt 4.15 min. LC/MS: (ES+): 354.2, (ES−): 352.1.

Intermediate 42: N-(3-chloroquinoxalin-2-yl)-4-fluorobenzenesulfonamide (Formula II)

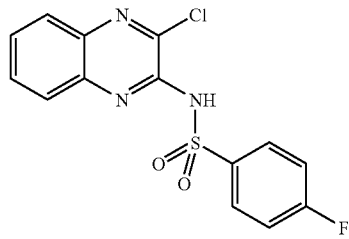

Following the protocol outlined in Procedure F, Intermediate 42 is obtained from 2,3-dichloroquinoxaline (1000 mg, 5.02 mmol, 1 eq.) and 4-fluorobenzenesulfonamide (880.1 mg, 5.0 mmol, 1 eq.) in the presence of $K_2CO_3$ (694.3 mg, 5 mmol, 1 eq.) in DMA (5 ml), to afford 540 mg (32%) of the title compound as a yellow solid. 1H NMR (DMSO-d6) δ 8.24 (dd, J=5.28, 9.05 Hz, 2H), 7.88 (br dd, 2H), 7.79-7.74 (m, 1H), 7.69-7.64 (m, 1H), 7.49-7.43 (m, 2H). HPLC (max plot) 89%; Rt 3.87 min. LC/MS: (ES+): 338.1, (ES−):336.1.

Intermediate 43: N-(3-chloroquinoxalin-2-yl)-4-methoxybenzenesulfonamide (Formula II)

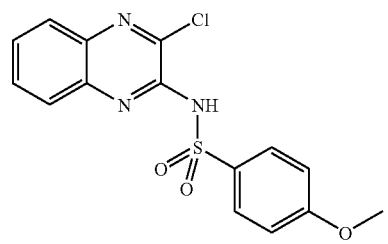

Following the protocol outlined in Procedure F, Intermediate 43 is obtained from 2,3-dichloroquinoxaline (1000 mg, 5.0 mmol, 1 eq.) and 4-methoxybenzenesulfonamide (940.6 mg, 5.0 mmol, 1 eq.) in the presence of $K_2CO_3$ (694.3 mg, 5.0 mmol, 1 eq.) in DMA (10 ml), to afford 782 mg (44%) of the title compound as a yellow solid. 1H NMR (DMSO-d6) δ 8.11 (d, J=8.4 Hz, 2H), 7.88 (d, J=8.4 Hz, 2H), 7.79-7.74 (m, 1H), 7.68-7.63 (m, 1H), 7.15-7.10 (m, 2H), 3.81 (s, 3H). HPLC (max plot) 92%; Rt 3.54 min. LC/MS: (ES+):350.1; (ES−): 348.1.

Intermediate 44: N-(3-chloroquinoxalin-2-yl)-4-methylbenzenesulfonamide (Formula II)

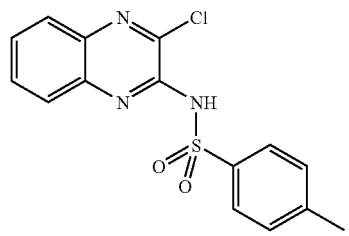

Following the protocol outlined in procedure F, intermediate 44 is obtained from 2,3-dichloroquinoxaline (500 mg, 2.51 mmol, 1 eq.) and p-toluenesulfonamide (430.1 mg, 2.5 mmol, 1 eq.) in the presence of $K_2CO_3$ (347.2 mg, 2.5 mmol, 1 eq.) in DMA (5 ml), to afford 680.6 mg (81%) of the title compound. 1H NMR (DMSO-d6) δ 11.51 (brs, 1H), 8.05 (d, J=7.9 Hz, 2H), 7.92-7.84 (m, 2H), 7.81-7.73 (m, 1H), 7.72-7.63 (m, 1H), 7.42 (d, J=8.3 Hz, 2H), 2.37 (s, 3H). HPLC (max plot) 88%; Rt 3.70 min. LC/MS: (ES+): 334.0, (ES−): 332.0.

Intermediate 45: 4-Bromo-N-(3-chloroquinoxalin-2-yl)benzenesulfonamide (Formula II)

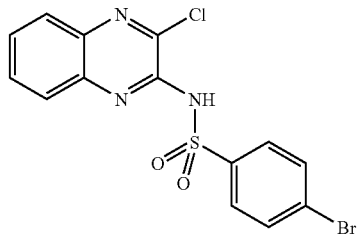

Following the protocol outlined in Procedure F, Intermediate 45 is obtained from 2,3-dichloroquinoxaline (1000 mg, 5.0 mmol, 1 eq.) and 4-bromobenzenesulfonamide (1186 mg, 5.0 mmol, 1 eq.) in the presence of $K_2CO_3$ (694.3 mg, 5.0 mmol, 1 eq.) in DMA (10 ml), to afford 1800 mg (90%) of the title compound as a yellow solid. 1H NMR (DMSO-d6) δ 8.08 (d, J=8.67 Hz, 2H), 7.88-7.82 (m, 2H), 7.84 (d, J=8.67 Hz, 2H), 7.78-7.73 (m, 1H), 7.68-7.63 (m, 1H). HPLC (max plot) 90%; Rt 4.21 min. LC/MS: (ES+): 400.0, (ES−): 398.0.

Intermediate 46: N-(3-chloroquinoxalin-2-yl)pyridine-3-sulfonamide (Formula II)

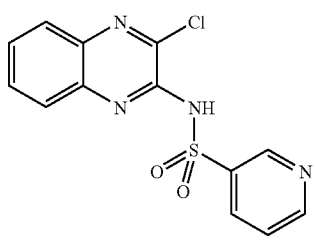

Following the protocol outlined in Procedure F, Intermediate 46 is obtained from 2,3-dichloroquinoxaline (165 mg, 0.8 mmol, 1 eq.) and pyridine-3-sulfonamide (131.1 mg, 0.8 mmol, 1 eq.) in the presence of $K_2CO_3$ (114.6 mg, 0.8 mmol, 1 eq.) in DMA (1.60 ml), to afford 200 mg (75%) of the title compound as an orange powder. 1H NMR (DMSO-d6) δ 9.28 (s, 1H), 8.80 (d, J=4.1 Hz, 1H), 8.57 (d, J=8.0 Hz, 1H), 7.95-7.55 (m, 5H). HPLC (max plot) 91%; Rt 2.54 min.

Intermediate 47: N-(3-chloroquinoxalin-2-yl)-4-cyanobenzenesulfonamide (Formula II)

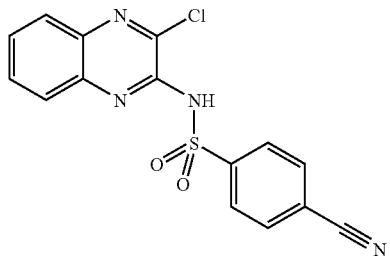

Following the protocol outlined in Procedure F, Intermediate 47 is obtained from 2,3-dichloroquinoxaline (600 mg, 3.0 mmol, 1 eq.) and 4-cyanobenzenesulfonamide (549.2 mg, 3.0 mmol, 1 eq., commercially available from Maybridge) in the presence of $K_2CO_3$ (416.6 mg, 3.0 mmol, 1 eq.) in DMA (6.0 ml), to afford 660.3 mg (64%) of the title compound as a yellowish solid. 1H NMR (DMSO-d6) δ 8.29 (d, J=8.2 Hz, 2H), 8.09 (d, J=8.3 Hz, 2H), 7.92-7.57 (m, 4H). HPLC (max plot) 93%; Rt 3.68 min. LC/MS: (ES+): 345.1, (ES−): 343.1.

Intermediate 48: N-(3-chloroquinoxalin-2-yl)methanesulfonamide (Formula II)

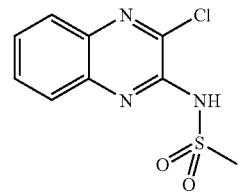

Following the protocol outlined in Procedure F, Intermediate 48 is obtained from 2,3-dichloroquinoxaline (300 mg, 1.5 mmol, 1 eq.) and methanesulfonamide (143.4 mg, 1.5 mmol; 1 eq.) in the presence of $K_2CO_3$ (208.3 mg, 1.5 mmol, 1 eq.) in DMA (3.0 ml), to afford 234.2 mg (60%) of the title compound as a yellow powder. 1H NMR (DMSO-d6) δ 11.05 (br s, 1H), 8.04-7.88 (m, 2H), 7.85-7.61 (m, 2H), 3.49 (s, 3H). HPLC (max plot) 90% Rt 2.35 min. LC/MS: (ES+): 258.0; (ES−): 256.0.

Intermediate 49: N-(3-chloroquinoxalin-2-yl)-4-(trifluoromethyl)benzenesulfonamide (Formula II)

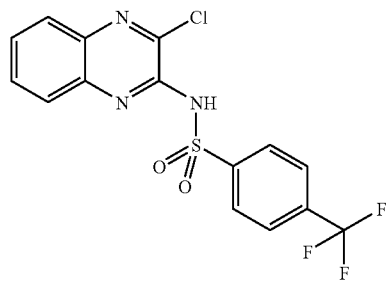

Following the protocol outlined in Procedure F, Intermediate 49 is obtained from 2,3-dichloroquinoxaline (500 mg, 2.5 mmol, 1 eq.) and (trifluoromethyl)benzenesulfonamide (565.7 mg, 2.5 mmol, 1 eq., commercially available from ABCR) in the presence of $K_2CO_3$ (347.2 mg; 2.5 mmol; 1 eq.) in DMA (5 ml), to afford 892.5 mg (92%) of the title compound. 1H NMR (DMSO-d6) δ 8.38 (d, J=8.3 Hz, 2H), 8.02 (d, J=8.6 Hz, 2H), 7.90-7.84 (m, 2H), 7.79-7.71 (m, 1H), 7.69-7.62 (m, 1H). HPLC (max plot) 83%; Rt 4.35 min. LC/MS: (ES+): 388.1, (ES−): 386.2.

Intermediate 50: N-(3-chloroquinoxalin-2-yl)-4-iodobenzenesulfonamide (Formula II)

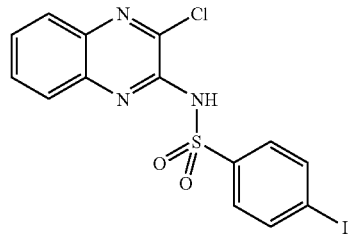

Following the protocol outlined in procedure F, intermediate 50 is obtained from 2,3-dichloroquinoxaline (500 mg, 2.5 mmol, 1 eq.) and 4-iodobenzenesulfonamide (711.1 mg, 2.5 mmol, 1 eq., commercially available from Apollo) in the presence of K₂CO₃ (347.2 mg, 2.5 mmol, 1 eq.) in DMA (5 ml), to afford 989.6 mg (88%) of the title compound. 1H NMR (DMSO-d6) δ 8.03 (d, J=8.3 Hz, 2H), 7.93 (d, J=8.6 Hz, 2H), 7.89 (d, J=8.7 Hz, 2H), 7.77 (m, 1H), 7.67 (m, 1H). HPLC (max plot) 91%; Rt 4.26 min. LC/MS: (ES+): 446.1, (ES−): 444.0.

Intermediate 51: 4,5-dichloro-N-(3-chloroquinoxalin-2-yl)thiophene-2-sulfonamide (Formula II)

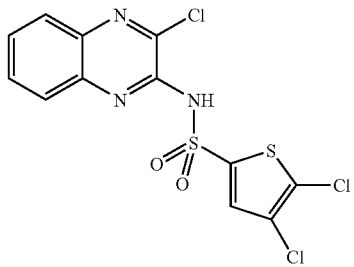

Following the protocol outlined in Procedure F, Intermediate 51 is obtained from 2,3-dichloroquinoxaline (250 mg, 1.3 mmol, 1 eq.) and 4,5-dichlorothiophene-2-sulfonamide (291.5 mg, 1.3 mmol, 1 eq.) in the presence of K₂CO₃ (173.6 mg, 1.3 mmol, 1 eq.) in DMA (3 ml), to afford 439 mg (89%) of the title compound. 1H NMR (DMSO-d6) δ 7.93-7.89 (m, 1H), 7.84-7.81 (m, 1H), 7.83 (s, 1H), 7.76-7.70 (m, 1H), 7.59-7.54 (m, 1H). HPLC (max plot) 95%; Rt 4.25 min. LC/MS: (ES+):395.9, (ES−):393.9.

Intermediate 52: 5-chloro-N-(3-chloroquinoxalin-2-yl)-1,3-dimethyl-1H-pyrazole-4-sulfonamide (Formula II)

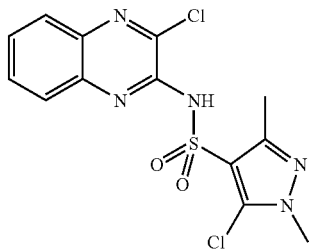

Following the protocol outlined in Procedure F, Intermediate 52 is obtained from 2,3-dichloroquinoxaline (300 mg, 1.5 mmol, 1 eq.) and 5-chloro-1,3-dimethyl-1H-pyrazole-4-sulfonamide (316 mg, 1.5 mmol, 1 eq.) in the presence of K₂CO₃ (208.3 mg, 1.5 mmol, 1 eq.) in DMA (3 ml), to afford 374.1 mg (67%) of the title compound as a yellow powder. 1H NMR (DMSO-d6) δ 8.00-7.5 (m, 4H), 3.75 (s, 3H), 2.46 (s, 3H). HPLC (max plot) 96%; Rt 3.09 min.

Intermediate 53: 4-acetyl-N-(3-chloroquinoxalin-2-yl)benzenesulfonamide (Formula II)

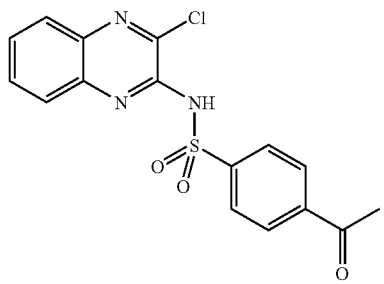

Following the protocol outlined in procedure F, intermediate 53 is obtained from 2,3-dichloroquinoxaline (250 mg, 1.3 mmol, 1 eq.) and 4-acetylbenzenesulfonamide (250.24 mg, 1.3 mmol, 1 eq.) in the presence of K₂CO₃ (173.59 mg, 1.3 mmol, 1 eq.) in DMA (3 ml), to afford 330 mg (73%) of the title compound. 1H NMR (DMSO-d6) δ 8.28 (d, J=8.7 Hz, 2H), 8.15 (d, J=8.7 Hz, 2H), 7.89-7.84 (m, 2H), 7.78-7.72 (m, 1H), 7.68-7.62 (m, 1H), 2.61 (s, 3H). HPLC (max plot) 94%; Rt 3.34 min. LC/MS: (ES+):362.1, (ES−):360.1.

Intermediate 54: methyl 3-(4-{[(3-chloroquinoxalin-2 yl)amino]sulfonyl}phenyl)propanoate (Formula II)

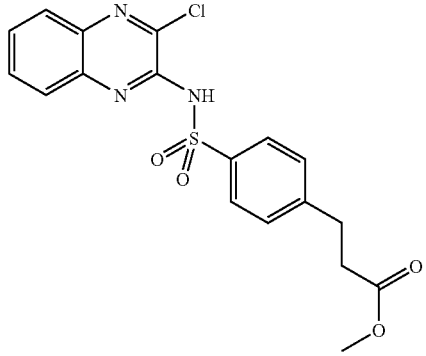

Following the protocol outlined in Procedure F, Intermediate 54 is obtained from 2,3-dichloroquinoxaline (200 mg, 1 mmol, 1 eq.) and methyl 3-[4-(aminosulfonyl)phenyl]propanoate (244.5 mg, 1 mmol, 1 eq.) in the presence of K₂CO₃ (138.9 mg, 1 mmol, 1 eq.) in DMA (2 ml), to afford 278.7 mg (68%) of the title compound as a yellow solid. 1H NMR (DMSO-d6) δ 11.50 (br s, 1H), 8.07 (d, J=7.9 Hz, 2H), 8-7.58 (m, 4H), 7.47 (d, J=7.9 Hz, 2H), 3.52 (s, 3H), 2.91 (t, J=7.5 Hz, 2H), 2.65 (t, J=7.5 Hz, 2H). HPLC (max plot) 81%; Rt 3.65 min.

Intermediate 55: 5-bromo-N-(3-chloroquinoxalin-2-yl)thiophene-2-sulfonamide (Formula II)

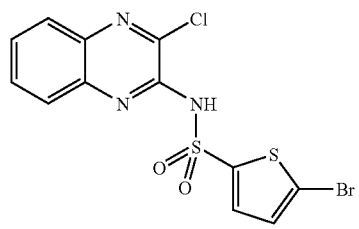

Following the protocol outlined in Procedure F, Intermediate 55 is obtained from 2,3-dichloroquinoxaline (740 mg, 3.7 mmol, 1 eq.) and 5-bromothiophene-2-sulfonamide (900.2 mg, 3.7 mmol, 1 eq.) in the presence of K₂CO₃ (513.8 mg, 3.7 mmol, 1 eq.) in DMA (7 ml), to afford 235 mg (16%) of the title compound. 1H NMR (DMSO-d6) δ 7.92-7.89 (m, 1H), 7.85-7.82 (m, 1H), 7.76-7.71 (m, 1H), 7.67 (d, J=4.1 Hz, 1H), 7.61-7.55 (m, 1H), 7.26 (d, J=4.1 Hz, 1H). HPLC (max plot) 97%; Rt 3.91 min. LC/MS: (ES+):405.9, (ES−):403.8.

Intermediate 56: 2-chloro-N-(3-chloroquinoxalin-2-yl)benzenesulfonamide (Formula II)

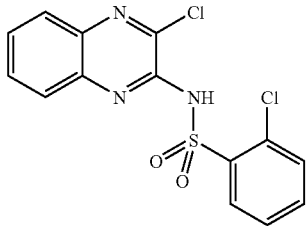

Following the protocol outlined in Procedure F, Intermediate 56 is obtained from 2,3-dichloroquinoxaline (700 mg, 3.5 mmol, 1 eq.), 2-chlorobenzenesulfonamide (674 mg, 3.5 mmol, 1 eq.) in the presence of $K_2CO_3$ (486 mg, 3.52 mmol, 1 eq.) in DMA (7 ml), to afford 1184.9 mg (95%) of the title compound as a white solid. 1H NMR (DMSO-d6) δ 8.32-8.26 (m, 1H), 7.87 (d, J=7.9 Hz, 1H), 7.75-7.57 (m, 7H). HPLC (max plot) 90%; Rt 3.64 min. LC/MS: (ES+): 354.2, (ES−): 352.2.

Intermediate 57: 3-chloro-N-(3-chloroquinoxalin-2-yl)benzenesulfonamide (Formula II)

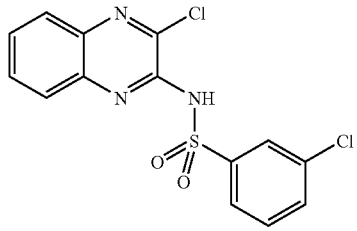

Following the protocol outlined in Procedure F, Intermediate 57 is obtained from 2,3-dichloroquinoxaline (500 mg, 2.5 mmol, 1 eq.) and 3-chlorobenzenesulfonamide (481.4 mg, 2.5 mmol, 1 eq., commercially available from Lancaster) in the presence of $K_2CO_3$ (347.2 mg, 2.5 mmol, 1 eq.) in DMA (5 ml), to afford 782 mg (88%) of the title compound as a yellow powder. 1H NMR (DMSO-d6) δ 8.18 (t, J=1.9 Hz, 1H), 8.12-8.09 (m, 1H), 7.89-7.87 (m, 1H), 7.83-7.71 (m, 3H), 7.68-7.63 (m, 2H). HPLC (max plot) 93%; Rt 4.15 min. LC/MS: (ES+):354.1, (ES−): 352.1.

Intermediate 58: N-(3,6-dichloroquinoxalin-2-yl)benzenesulfonamide (Formula II)

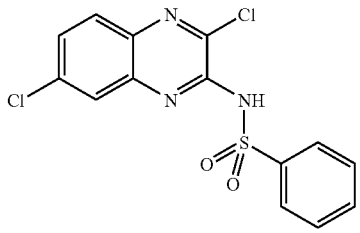

Following the protocol outlined in Procedure F, Intermediate 58 is obtained from 2,3,6-trichloroquinoxaline (300 mg, 1.3 mmol, 1 eq., commercially available from Acros) and benzenesulfonamide (202 mg, 1.3 mmol, 1 eq.) in the presence of $K_2CO_3$ (177.6 mg, 1.3 mmol, 1 eq.) in DMA (9 ml), then washing with hot ACN to afford 97.6 mg (21%) of the title compound as a beige solid. 1H NMR (DMSO-d6) δ 8-30-8.10 (m, 2H), 8-7.75 (m, 2H), 7.70-7.50 (m, 4H), Rt 3.85 min. HPLC (max plot) 99%; Rt 3.86 min.

Intermediate 59: methyl 5-{[(3-chloroquinoxalin-2-yl)amino]sulfonyl}-4-methylthiophene-2-carboxylate (Formula II)

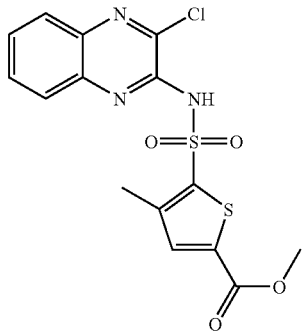

Following the protocol outlined in procedure F, intermediate 59 is obtained from 2,3-dichloroquinoxaline (295 mg; 1.48 mmol; 1 eq) and methyl 5-(aminosulfonyl)-4-methylthiophene-2-carboxylate (348.22 mg; 1.48 mmol; 1 eq) in the presence of $K_2CO_3$ (204.54 mg; 1.48 mmol; 1 eq) in DMA (4 ml), to afford 426.2 mg (72%) of the title compound. 1H NMR (DMSO-d6) δ 7.90-7.58 (m, 5H), 3.84 (s, 3H), 2.51 (s, 3H). HPLC (max plot) 99%; Rt 4.05 min. LC/MS: (ES+): 398.1, (ES−): 396.1.

Intermediate 60: methyl 5-{[(3-chloroquinoxalin-2-yl)amino]sulfonyl}-1-methyl-1H-pyrrole-2-carboxylate (Formula II)

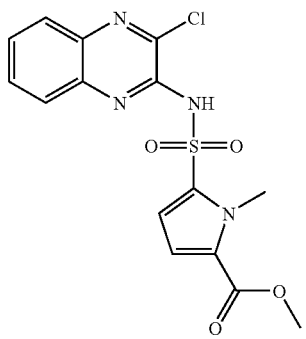

Following the protocol outlined in procedure F, intermediate 60 is obtained from 2,3-dichloroquinoxaline (500 mg; 2.51 mmol; 1 eq) and methyl 5-(aminosulfonyl)-1-methyl-1H-pyrrole-2-carboxylate (548.22 mg; 2.51 mmol; 1 eq) in the presence of $K_2CO_3$ (347.18 mg; 2.51 mmol; 1 eq) in DMA (5 ml), to afford 545.3 mg (57%) of the title compound. 1H NMR (DMSO-d6) δ 11.21 (br s, 1H), 8.08 (d, J=7.9 Hz, 1H), 8.04 (s, 1H), 7.91 (d, J=7.9 Hz, 1H), 7.82 (t, J=7.4 Hz, 1H), 7.69 (t, J=7.4 Hz, 1H), 7.31 (d, J=1.9 Hz, 1H), 3.92 (s, 3H), 3.76 (s, 3H). HPLC (max plot) 99%; Rt 3.32 min. LC/MS: (ES+): 381.2, (ES−): 379.2.

Intermediate 61: N-(3-chloroquinoxalin-2-yl)thiophene-2-sulfonamide (Formula II)

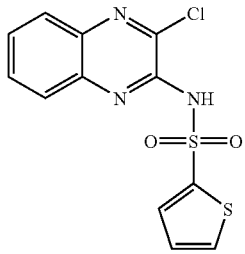

Following the protocol outlined in procedure F, intermediate 61 is obtained from 2,3-dichloroquinoxaline (650.00 mg; 3.27 mmol; 1.00 eq) and thiophene-2-sulfonamide (533.03 mg; 3.27 mmol; 1.00 eq) in the presence of $K_2CO_3$ (451.33 mg; 3.27 mmol; 1.00 eq) in DMA (7 ml), to afford 693 mg (65.13%) of the title compound. 1H NMR (DMSO-d6) δ 7.99-7.97 (m, 3H), 7.91-7.88 (m, 1H), 7.82-7.75 (m, 1H), 7.70-7.65 (m, 1H), 7.19-7.16 (m, 1H). HPLC (max plot) 87.42%; Rt 3.51 min. LC/MS: (ES+): 326.1, (ES−): 324.1.

Intermediate 62: 2-chloro-N-(3-chloroquinoxalin-2-yl)-4-fluorobenzenesulfonamide (Formula II)

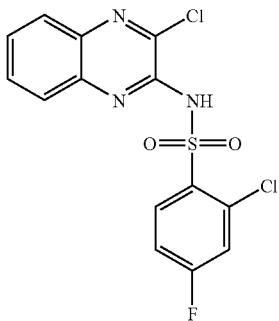

Following the protocol outlined in procedure F, intermediate 62 is obtained from 2,3-dichloroquinoxaline (300.00 mg; 1.51 mmol; 1 eq) and 2-chloro-4-fluorobenzenesulfonamide (315.96 mg; 1.51 mmol; 1 eq) in the presence of $K_2CO_3$ (208.31 mg; 1.51 mmol; 1 eq) in DMA (3 ml), to afford 479.8 mg (85.5%) of the title compound as a beige solid. 1H NMR (DMSO-d6) δ 8.35 (dd, J=9.0, 3.0 Hz, 1H), 7.86 (d, J=8.3 Hz, 1H), 7.71 (d, J=4.9 Hz, 2H), 7.69-7.56 (m, 2H), 7.48 (dt, J=8.4, 2.4 Hz, 1H), (, H). HPLC (max plot) 90.5%; Rt 3.76 min. LC/MS: (ES+): 372.2, (ES−): 370.2.

Intermediate 63: N-(3-chloroquinoxalin-2-yl)-5-[(1,3-dioxo-1,3-dihydro-2H-isoindol-2-yl)methyl]thiophene-2-sulfonamide (Formula II)

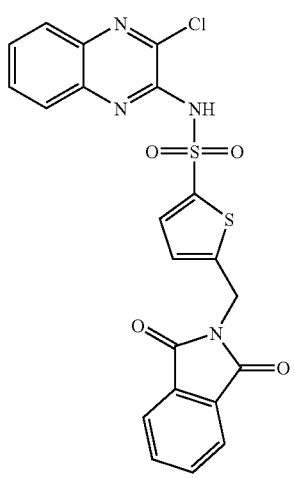

Following the protocol outlined in procedure F, intermediate 63 is obtained from 2,3-dichloroquinoxaline (800 mg; 4.02 mmol; 1 eq) and 5-[(1,3-dioxo-1,3-dihydro-2H-isoindol-2-yl)methyl]thiophene-2-sulfonamide (1295.68 mg; 4.02 mmol; 1 eq) in the presence of $K_2CO_3$ (555.48 mg; 4.02 mmol; 1 eq) in DMA (8 ml), to afford 647 mg (33%) of the title compound. 1H NMR (DMSO-d6) δ 7.92-7.79 (m, 7H), 7.72-7.61 (m, 2H), 7.14 (d, J=3.8 Hz, 1H), 4.98 (s, 2H). HPLC (max plot) 88%; Rt 3.95 min. LC/MS: (ES+): 485.2, (ES−): 483.2.

Intermediate 64: N-(3-chloroquinoxalin-2-yl)-3-cyano-4-fluorobenzenesulfonamide (Formula II)

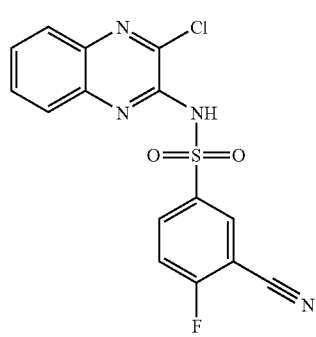

Following the protocol outlined in procedure F, intermediate 64 is obtained from 2,3-dichloroquinoxaline (1000 mg; 5.02 mmol; 1 eq) and 3-cyano-4-fluorobenzenesulfonamide (1005.79 mg; 5.02 mmol; 1 eq) in the presence of $K_2CO_3$ (694.35 mg; 5.02 mmol; 1 eq) in DMA (40 ml), to afford 541 mg (30%) of the title compound as a yellow solid. 1H NMR (DMSO-d6) δ 8.65 (dd, J=6.0, 2.2 Hz, 1H), 8.54-8.47 (m, 1H), 7.89-7.83 (m, 2H), 7.79-7.71 (m, 2H), 7.67-7.59 (m, 1H). HPLC (max plot) 97%; Rt 3.57 min. LC/MS: (ES+): 363.2, (ES−): 361.2.

Intermediate 65: 6-chloro-N-(3-chloroquinoxalin-2-yl)pyridine-3-sulfonamide (Formula II)

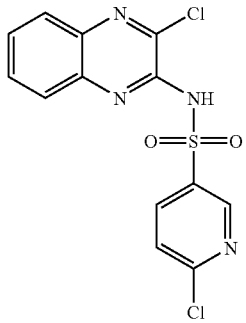

Following the protocol outlined in procedure F, intermediate 65 is obtained from 2,3-dichloroquinoxaline (200 mg; 1 mmol; 1 eq) and 6-Chloropyridine-3-sulfonamide (193.55 mg; 1 mmol; 1 eq) in the presence of $K_2CO_3$ (138.87 mg; 1 mmol; 1 eq) in DMA (2 ml), to afford 292 mg (82%) of the title compound as a powder. 1H NMR (DMSO-d6) δ 9.09 (d, J=2.3 Hz, 1H), 8.52 (dd, J=2.6, 8.3 Hz, 1H), 7.85 (dd, J=1.1, 8.3 Hz, 2H), 7.77-7.71 (m, 2H), 7.65-7.60 (m, 1H). HPLC (max plot) 97%; Rt 3.45 min. LC/MS: (ES+): 355.2, (ES−): 353.2.

Intermediate 66: N-(3-chloroquinoxalin-2-yl)-6-(dimethylamino)pyridine-3-sulfonamide (Formula II)

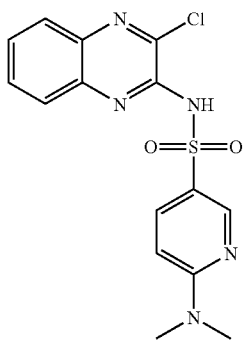

Following the protocol outlined in procedure F, intermediate 66 is obtained from 2,3-dichloroquinoxaline (250 mg; 1.26 mmol; 1 eq) and 6-dimethylamino-pyridine-3-sulfonic acid amide (252.77 mg; 1.26 mmol; 1 eq) in the presence of $K_2CO_3$ (173.59 mg; 1.26 mmol; 1 eq) in DMA (3 ml), to afford 252 mg (55%) of the title compound as a powder. 1H NMR (DMSO-d6) δ 11.26 (br s, 1H), 8.76 (d, J=2.3 Hz, 1H), 8.14 (dd, J=2.3, 9.0 Hz, 1H), 7.90-7.87 (m, 2H), 7.81-7.76 (m, 1H), 7.66 (t, J=7.5 Hz, 1H), 6.74 (d, J=9.0 Hz, 1H), 3.08 (s, 6H). HPLC (max plot) 89.63%; Rt 2.39 min. LC/MS: (ES+): 364.3, (ES−): 362.3.

Intermediate 67: N-(3-chloroquinoxalin-2-yl)-6-[(3-methoxypropyl)amino]pyridine-3-sulfonamide (Formula II)

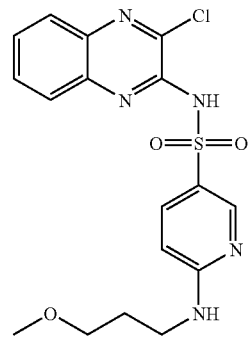

Following the protocol outlined in procedure F, intermediate 67 is obtained from 2,3-dichloroquinoxaline (250 mg; 1.26 mmol; 1 eq) and 6-[(3-methoxypropyl)amino]pyridine-3-sulfonamide (308.11 mg; 1.26 mmol; 1 eq) in the presence of $K_2CO_3$ (173.59 mg; 1.26 mmol; 1 eq) in DMA (3 ml), to afford 388 mg (76%) of the title compound as a powder. 1H NMR (DMSO-d6) δ (, H), 11.29 (br s, 1H), 8.68 (d, J=1.9 Hz, 1H), 8.04 (d, J=8.7 Hz, 1H), 7.90-7.85 (m, 2H), 7.79-7.74 (m, 1H), 7.67-7.62 (m, 2H), 6.56 (d, J=9.0 Hz, 1H), 3.35-3.27 (m, 4H), 3.19 (s, 3H), 1.76-1.67 (m, 2H). HPLC (max plot) 84.5%; Rt 2.44 min. LC/MS: (ES+): 408.3, (ES−): 406.3.

Intermediate 68: N-(3-chloroquinoxalin-2-yl)-6-methoxypyridine-3-sulfonamide (Formula II)

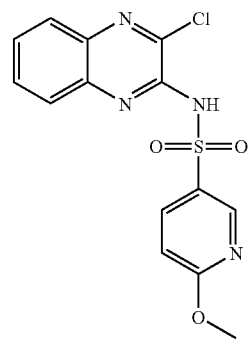

Following the protocol outlined in procedure F, intermediate 68 is obtained from 2,3-dichloroquinoxaline (250.00 mg; 1.26 mmol; 1 eq) and 6-methoxypyridine-3-sulfonamide (236.39 mg; 1.26 mmol; 1 eq) in the presence of $K_2CO_3$ (173.59 mg; 1.26 mmol; 1 eq) in DMA (3 ml), to afford 230 mg (52%) of the title compound as a powder. 1H NMR (DMSO-d6) δ 8.92 (d, J=2.26 Hz, 1H), 8.43-8.39 (m, 1H), 7.91-7.86 (m, 2H), 7.80-7.75 (m, 1H), 7.69-7.64 (m, 1H), 7.02 (d, J=9.04 Hz, 1H), 3.91 (s, 3H). HPLC (max plot) 80%; Rt 3.28 min. LC/MS: (ES+): 351.1, (ES−): 349.2.

Intermediate 69: N-(3-chloroquinoxalin-2-yl)-6-methylpyridine-3-sulfonamide (Formula II)

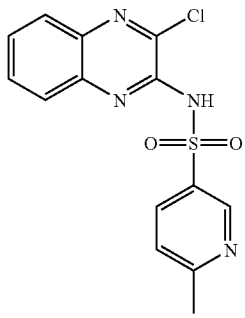

Following the protocol outlined in procedure F, intermediate 69 is obtained from 2,3-dichloroquinoxaline (500 mg; 2.51 mmol; 1 eq.), 6-methyl-pyridine-3-sulfonic acid pyridine (432.59 mg; 2.51 mmol; 1 eq.) in the presence of $K_2CO_3$ (347.18 mg; 2.51 mmol; 1 eq.) in DMA (5 ml), to afford 451 mg (54%) of the title compound as a red powder. HPLC (max plot) 94%; Rt 2.72 min. LC/MS: (ES+): 335.1, (ES−): 333.1.

Intermediate 70: methyl 5-{[(3-chloroquinoxalin-2-yl)amino]sulfonyl}pyridine-2-carboxylate (Formula II)

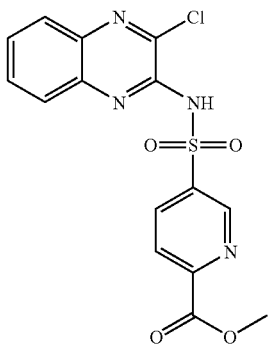

Following the protocol outlined in procedure F, intermediate 70 is obtained from 2,3-dichloroquinoxaline (92.06 mg; 0.46 mmol; 1 eq.) and methyl 5-(aminosulfonyl)pyridine-2-carboxylate (100 mg; 0.46 mmol; 1 eq.) in the presence of $K_2CO_3$ (63.92 mg; 0.46 mmol; 1 eq.) in DMA (1.5 ml), to afford 112 mg (65%) of the title compound as a brown powder. 1H NMR (DMSO-d6) δ 9.30 (d, J=3 Hz, 1H), 8.70 (dd, J=9 and 3 Hz, 1H), 8.25 (d, J=9 Hz, 1H), 7.76 (m, 2H), 7.60 (m, 2H), 3.90 (s, 3H). HPLC (max plot) 83%; Rt 3.22 min. LC/MS: (ES+): 379 and (ES−): 377.

Intermediate 71: N-(3-chloroquinoxalin-2-yl)-3-(morpholin-4-ylcarbonyl)benzenesulfonamide (Formula II)

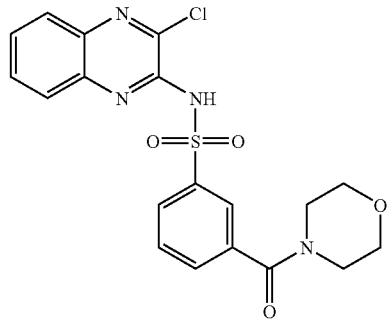

Following the protocol outlined in procedure F, intermediate 71 is obtained from 2,3-dichloroquinoxaline (800 mg; 4.02 mmol; 1 eq.) and 3-(morpholine-4-carbonyl)-benzenesulfonamide (1086.45 mg; 4.02 mmol; 1 eq.) in the presence of $K_2CO_3$ (555.48 mg; 4.02 mmol; 1 eq.) in DMA (8 ml), to afford 1267 mg (73%) of the title compound as a yellow solid. 1H NMR (DMSO-d6) δ 8.22-8.18 (m, 2H), 7.89-7.83 (m, 2H), 7.78-7.73 (m, 1H), 7.70-7.63 (m, 3H), 3.63-3.27 (m, 8H). HPLC (max plot) 92%; Rt 3.13 min. LC/MS: (ES+): 433.2, (ES−): 431.2.

Intermediate 72: N-(3-chloroquinoxalin-2-yl)-1-methyl-1H-imidazole-4-sulfonamide (Formula II)

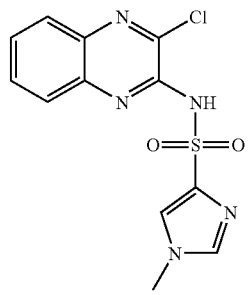

Following the protocol outlined in procedure F, intermediate 72 is obtained from 2,3-dichloroquinoxaline (500 mg; 2.51 mmol; 1 eq.) and 1-methyl-1H-imidazole-4-sulfonamide (404.9 mg; 2.51 mmol; 1 eq.) in the presence of $K_2CO_3$ (347.18 mg; 2.51 mmol; 1 eq.) in DMA (5 ml), to afford 3516 mg (65.5%) of the title compound. 1H NMR (DMSO-d6) δ 8.15 (s, 1H), 7.87 (m, 3H), 7.74 (m, 1H), 7.61 (m, 1H), 3.73 (s, 3H). HPLC (max plot) 92%; Rt 2.41 min. LC/MS: (ES+): 324.0, (ES−): 321.9.

Intermediate 73: 1,4-Dihydropyrido[3,4-b]pyrazine-2,3-dione (Formula VIII)

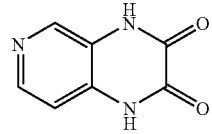

To a suspension of 3,4-diaminopyridine (10 g, 0.068 mol) in 4N aqueous HCl (100 ml) is added oxalic acid (10.4 g, 0.082 mol) and the reaction mixture is refluxed for 20 h. The reaction mixture is cooled down and the solid precipitated is filtered, washed with water then dried under vacuum to afford 9 g (80%) of the title compound as a solid. HPLC (max plot) 98%. LC/MS: (ES+): 164.3.

Intermediate 74: 2,3-Dichloro-pyrido(3,4-b)pyrazine (Formula IV)

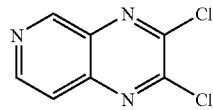

To a solution of 1,4-dihydropyrido[3,4-b]pyrazine-2,3-dione (9 g, 0.055 mol) in POCl$_3$ (90 ml) is added Et$_3$N (6.7 g, 0.066 mol) and the reaction mixture is refluxed for 20 h under N$_2$. The reaction mixture is cooled down and carefully quenched with ice-water (1 kg) and the product is extracted with EtOAc (3×150 ml). The combined organic layer is washed with water, dried over MgSO$_4$ and evaporated under reduced pressure to afford 6 g (54%) of the title compound as a solid. TLC—Chloroform/methanol (9/1): R$_f$=0.8, HPLC (max plot) 98%.

Intermediate 75: 1,4-Dihydropyrido[2,3-b]pyrazine-2,3-dione (Formula VIII)

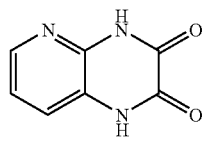

To a suspension of 2,3-diaminopyridine (20 g, 0.136 mol) in 4N aqueous HCl (200 ml) is added oxalic acid (20.7 g, 0.164 mol) and the reaction mixture is refluxed for 20 h. The reaction mixture is cooled and the solid precipitated is filtered, washed with water and dried under vacuum to afford 20 g (89%) of the title compound as a solid. HPLC (max plot) 98%.

Intermediate 76: 2,3-Dichloro-pyrido(2,3-b)pyrazine (Formula IV)

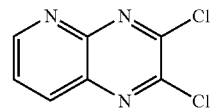

To a solution of 1,4-dihydropyrido[2,3-b]pyrazine-2,3-dione (10 g, 0.0613 mol) in POCl$_3$ (100 ml) was added Et$_3$N (9 g, 0.092 mol) and the reaction mixture refluxed for 18 h under nitrogen. The reaction mixture is cooled and carefully quenched with ice-water (1 kg) and the product was extracted with EtOAc (3×150 ml). The combined organic layer is washed with water, dried over MgSO4 and evaporated under reduced pressure to afford 8 g (65%) of the title compound as a solid. TLC—Chloroform/methanol (9/1): R$_f$=0.8, HPLC (max plot) 98%.

Intermediate 77: N-(2-chloropyrido[3,4-b]pyrazin-3-yl)benzenesulfonamide (Formula II)

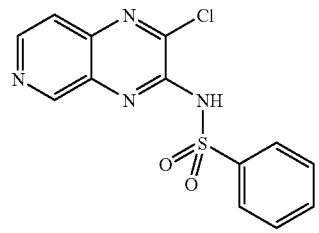

2,3-dichloro-pyrido(3,4-b)pyrazine (300 mg, 1.5 mmol, 1 eq.), benzenesulfonamide (235.8 mg, 1.5 mmol, 1 eq.) and K$_2$CO$_3$ (207.3 mg, 1.5 mmol, 1 eq.) are taken up in anhydrous DMA (10 ml) under argon. The reaction mixture is stirred at room temperature for 3 days, then water (15 ml) is added. The aqueous phase is washed with EtOAc (4×10 ml) then lyophilized. The solid residue obtained is extracted with DCM and the solvent is evaporated to near dryness then purified by preparative HPLC using a gradient of H2O, TFA 0.1% ACN, TFA 0.1%, to afford 21.7 mg (5%) of the title compound. 1H NMR (DMSO-d6) δ 9.13 (s, 1H), 8.42 (d, J=6.7 Hz, 1H), 8.03-7.97 (m, 2H), 7.56 (d, J=6.8 Hz, 1H), 7.51-7.45 (m, 3H). HPLC (max plot) 95%; Rt 1.71 min. LC/MS: (ES+): 321.0, (ES−): 319.0.

Intermediate 78: N-(3-chloropyrido[2,3-b]pyrazin-2-yl)benzenesulfonamide (Formula II)

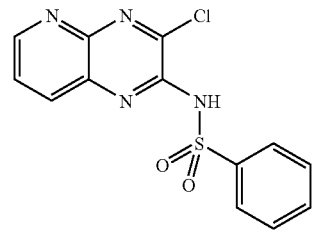

2,3-dichloro-pyrido(2,3-b)pyrazine (300 mg; 1.5 mmol; 1 eq.), benzenesulfonamide (235.8 mg, 1.5 mmol, 1 eq.) and K$_2$CO$_3$ (207.3 mg, 1.5 mmol, 1 eq.) are taken up in anhydrous DMA (10 ml) under argon. The reaction mixture is stirred at room temperature for 7 days. The solvent is evaporated and the residue obtained is purified by prep HPLC using a gradient of H2O, TFA 0.1%/ACN, TFA 0.1%, to afford 82.1 mg (17%) of the title compound. 1H NMR (DMSO-d6) δ 8.67 (dd, J=5.7, 1.5 Hz, 1H), 8.57 (dd, J=7.9, 1.5 Hz, 1H), 8.08 (dd, J=8.0 Hz, 1.8 Hz, 2H), 7.57 (dd, J=7.9, 5.7 Hz, 1H), 7.54-7.46 (m, 4H). HPLC (max plot) 94%; Rt 1.96 min. LC/MS: (ES+): 321.0, (ES−): 319.0.

Procedure G

Intermediate 79: N-{3-[(3,5-dimethoxyphenyl)amino]quinoxalin-2-yl}-4-[(4-methylpiperazin-1-yl)carbonyl]benzenesulfonamide (Formula I)

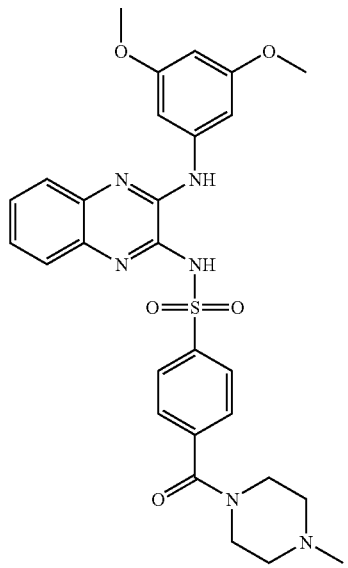

4-[({3-[(3,5-dimethoxyphenyl)amino]quinoxalin-2-yl}amino)sulfonyl]benzoic acid (162 mg; 0.34 mmol; 1 eq.), EDC-HCl (71.10 mg; 0.37 mmol; 1.10 eq.) and HOBT (50.11 mg; 0.37 mmol; 1.10 eq.) were taken up in DCM (6 ml) then DIEA (84.89 μl; 0.51 mmol; 1.50 eq.) and 1-methylpiperazine (37.52 μl; 0.34 mmol; 1 eq.) were added. The mixture was stirred at rt for 5 h. The solution was washed successively with a saturated solution of NaHCO$_3$, NH$_4$Cl and NaCl. The organic phase was dried over MgSO$_4$ and concentrated to near dryness to afford 171 mg (90%) of the title compound as a yellow powder. 1H NMR (DMSO-d6) δ 10.06 (br s, 1H), 8.80 (s, 1H), 8.13 (d, J=8.3 Hz, 2H), 7.47 (d, J=8.3 Hz, 2H), 7.44-7.41 (m, 1H), 7.39-7.34 (m, 1H), 7.31 (br d, 2H), 7.21-7.14 (m, 2H), 6.15 (t, J=2.3 Hz, 1H), 3.76 (s, 6H), 3.65-3.35 (m, 4H), 3.10-2.85 (m, 4H), 2.63 (s, 3H). HPLC (max plot) 97.1%; Rt 3.55 min. LC/MS: (ES+): 563.4, (ES−): 561.2.

Intermediate 80: N-{3-[(3,5-dimethoxyphenyl)amino]quinoxalin-2-yl}-4-(morpholin-4-ylcarbonyl)benzenesulfonamide) (Formula I)

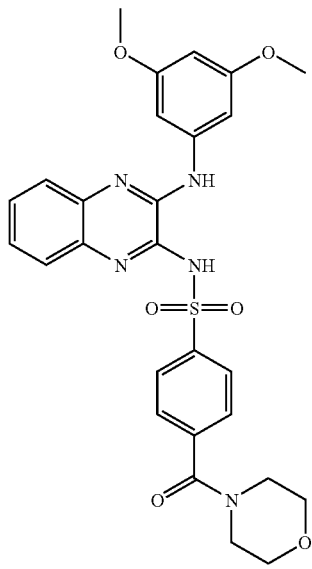

Following the protocol outlined in Procedure G, Example 80 is obtained from 4-[({3-[(3,5-dimethoxyphenyl)amino]quinoxalin-2-yl}amino)sulfonyl]benzoic acid (160 mg; 0.33 mmol; 1 eq.), EDC-HCl (70.22 mg; 0.37 mmol; 1.10 eq.), HOBT (49.49 mg; 0.37 mmol; 1.10 eq.), DIEA (83.84 μl; 0.5 mmol; 1.50 eq.) and morpholine (29.01 μl; 0.33 mmol; 1 eq.) in DCM (6 ml) to afford the title compound as a parent. Treatment of the parent with HCl in MeOH affords 165 mg (90%) of the title compound as a yellow powder. 1H NMR (DMSO-d6) δ 12.34 (s, 1H), 8.94 (s, 1H), 8.16 (d, J=8.3 Hz, 2H), 7.90 (br s, 1H), 7.61-7.55 (m, 3H), 7.40-7.34 (m, 4H), 6.23 (t, J=2.3 Hz, 1H), 3.75 (s, 6H), 3.62-3.27 (m, 8H). HPLC (max plot) 98.4%; Rt 4.19 min. LC/MS: (ES+): 550.2, (ES−): 548.8.

Intermediate 81: 4-[({3-[(3,5-dimethoxyphenyl)amino]quinoxalin-2-yl}amino)sulfonyl]-N,N-dimethylbenzamide (Formula I)

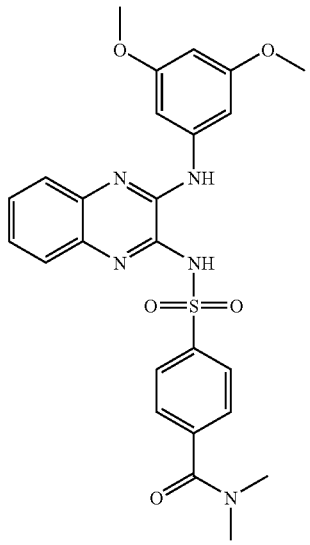

Following the protocol outlined in Procedure G, Example 81 is obtained from 4-[({3-[(3,5-dimethoxyphenyl)amino]quinoxalin-2-yl}amino)sulfonyl]benzoic acid (166 mg; 0.35 mmol; 1 eq.), EDC-HCl (72.85 mg; 0.38 mmol; 1.1 eq.), HOBT (51.35 mg; 0.38 mmol; 1.1 eq.), DIEA (86.98 μl; 0.52 mmol; 1.50 eq.) and dimethylamine (172.74 μl; 2 M; 0.35 mmol; 1 eq.) in DCM (6 ml) to afford 155 mg (88%) of the title compound as a parent (yellow powder). 1H NMR (DMSO-d6) δ 12.36 (br s, 1H), 8.94 (s, 1H), 8.15 (d, J=8.3 Hz, 2H), 7.90 (br s, 1H), 7.58 (d, J=8.3 Hz, 2H), 7.57-7.55 (m, 1H), 7.38-7.34 (m, 4H), 6.22 (t, J=2.3 Hz, 1H), 3.75 (s, 6H), 2.97 (s, 3H), 2.86 (s, 3H). HPLC (max plot) 98%; Rt 4.38 min. LC/MS: (ES+): 508.1, (ES−): 506.1.

Intermediate 82: 3-[({3-[(3,5-dimethoxyphenyl)amino]quinoxalin-2-yl}amino)sulfonyl]-N,N-dimethylbenzamide (Formula I)

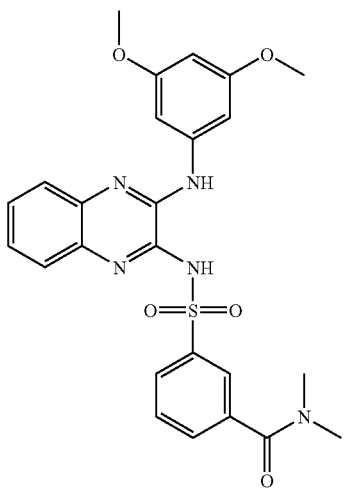

Following the protocol outlined in Procedure G, Example 82 is obtained from 3-[({3-[(3,5-dimethoxyphenyl)amino]quinoxalin-2-yl}amino)sulfonyl]benzoic acid (110 mg; 0.23 mmol; 1 eq.), EDC-HCl (48.28 mg; 0.25 mmol; 1.1 eq.), HOBT (34.03 mg; 0.25 mmol; 1.1 eq.), DIEA (57.64 µl; 0.34 mmol; 1.5 eq.) and dimethylamine (114.46 µl; 2 M; 0.23 mmol; 1 eq.) in DCM (4.5 ml) to afford 102 mg (88%) of the title compound as a parent (yellow powder). 1H NMR (DMSO-d6) δ 12.34 (br s, 1H), 8.95 (s, 1H), 8.17-8.12 (m, 2H), 7.90 (br s, 1H), 7.66-7.63 (m, 2H), 7.58-7.55 (m, 1H), 7.41-7.34 (m, 4H), 6.22 (t, J=2.3 Hz, 1H), 3.75 (s, 6H), 2.97 (s, 3H), 2.87 (s, 3H). HPLC (max plot) 98%; Rt 4.34 min. LC/MS: (ES+): 508.3, (ES–): 506.1.

Intermediate 83: 6-(chloromethyl)-N-{3-[(3,5-dimethoxyphenyl)amino]quinoxalin-2-yl}pyridine-3-sulfonamide (Formula I)

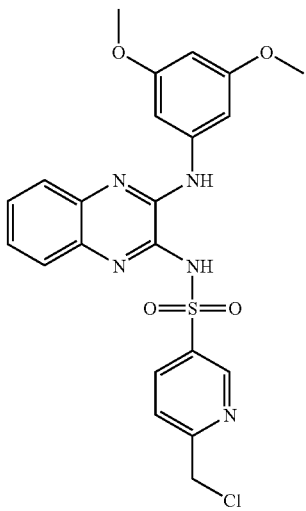

N-{3-[(3,5-dimethoxyphenyl)amino]quinoxalin-2-yl}-6-(hydroxymethyl)pyridine-3-sulfonamide (90 mg; 0.19 mmol; 1 eq.) is dissolved in CHCl₃ (10 ml) at rt. Thionyl chloride (0.05 ml; 0.39 mmol; 2 eq.) is added and reaction mixture is stirred for 1 h30. Water and aqueous NaHCO₃ are added and the product is extracted with DCM. The organic phase is dried over magnesium sulfate and the solvent is evaporated under reduced pressure to afford 100 mg (108%) of the title compound as a powder. It was used as such in the next step. HPLC (max plot) 35%; Rt 4.78 min, LC/MS: (ES+) 486.22, (ES–) 484.22.

Intermediate 84: methyl 5-[({3-[(3,5-dimethoxyphenyl)amino]quinoxalin-2-yl}amino)sulfonyl]-4-methylthiophene-2-carboxylate (Formula I)

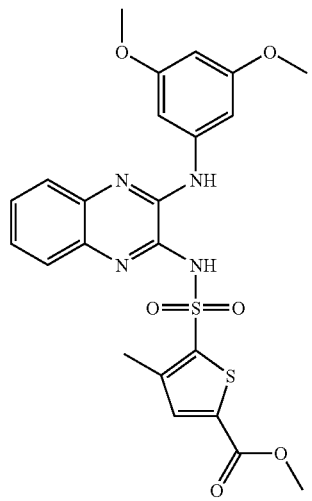

Methyl 5-{[(3-chloroquinoxalin-2-yl)amino]sulfonyl}-4-methylthiophene-2-carboxylate (100 mg; 0.25 mmol; 1 eq) and 3,5-dimethoxyaniline (42.35 mg; 0.28 mmol; 1.1 eq) are taken up in EtOH (2 ml) and the resulting suspension is heated up to 170° C. for 6 min on high absorption in the microwave. The precipitate formed is filtered off and washed with EtOH then dried under vacuum at 40° C. for 1 day. The solid is washed with hot EtOH then THF to afford, after cooling at 4° C., 103.6 mg (80%) of the title compound as a powder. 1H NMR (DMSO-d6) δ 12.64 (brs, 1H), 8.91 (s, 1H), 7.89 (brs, 1H), 7.71 (s, 1H), 7.60 (dd, J=7.7, 1.7 Hz, 1H), 7.46-7.34 (m, 2H), 7.32 (d, J=1.9 Hz, 2H), 6.26 (t, J=1.9 Hz, 1H), 3.83 (s, 3H), 3.77 (s, 6H), 2.48 (s, 3H). HPLC (max plot) 95%; Rt 4.93 min. LC/MS: ES+ 515.2, ES– 512.9.

Procedure H

Example 1

N-[3-(3,5-Dimethoxy-phenylamino)-quinoxalin-2-yl]-3-methanesulfonyl-benzenesulfonamide (1) (Scheme 5)

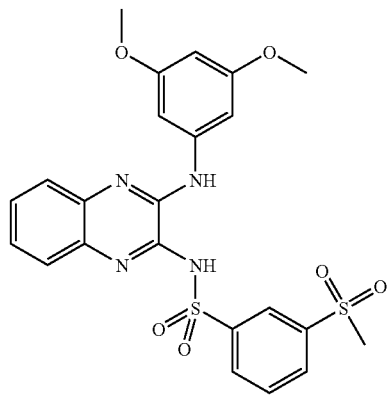

N-(3,5-dimethoxyphenyl)quinoxaline-2,3-diamine (50 mg, 0.17 mmol), 3-(methylsulfonyl)benzenesulfonyl chloride (64 mg, 0.26 mmol, commercially available from Matrix) are dissolved in a 1 to 1 mixture of pyridine and 1,2-dichlorobenzene (0.4 ml) and the reaction mixture is heated at 100° C. in the microwave for 20 min. When TLC confirms the total consumption of the starting material, the reaction mixture is cooled down to rt. The precipitate formed is filtered and purified by column chromatography, using CHCl3: MeOH as eluent, to afford 18 mg (21%) of the title compound as a light brown solid. HPLC (max plot) 84%, rt. 4.2 min. LC/MS: (ES+): 515.

Example 2

N-{3-[(3,5-dimethoxyphenyl)amino]quinoxalin-2-yl}thiophene-3-sulfonamide (2) (Scheme 5)

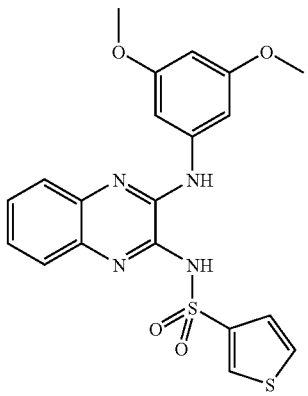

Following the general protocol outlined in Procedure H, Example 2 is obtained from N-(3,5-dimethoxyphenyl)quinoxaline-2,3-diamine and thiophene-3-sulfonyl chloride (commercially available from ABCR) in a 1 to 2 mixture of pyridine:dichlorobenzene (yellow solid, 8 mg, 11%). HPLC (max plot) 94%, rt. 4.51 min. LC/MS: (ES+): 443.

Example 3

N-{3-[(2,5-dimethoxyphenyl)amino]quinoxalin-2-yl}-6-morpholin-4-yl pyridine-3-sulfonamide (3) (Scheme 5)

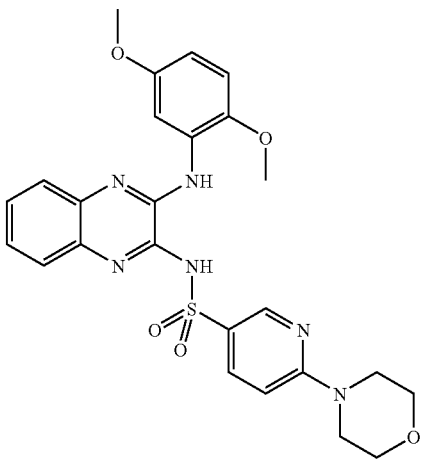

Following the general protocol outlined in Procedure H, Example 3 is obtained from N-(2,5-dimethoxyphenyl)quinoxaline-2,3-diamine (65 mg, 0.22 mmol, 1 eq.) and 6-morpholin-4-sulfonyl chloride (86.4 mg, 0.33 mmol, 1.5 eq., commercially available from ASDI) in a 1 to 2 mixture of pyridine:dichloro-benzene to afford 12.2 mg (11%) of the title compound as a brown solid. 1H NMR (DMSO-d6) δ 12.40-12.20 (br s, 1H), 9.15 (s, 1H), 8.75-8.65 (m, 1H), 8.58-8.45 (m, 1H), 8.15-7.83 (m, 2H), 7.70-750 (m, 1H), 7.45-7.25 (m, 2H), 7.10-6.75 (m, 2H), 6.68-6.5 (m, 1H), 3.81 (s, 3H), 3.76 (s, 3H), 3.70-3.54 (m, 8H). HPLC (max plot) 95%; Rt 4.36 min. LC/MS: (ES+): 523.3; (ES-): 521.3.

Procedure I

Example 4

N-{3-[({3-[(3,5-dimethoxyphenyl)amino]quinoxalin-2-yl}amino)sulfonyl]phenyl}acetamide (4) (Scheme 5)

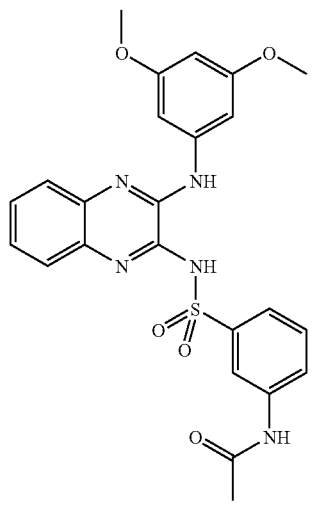

N-(3,5-dimethoxyphenyl)quinoxaline-2,3-diamine (50 mg, 0.168 mmol), 3-Acetylaminobenzene sulfonylchloride (59 mg, 0.5 mmol, commercially available from INTERCHIM) are dissolved in a 1 to 2 mixture of pyridine: dichlorobenzene (0.3 ml) and the reaction mixture is heated to 150° C. overnight in an orbital shaker. When TLC confirms the total consumption of the starting material, the reaction mixture is cooled down to rt. The precipitate formed is filtered and purified by column chromatography, using Pet.Ether: EtOAc as eluent, to afford 20 mg (24%) of the title compound as a yellow solid. HPLC (max plot) 89%, rt. 4.08 min. LC/MS: (ES+): 494.

Example 5

N-{3-[(2,5-dimethoxyphenyl)amino]quinoxalin-2-yl}-2-(methylsulfonyl)benzenesulfonamide (5) (Scheme 5)

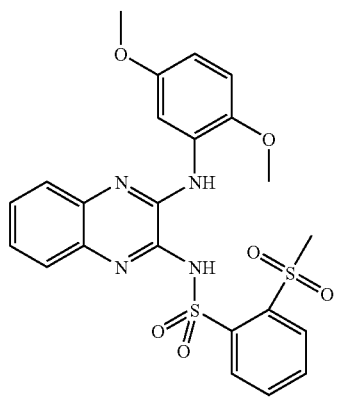

Following the general protocol outlined in Procedure I, Example 5 is obtained from N-(2,5-dimethoxyphenyl)quinoxaline-2,3-diamine and 2-(methylsulfonyl)benzenesulfonyl chloride (commercially available from Acros) in a 1 to 2 mixture of pyridine:dichlorobenzene (dark yellow solid, 10 mg, 14%). HPLC (max plot) 96%, rt. 4.48 min. LC/MS: (ES+): 515.

Example 6

N-{3-[(3,5-dimethoxyphenyl)amino]quinoxalin-2-yl}-2-(methylsulfonyl)benzenesulfonamide (6) (Scheme 5)

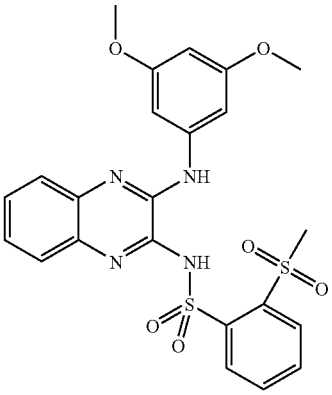

Following the general protocol outlined in Procedure I, Example 6 is obtained from N-(3,5-dimethoxyphenyl)quinoxaline-2,3-diamine and 2-(methylsulfonyl)benzenesulfonyl chloride in pyridine (yellow solid, 20 mg, 24%). HPLC (max plot) 89%, rt. 4.47 min. LC/MS: (ES+): 515.

Example 7

N-{3-[(2,5-dimethoxyphenyl)amino]quinoxalin-2-yl}-2,3-dihydro-1,4-benzodioxine-6-sulfonamide (7) (Scheme 5)

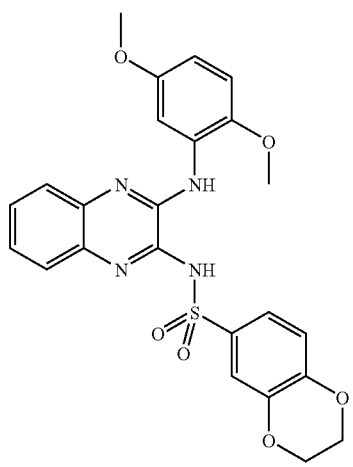

Following the general protocol outlined in Procedure I, Example 7 is obtained from N-(2,5-dimethoxyphenyl)quinoxaline-2,3-diamine and 2,3-dihydro-1,4-benzodioxine-6-sulfonyl chloride (commercially available from Acros) in a 1 to 2 mixture of pyridine:dichlorobenzene (brown solid, 30 mg, 36%). HPLC (max plot) 98%, rt. 4.71 min. LC/MS: (ES+): 495.2.

Example 8

N-{3-[(2,5-dimethoxyphenyl)amino]quinoxalin-2-yl}-4-(pyrrolidin-1-yl sulfonyl)benzenesulfonamide (8) (Scheme 5)

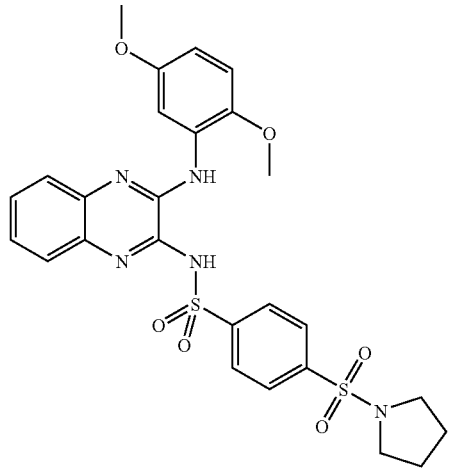

Following the general protocol outlined in Procedure I, Example 8 is obtained from N-(2,5-dimethoxyphenyl)quinoxaline-2,3-diamine and 4-(pyrrolidin-1 ylsulfonyl)benzene sulfonyl chloride (commercially available from Acros) in a 1 to 2 mixture of pyridine:dichlorobenzene (dark brown solid, 18 mg, 19%). HPLC (max plot) 94%, rt. 4.73 min. LC/MS: (ES+): 570.

Example 9

N-{3-[(2,5-dimethoxyphenyl)amino]quinoxalin-2-yl}thiophene-3-sulfonamide (9) (Scheme 5)

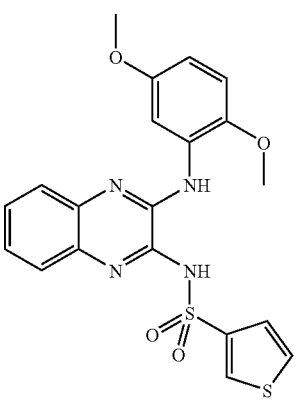

Following the general protocol outlined in Procedure I, Example 9 is obtained from N-(2,5-dimethoxyphenyl)quinoxaline-2,3-diamine and thiophene-3-sulfonyl chloride in a 1 to 2 mixture of pyridine:dichlorobenzene (yellow solid, 15 mg, 20%). HPLC (max plot) 98%, rt. 4.64 min. LC/MS: (ES+):): 443.

Example 10

2-Cyano-N-{3-[(2,5-dimethoxyphenyl)amino]quinoxalin-2-yl}benzene sulfonamide (10) (Scheme 5)

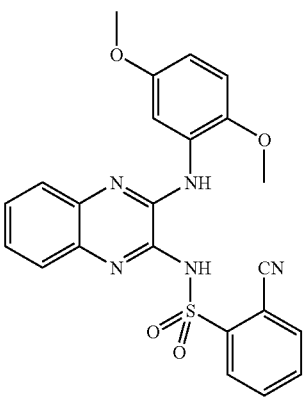

Following the general protocol outlined in Procedure I, Example 10 is obtained from N-(2,5-dimethoxyphenyl)quinoxaline-2,3-diamine and 2-cyanobenzenesulfonyl chloride in a 1 to 2 mixture of pyridine:dichlorobenzene (yellow solid, 15 mg, 19%). HPLC (max plot) 95%, rt. 4.56 min. LC/MS: (ES+): 462.2.

Example 11

3-Cyano-N-{3-[(2,5-dimethoxyphenyl)amino]quinoxalin-2-yl}benzene sulfonamide (11) (Scheme 5)

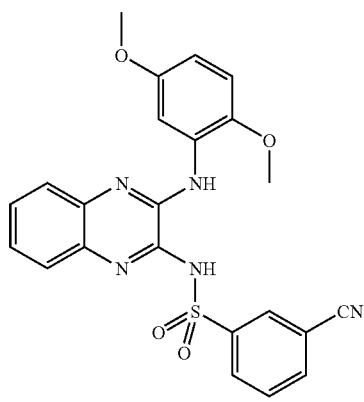

Following the general protocol outlined in Procedure I, Example 11 is obtained from N-(2,5-dimethoxyphenyl)quinoxaline-2,3-diamine and 3-cyanobenzenesulfonyl chloride in a 1 to 2 mixture of pyridine:dichlorobenzene (brown solid, 20 mg, 26%). HPLC (max plot) 93%, rt. 4.65 min. LC/MS: (ES+): 462.2.

Example 12

N-{3-[(2,5-dimethoxyphenyl)amino]quinoxalin-2-yl}-3-methoxybenzene sulfonamide (12) (Scheme 5)

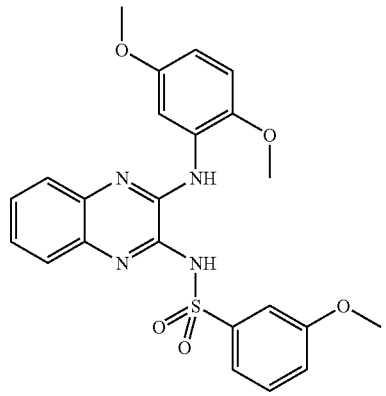

Following the general protocol outlined in Procedure I, Example 12 is obtained from N-(2,5-dimethoxyphenyl)quinoxaline-2,3-diamine and 3-methoxybenzenesulfonyl chloride in a 1 to 2 mixture of pyridine:dichlorobenzene (brown solid, 20 mg, 25%). HPLC (max plot) 88%, rt. 4.84 min. LC/MS: (ES+): 467.1.

Procedure J

Example 13

N-{3-[(2,5-dimethoxyphenyl)amino]quinoxalin-2-yl}-1-methyl-1H-imidazole-4-sulfonamide (13) (Scheme 5)

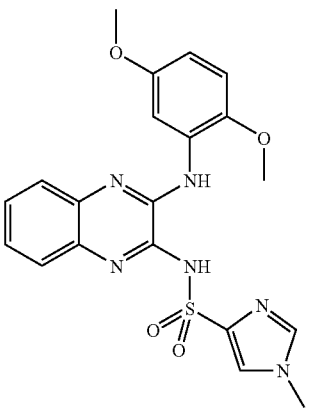

N-(2,5-dimethoxyphenyl)quinoxaline-2,3-diamine (50 mg, 0.17 mmol), 1-methylimidazole-4-sulfonylchloride (91.4 mg, 0.51 mmol, commercially available from Acros) are dissolved in pyridine (0.3 ml) and the reaction mixture was stirred at rt, overnight. When TLC confirms the total consumption of N-(2,5-dimethoxyphenyl)quinoxaline-2,3-diamine, the product is extracted with CHCl$_3$. The organic layer is washed with water, 1.5N HCl and brine then dried over Na$_2$SO$_4$. The solvent is removed under reduced pressure and the residue obtained is purified by recrystallization from MeOH to afford 47 mg (64%) of the title compound as a yellow solid. HPLC (max plot) 95%, rt. 3.91 min. LC/MS: (ES+): 441.2.

Example 14

N-{3-[(2,5-dimethoxyphenyl)amino]quinoxalin-2-yl}-2-fluorobenzene sulfonamide (14) (Scheme 5)

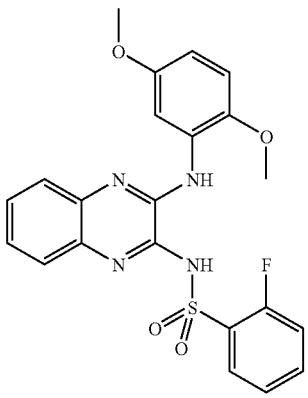

Following the general protocol outlined in Procedure J, Example 14 is obtained from N-(2,5-dimethoxyphenyl)quinoxaline-2,3-diamine and 2-fluorobenzenesulfonyl chloride in pyridine (light brown solid, 18.3 mg, 30%). HPLC (max plot) 91%, rt. 4.79 min. LC/MS: (ES+): 455.5.

Example 15

N-{3-[(3,5-dimethoxyphenyl)amino]quinoxalin-2-yl}-2-fluorobenzene sulfonamide (15) (Scheme 5)

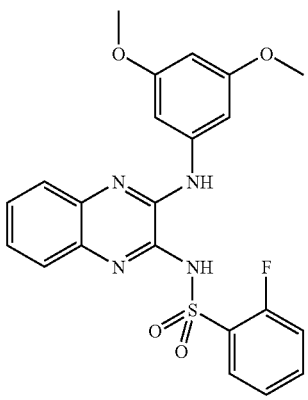

Following the general protocol outlined in Procedure J, Example 15 is obtained from N-(3,5-dimethoxyphenyl)quinoxaline-2,3-diamine and 2-fluorobenzenesulfonyl chloride in pyridine (light brown solid, 20 mg, 30%). HPLC (max plot) 98%, rt. 4.65 min. LC/MS: (ES+): 455.2.

Example 16

N-{3-[(3,5-dimethoxyphenyl)amino]quinoxalin-2-yl}-4-(methylsulfonyl)benzenesulfonamide (16) (Scheme 5)

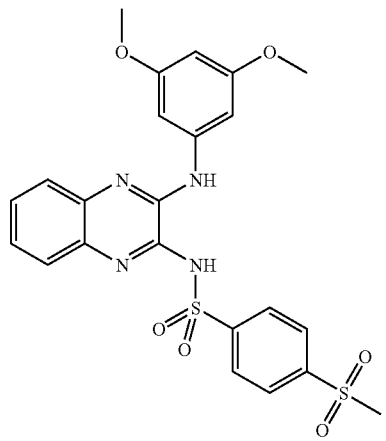

Following the general protocol outlined in Procedure J, Example 16 is obtained from N-(3,5-dimethoxyphenyl)quinoxaline-2,3-diamine and 4-(methylsulfonyl)benzenesulfonyl chloride in pyridine (yellow solid, 5 mg, 9%). HPLC (max plot) 98%, rt. 6.21 min. LC/MS: (ES+): 515.

Example 17

N-{3-[(3,5-dimethoxyphenyl)amino]quinoxalin-2-yl}-4-(pyrrolidin-1-yl sulfonyl)benzenesulfonamide (17) (Scheme 5)

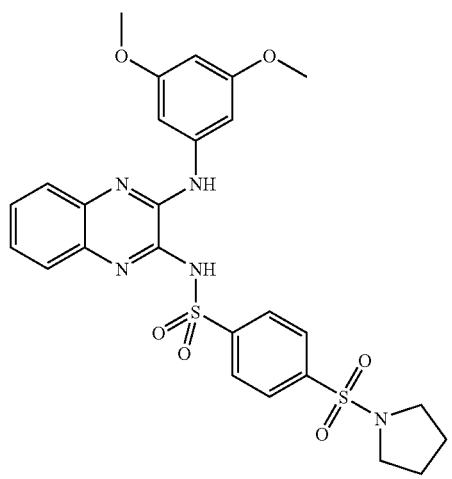

Following the general protocol outlined in Procedure J, Example 17 is obtained from N-(3,5-dimethoxyphenyl)quinoxaline-2,3-diamine and 4-(pyrrolidin-1-ylsulfonyl)benzene sulfonyl chloride in pyridine (yellow solid, 32 mg, 33%). HPLC (max plot) 89%, rt. 4.6 min. LC/MS: (ES+): 570.

Example 18

N-{3-[(2,5-dimethoxyphenyl)amino]quinoxalin-2-yl}-3-(methylsulfonyl)benzenesulfonamide (18)
(Scheme 5)

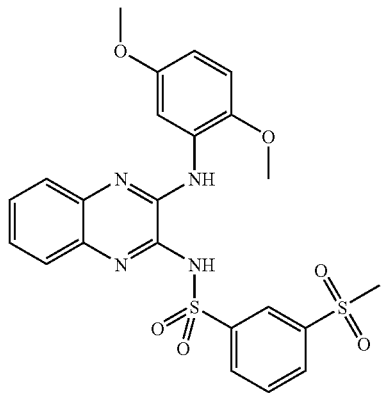

Following the general protocol outlined in Procedure J, Example 18 is obtained from N-(2,5-dimethoxyphenyl)quinoxaline-2,3-diamine and 3-(methylsulfonyl)benzenesulfonyl chloride in pyridine (dark yellow solid, 27 mg, 31%). HPLC (max plot) 94%, rt. 4.31 min. LC/MS: (ES+): 515.

Example 19

N-{3-[(2,5-dimethoxyphenyl)amino]quinoxalin-2-yl}-2,1,3-benzothiadiazole-4-sulfonamide (19)
(Scheme 5)

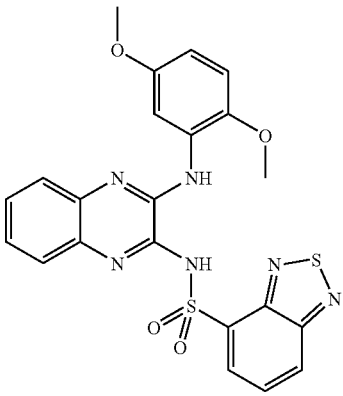

Following the general protocol outlined in Procedure J, Example 19 is obtained from N-(2,5-dimethoxyphenyl)quinoxaline-2,3-diamine and 2,1,3-benzothiadiazole-4-sulfonyl chloride (commercially available from ACROS) in pyridine (yellow solid, 40 mg, 48%). HPLC (max plot) 89%, rt. 4.79 min. LC/MS: (ES+): 495.1.

Example 20

N-{3-[(3,5-dimethoxyphenyl)amino]quinoxalin-2-yl}-1-methyl-1H-imidazole-4-sulfonamide (20)
(Scheme 5)

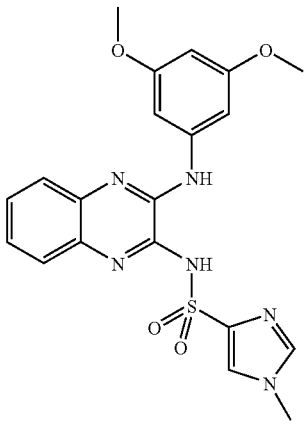

Following the general protocol outlined in Procedure J, Example 20 is obtained from N-(3,5-dimethoxyphenyl)quinoxaline-2,3-diamine and 1-methyl-1H-imidazole-4-sulfonyl chloride in pyridine (yellow solid, 53 mg, 67%). HPLC (max plot) 99%, rt. 3.81 min. LC/MS: (ES+): 441.2.

Example 21

N-{3-[(3,5-dimethoxyphenyl)amino]quinoxalin-2-yl}-2,1,3-benzoxadiazole-4-sulfonamide (21)
(Scheme 5)

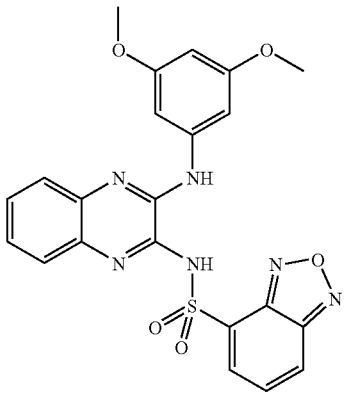

Following the general protocol outlined in Procedure J, Example 21 is obtained from N-(3,5-dimethoxyphenyl)quinoxaline-2,3-diamine and 2,1,3-benzoxadiazole-4-sulfonyl chloride (commercially available from ACROS) in pyridine (yellow solid, 20 mg, 25%). HPLC (max plot) 90%, rt. 4.57 min. LC/MS: (ES+): 479.

Example 22

N-{3-[(2,5-dimethoxyphenyl)amino]quinoxalin-2-yl}-1-pyridin-2-yl methanesulfonamide (22) (Scheme 5)

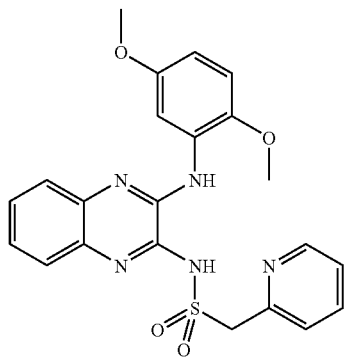

Following the general protocol outlined in Procedure J, Example 22 is obtained from N-(2,5-dimethoxyphenyl)quinoxaline-2,3-diamine and pyridin-2-ylmethanesulfonyl chloride triflate (commercially available from ARRAY) in pyridine (yellow solid, 11 mg, 14%). HPLC (max plot) 94%, rt. 3.85 min. LC/MS: (ES+): 452.

Example 23

N-{3-[(3,5-dimethoxyphenyl)amino]quinoxalin-2-yl}-1-pyridin-2-yl methanesulfonamide (23) (Scheme 5)

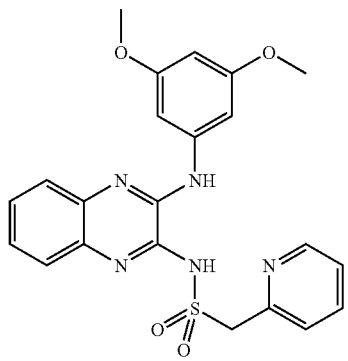

Following the general protocol outlined in Procedure J, Example 23 is obtained from N-(3,5-dimethoxyphenyl)quinoxaline-2,3-diamine and pyridin-2-ylmethanesulfonyl chloride triflate (commercially available from ARRAY) in pyridine (yellow solid, 10 mg, 13%). HPLC (max plot) 94%, rt. 3.75 min. LC/MS: (ES+): 452.

Example 24

N-{3-[(2,5-dimethoxyphenyl)amino]quinoxalin-2-yl}-1-pyridin-3-yl methanesulfonamide (24) (Scheme 5)

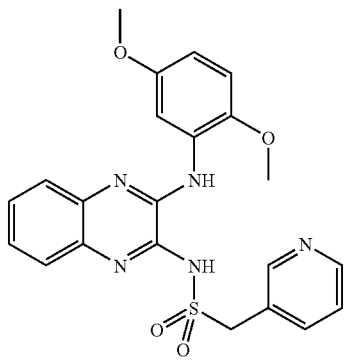

Following the general protocol outlined in Procedure J, Example 24 is obtained from N-(2,5-dimethoxyphenyl)quinoxaline-2,3-diamine and pyridin-3-ylmethanesulfonyl chloride triflate (commercially available from ARRAY) in pyridine (yellow solid, 30 mg, 39%). HPLC (max plot) 97%, rt. 3.57 min. LC/MS: (ES+): 452.

Example 25

N-{3-[(3,5-dimethoxyphenyl)amino]quinoxalin-2-yl}-1-pyridin-3-yl methanesulfonamide (25) (Scheme 5)

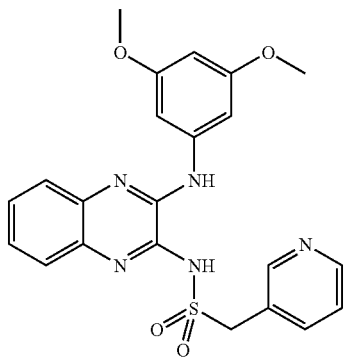

Following the general protocol outlined in Procedure J, Example 25 is obtained from N-(3,5-dimethoxyphenyl)quinoxaline-2,3-diamine and pyridin-3-ylmethanesulfonyl chloride triflate (commercially available from ARRAY) in pyridine (yellow solid, 30 mg, 20%). HPLC (max plot) 96%, rt. 3.49 min. LC/MS: (ES+): 452.5.

Example 26

N-{3-[(2,5-dimethoxyphenyl)amino]quinoxalin-2-yl}-1,2-dimethyl-1H-imidazole-5-sulfonamide (26) (Scheme 5)

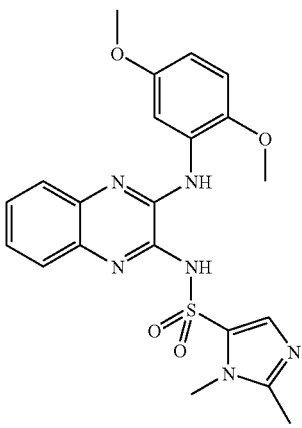

Following the general protocol outlined in Procedure J, Example 26 is obtained from N-(2,5-dimethoxyphenyl)quinoxaline-2,3-diamine and 1,2-dimethyl-1H-imidazole-5-sulfonyl chloride (commercially available from Apollo) in pyridine (yellow solid, 10 mg, 13%). HPLC (max plot) 95%, rt. 3.77 min. LC/MS: (ES+): 455.2.

Example 27 methyl 3-[({3-[(2,5-dimethoxyphenyl)amino]quinoxalin-2-yl}amino)sulfonyl]thiophene-2-carboxylate (27) (Scheme 5)

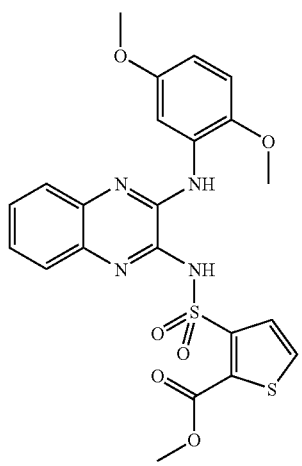

Following the general protocol outlined in Procedure J, Example 27 is obtained from N-(2,5-dimethoxyphenyl)quinoxaline-2,3-diamine and methyl 3-(chlorosulfonyl)thiophene-2-carboxylate in pyridine (yellow solid, 20 mg, 24%). HPLC (max plot) 94%, rt. 4.72 min. LC/MS: (ES+): 501.

Example 28 methyl 3-[({3-[(3,5-dimethoxyphenyl)amino]quinoxalin-2-yl}amino)sulfonyl]thiophene-2-carboxylate (28) (Scheme 5)

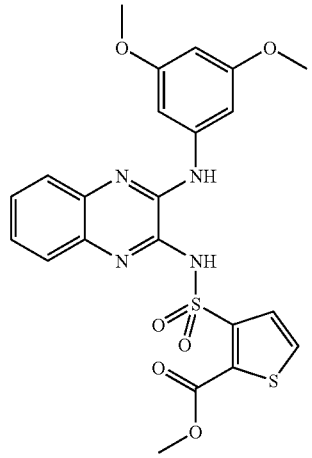

Following the general protocol outlined in Procedure J, Example 28 is obtained from N-(3,5-dimethoxyphenyl)quinoxaline-2,3-diamine and methyl 3-(chlorosulfonyl)thiophene-2-carboxylate in pyridine (yellow solid, 7 mg, 8%). HPLC (max plot) 91%, rt. 4.61 min. LC/MS: (ES+): 501.5.

Example 29

N-{3-[(2,5-dimethoxyphenyl)amino]quinoxalin-2-yl}-3-methyl-2-oxo-2,3-dihydro-1,3-benzothiazole-6-sulfonamide (29) (Scheme 5)

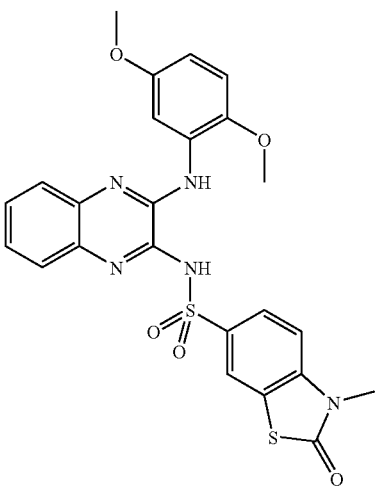

Following the general protocol outlined in Procedure J, Example 29 is obtained from N-(2,5-dimethoxyphenyl)quinoxaline-2,3-diamine and 3-methyl-2-oxo-2,3-dihydro-1,3-benzothiazole-6-sulfonyl chloride (commercially available from CBI) in pyridine (yellow solid, 22 mg, 28%). HPLC (max plot) 98%, rt. 4.62 min. LC/MS: (ES+): 524.5.

Example 30

N-{3-[(3,5-dimethoxyphenyl)amino]quinoxalin-2-yl}-3-methyl-2-oxo-2,3-dihydro-1,3-benzothiazole-6-sulfonamide (30) (Scheme 5)

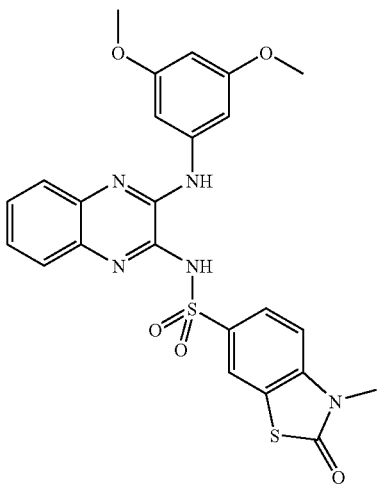

Following the general protocol outlined in Procedure J, Example 30 is obtained from N-(3,5-dimethoxyphenyl)quinoxaline-2,3-diamine and 3-methyl-2-oxo-2,3-dihydro-1,3-benzo thiazole-6-sulfonyl chloride in pyridine (yellow solid, 110 mg, 62%). HPLC (max plot) 92%, rt. 4.47 min. LC/MS: (ES+): 524.5.

Example 31

2-cyano-N-{3-[(3,5-dimethoxyphenyl)amino]quinoxalin-2-yl}benzene sulfonamide (31) (Scheme 5)

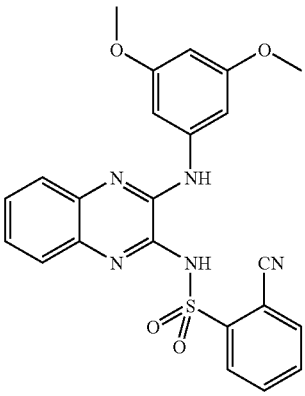

Following the general protocol outlined in Procedure J, Example 31 is obtained from N-(3,5-dimethoxyphenyl)quinoxaline-2,3-diamine and 2-cyanobenzenesulfonyl chloride in pyridine (yellow solid, 10 mg, 13%). HPLC (max plot) 94%, rt. 4.5 min. LC/MS: (ES+): 462.2.

Example 32

3-cyano-N-{3-[(3,5-dimethoxyphenyl)amino]quinoxalin-2-yl}benzene sulfonamide (32) (Scheme 5)

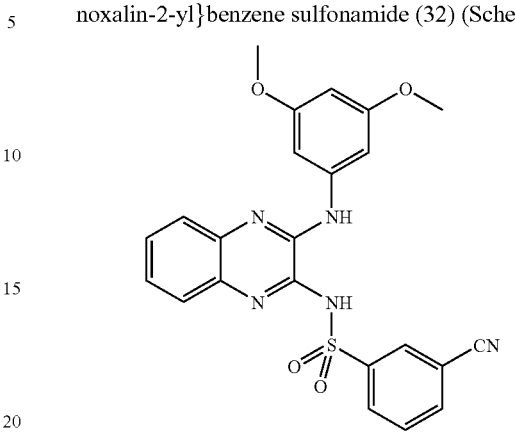

Following the general protocol outlined in Procedure J, Example 32 is obtained from N-(3,5-dimethoxyphenyl)quinoxaline-2,3-diamine and 3-cyanobenzenesulfonyl chloride in pyridine (yellow solid, 15 mg, 19%). 1H NMR (DMSO-d6) δ 12.45 (br s, 1H), 8.97 (s, 1H), 8.63 (t, J=1.5 Hz, 1H), 8.39 (dt, J=8.3, 1.5 Hz, 1H), 8.11 (dt, J=7.9, 1.5 Hz, 1H), 7.89 (br d, J=6.7 Hz, 1H), 7.81 (t, J=7.9 Hz, 1H), 7.60-7.57 (m, 1H), 7.44-7.35 (m, 2H), 7.35 (d, J=2.3 Hz, 2H), 6.24 (t, J=2.3 Hz, 1H), 3.76 (s, 6H); HPLC (max plot) 86%, rt. 4.5 min. LC/MS: (ES+): 462.5.

Example 33

N-{3-[(3,5-dimethoxyphenyl)amino]quinoxalin-2-yl}-3-methoxybenzene sulfonamide (33) (Scheme 5)

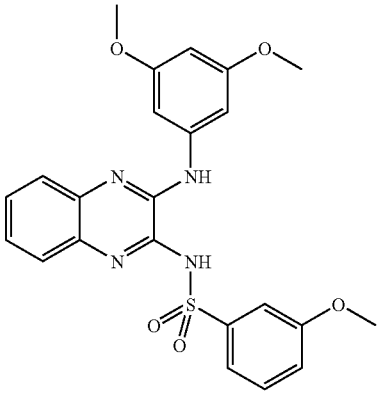

Following the general protocol outlined in Procedure J, Example 33 is obtained from N-(3,5-dimethoxyphenyl)quinoxaline-2,3-diamine and 3-methoxybenzenesulfonyl chloride in pyridine (dark yellow solid, 10 mg, 13%). HPLC (max plot) 92%, rt. 4.71 min. LC/MS: (ES+): 467.1.

Example 34 methyl 3-[({3-[(2,5-dimethoxyphenyl)amino]quinoxalin-2-yl}amino)sulfonyl]benzoate (34) (Scheme 5)

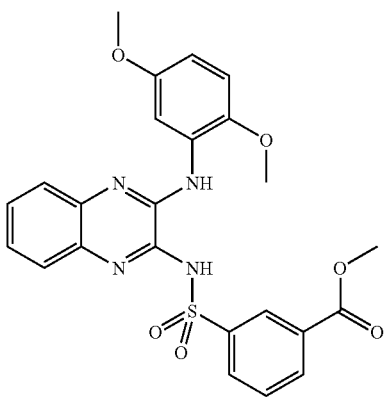

Following the general protocol outlined in Procedure J, Example 34 is obtained from N-(2,5-dimethoxyphenyl)quinoxaline-2,3-diamine and methyl 3-(chlorosulfonyl)benzoate in pyridine (brown solid, 8 mg, 27%). HPLC (max plot) 90%, rt. 4.79 min. LC/MS: (ES+): 495.1.

Example 35 methyl 3-[({3-[(3,5-dimethoxyphenyl)amino]quinoxalin-2-yl}amino)sulfonyl]benzoate (35) (Scheme 5)

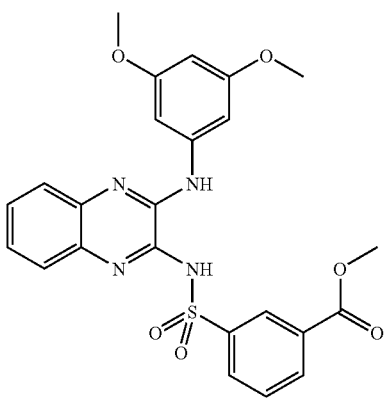

Following the general protocol outlined in Procedure J, Example 35 is obtained from N-(3,5-dimethoxyphenyl)quinoxaline-2,3-diamine and methyl 3-(chlorosulfonyl)benzoate in pyridine (yellow solid, 5 mg, 17%). HPLC (max plot) 99%, rt. 4.65 min. LC/MS: (ES+): 495.1.

Procedure K

Example 36

N-[3-(2,5-Dimethoxy-phenylamino)-quinoxalin-2-yl]-3-fluorobenzene sulfonamide (36) (Scheme 1)

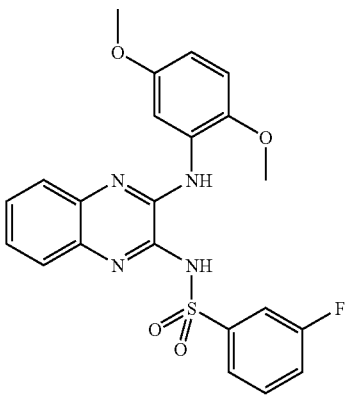

N-(3-chloroquinoxalin-2-yl)-3-fluorobenzenesulfonamide (125 mg, 0.4 mmole) and 2,5-dimethoxyaniline (170.4 mg, 1.1 mmole) are taken in 0.5 ml of EtOH and the resulting suspension is stirred at 100° C. in an orbital shaker, overnight. The precipitate obtained is filtered and washed with EtOH then ether to afford the title compound as a dark green solid (163 mg, 97%). HPLC (max plot) 96%, rt. 4.88 min. LC/MS: (ES+): 455.2.

Example 37

N-{3-[(3,5-dimethoxyphenyl)amino]quinoxalin-2-yl}-3-fluorobenzene sulfonamide (37) (Scheme 1)

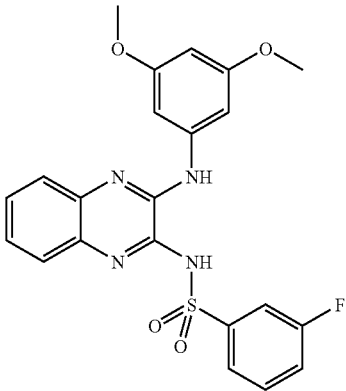

Following the general protocol outlined in Procedure K, example 37 is obtained from N-(3-chloroquinoxalin-2-yl)-3-fluorobenzenesulfonamide and 3,5-dimethoxyaniline in EtOH (yellow solid, 105 mg, 90%). HPLC (max plot) 96%, rt. 4.71 min. LC/MS: (ES+): 455.2.

Example 38

2-chloro-N-{3-[(3,5-dimethoxyphenyl)amino]qui-noxalin-2-yl}benzene sulfonamide (38) (Scheme 1)

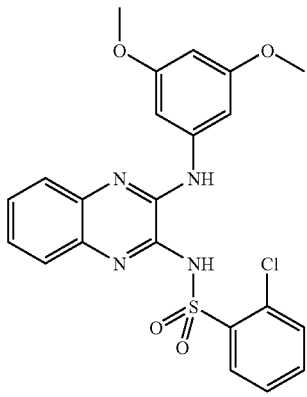

Following the general protocol outlined in Procedure K, Example 38 is obtained from 2-chloro-N-(3-chloroquinoxa-lin-2-yl)benzenesulfonamide and 3,5-dimethoxyaniline in EtOH (yellow solid, 52 mg, 78%). HPLC (max plot) 93%, rt. 4.82 min. LC/MS: (ES+): 471.

Example 39

4-cyano-N-{3-[(3,5-dimethoxyphenyl)amino]qui-noxalin-2-yl}benzene sulfonamide (39) (Scheme 1)

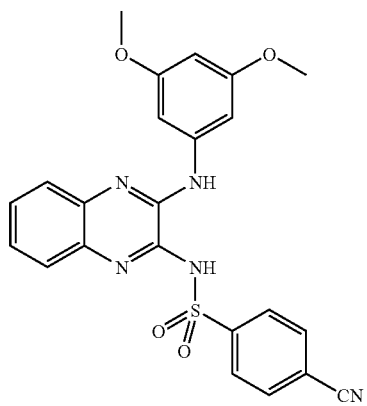

Following the general protocol outlined in Procedure K, Example 39 is obtained from 4-cyano-N-(3-chloroquinoxa-lin-2-yl)benzenesulfonamide and 3,5-dimethoxyaniline in EtOH (yellow solid, 22 mg, 50%). 1H NMR (DMSO-d6) δ 12.44 (br s, 1H), 8.95 (s, 1H), 8.27 (d, J=8.3 Hz, 2H), 8.06 (d, J=8.3 Hz, 2H), 7.95-7.80 (m, 1H), 7.62-7.50 (m, 1H), 7.45-7.25 (m, 4H), 6.23 (s, 1H), 3.75 (s, 6H). HPLC (max plot) 87%, rt. 4.45 min. LC/MS: (ES+): 462.5.

Example 40

3-chloro-N-{3-[(2,5-dimethoxyphenyl)amino]qui-noxalin-2-yl}benzene sulfonamide (40) (Scheme 1)

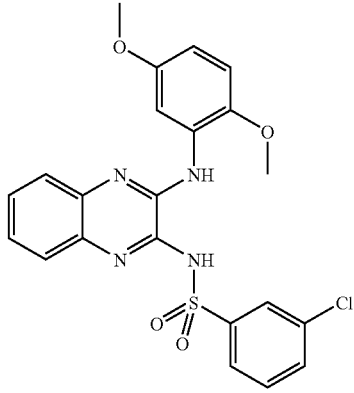

Following the general protocol outlined in Procedure K, Example 40 is obtained from 3-chloro-N-(3-chloroquinoxa-lin-2-yl)benzenesulfonamide and 2,5-dimethoxyaniline in EtOH (greenish black solid, 66 mg, 83%). HPLC (max plot) 97%, rt. 5.1 min. LC/MS: (ES+): 471.5.

Example 41

3-chloro-N-{3-[(3,5-dimethoxyphenyl)amino]qui-noxalin-2-yl}benzene sulfonamide (41) (Scheme 1)

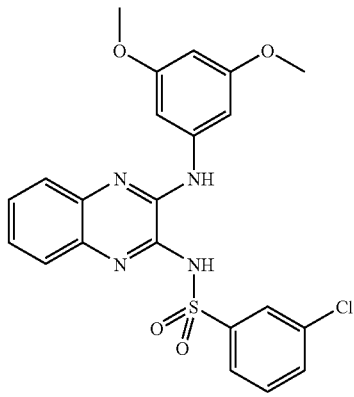

Following the general protocol outlined in Procedure K, Example 41 is obtained from 3-chloro-N-(3-chloroquinoxa-lin-2-yl)benzenesulfonamide and 3,5-dimethoxyaniline in EtOH (yellow solid, 66 mg, 83%). HPLC (max plot) 99%, rt. 4.89 min. LC/MS: (ES+): 471.5.

Example 42

2-chloro-N-{3-[(2,5-dimethoxyphenyl)amino]quinoxalin-2-yl}benzene sulfonamide (42)

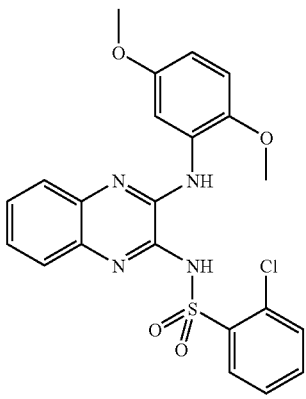

Following the general protocol outlined in Procedure K, Example 42 is obtained from 2-chloro-N-(3-chloroquinoxalin-2-yl)benzenesulfonamide and 3,5-dimethoxyaniline in EtOH (greenish black solid, 50 mg, 98%). HPLC (max plot) 94%, rt. 4.94 min. LC/MS: (ES+): 471.5.

Example 43

N-{3-[(2,5-dimethoxyphenyl)amino]quinoxalin-2-yl}propane-1-sulfonamide (43) (Scheme 1)

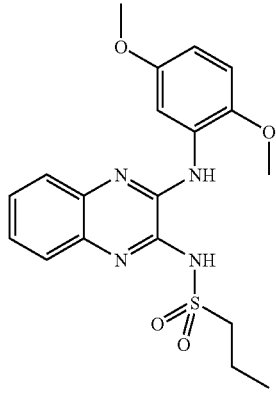

Following the general protocol outlined in Procedure K, example 43 is obtained from N-(3-chloroquinoxalin-2-yl)propane-1-sulfonamide and 2,5-dimethoxyaniline in EtOH (light green solid, 12 mg, 40%). HPLC (max plot) 97%, rt. 4.62 min. LC/MS: (ES+): 403.5.

Example 44

N-{3-[(3,5-dimethoxyphenyl)amino]quinoxalin-2-yl}propane-1-sulfonamide (44) (Scheme 1)

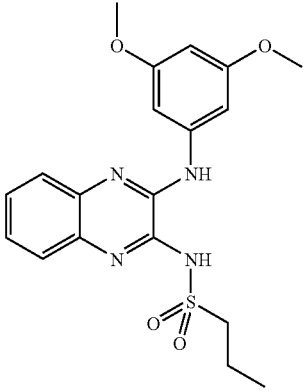

Following the general protocol outlined in Procedure K, Example 44 is obtained from N-(3-chloroquinoxalin-2-yl)propane-1- and 3,5-dimethoxyaniline in EtOH (yellow solid, 15 mg, 43%). HPLC (max plot) 98%, rt. 4.47 min. LC/MS: (ES+): 403.5.

Example 45

N-(3-{[5-methoxy-2-(1H-pyrrol-1-yl)phenyl]amino}quinoxalin-2-yl)Benzenesulfonamide (45) (Scheme 1)

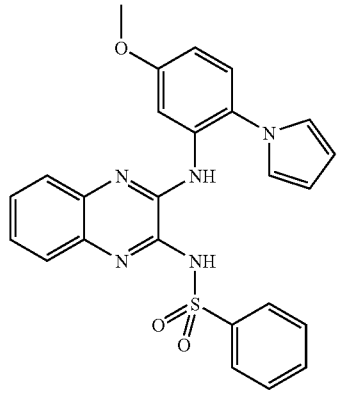

Following the general protocol outlined in Procedure K, Example 45 is obtained from N-(3-chloroquinoxalin-2-yl)benzenesulfonamide and 5-methoxy-2-(1H-pyrrol-1-yl)aniline (commercially available from Bionet) in EtOH (yellow solid, 25 mg, 34%). HPLC (max plot) 99%, rt. 5.11 min. LC/MS: (ES+): 472.

Example 46

N-{3-[(2-chloro-5-methoxyphenyl)amino]quinoxalin-2-yl}benzene sulfonamide (46) (Scheme 1)

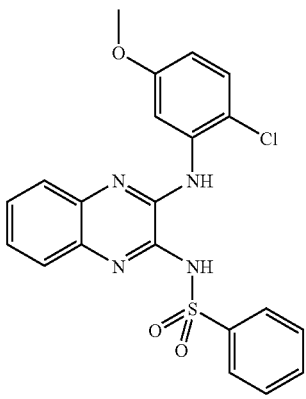

Following the general protocol outlined in Procedure K, Example 46 is obtained from N-(3-chloroquinoxalin-2-yl)-benzenesulfonamide and 2-chloro-5-methoxyaniline (commercially available from Pflatz Bauer) in EtOH (light green solid, 10 mg, 10%). HPLC (max plot) 100%, rt. 5.09 min. LC/MS: (ES+): 441.2.

Example 47

N-{3-[(5-methoxy-2-methylphenyl)amino]quinoxalin-2-yl}benzene sulfonamide (47) (Scheme 1)

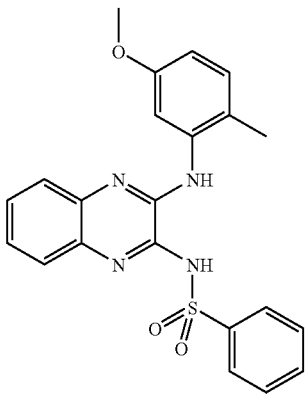

Following the general protocol outlined in Procedure K, Example 47 is obtained from N-(3-chloroquinoxalin-2-yl)-benzenesulfonamide and 5-methoxy-2-methylaniline in EtOH (yellow solid, 35 mg, 53%). HPLC (max plot) 99%, rt. 12.2 min. LC/MS: (ES+): 421.

Example 48

Methyl 4-[({3-[(2,5-dimethoxyphenyl)amino]quinoxalin-2-yl}amino)sulfonyl]benzoate (48) (Scheme 1)

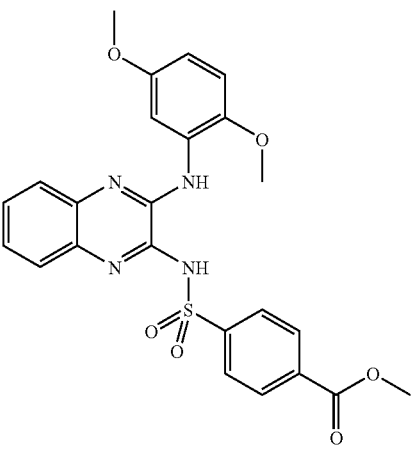

Following the general protocol outlined in Procedure K, Example 48 is obtained from methyl 4-{[(3-chloroquinoxalin-2-yl)amino]sulfonyl}benzoate and 2,5-dimethoxyaniline in EtOH (greenish black solid, 57 mg, 60%). HPLC (max plot) 96%, rt. 4.8 min. LC/MS: (ES+): 495.5.

Example 49

Methyl 4-[({3-[(3,5-dimethoxyphenyl)amino]quinoxalin-2-yl}amino)sulfonyl]benzoate (49) (Scheme 1)

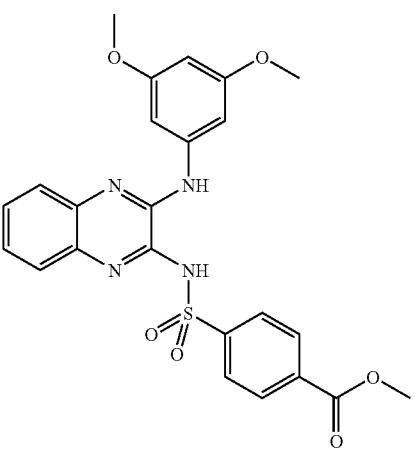

Following the general protocol outlined in Procedure K, Example 49 is obtained from methyl 4-{[(3-chloroquinoxalin-2-yl)amino]sulfonyl}benzoate and 3,5-dimethoxyaniline in EtOH (yellow solid, 8 mg, 35%). HPLC (max plot) 89%, rt. 4.64 min. LC/MS: (ES+): 495.5.

Example 50

Methyl 4-[({3-[(2,5-dimethoxyphenyl)amino]quinoxalin-2-yl}amino)sulfonyl]butanoate (50) (Scheme 1)

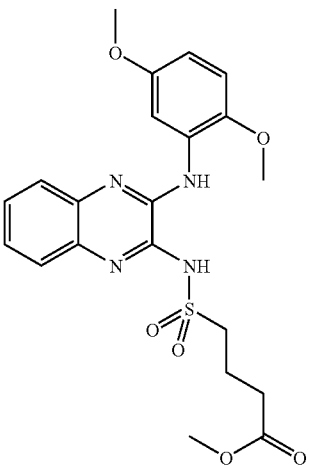

Following the general protocol outlined in Procedure K, Example 50 is obtained from methyl 4-{[(3-chloroquinoxalin-2-yl)amino]sulfonyl}butanoate and 2,5-dimethoxyaniline in EtOH (greenish black solid, 10 mg, 45%). HPLC (max plot) 98%, rt. 4.32 min. LC/MS: (ES+): 460.5.

Example 51

Methyl 4-[({3-[(3,5-dimethoxyphenyl)amino]quinoxalin-2-yl}amino)sulfonyl]butanoate (51) (Scheme 1)

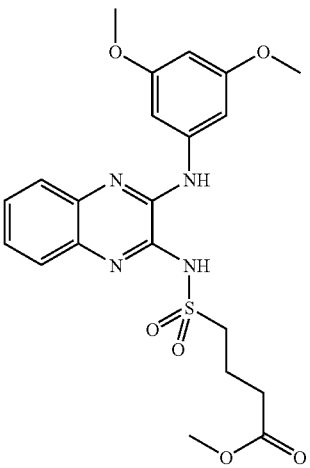

Following the general protocol outlined in Procedure K, Example 51 is obtained from methyl 4-{[(3-chloroquinoxalin-2-yl)amino]sulfonyl}butanoate and 3,5-dimethoxyaniline in EtOH (yellow solid, 10 mg, 23%). HPLC (max plot) 94%, rt. 4.2 min. LC/MS: (ES+): 460.5.

Procedure L

Example 52

N-{3-[(3,5-dimethoxyphenyl)amino]quinoxalin-2-yl}benzenesulfonamide (52)—potassium salt (Scheme 1)

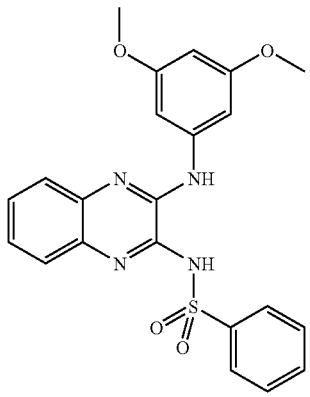

N-(3-chloro-2-quinoxalinyl)benzenesulfonamide (500 mg, 1.6 mmol, 1 eq.) and 3,5-dimethoxyaniline (263.5 mg, 1.7 mmol, 1.1 eq.) are taken up in EtOH (7 ml) and the resulting suspension is heated up to 170° C. for 6 min on high absorption in the microwave. The precipitate formed is filtered off and washed with EtOH then dried under vacuum at 40° C. for 1 day. The solid is washed with hot EtOH then THF to afford, after cooling at 4° C., 397 mg (58%) of the title compound as parent. The parent (397 mg, 0.9 mmol, 1 eq.) is suspended in water (8 ml) then potassium hydroxide (0.18 ml, 0.5 M, 0.9 mmol, 1 eq.) is added and the mixture is lyophilised to afford 453 mg (100%) of the title compound as a yellow powder. 1H NMR (DMSO-d6) δ 8.79 (s, 1H), 8.05-8.01 (m, 2H), 7.40-7.35 (m, 4H), 7.30 (br s, 2H), 7.26-7.23 (m, 1H), 7.16-7.06 (m, 2H), 6.12 (t, J=2.3 Hz, 1H), 3.77 (s, 6H). HPLC (max plot) 97%; Rt 4.61 min. LC/MS: (ES+) 437.3, (ES−): 435.3.

Example 53

N-{3-[(2,5-dimethoxyphenyl)amino]quinoxalin-2-yl}-3 methylbenzene sulfonamide (53)—potassium salt (Scheme 1)

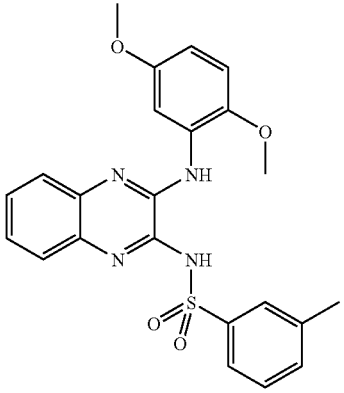

Following the protocol outlined in Procedure L, Example 53 is obtained from N-(3-chloroquinoxalin-2-yl)-3-methylbenzenesulfonamide (100 mg, 0.3 mmol, 1 eq.) and 2,5-

1dimethoxyaniline (50.5 mg, 0.33 mmol, 1.10 eq.) in EtOH (2 ml), to afford 108 mg (80%) of the title compound as a parent. Treatment of the parent (97.4 mg, 0.2 mmol, 1 eq.) with an aqueous solution of potassium hydroxide (432 µl, 0.5 M, 0.2 mmol, 1 eq.) affords 106.5 mg (100%) of the title compound as a yellow powder. 1H NMR (DMSO-d6) δ 9.25 (s, 1H), 8.80 (s, 1H), 7.89 (s, 1H), 7.83 (d, J=7.9 Hz, 1H), 7.43 (d, J=7.5 Hz, 1H), 7.29 (t, J=7.3 Hz, 2H), 7.24-7.10 (m, 3H), 6.94 (d, J=8.7 Hz, 1H), 6.49 (dd, J=9.1, 3.0 Hz, 1H), 3.86 (s, 3H), 3.76 (s, 3H), 2.35 (s, 3H). HPLC (max plot) 98%; Rt 4.74 min. LC/MS: (ES+): 451.4, (ES−): 449.2.

Example 54

4-Chloro-N-{3-[(3,5-dimethoxyphenyl)amino]quinoxalin-2-yl}benzene Sulfonamide (54)—potassium salt (Scheme 1)

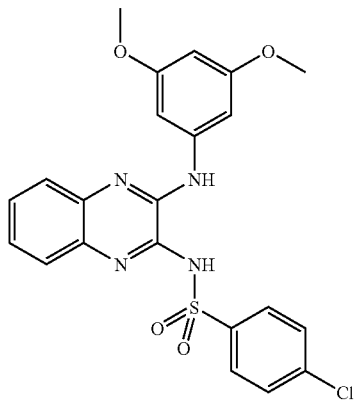

Following the protocol outlined in Procedure L, Example 54 is obtained from 4-chloro-N-(3-chloroquinoxalin-2-yl)benzenesulfonamide (200 mg, 0.56 mmol, 1 eq.) and 3,5-dimethoxyaniline (95.1 mg, 0.62 mmol, 1.1 eq.) in EtOH (3 ml), to afford 179 mg (67.3%) of the title compound as a parent. Treatment of the parent (179 mg, 0.4 mmol, 1 eq.) with an aqueous solution of potassium hydroxide (760.2 µl, 0.5 M, 0.4 mmol, 1 eq.) affords 184 mg (95%) of the title compound as a beige solid. 1H NMR (DMSO-d6) δ 8.74 (s, 1H), 8.04-8.01 (m, 2H), 7.44-7.38 (m, 3H), 7.31-7.25 (m, 3H), 7.15-7.08 (m, 2H), 6.13 (t, J=2.3 Hz, 1H), 3.77 (s, 6H). HPLC (max plot) 98%; Rt 4.77 min. LC/MS: (ES+): 471.3, (ES−): 469.3.

Example 55

4-fluoro-N-{3-[(3-methoxyphenyl)amino]quinoxalin-2-yl}benzene sulfonamide (55)—potassium salt (Scheme 1)

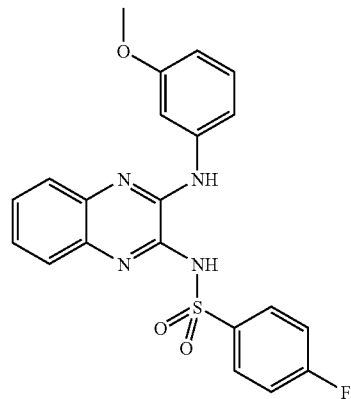

Following the protocol outlined in Procedure L, Example 55 is obtained from N-(3-chloroquinoxalin-2-yl)-4-fluorobenzenesulfonamide (170 mg, 0.5 Mmol, 1 eq.) and m-anisidine (62 µl, 0.55 mmol, 1.10 eq.) in EtOH (3 ml), to afford 149 mg (70%) of the title compound as a parent. Treatment of the parent (140 mg, 0.3 mmol, 1 eq.) with an aqueous solution of potassium hydroxide (659.7 µl, 0.5 M, 0.3 mmol, 1 eq.) affords 149 mg (98%) of the title compound as an orange solid. 1H NMR (DMSO-d6) δ 8.77 (s, 1H), 8.11-8.06 (m, 2H), 7.84-7.83 (m, 1H), 7.46-7.39 (m, 2H), 7.29-7.04 (m, 6H), 6.55 (dd, J=1.9, 7.9 Hz, 1H), 3.79 (s, 3H). HPLC (max plot) 100%; Rt 4.51 min. LC/MS: (ES+): 425.3, (ES−): 423.3.

Example 56

N-{3-[(3,5-dimethoxyphenyl)amino]quinoxalin-2-yl}-4-fluorobenzene Sulfonamide (56)—potassium salt (Scheme 1)

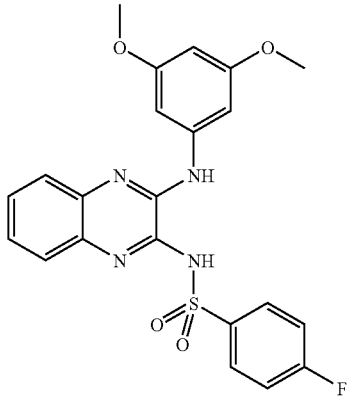

Following the protocol outlined in Procedure L, Example 56 is obtained from N-(3-chloroquinoxalin-2-yl)-4-fluorobenzenesulfonamide (170 mg, 0.5 Mmol, 1 eq.) and 3,5-dimethoxyaniline (84.8 mg, 0.55 mmol, 1.1 eq.) in EtOH (3 ml), to afford 157 mg (69%) of the title compound as a parent. Treatment of the parent (145 mg, 0.32 mmol, 1 eq.) with an aqueous solution of potassium hydroxide (638.1 µl, 0.5 M, 0.32 mmol, 1 eq.) affords 161 mg (100%) of the title compound as a light brown. 1H NMR (DMSO-d6) δ 8.76 (s, 1H), 8.10-8.06 (m, 2H), 7.41-7.38 (m, 1H), 7.31-7.08 (m, 7H), 6.13-6.12 (m, 1H), 3.77 (s, 6H). HPLC (max plot) 97%; Rt 4.54 min. LC/MS: (ES+): 455.3, (ES−): 453.2.

Example 57

N-{3-[(2,5-dimethoxyphenyl)amino]quinoxalin-2-yl}-4-methoxybenzene Sulfonamide (57)—potassium salt (Scheme 1)

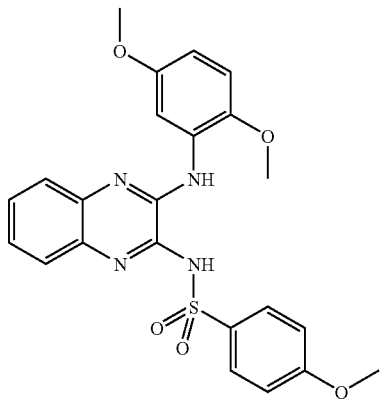

Following the protocol outlined in Procedure L, Example 57 is obtained from N-(3-chloroquinoxalin-2-yl)-4-methoxybenzenesulfonamide (200 mg, 0.57 mmol, 1 eq.) and 2,5-dimethoxyaniline (96.3 mg, 0.63 mmol, 1.1 eq.) in EtOH (3 ml), to afford 173 mg (65%) of the title compound as a parent. Treatment of the parent (173 mg, 0.37 mmol, 1 eq.) with an aqueous solution of potassium hydroxide (0.74 ml, 0.5 M, 0.37 mmol, 1 eq.) affords 160 mg (86%) of the title compound as a green solid. 1H NMR (DMSO-d6) δ 9.24 (s, 1H), 8.80 (d, J=3.4 Hz, 1H), 7.98-7.95 (m, 2H), 7.44-7.39 (m, 1H), 7.29-7.26 (m, 1H), 7.17-7.02 (m, 2H), 6.94-6.89 (m, 3H), 6.47 (dd, J=3.0, 8.7 Hz, 1H), 3.87 (s, 3H), 3.75 (s, 3H), 3.74 (s, 3H). HPLC (max plot) 98%; Rt 4.82 min. LC/MS: (ES+): 467.4, (ES−): 465.3.

Example 58

N-{3-[(2,5-dimethoxyphenyl)amino]quinoxalin-2-yl}-4-methylbenzene Sulfonamide (58)—potassium salt (Scheme 1)

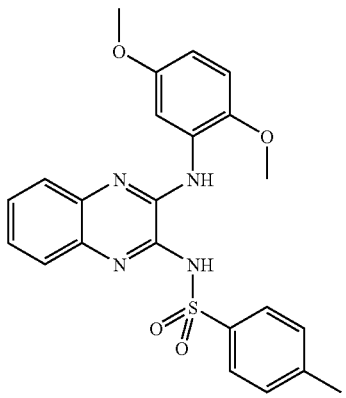

Following the protocol outlined in Procedure L, Example 58 is obtained from N-(3-chloroquinoxalin-2-yl)-4-methylbenzenesulfonamide (100 mg, 0.3 mmol, 1 eq.) and 2,5-dimethoxyaniline (50.5 mg, 0.33 mmol, 1.1 eq.) in EtOH (2 ml), to afford 105.6 mg (78%) of the title compound as a parent. Treatment of the parent (75.6 mg; 0.17 mmol; 1 eq.) with an aqueous solution of potassium hydroxide (335.6 µl, 0.5 M, 0.17 mmol, 1 eq.) affords 82.4 mg (100%) of the title compound as a yellow powder. 1H NMR (DMSO-d6) δ 9.26 (s, 1H), 8.80 (d, J=3.1 Hz, 1H), 7.93 (d, J=8.3 Hz, 2H), 7.41 (dd, J=7.6, 1.9 Hz, 1H), 7.27 (dd, J=7.5, 1.9 Hz, 1H), 7.19 (d, 2H), 7.18-7.06 (m, 2H), 6.95 (d, J=9.0 Hz, 1H), 6.48 (dd, J=8.6, 3.0 Hz, 1H), 3.88 (s, 3H), 3.76 (s, 3H), 2.29 (s, 3H). HPLC (max plot) 98%; Rt 4.75 min. LC/MS: (ES+): 451.3, (ES−): 449.3.

Example 59

4-Bromo-N-{3-[(2,5-dimethoxyphenyl)amino]quinoxalin-2-yl}benzene Sulfonamide (59)—potassium salt (Scheme 1)

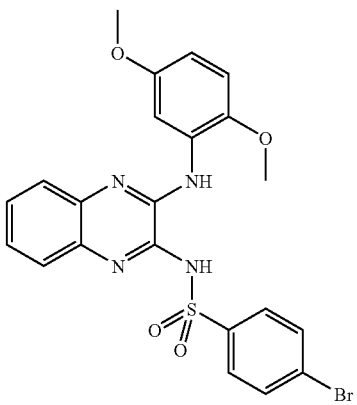

Following the protocol outlined in Procedure L, Example 59 is obtained from 4-bromo-N-(3-chloroquinoxalin-2-yl)

benzenesulfonamide (200 mg, 0.5 Mmol, 1 eq.) and 2,5-dimethoxyaniline (84.5 mg, 0.55 mmol, 1.1 eq.) in EtOH (3 ml), to afford 184 mg (71%) of the title compound as a parent. Treatment of the parent (192 mg; 0.37 mmol; 1 eq.) with an aqueous solution of potassium hydroxide (745.1 µl, 0.5 M, 0.37 mmol, 1 eq.) affords 193 mg (94%) of the title compound as an orange solid. 1H NMR (DMSO-d6) δ 9.18 (s, 1H), 8.74 (br s, 1H), 7.97-7.94 (m, 2H), 7.64-7.19 (m, 6H), 6.95 (d, J=9.1 Hz, 1H), 6.52-6.48 (m, 1H), 3.84 (s, 3H), 3.75 (s, 3H). HPLC (max plot) 97%; Rt 5.12 min. LC/MS: (ES+): 515.3, (ES−): 513.3.

Example 60

4-chloro-N-{3-[(3-methoxyphenyl)amino]quinoxalin-2-yl}benzene sulfonamide (60)—potassium salt (Scheme 1)

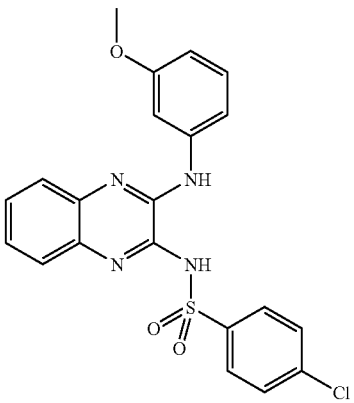

Following the protocol outlined in Procedure L, Example 60 is obtained from 4-chloro-N-(3-chloroquinoxalin-2-yl) benzenesulfonamide (200 mg, 0.56 mmol, 1 eq.) and m-anisidine (69.5 µl, 0.62 mmol, 1.1 eq.) in EtOH (3 ml), to afford 186 mg (75%) of the title compound as a parent. Treatment of the parent (186 mg; 0.42 mmol; 1 eq.) with an aqueous solution of potassium hydroxide (843.7 µl, 0.5 M, 0.42 mmol, 1 eq.) affords 200 mg (99%) of the title compound as a beige solid. 1H NMR (DMSO-d6) δ 8.76 (s, 1H), 8.04-8.02 (m, 2H), 7.84 (t, J=2.3 Hz, 1H), 7.47-7.39 (m, 4H), 7.29-7.09 (m, 4H), 6.56-6.53 (m, 1H), 3.79 (s, 3H). HPLC (max plot) 98%; Rt 4.72 min. LC/MS: (ES+): 441.1, (ES−): 439.3.

Example 61

4-Chloro-N-{3-[(2,5-dimethoxyphenyl)amino]quinoxalin-2-yl}benzene Sulfonamide (61)—potassium salt (Scheme 1)

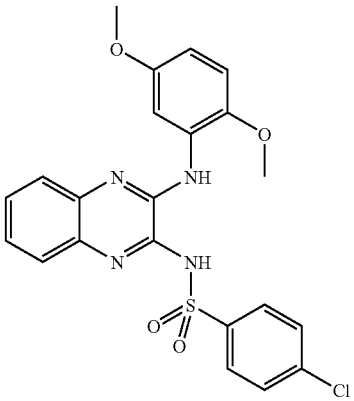

Following the protocol outlined in Procedure L, Example 61 is obtained from 4-chloro-N-(3-chloroquinoxalin-2-yl)

benzenesulfonamide (200 mg, 0.56 mmol, 1 eq.) and 2,5-dimethoxy aniline (95.1 mg, 0.62 mmol, 1.10 eq.) in EtOH (3 ml), to afford 184 mg (69%) of the title compound as a parent. Treatment of the parent (184 mg, 0.39 mmol, 1 eq.) with an aqueous solution of potassium hydroxide (781.4 μl, 0.5 M, 0.39 mmol, 1 eq.) affords 183 mg (92%) of the title compound as a green solid. 1H NMR (DMSO-d6) δ 9.20 (s, 1H), 8.80 (d, J=3.0 Hz, 1H), 8.04-8.01 (m, 2H), 7.45-7.40 (m, 3H), 7.29-7.25 (m, 1H), 7.18-7.09 (m, 2H), 6.94 (d, J=8.6 Hz, 1H), 6.48 (dd, J=3.0, 8.6 Hz, 1H), 3.87 (s, 3H), 3.75 (s, 3H). HPLC (max plot) 97%; Rt 4.85 min. LC/MS: (ES+): 471.3, (ES−): 469.2.

Example 62

N-{3-[(2,5-dimethoxyphenyl)amino]quinoxalin-2-yl}-4-fluorobenzene sulfonamide(62)-potassium salt
(Scheme 1)

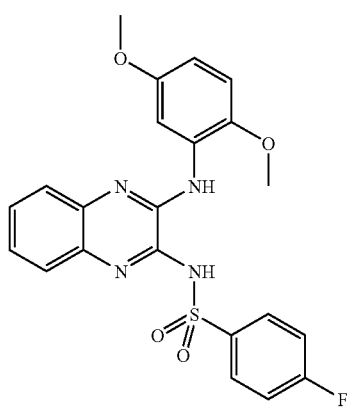

Following the protocol outlined in Procedure L, Example 62 is obtained from N-(3-chloro quinoxalin-2-yl)-4-fluorobenzenesulfonamide (170 mg, 0.5 Mmol, 1 eq.) and 2,5-dimethoxy aniline (84.8 mg, 0.55 mmol, 1.1 eq.) in EtOH (3 ml), to afford 167 mg (73%) of the title compound as a parent. Treatment of the parent (161 mg, 0.35 mmol, 1 eq.) with an aqueous solution of potassium hydroxide (708.5 μl, 0.5 M, 0.35 mmol, 1 eq.) affords 144 mg (83%) of the title compound as a beige solid. 1H NMR (DMSO-d6) δ 9.22 (s, 1H), 8.79 (d, J=3.0 Hz, 1H), 8.10-8.05 (m, 2H), 7.43-7.40 (m, 1H), 7.29-7.08 (m, 5H), 6.94 (d, J=9.1 Hz, 1H), 6.48 (dd, J=3.0, 8.6 Hz, 1H), 3.87 (s, 3H), 3.75 (s, 3H). HPLC (max plot) 99.64%; Rt 4.65 min. LC/MS: (ES+): 455.3, (ES−): 453.3.

Example 63

N-{3-[(2,5-dimethoxyphenyl)amino]quinoxalin-2-yl}benzene sulfonamide (63)—potassium salt
(Scheme 1)

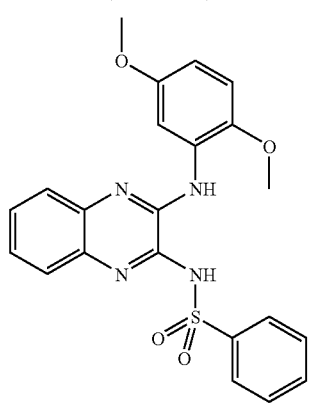

Following the protocol outlined in procedure L, example 63 is obtained from N-(3-chloro quinoxalin-2-yl)benzene-sulfonamide (500 mg, 1.56 mmol, 1 eq.) and 2,5-dimethoxy aniline (263.5 mg, 1.72 mmol, 1.1 eq.) in EtOH (6 ml), to afford 477.6 mg (70%) of the title compound as a parent. Treatment of the parent (372.8 mg, 0.85 mmol, 1 eq.) with an aqueous solution of potassium hydroxide (1.7 ml, 0.5 M, 0.85 mmol, 1 eq.) affords 483.8 mg (97%) of the title compound as a yellow powder. 1H NMR (DMSO-d6) δ 9.25 (s, 1H), 8.80 (d, J=3 Hz, 1H), 8.10-7.93 (m, 2H), 7.50-7.32 (m, 4H), 7.31-720 (m, 1H), 7.19-7.02 (m, 2H), 6.93 (d, J=8.7 Hz, 1H), 6.48 (dd, J=9, 3 Hz, 1H), 3.86 (s, 3H), 3.75 (s, 3H). HPLC (max plot) 99%; Rt 4.71 min. LC/MS: (ES+): 437.0, (ES−): 435.1. CHN analysis: Calc: C 54.58%; H 4.19%; N 11.51%; Exp.: C 54.80%; H 3.73%; N 11.50%.

Example 64

N-{3-[(3-methoxyphenyl)amino]quinoxalin-2-yl}benzene sulfonamide(64)—potassium salt
(Scheme 1)

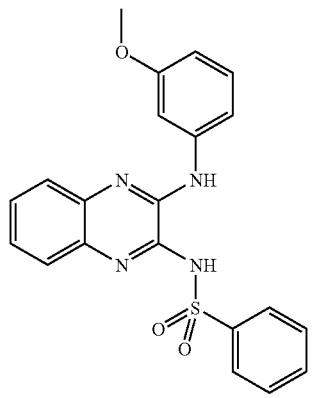

Following the protocol outlined in Procedure L, Example 64 is obtained from N-(3-chloro quinoxalin-2-yl)benzene-sulfonamide (150 mg; 0.47 mmol; 1 eq.) and m anisidine (58 μl, 0.52 mmol, 1.10 eq.) in EtOH (2.5 ml), to afford 127 mg (67%) of the title compound as a parent. Treatment of the parent (126 mg, 0.31 mmol, 1 eq.) with an aqueous solution of potassium hydroxide (620 μl, 0.5 M, 0.31 mmol, 1 eq.) affords 142 mg (100%) of the title compound as a yellow powder. 1H NMR (DMSO-d6) δ 8.83 (s, 1H), 8.06-8.03 (m, 2H), 7.82 (s, 1H), 7.47-7.15 (m, 9H), 6.56 (d, J=7.9 Hz, 1H), 3.76 (s, 3H). HPLC (max plot) 99%; Rt 4.58 min. LC/MS: (ES+): 407.2, (ES−): 405.2.

Example 65

N-{3-[(2,5-dimethoxyphenyl)amino]quinoxalin-2-yl}pyridine-3-sulfonamide (65)—potassium salt
(Scheme 1)

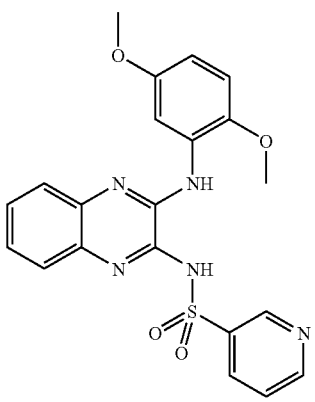

Following the protocol outlined in Procedure L, Example 65 is obtained from N-(3-chloroquinoxalin-2-yl)pyridine-3- sulfonamide (200 mg, 0.62 mmol, 1 eq.) and 2,5-dimethoxyaniline (105.1 mg, 0.69 mmol, 1.1 eq.) in EtOH (2.50 ml), to afford 186.1 mg (68%) of the title compound as a parent. Treatment of the parent (186 mg, 0.43 mmol, 1 eq.) with an aqueous solution of potassium hydroxide (850.3 µl, 0.5 M, 0.43 mmol, 1 eq.) affords 200.9 mg (99%) of the title compound as a yellow powder. 1H NMR (DMSO-d6) δ 9.19 (s, 1H), 9.15 (d, J=1.9 Hz, 1H), 8.79 (d, J=3.1 Hz, 1H), 8.53 (dd, J=4.9, 1.9 Hz, 1H), 8.36 (dt, J=7.9, 1.9 Hz, 1H), 7.48-7.35 (m, 2H), 7.29-1.21 (m, 1H), 7.20-7.07 (m, 2H), 6.94 (d, J=9 Hz, 1H), 6.48 (dd, J=9, 3 Hz, 1H), 3.88 (s, 3H), 3.75 (s, 3H). HPLC (max plot) 98%; Rt 4.03 min. LC/MS: (ES+): 438.7, (ES−): 436.2. CHN analysis: Calc: C 50.54%, H 3.64%, N 14.03%; Found: C 50.49%, H 3.59%, N 13.94%.

Example 66

4-Cyano-N-{3-[(2,5-dimethoxyphenyl)amino]quinoxalin-2-yl}benzene Sulfonamide (66)—potassium salt (Scheme 1)

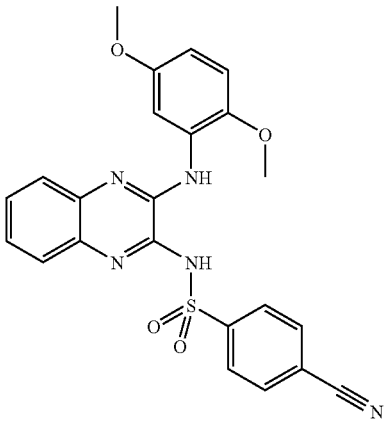

Following the protocol outlined in Procedure L, Example 66 is obtained from N-(3-chloroquinoxalin-2-yl)-4-cyanobenzenesulfonamide (200 mg, 0.58 mmol, 1 eq.) and 2,5-dimethoxyaniline (97.8 mg, 0.64 mmol, 1.1 eq.) in EtOH (3 ml), to afford 196.5 mg (73%) of the title compound as a parent. Treatment of the parent (80 mg, 0.17 mmol, 1 eq.) with an aqueous solution of potassium hydroxide (346.7 µl, 0.5 M, 0.17 mmol, 1 eq.) affords 87.8 mg (100%) of the title compound as a yellow fluffy solid. 1H NMR (DMSO-d6) δ 9.18 (s, 1H), 8.78 (d, J=3 Hz, 1H), 8.17 (d, J=8.3 Hz, 2H), 7.86 (d, J=8.6 Hz, 2H), 7.45-7.35 (m, 1H), 7.28-7.18 (m, 1H), 7.17-7.06 (m, 2H), 6.95 (d, J=8.6 Hz, 1H), 6.49 (dd, J=8.7, 3 Hz, 1H), 3.87 (s, 3H), 3.75 (s, 3H). HPLC (max plot) 98.51%; Rt 4.77 min. LC/MS: (ES+): 4.62, (ES−): 460.3.

Example 67

N-{3-[(3,5-Dimethoxyphenyl)amino]quinoxalin-2-yl}methane sulfonamide (67)—potassium salt (Scheme 1)

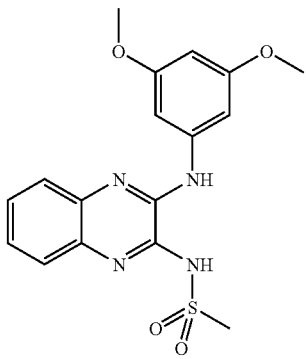

Following the protocol outlined in Procedure L, Example 67 is obtained from N-(3-chloroquinoxalin-2-yl)methanesulfonamide (100 mg, 0.39 mmol, 1 eq.) and 3,5-dimethoxyaniline (65.4 mg, 0.43 mmol, 1.1 eq.) in EtOH (1.5 ml), to afford 86.8 mg (60%) of the title compound as a parent. Treatment of the parent (86.8 mg, 0.23 mmol, 1 eq.) with an aqueous solution of potassium hydroxide (0.46 ml, 0.5 M, 0.23 mmol, 1 eq.) affords 91.5 mg (96%) of the title compound as a yellow powder. 1H NMR (DMSO-d6) δ 8.81 (s, 1H), 7.44 (dd, J=7.5, 1.5 Hz, 1H), 7.35 (dd, J=7.9, 1.5 Hz, 1H), 7.30 (d, J=1.5 Hz, 2H), 7.23-7.08 (m, 2H), 6.12 (t, J=2.3 Hz, 1H), 3.77 (s, 6H), 3.06 (s, 3H). HPLC (max plot) 96%; Rt 3.96 min. LC/MS: (ES+): 375.2, (ES−): 373.3.

Example 68

N-{3-[(2,5-dimethoxyphenyl)amino]quinoxalin-2-yl}methane sulfonamide (68)—potassium salt (Scheme 1)

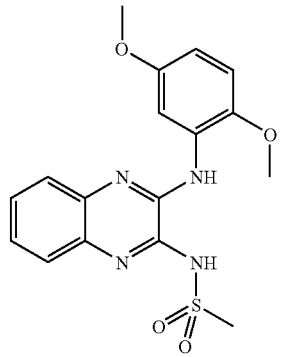

Following the protocol outlined in Procedure L, Example 68 is obtained from N-(3-chloro quinoxalin-2-yl)methanesulfonamide (100 mg, 0.39 mmol, 1 eq.) and 2,5-dimethoxyaniline (65.4 mg, 0.43 mmol, 1.10 eq.) in EtOH (1.5 ml), to afford 87.7 mg (60%) of the title compound as a parent. Treatment of the parent (87.7 mg, 0.23 mmol, 1 eq.) with an aqueous solution of potassium hydroxide (0.47 ml, 0.5 M, 0.23 mmol, 1 eq.) affords 92 mg (95%) of the title compound as a yellow powder. 1H NMR (DMSO-d6) δ 9.26 (s, 1H), 8.84 (d, J=2.6 Hz, 1H), 7.46 (dd, J=7.6, 1.1 Hz, 1H), 7.42-7.25 (m, 1H), 7.23-7.05 (m, 2H), 6.93 (d, J=9 Hz, 1H), 6.48 (dd, J=9, 3 Hz, 1H), 3.85 (s, 3H), 3.77 (s, 3H), 3.06 (s, 3H). HPLC (max plot) 95%; Rt 4.12 min. LC/MS: (ES+): 375.3, (ES−): 373.2.

Example 69

N-{3-[(3-methoxyphenyl)amino]quinoxalin-2-yl}methane sulfonamide(69)—potassium salt (Scheme 1)

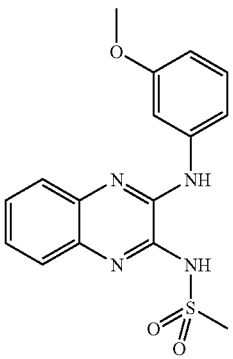

Following the protocol outlined in Procedure L, Example 69 is obtained from N-(3-chloro quinoxalin-2-yl)methanesulfonamide (30 mg, 0.12 mmol, 1 eq.) and m-anisidine (14.4 µl, 0.13 mmol, 1.1 eq.) in EtOH (1.0 ml), to afford 25 mg (62%) of the title compound as a parent. Treatment of the parent (25 mg, 0.07 mmol, 1 eq.) with an aqueous solution of potassium hydroxide (145 µl, 0.5 M; 0.07 mmol, 1 eq.) affords 26.9 mg (97%) of the title compound as a yellow powder. 1H NMR (DMSO-d6) δ 8.83 (s, 1H), 7.84 (t, J=2.2 Hz, 1H), 7.50-7.39 (m, 2H), 7.34 (dd, J=7.9, 1.9 Hz, 1H), 7.27-7.06 (m, 3H), 6.55 (dd, J=7.5, 1.8 Hz, 1H), 3.79 (s, 3H), 3.06 (s, 3H). HPLC (max plot) 99.54%; Rt 3.65 min. LC/MS: (ES+): 345.2, (ES−): 343.2.

Example 70

4-Methoxy-N-{3-[(3-methoxyphenyl)amino]quinoxalin-2yl}benzene sulfonamide (70)—potassium salt (Scheme 1)

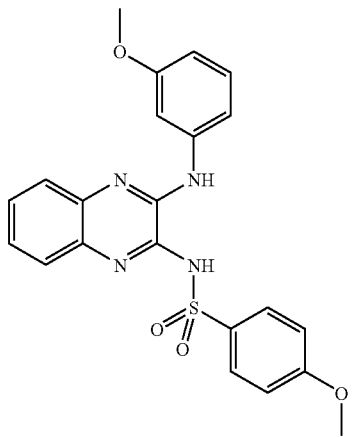

Following the protocol outlined in Procedure L, Example 70 is obtained from N-(3-chloroquinoxalin-2-yl)-4-methoxybenzenesulfonamide (200 mg, 0.57 mmol, 1 eq.) and m-anisidine (0.07 ml, 0.63 mmol, 1.10 eq.) in EtOH (3.0 ml), to afford 162 mg (65%) of the title compound as a parent. Treatment of the parent (162 mg, 0.37 mmol, 1 eq.) with an aqueous solution of potassium hydroxide (0.74 ml, 0.5 M, 0.37 mmol, 1 eq.) affords 171 mg (97%) of the title compound as a beige solid. 1H NMR (DMSO-d6) δ 8.80 (s, 1H), 8.01-7.96 (m, 2H), 7.84 (t, J=2.3 Hz, 1H), 7.45-7.38 (m, 2H), 7.29-7.06 (m, 4H), 6.91-6.87 (m, 2H), 6.54 (dd, J=1.8, 7.9 Hz, 1H), 3.79 (s, 3H), 3.73 (s, 3H). HPLC (max plot) 99%; Rt 4.77 min. LC/MS: (ES+): 437.2, (ES−): 435.2.

Example 71

4-Bromo-N-{3-[(3-methoxyphenyl)amino]quinoxalin-2-yl}benzene sulfonamide (71)—potassium salt (Scheme 1)

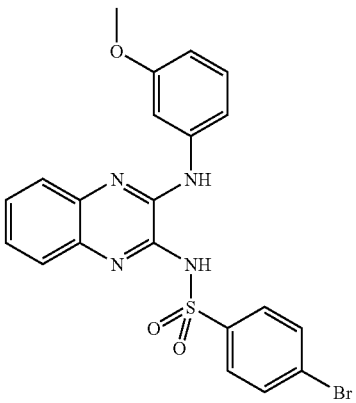

Following the protocol outlined in Procedure L, Example 71 is obtained from 4-bromo-N-(3-chloroquinoxalin-2-yl)benzenesulfonamide (200 mg, 0.5 mmol, 1 eq.) and m-anisidine (61.78 µl, 0.55 mmol, 1.10 eq.) in EtOH (3.0 ml), to afford 178 mg (73%) of the title compound as a parent. Treatment of the parent (178 mg, 0.37 mmol, 1 eq.) with an aqueous solution of potassium hydroxide (733.47 µl, 0.5 M, 0.37 mmol, 1 eq.) affords 183 mg (95%) of the title compound as a beige solid. 1H NMR (DMSO-d6) δ 8.76 (s, 1H), 7.98-7.95 (m, 2H), 7.84-7.83 (m, 1H), 7.59-7.56 (m, 2H), 7.47-7.39 (m, 2H), 7.29-7.09 (m, 4H), 6.57-6.53 (m, 1H), 3.79 (s, 3H). HPLC (max plot) 98%; Rt 4.78 min. LC/MS: (ES+): 487.2, (ES−):485.2.

Example 72

4-Bromo-N-{3-[(3,5-dimethoxyphenyl)amino]quinoxalin-2-yl}benzene Sulfonamide (72)-potassium salt (Scheme 1)

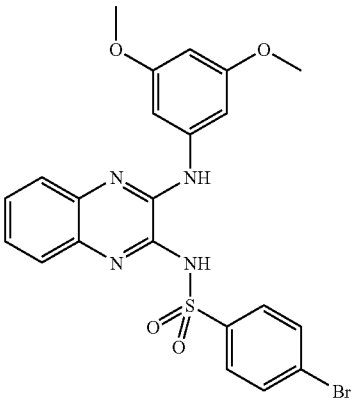

Following the protocol outlined in Procedure L, Example 72 is obtained from 4-bromo-N-(3-chloroquinoxalin-2-yl)benzenesulfonamide (200 mg, 0.5 mmol, 1 eq.) and 3,5-dimethoxyaniline (84.53 mg, 0.55 mmol, 1.10 eq.) in EtOH (3.0 ml), to afford 176 mg (68%) of the title compound as a parent. Treatment of the parent (176 mg, 0.34 mmol, 1 eq.) with an aqueous solution of potassium hydroxide (683 µl, 0.5 M, 0.34 mmol, 1 eq.) affords 176 mg (93%) of the title compound as a yellow solid. 1H NMR (DMSO-d6) δ 8.74 (s, 1H), 7.96 (dt, J=1.9, 8.3 Hz, 2H), 7.57 (dt, J=1.9, 8.3 Hz, 2H), 7.42-7.38 (m, 1H), 7.31-7.26 (m, 3H), 7.18-7.09 (m, 2H), 6.13-6.12 (m, 1H), 3.77 (s, 3H). HPLC (max plot) 97%; Rt 4.82 min. LC/MS: (ES+):515.3, (ES−):513.2.

Example 73

N-{3-[(2,5-dimethoxyphenyl)amino]quinoxalin-2-yl}-4-(trifluoromethyl) Benzenesulfonamide (73)—potassium salt (Scheme 1)

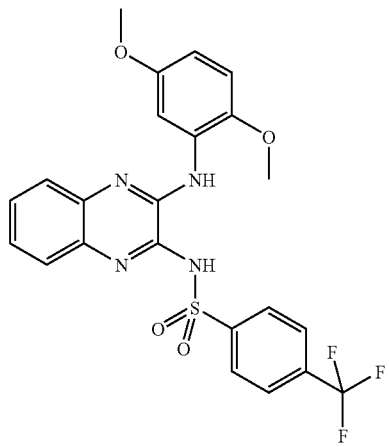

Following the protocol outlined in Procedure L, Example 73 is obtained from N-(3-chloroquinoxalin-2-yl)-4-(trifluoromethyl)benzenesulfonamide (100 mg, 0.26 mmol, 1 eq.) and 2,5-dimethoxyaniline (43.5 mg, 0.28 mmol, 1.1 eq.) in EtOH (2.0 ml), to afford 108.1 mg (83%) of the title compound as a parent. Treatment of the parent (101.70 mg, 0.20 mmol, 1 eq.) with an aqueous solution of potassium hydroxide (403.2 µl, 0.5 M, 0.20 mmol, 1 eq.) affords 101.4 mg (99%) of the title compound as a yellow solid. 1H NMR (DMSO-d6) δ 9.22 (s, 1H), 8.81 (d, J=3.0 Hz, 1H), 8.24 (d, J=8.3 Hz, 2H), 7.78 (d, J=8.3 Hz, 2H), 7.46-7.41 (m, 1H), 7.30-7.25 (m, 1H), 7.20-7.10 (m, 2H), 6.96 (d, J=9.0 Hz, 1H), 6.50 (dd, J=9.1, 3.0 Hz, 1H), 3.88 (s, 3H), 3.76 (s, 3H). HPLC (max plot) 98%; Rt 5.21 min. LC/MS: (ES+): 505.4, (ES−): 503.4.

Example 74

N-{3-[(3,5-dimethoxyphenyl)amino]quinoxalin-2-yl}-4-iodobenzene Sulfonamide (74)—potassium salt (Scheme 1)

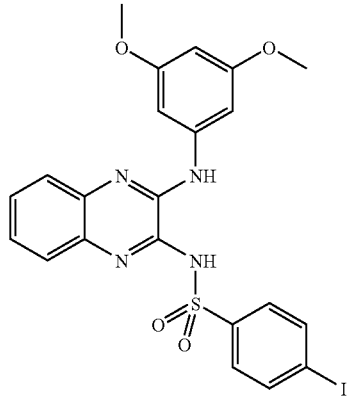

Following the protocol outlined in Procedure L, Example 74 is obtained from N-(3-chloroquinoxalin-2-yl)-4-iodobenzenesulfonamide (100 mg, 0.22 mmol, 1 eq.) and 3,5-dimethoxyaniline (37.8 mg, 0.25 mmol, 1.1 eq.) in EtOH (2.0 ml), to afford 95.2 mg (75%) of the title compound as a parent. Treatment of the parent (74.2 mg, 0.13 mmol, 1 eq.) with an aqueous solution of potassium hydroxide (263.9 µl, 0.5 M, 0.13 mmol, 1 eq.) affords 78.1 mg (98%) of the title compound as a yellow powder. 1H NMR (DMSO-d6) δ 8.76 (s, 1H), 7.84-7.73 (m, 4H), 7.44-7.39 (m, 1H), 7.34-7.24 (m, 3H), 7.21-7.09 (m, 2H), 6.14 (t, J=2.2 Hz, 1H), 3.78 (s, 6H). HPLC (max plot) 98%; Rt 5.09 min. LC/MS: (ES+): 563.3, (ES−): 561.2.

Example 75

N-{3-[(2,5-dimethoxyphenyl)amino]quinoxalin-2-yl}-4-iodobenzene sulfonamide (75)-potassium salt (Scheme 1)

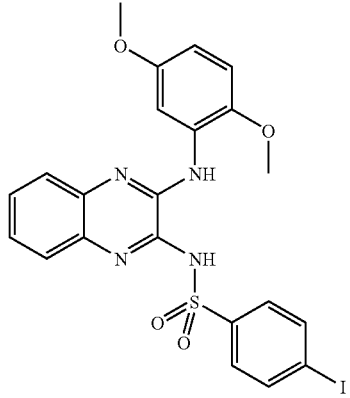

Following the protocol outlined in Procedure L, Example 75 is obtained from N-(3-chloroquinoxalin-2-yl)-4-iodobenzenesulfonamide (100 mg, 0.22 mmol, 1 eq.) and 2,5-dimethoxyaniline (37.8 mg, 0.25 mmol, 1.1 eq.) in EtOH (2.0 ml), to afford 100.4 mg (80%) of the title compound as a parent. Treatment of the parent (98 mg, 0.17 mmol, 1 eq.) with an aqueous solution of potassium hydroxide (348.5 µl, 0.5 M, 0.17 mmol, 1 eq.) affords 103.5 mg (99%) of the title compound as an orange powder. 1H NMR (DMSO-d6) δ 9.21 (s, 1H), 8.80 (d, J=3.0 Hz, 1H), 7.84-7.73 (m, 4H), 7.45-7.40 (m, 1H), 7.30-7.25 (m, 1H), 7.20-7.09 (m, 2H), 6.95 (d, J=9.1 Hz, 1H), 6.49 (dd, J=8.6, 3.0 Hz, 1H), 3.88 (s, 3H), 3.76 (s, 3H). HPLC (max plot) 98%; Rt 5.20 min. LC/MS: (ES+): 563.2, (ES−): 561.3.

Example 76

4,5-Dichloro-N-{3-[(2,5-dimethoxyphenyl)amino]quinoxalin-2-yl}thiophene-2-sulfonamide (76)-potassium salt (Scheme 1)

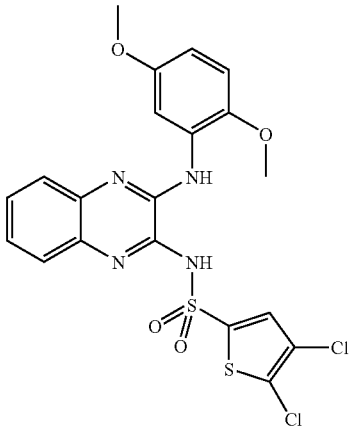

Following the protocol outlined in Procedure L, Example 76 is obtained from 4,5-dichloro-N-(3-chloroquinoxalin-2- yl)thiophene-2-sulfonamide (100 mg, 0.25 mmol, 1 eq.) and 2,5-dimethoxyaniline (42.7 mg, 0.28 mmol, 1.1 eq.) in EtOH (2 ml), to afford 96 mg (74%) of the title compound as a parent. Treatment of the parent (96 mg, 0.19 mmol, 1 eq.) with an aqueous solution of potassium hydroxide (375.4µl, 0.5 M, 0.19 mmol; 1 eq.) affords 108 mg (100%) of the title compound as a yellow powder. 1H NMR (DMSO-d6) δ 9.07 (s, 1H), 8.75 (s, 1H), 7.66-7.53 (m, 3H), 7.30-7.28 (m, 2H), 6.97 (d, J=8.7 Hz, 1H), 6.54-6.51 (m, 1H), 3.86 (s, 3H), 3.76 (s, 3H). HPLC (max plot) 99%; Rt 5.34 min. LC/MS: (ES+): 511.1, (ES−): 509.3.

Example 77

4-Acetyl-N-{3-[(3,5-dimethoxyphenyl)amino]quinoxalin-2-yl}benzene Sulfonamide (77)—potassium salt (Scheme 1)

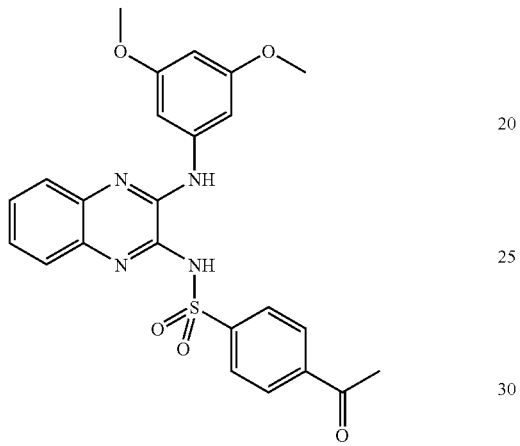

Following the protocol outlined in Procedure L, Example 77 is obtained from 4-acetyl-N-(3-chloroquinoxalin-2-yl)benzenesulfonamide (100 mg, 0.28 mmol, 1 eq.) and 3,5-dimethoxyaniline (46.6 mg, 0.30 mmol, 1.1 eq.) in EtOH (2 ml), to afford 90 mg (68%) of the title compound as a parent. Treatment of the parent (90 mg, 0.19 mmol, 1 eq.) with an aqueous solution of potassium hydroxide (376.1 µl, 0.5 M, 0.19 mmol, 1 eq.) affords 100 mg (100%) of the title compound as a yellow powder. 1H NMR (DMSO-d6) δ 8.76 (s, 1H), 8.14 (d, J=8.3 Hz, 2H), 7.95 (d, J=8.3 Hz, 2H), 7.41-7.38 (m, 1H), 7.31 (d, J=2.2 Hz, 2H), 7.27-7.24 (m, 1H), 7.17-7.08 (m, 2H), 6.14-6.12 (m, 1H), 3.77 (s, 6H), 2.55 (s, 3H). HPLC (max plot) 94%; Rt 4.53 min. LC/MS: (ES+):479.3, (ES−): 477.3.

Example 78

4-Acetyl-N-{3-[(2,5-dimethoxyphenyl)amino]quinoxalin-2-yl}benzene Sulfonamide (78)—potassium salt (Scheme 1)

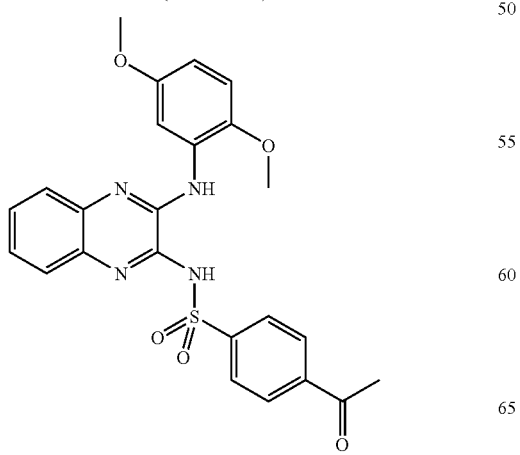

Following the protocol outlined in Procedure L, Example 78 is obtained from 4-acetyl-N-(3-chloroquinoxalin-2-yl)benzenesulfonamide (100 mg, 0.28 mmol, 1 eq.) and 2,5-dimethoxyaniline (46.6 mg; 0.30 mmol; 1.1 eq.) in EtOH (2.0 ml), to afford 78 mg (59%) of the title compound as a parent. Treatment of the parent (78 mg; 0.16 mmol, 1 eq.) with an aqueous solution of potassium hydroxide (326 µl, 0.5 M, 0.16 mmol, 1 eq.) affords 81 mg (96%) of the title compound as a beige powder. 1H NMR (DMSO-d6) δ 9.22 (s, 1H), 8.80 (d, J=3.0 Hz, 1H), 8.13 (d, J=8.7 Hz, 2H), 7.96 (d, J=8.7 Hz, 2H), 7.43-7.39 (m, 1H), 7.27-7.24 (m, 1H), 7.17-7.08 (m, 2H), 6.95 (d, J=9.0 Hz, 1H), 6.50-6.46 (m, 1H), 3.88 (s, 3H), 3.75 (s, 3H), 2.56 (s, 3H). HPLC (max plot) 93%; Rt 4.62 min. LC/MS: (ES+):479.4, (ES−):477.3.

Example 79

Methyl 3-{4-[({3-[(3,5-dimethoxyphenyl)amino]quinoxalin-2-yl}amino)sulfonyl]phenyl}propanoate (79) (Scheme 1)

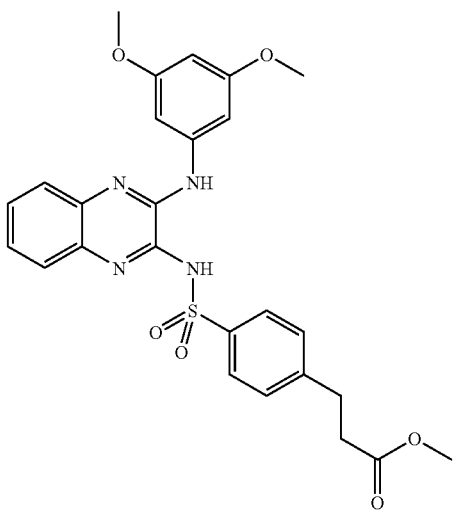

Following the protocol outlined in Procedure L, Example 79 is obtained from methyl 3-(4-{[(3-chloroquinoxalin-2-yl)amino]sulfonyl}phenyl)propanoate (270 mg, 0.67 mmol, 1 eq.) and 3,5-dimethoxyaniline (112.1 mg, 0.73 mmol, 1.1 eq.) in MeOH (3.0 ml), to afford 192.8 mg (55%) of the title compound as a parent (yellow powder). 1H NMR (DMSO-d6) δ 12.21 (br s, 1H), 8.91 (s, 1H), 8.02 (d, J=7.9 Hz, 2H), 7.95-7.8 (m, 1H), 7.65-7.20 (m, 7H), 6.23 (t, J=2.2 Hz, 1H), 3.75 (s, 6H), 3.54 (s, 3H), 2.91 (t, J=7.5 Hz, 2H), 2.66 (t, 2H). HPLC (max plot) 96%; Rt 4.56 min. LC/MS: (ES+): 523.4; (ES−): 521.4.

Example 80

5-Chloro-N-{3-[(2,5-dimethoxyphenyl)amino]quinoxalin-2-yl}-1,3-dimethyl-1H-pyrazole-4-sulfonamide (80)—potassium salt (Scheme 1)

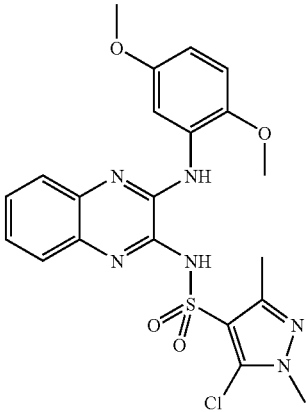

Following the protocol outlined in Procedure L, Example 80 is obtained from 5-chloro-N-(3-chloroquinoxalin-2-yl)-1,3-dimethyl-1H-pyrazole-4-sulfonamide (100 mg, 0.27 mmol, 1 eq) and 2,5-dimethoxyaniline (45.3 mg, 0.30 mmol, 1.1 eq.) in EtOH (1.5 ml), to afford 88.1 mg (67%) of the title compound as a parent. Treatment of the parent (88.1 mg, 0.18 mmol, 1 eq.) with an aqueous solution of potassium hydroxide (0.36 ml, 0.5M, 0.18 mmol, 1 eq.) affords 92 mg (97%) of the title compound as a greenish powder. 1H NMR (DMSO-d6) δ 9.22 (s, 1H), 8.78 (d, J=3 Hz, 1H), 7.41 (dd, J=7.1, 2.9 Hz, 1H), 7.23 (dd, J=7.6, 2.2 Hz, 1H), 7.17-7.05 (m, 2H), 6.93 (d, J=9 Hz, 1H), 6.48 (dd, J=8.6, 3 Hz, 1H), 3.86 (s, 3H), 3.75 (s, 3H), 3.64 (s, 3H), 2.44 (s, 3H). HPLC (max plot) 98%; Rt 4.43 min. LC/MS: (ES+) 489.4; (ES−): 487.5.

Example 81

5-Chloro-N-{3-[(3,5-dimethoxyphenyl)amino]quinoxalin-2-yl}-1,3-dimethyl-1H-pyrazole-4-sulfonamide (81)—potassium salt (Scheme 1)

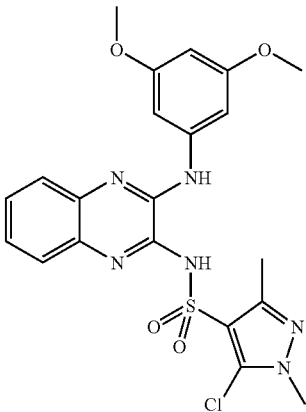

Following the protocol outlined in Procedure L, Example 81 is obtained from 5-chloro-N-(3-chloroquinoxalin-2-yl)-1,3-dimethyl-1H-pyrazole-4-sulfonamide (100 mg, 0.27 mmol, 1 eq.) and 3,5-dimethoxyaniline (45.3 mg, 0.30 mmol, 1.1 eq.) in EtOH (1.5 ml), to afford 93.1 mg (71%) of the title compound as a parent. Treatment of the parent (93.1 mg, 0.19 mmol, 1 eq.) with an aqueous solution of potassium hydroxide (380.8 µl, 0.5M, 0.19 mmol, 1 eq.) affords 100 mg (99%) of the title compound as a yellow solid. 1H NMR (DMSO-d6) δ 8.77 (s, 1H), 7.39 (dd, J=7.2, 2.0 Hz, 1H), 7.29 (d, J=2.3 Hz, 2H), 7.23 (d, J=7.9, 2.7 Hz, 1H), 7.15-7.05 (m, 2H), 6.13 (t, J=2.2 Hz, 1H), 3.77 (s, 6H), 3.64 (s, 3H), 2.45 (s, 3H). HPLC (max plot) 94%; Rt 4.30 min. LC/MS: (ES+): 489.3; (ES−): 487.3.

Example 82

N-{3-[(3,5-dimethoxyphenyl)amino]quinoxalin-2-yl}-4-methylbenzene Sulfonamide (82)—potassium salt (Scheme 1)

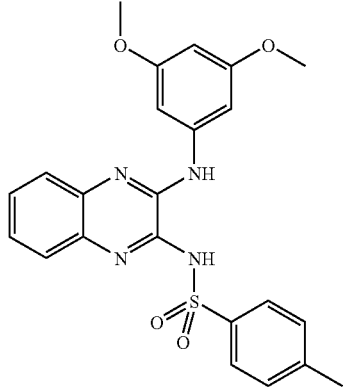

Following the protocol outlined in Procedure L, Example 82 is obtained from N-(3-chloroquinoxalin-2-yl)-4-methylbenzenesulfonamide (100 mg, 0.30 mmol, 1 eq.) and 3,5-dimethoxyaniline (50.5 mg, 0.33 mmol, 1.1 eq.) in EtOH (2.0 ml), to afford 113.9 mg (84%) of the title compound as a parent. Treatment of the parent (84.5 mg, 0.19 mmol, 1 eq.) with an aqueous solution of potassium hydroxide (375.1 µl, 0.5M, 0.19 mmol, 1 eq.) affords 85.3 mg (100%) of the title compound as a yellow powder. 1H NMR (DMSO-d6) δ 8.80 (s, 1H), 7.93 (d, J=8.3 Hz, 2H), 7.39 (dd, J=7.8, 1.7 Hz, 1H), 7.30 (d, J=1.8 Hz, 2H), 7.26 (dd, J=7.7, 1.7 Hz, 1H), 7.20-7.13 (m, 4H), 6.13 (t, J=2.3 Hz, 1H), 3.78 (s, 6H), 2.28 (s, 3H). HPLC (max plot) 97%; Rt 4.64 min. LC/MS: (ES+): 451.4, (ES−): 449.3.

Example 83

N-{3-[(3,5-dimethoxyphenyl)amino]quinoxalin-2-yl}-3-methylbenzene Sulfonamide (83)—potassium salt (Scheme 1)

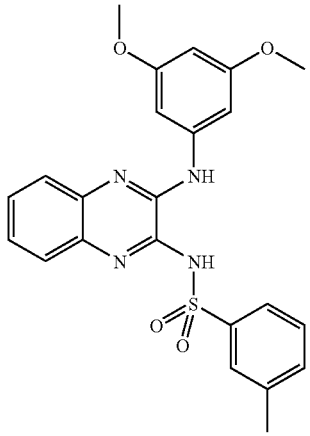

Following the protocol outlined in Procedure L, Example 83 is obtained from N-(3-chloroquinoxalin-2-yl)-3-methylbenzenesulfonamide (100 mg, 0.30 mmol, 1 eq.) and 3,5-dimethoxyaniline (50.5 mg, 0.33 mmol, 1.1 eq.) in EtOH (2.0 ml), to afford 102.1 mg (76%) of the title compound as a parent. Treatment of the parent (91.4 mg, 0.20 mmol, 1 eq.) with an aqueous solution of potassium hydroxide (405.7 µl; 0.5M; 0.20 mmol; 1 eq) affords 100.3 mg (100%) of the title compound as a yellow powder. 1H NMR (DMSO-d6) δ 8.80 (s, 1H), 7.91 (s, 1H), 7.82 (d, J=7.6 Hz, 1H), 7.40 (dd, J=7.6, 1.5 Hz, 1H), 7.30 (d, J=2.2 Hz, 2H), 7.26 (t, J=7.7 Hz, 2H), 7.20-7.06 (m, 3H), 6.13 (t, J=2.2 Hz, 1H), 3.78 (s, 6H), 2.34 (s, 3H). HPLC (max plot) 99%; Rt 4.63 min. LC/MS: (ES+): 451.4, (ES−): 449.4.

Example 84

5-Bromo-N-{3-[(3,5-dimethoxyphenyl)amino]quinoxalin-2-yl}thiophene-2-sulfonamide (84)-potassium salt (Scheme 1)

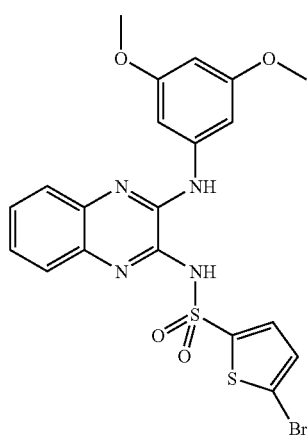

Following the protocol outlined in procedure L, example 84 is obtained from 5-bromo-N-(3-chloroquinoxalin-2-yl)thiophene-2-sulfonamide (230 mg, 0.57 mmol, 1 eq.) and 3,5-dimethoxy aniline (95.8 mg, 0.63 mmol, 1.1 eq.) in EtOH (4.0 ml), to afford 238 mg (80%) of the title compound as a parent. Treatment of the parent (35 mg, 0.07 mmol, 1 eq.) with an aqueous solution of potassium hydroxide (134.2 µl, 0.5M, 0.07 mmol, 1 eq.) affords 36 mg (96%) of the title compound as a yellow powder. 1H NMR (DMSO-d6) δ 8.65 (s, 1H), 7.51-7.46 (m, 3H), 7.32-7.17 (m, 4H), 7.10-7.09 (m, 1H), 6.14-6.13 (m, 1H), 3.76 (s, 6H). HPLC (max plot) 95%; Rt 5.09 min. LC/MS: (ES+):523.2, (ES−):521.1.

Example 85

N-{3-[(3,5-dimethoxyphenyl)amino]pyrido[2,3-b]pyrazin-2-yl}benzene Sulfonamide (85)—potassium salt (Scheme 1)

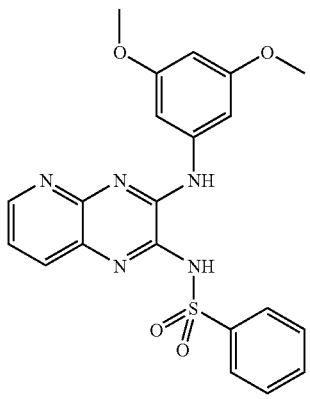

Following the protocol outlined in Procedure L, Example 85 is obtained from N-(3-chloropyrido[2,3-b]pyrazin-2-yl)benzenesulfonamide (100 mg, 0.31 mmol, 1 eq.) and 3,5-dimethoxyaniline (52.5 mg, 0.34 mmol, 1.1 eq.) in EtOH (2 ml), to afford 74 mg (54%) of the title compound as a yellow solid. Treatment of the parent (63.1 mg, 0.14 mmol, 1 eq.) with an aqueous solution of potassium hydroxide (288.5 µl, 0.5M, 0.14 mmol, 1 eq.) affords 67.3 mg (98%) of the title compound as a yellow powder. 1H NMR (DMSO-d6) δ 8.98 (s, 1H), 8.33 (m, 1H), 8.12-8.05 (m, 2H), 7.94 (d, J=7.9 Hz, 1H), 7.45-7.40 (m, 3H), 7.32 (d, J=1.9 Hz, 2H), 7.23 (dd, J=7.9, 4.9 Hz, 1H), 6.20 (m, 1H), 3.78 (s, 6H). HPLC (max plot) 100%; Rt 3.54 min. LC/MS: (ES+): 438.4, (ES−): 436.3.

Example 86

N-{3-[(2,5-dimethoxyphenyl)amino]pyrido[2,3-b]pyrazin-2-yl}benzene sulfonamide (86) (Scheme 1)

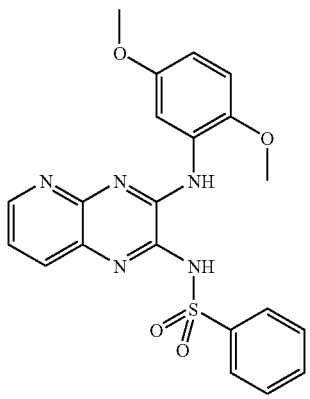

Following the protocol outlined in Procedure L, Example 86 is obtained from N-(2-chloropyrido[2,3-b]pyrazin-2-yl)benzenesulfonamide (73.6 mg, 0.23 mmol, 1 eq.) and 2,5-dimethoxyaniline (38.7 mg, 0.25 mmol; 1.1 eq.) in EtOH (1 ml), to afford 53.5 mg (53%) of the title compound as parent (yellow solid). 1H NMR (DMSO-d6) δ 14.89 (brs, 1H), 9.46 (singulet, 1H), 8.58 (d, J=3.0 Hz, 1H), 8.34 (dd, J=7.9, 1.1 Hz, 1H), 8.29 (d, J=6.0 Hz, 1H), 8.10 (dd, J=7.3, 2.1 Hz, 2H), 7.55-7.49 (m, 3H), 7.46 (dd, J=6.1, 7.9 Hz, 1H), 7.01 (d, J=9.0 Hz, 1H), 6.63 (dd, J=9.1, 3.0 Hz, 1H), 3.84 (s, 3H), 3.77 (s, 3H). HPLC (max plot) 97%; Rt 3.73 min. LC/MS: (ES+): 438.3, (ES−): 436.1.

Example 87

N-{2-[(2,5-dimethoxyphenyl)amino]pyrido[3,4-b]pyrazin-3-yl}benzene Sulfonamide (87) (Scheme 1)

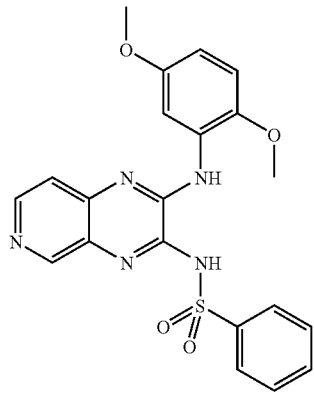

Following the protocol outlined in Procedure L, Example 87 is obtained from N-(2-chloropyrido[3,4-b]pyrazin-3-yl)benzenesulfonamide (17.3 mg, 0.05 mmol, 1 eq.) and 2,5-dimethoxyaniline (9.1 mg, 0.06 mmol, 1.1 eq.) in EtOH (0.3 ml), to afford 12.5 mg (53%) of the title compound as parent (yellow solid). 1H NMR (DMSO-d6) δ 14.43 (br s, 1H), 9.47 (s, 1H), 8.91 (s, 1H), 8.55 (d, J=2.7 Hz, 1H), 8.27 (d, J=6.4 Hz, 1H), 8.06-8.01 (m, 2H), 7.54-7.48 (m, 4H), 7.02 (d, J=9.0 Hz, 1H), 6.63 (dd, J=9.0, 2.8 Hz, 1H), 3.86 (s, 3H), 3.77 (s, 3H). HPLC (max plot) 85%; Rt 3.17 min. LC/MS: (ES+): 438.3, (ES−): 436.2.

Example 88

N-{7-chloro-3-[(3,5-dimethoxyphenyl)amino]quinoxalin-2-yl}benzene Sulfonamide (88)—potassium salt (Scheme 1)

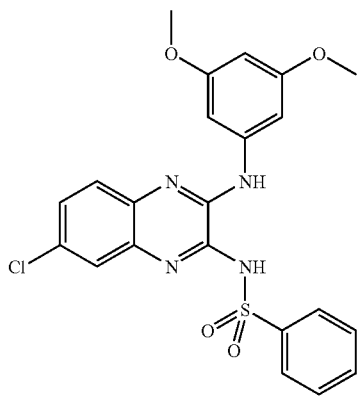

Following the protocol outlined in Procedure L, Example 88 is obtained from N-(3,7-dichloroquinoxalin-2-yl)benzenesulfonamide (50 mg, 0.14 mmol, 1 eq.) and 3,5-dimethoxyaniline (23.8 mg, 0.16 mmol, 1.1 eq.) in EtOH (0.75 ml), to afford 38.6 mg (58%) of the title compound as a parent. Treatment of the parent (38.6 mg, 0.08 mmol, 1 eq.) with an aqueous solution of potassium hydroxide (163.9 μl; 0.50M; 0.08 mmol; 1 eq) affords 38.6 mg (93%) of the title compound as a yellow powder. 1H NMR (DMSO-d6) δ 8.85 (s, 1H), 8.10-7.95 (m, 2H), 7.50-6.95 (m, 8H), 6.18-6.10 (m, 1H), 3.76 (s, 6H). HPLC (max plot) 98%; Rt 4.69 min. LC/MS: (ES+): 471.4, (ES−): 469.2.

Example 89 methyl 5-[({3-[(2,5-dimethoxyphenyl)amino]quinoxalin-2-yl}amino)sulfonyl]-4-methylthiophene-2-carboxylate (89)—potassium salt (Scheme 1)

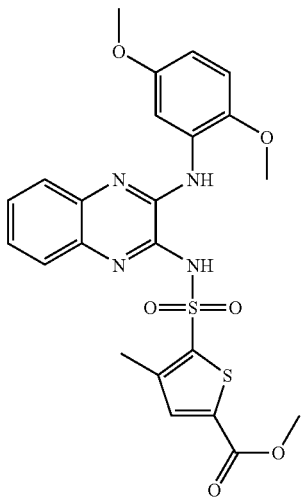

Following the protocol outlined in Procedure L, Example 89 is obtained from methyl 5-{[(3-chloroquinoxalin-2-yl)amino]sulfonyl}-4-methylthiophene-2-carboxylate (100 mg; 0.25 mmol; 1 eq) and 2,5-dimethoxyaniline (42.35 mg; 0.28 mmol; 1.1 eq) in EtOH (2 ml) to afford 105.1 mg (81%) of the title compound as a parent. Treatment of the parent (30.80 mg; 0.06 mmol; 1 eq) with an aqueous solution of potassium hydroxide (118.43 μl; 0.50 M; 0.06 mmol; 1 eq) affords 33.6 mg (100%) of the title compound as a yellow greenish powder. 1H NMR (DMSO-d6) δ 9.18 (s, 1H), 8.80 (s, 1H), 7.52-7.44 (m, 2H), 7.25-7.15 (m, 3H), 6.97 (d, J=9.0 Hz, 1H), 6.51 (dd, J=9.0, 2.3 Hz, 1H), 3.89 (s, 3H), 3.81 (s, 3H), 3.77 (s, 3H), 2.41 (s, 3H). HPLC (max plot) 91%; Rt 5.06 min. LC/MS: ES+ 515.3, ES− 513.3.

Example 90 methyl 5-[({3-[(2,5-dimethoxyphenyl)amino]quinoxalin-2-yl}amino)sulfonyl]-1-methyl-1H-pyrrole-2-carboxylate (90) (Scheme 1)

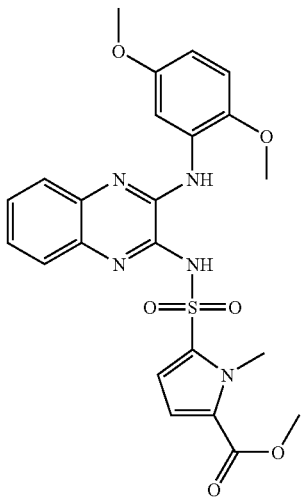

Following the protocol outlined in Procedure L, Example 90 is obtained from methyl 5-{[(3-chloroquinoxalin-2-yl)amino]sulfonyl}-1-methyl-1H-pyrrole-2-carboxylate (200 mg; 0.53 mmol; 1 eq) and 2,5-dimethoxyaniline (88.49 mg, 0.58 mmol; 1.1 eq) in MeOH (4 ml) to afford 188.8 mg (72%) of the title compound as a green powder. 1H NMR (DMSO-d6) δ 12.26 (br s, 1H), 9.19 (s, 1H), 8.57 (d, J=3.0 Hz, 1H), 7.96 (br d, J=6.7 Hz, 1H), 7.88 (d, J=1.9 Hz, 1H), 7.65-7.59 (m, 1H), 7.43-7.32 (m, 2H), 7.29 (d, J=2.3 Hz, 1H), 7.01 (d, J=9.0 Hz, 1H), 6.61 (dd, J=8.7, 3.0 Hz, 1H), 3.90 (s, 3H), 3.85 (s, 3H), 3.77 (s, 6H). HPLC (max plot) 99%; Rt 4.44 min. LC/MS: (ES+): 498.6, (ES−): 496.4.

Example 91 methyl 5-[({3-[(3,5-dimethoxyphenyl)amino]quinoxalin-2-yl}amino)sulfonyl]-1-methyl-1H-pyrrole-2-carboxylate (91) (Scheme 1)

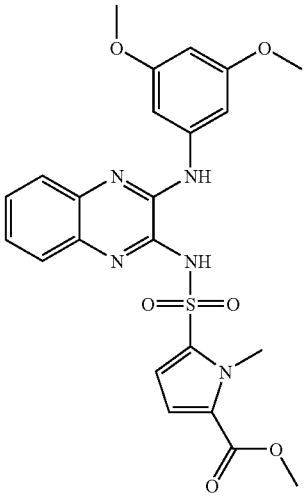

Following the protocol outlined in Procedure L, Example 91 is obtained from methyl 5-{[(3-chloroquinoxalin-2-yl)amino]sulfonyl}-1-methyl-1H-pyrrole-2-carboxylate (200 mg; 0.53 mmol; 1 eq) and 3,5-dimethoxyaniline (88.49 mg; 0.58 mmol; 1.1 eq) in MeOH (4 ml) to afford 181 mg (69%) of the title compound as yellow powder. 1H NMR (DMSO-d6) δ 12.02 (br s, 1H), 8.89 (s, 1H), 7.92 (br s, 2H), 7.59-7.54 (m, 1H), 7.40-7.33 (m, 5H), 6.24 (t, J=2.2 Hz, 1H), 3.88 (s, 3H), 3.77 (s, 6H), 3.75 (s, 3H). HPLC (max plot) 96%; Rt 4.35 min. LC/MS: (ES+): 498.4, (ES−): 496.4.

Example 92

N-{3-[(2,5-dimethoxyphenyl)amino]quinoxalin-2-yl}thiophene-2-sulfonamide (92)—potassium salt (Scheme 1)

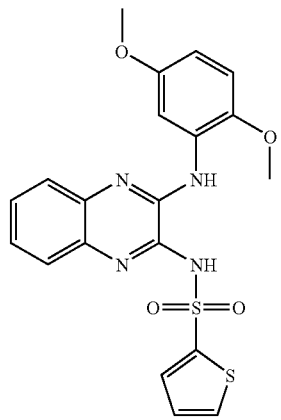

Following the protocol outlined in Procedure L, Example 92 is obtained from N-(3-chloroquinoxalin-2-yl)thiophene-2-sulfonamide (200 mg; 0.61 mmol; 1 eq) and 2,5-dimethoxyaniline (94.03 mg; 0.61 mmol; 1 eq) in EtOH (3 ml) to afford 150 mg (55%) of the title compound as a parent (yellow powder). Treatment of the parent (150 mg; 0.34 mmol; 1 eq) with an aqueous solution of potassium hydroxide (677.94 μl; 0.5 M; 0.34 mmol; 1 eq) affords 163 mg (100%) of the title compound as a yellow powder. 1H NMR (DMSO-d6) δ 9.16 (s, 1H), 8.81 (d, J=3.0 Hz, 1H), 7.70-7.68 (m, 1H), 7.57-7.55 (m, 1H), 7.48-7.43 (m, 2H), 7.24-7.14 (m, 2H), 6.98-6.92 (m, 1H), 6.94 (d, J=9.0 Hz, 1H), 6.48 (dd, J=3.0, 9.0 Hz, 1H), 3.87 (s, 3H), 3.76 (s, 3H). HPLC (max plot) 99%; Rt 4.49 min. LC/MS: (ES+): 443.4, (ES−): 441.3.

Example 93

2-chloro-N-{3-[(2,5-dimethoxyphenyl)amino]quinoxalin-2-yl}-4-fluorobenzenesulfonamide (93)-potassium salt (Scheme 1)

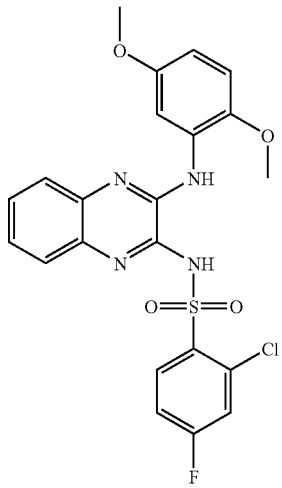

Following the protocol outlined in Procedure L, Example 93 is obtained from 2-chloro-N-(3-chloroquinoxalin-2-yl)-4- fluorobenzenesulfonamide (150 mg; 0.4 mmol; 1 eq) and 2,5-dimethoxyaniline (67.91 mg; 0.44 mmol; 1.1 eq) in EtOH (3 ml) to afford 146.8 mg (74%) of the title compound as a parent (yellow powder). Treatment of the parent (137.5 mg; 0.28 mmol; 1 eq) with an aqueous solution of potassium hydroxide (562.46 µl; 0.50 M; 0.28 mmol; 1 eq) affords 157.8 mg (100%) of the title compound as a yellow powder. 1H NMR (DMSO-d6) δ 9.26 (s, 1H), 8.78 (d, J=3.0 Hz, 1H), 8.26 (dd, J=8.3, 6.4 Hz, 1H), 7.44-7.39 (m, 1H), 7.34-7.26 (m, 2H), 7.13-7.02 (m, 3H), 6.96 (d, J=9.1 Hz, 1H), 6.49 (dd, J=8.9, 3.2 Hz, 1H), 3.86 (s, 3H), 3.77 (s, 3H). HPLC (max plot) 99.5%; Rt 4.76 min. LC/MS: (ES+): 489.4, (ES−): 487.4.

Example 94

2-chloro-N-{3-[(3,5-dimethoxyphenyl)amino]quinoxalin-2-yl}-4-fluorobenzenesulfonamide (94)—potassium salt (Scheme 1)

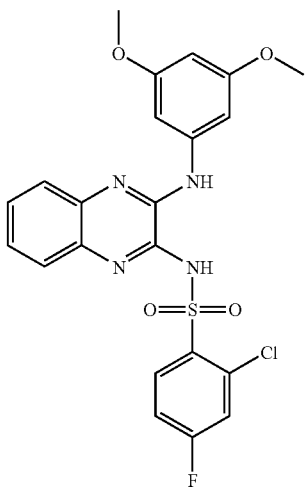

Following the protocol outlined in Procedure L, Example 94 is obtained from 2-chloro-N-(3-chloroquinoxalin-2-yl)-4-fluorobenzenesulfonamide (150 mg; 0.4 mmol; 1 eq) and 3,5-dimethoxyaniline (67.91 mg; 0.44 mmol; 1.1 eq) in EtOH (3 ml) to afford 145 mg (74%) of the title compound as a parent (yellow powder). Treatment of the parent (133 mg; 0.27 mmol; 1 eq) with an aqueous solution of potassium hydroxide (544.05 µl; 0.50 M; 0.27 mmol; 1 eq) affords 154.9 mg (100%) of the title compound as a yellow powder. 1H NMR (DMSO-d6) δ 8.80 (s, 1H), 8.28 (dd, J=9.4, 6.4 Hz, 1H), 7.43-7.37 (m, 1H), 7.33-7.26 (m, 4H), 7.13-7.08 (m, 2H), 7.05-7 (m, 1H), 6.15 (t, J=2.3 Hz, 1H), 3.78 (s, 6H). HPLC (max plot) 97%; Rt 4.67 min. LC/MS: (ES+): 489.3, (ES−): 487.4.

Example 95

N-{3-[(3,5-dimethoxyphenyl)amino]quinoxalin-2-yl}pyridine-3-sulfonamide (95)—potassium salt (Scheme 1)

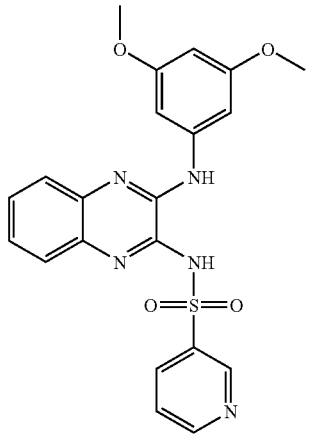

Following the protocol outlined in Procedure L, Example 95 is obtained from N-(3-chloroquinoxalin-2-yl)pyridine-3-sulfonamide (150 mg; 0.47 mmol; 1 eq) and 3,5-dimethoxyaniline (78.80 mg; 0.51 mmol; 1.1 eq) in EtOH (2 ml) to afford 112 mg (55%) of the title compound as a parent (yellow powder). Treatment of the parent (112 mg; 0.26 mmol; 1 eq) with an aqueous solution of potassium hydroxide (512.02 µl; 0.50 M; 0.26 mmol; 1 eq) affords 120 mg (98.5%) of the title compound as a yellow powder. 1H NMR (DMSO-d6) δ 9.13 (d, J=1.5 Hz, 1H), 8.73 (s, 1H), 8.52 (dd, J=1.9, 4.9 Hz, 1H), 8.37 (dt, J=1.9, 7.9 Hz, 1H), 7.44-7.38 (m, 2H), 7.31 (d, J=2.3 Hz, 2H), 7.28-7.24 (m, 1H), 7.18-7.09 (m, 2H), 6.13 (t, J=2.3 Hz, 1H), 3.77 (s, 6H). HPLC (max plot) 99%; Rt 3.94 min. LC/MS: (ES+): 438.4, (ES−): 436.4.

Example 96

3-cyano-N-{3-[(3,5-dimethoxyphenyl)amino]quinoxalin-2-yl}-4-fluorobenzenesulfonamide (96)—potassium salt (Scheme 1)

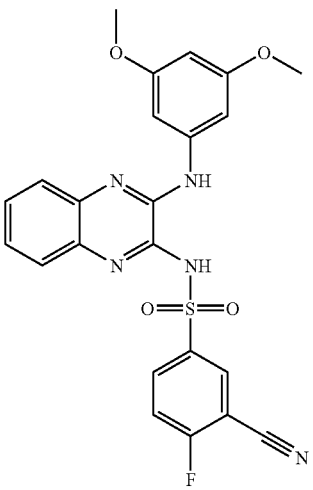

Following the protocol outlined in Procedure L, Example 96 is obtained from N-(3-chloroquinoxalin-2-yl)-3-cyano-4-fluorobenzenesulfonamide (541 mg; 1.49 mmol; 1 eq) and 3,5-dimethoxyaniline (251.28 mg; 1.64 mmol; 1.0 eq) in EtOH (8 ml) to afford 425 mg (59.44%) of the title compound as a parent (yellow powder). Treatment of the parent (100 mg; 0.21 mmol; 1 eq) with an aqueous solution of potassium hydroxide (417.11 µl; 0.50 M; 0.21 mmol; 1 eq) affords 99 mg (91.71%) of the title compound as a yellow powder. 1H NMR (DMSO-d6) δ 8.71 (br s, 1H), 8.57 (br d, 1H), 8.40-8.35 (m, 1H), 7.57-7.51 (m, 1H), 7.44-7.42 (m, 1H), 7.35-7.30 (br s, 1H), 7.31 (d, J=1.9 Hz, 2H), 7.23-7.16 (m, 2H), 6.14 (br d, 1H), 3.76 (s, 6H). HPLC (max plot) 95%; Rt 4.48 min. LC/MS: (ES+): 480.4, (ES−): 478.4.

Example 97

3-cyano-N-{3-[(2,5-dimethoxyphenyl)amino]quinoxalin-2-yl}-4-fluorobenzenesulfonamide (97)—potassium salt (Scheme 1)

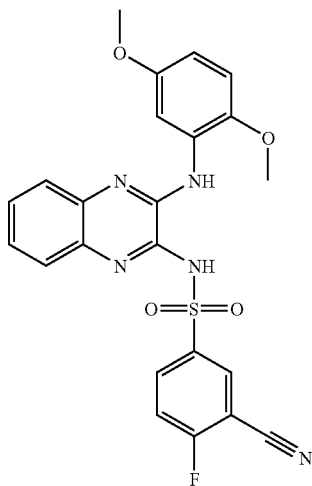

Following the protocol outlined in Procedure L, Example 97 is obtained from N-(3-chloroquinoxalin-2-yl)-3-cyano-4-fluorobenzenesulfonamide (84.1 mg; 0.23 mmol; 1 eq) and 2,5-dimethoxyaniline (39.06 mg; 0.26 mmol; 1.1 eq) in EtOH (2 ml) to afford 88.5 mg (80%) of the title compound as a parent (green powder). Treatment of the parent (80 mg; 0.17 mmol; 1 eq) with an aqueous solution of potassium hydroxide (333.7 µl; 0.5 M; 0.17 mmol; 1 eq) affords 87.4 mg (100%) of the title compound as a green powder. 1H NMR (DMSO-d6) δ 9.16 (s, 1H), 8.79 (d, J=3.0 Hz, 1H), 8.56 (dd, J=6.5, 2.3 Hz, 1H), 8.43-8.35 (m, 1H), 7.54 (t, J=9.0 Hz, 1H), 7.45 (dd, J=7.4, 1.7 Hz, 1H), 7.31 (dd, J=7.8, 1.7 Hz, 1H), 7.24-7.12 (m, 2H), 6.96 (d, J=8.7 Hz, 1H), 6.50 (dd, J=8.7, 3.0 Hz, 1H), 3.89 (s, 3H), 3.76 (s, 3H). HPLC (max plot) 99%; Rt 4.59 min. LC/MS: (ES+): 480.4, (ES−): 478.5.

Example 98

6-chloro-N-{3-[(3,5-dimethoxyphenyl)amino]quinoxalin-2-yl}pyridine-3-sulfonamide (98)—potassium salt (Scheme 1)

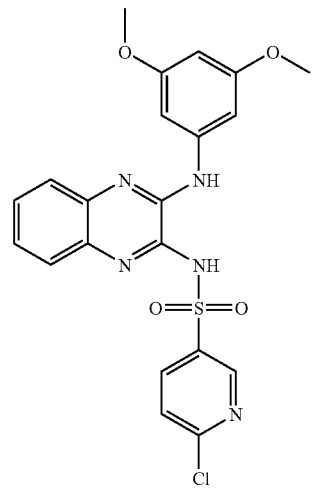

Following the protocol outlined in Procedure L, Example 98 is obtained from 6-chloro-N-(3-chloroquinoxalin-2-yl)pyridine-3-sulfonamide (237 mg; 0.67 mmol; 1 eq) and 3,5-dimethoxyaniline (107.32 mg; 0.70 mmol; 1.05 eq) in EtOH (6 ml) to afford 59 mg (19%) of the title compound as a parent (yellow powder). Treatment of the parent (58 mg; 0.12 mmol; 1 eq) with an aqueous solution of potassium hydroxide (245.8 µl; 0.5 M; 0.12 mmol; 1 eq) affords 63 mg (100%) of the title compound as a yellow powder. 1H NMR (DMSO-d6) δ 8.97 (d, J=2.3 Hz, 1H), 8.69 (s, 1H), 8.41 (dd, J=8.3, 2.3 Hz, 1H), 7.54 (d, J=8.6 Hz, 1H), 7.44-7.41 (m, 1H), 7.31 (d, J=2.3 Hz, 2H), 7.31-7.28 (br s, 1H), 7.21-7.13 (m, 2H), 6.14-6.13 (m, 1H), 3.77 (s, 6H). HPLC (max plot) 95%; Rt 4.49 min. LC/MS: (ES+): 472.4, (ES−): 470.4.

Example 99

N-{3-[(3,5-dimethoxyphenyl)amino]quinoxalin-2-yl}-6-(dimethylamino)pyridine-3-sulfonamide (99)—potassium salt (Scheme 1)

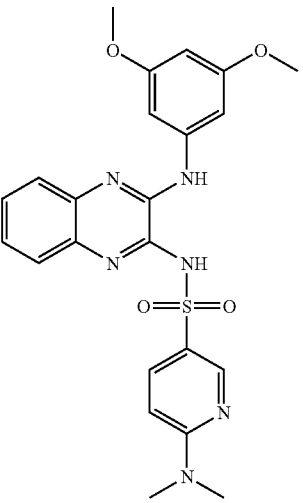

Following the protocol outlined in Procedure L, Example 99 is obtained from N-(3-chloroquinoxalin-2-yl)-6-(dimethylamino)pyridine-3-sulfonamide (150 mg; 0.41 mmol; 1 eq) and 3,5-dimethoxyaniline (69.47 mg; 0.45 mmol; 1.1 eq) in EtOH (2 ml) to afford 144 mg (73%) of the title compound as a parent (yellow powder). Treatment of the parent (144 mg; 0.3 mmol; 1 eq) with an aqueous solution of potassium hydroxide (599.32 μl; 0.5 M; 0.3 mmol; 1 eq) affords 142.6 mg (92%) of the title compound as a yellow powder. 1H NMR (DMSO-d6) δ 8.78 (s, 1H), 8.66 (s, 1H), 8.10 (dd, J=9.0, 2.6 Hz, 1H), 7.41-7.30 (m, 4H), 7.07-6.93 (m, 2H), 6.56 (br d, 1H), 6.13 (s, 1H), 3.77 (s, 6H), 3.01 (s, 6H). HPLC (max plot) 98%; Rt 3.54 min. LC/MS: (ES+): 481.5, (ES−): 479.4.

Example 100

N-{3-[(3,5-dimethoxyphenyl)amino]quinoxalin-2-yl}-6-[(3-methoxypropyl)amino]pyridine-3-sulfonamide (100)—HCl salt (Scheme 1)

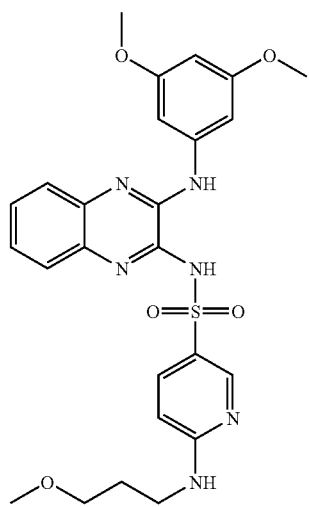

Following the protocol outlined in Procedure L, Example 100 is obtained from N-(3-chloroquinoxalin-2-yl)-6-[(3-methoxypropyl)amino]pyridine-3-sulfonamide (100 mg; 0.25 mmol; 1 eq) and 3,5-dimethoxyaniline (41.31 mg; 0.27 mmol; 1.1 eq) in EtOH (1.5 ml) to afford 79.5 mg (62%) of the title compound as a parent (yellow powder). Treatment of the parent (79.5 mg; 0.15 mmol; 1 eq) in solution in DCM (3 ml) with hydrochloric acid in MeOH (1 ml; 1.25 M; 1.25 mmol; 8.25 eq) affords 79.6 mg (94%) of the title compound as a yellow powder. 1H NMR (DMSO-d6) δ 12.03 (br s, 1H), 8.93 (s, 1H), 8.62 (d, J=1.9 Hz, 1H), 8.10-7.76 (m, 3H), 7.63-7.50 (m, 1H), 7.47-7.25 (m, 4H), 6.67 (d, J=9.4 Hz, 1H), 6.23 (t, J=1.9 Hz, 1H), 3.75 (s, 6H), 3.40-2.27 (m, 4H), 3.20 (s, 3H), 1.82-1.68 (m, 2H). HPLC (max plot) 98%; Rt 3.48 min. LC/MS: ES+ 525.6, ES− 523.6, 1.73 min, 98.37%.

Example 101

N-{3-[(5-methoxy-2-methylphenyl)amino]quinoxalin-2-yl}pyridine-3-sulfonamide (101) (Scheme 1)

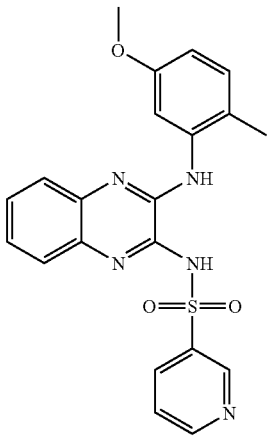

Following the protocol outlined in Procedure L, Example 101 is obtained from N-(3-chloroquinoxalin-2-yl)pyridine-3-sulfonamide (150 mg; 0.47 mmol; 1 eq) and 5-methoxy-2-methylaniline (70.57 mg; 0.51 mmol; 1.1 eq) in EtOH (2 ml) to afford 87 mg (44%) of the title compound as a parent (yellow powder). 1H NMR (DMSO-d6) δ 12.65 (br s, 1H), 9.23 (d, J=2.3 Hz, 1H), 8.83-8.81 (m, 1H), 8.71 (br s, 1H), 8.48-8.44 (m, 1H), 7.96-7.91 (m, 2H), 7.67-7.62 (m, 1H), 7.55-7.52 (m, 1H), 7.41-7.32 (m, 2H), 7.13 (d, J=8.7 Hz, 1H), 6.66-6.63 (m, 1H), 3.75 (s, 3H), 2.05 (s, 3H). HPLC (max plot) 99%; Rt 3.72 min. LC/MS: (ES+): 422.4, (ES−): 420.4.

Example 102

N-{3-[(2-chloro-5-methoxyphenyl)amino]quinoxalin-2-yl}-4-cyanobenzenesulfonamide (102)—potassium salt (Scheme 1)

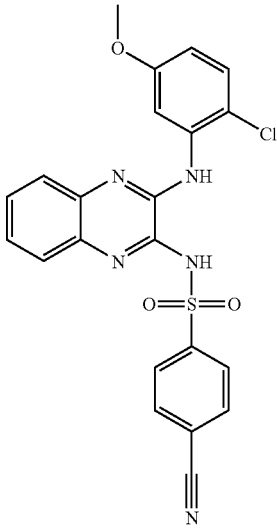

Following the protocol outlined in Procedure L, Example 102 is obtained from N-(3-chloroquinoxalin-2-yl)-4-cy anobenzenesulfonamide (150 mg; 0.44 mmol; 1 eq) and 2-chloro-5-methoxyaniline (75.42 mg; 0.48 mmol; 1.1 eq) in EtOH (2.50 ml) to afford 72.8 mg (36%) of the title compound as a parent (yellow powder). Treatment of the parent (55.2 mg; 0.12 mmol; 1 eq) with an aqueous solution of potassium hydroxide (0.24 ml; 0.5 M; 0.12 mmol; 1 eq) affords 44.4 mg (74%) of the title compound as a yellow powder. 1H NMR (DMSO-d6) δ 9.35 (s, 1H), 8.88 (s, 1H), 8.18 (d, J=7.9 Hz, 2H), 7.89 (d, J=7.2 Hz, 2H), 7.60-7.05 (m, 5H), 6.61 (dd, J=8.7, 2.7 Hz, 1H), 3.82 (s, 3H). HPLC (max plot) 98%; Rt 4.64 min. LC/MS: (ES+): 466.3, (ES−): 464.3, 1.89 min, 99%.

Example 103

N-{3-[(2-chloro-5-methoxyphenyl)amino]quinoxalin-2-yl}pyridine-3-sulfonamide (103)—potassium salt (Scheme 1)

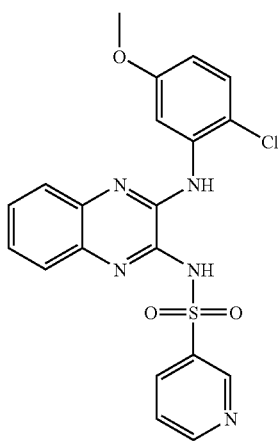

Following the protocol outlined in Procedure L, Example 103 is obtained from N-(3-chloroquinoxalin-2-yl)pyridine-3-sulfonamide (200 mg; 0.62 mmol; 1 eq.) and 2-chloro-5-methoxyaniline (108.09 mg; 0.69 mmol; 1.1 eq.) in EtOH (3 ml) to afford 69 mg (25%) of the title compound as a parent (yellow powder). Treatment of the parent (69 mg; 0.16 mmol; 1 eq.) with an aqueous solution of potassium hydroxide (312.29 µl; 0.5 M; 0.16 mmol; 1 eq.) affords 70 mg (93%) of the title compound as a yellow powder. 1H NMR (DMSO-d6) δ 9.34 (s, 1H), 9.16 (d, J=1.9 Hz, 1H), 8.86 (br s, 1H), 8.59 (br s, 1H), 8.38 (dt, J=1.9, 7.9 Hz, 1H), 7.51-7.44 (m, 3H), 7.40 (d, J=8.7 Hz, 1H), 7.25-7.20 (m, 2H), 6.63-6.59 (m, 1H), 3.81 (s, 3H). HPLC (max plot) 100%; Rt 4.11 min. LC/MS: (ES+): 442.1, (ES−): 440.2.

Example 104

N-{3-[(3,5-dimethoxyphenyl)amino]quinoxalin-2-yl}-6-methoxypyridine-3-sulfonamide (104)—potassium salt (Scheme 1)

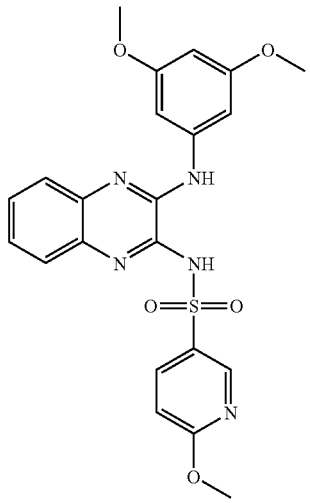

Following the protocol outlined in Procedure L, Example 104 is obtained from N-(3-chloroquinoxalin-2-yl)-6-methoxypyridine-3-sulfonamide (228 mg; 0.65 mmol; 1 eq.) and 3,5-dimethoxyaniline (109.52 mg; 0.71 mmol; 1.1 eq.) in EtOH (3 ml) to afford 46 mg (15%) of the title compound as a parent (yellow powder) after preparative HPLC. Treatment of the parent (46 mg; 0.1 mmol; 1 eq.) with an aqueous solution of potassium hydroxide (196.79 µl; 0.50 M; 0.1 mmol; 1 eq.) affords 48 mg (96.5%) of the title compound as a yellow powder. 1H NMR (DMSO-d6) δ 8.79 (br d, 2H), 8.31 (dd, J=2.3, 8.7 Hz, 1H), 7.44-7.21 (m, 6H), 6.84 (br d, 1H), 6.15 (s, 1H), 3.85 (s, 3H), 3.76 (s, 6H). HPLC (max plot) 98%; Rt 4.38 min. LC/MS: (ES+): 468.4, (ES−): 466.2.

Example 105

N-{3-[(3,5-dimethoxyphenyl)amino]quinoxalin-2-yl}-6-oxo-1,6-dihydropyridine-3-sulfonamide (105) (Scheme 1)

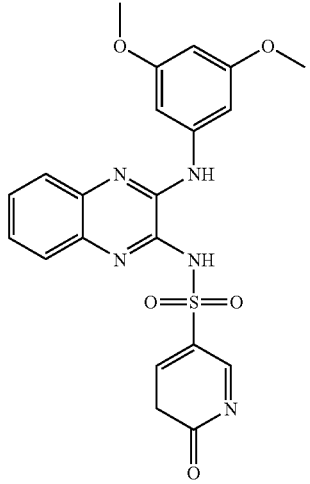

Following the protocol outlined in Procedure L, Example 105 is obtained from N-(3-chloroquinoxalin-2-yl)-6-methoxypyridine-3-sulfonamide (228 mg; 0.65 mmol; 1 eq.) and 3,5-dimethoxyaniline (109.52 mg; 0.71 mmol; 1.10 eq.) in EtOH (3 ml) to afford 32 mg, (12%) of the title compound as a parent (yellow powder) after preparative HPLC. 1H NMR (DMSO-d6) δ 8.94 (s, 1H), 8.21 (s, 1H), 7.93 (dd, J=2.6, 9.8 Hz, 2H), 7.58-7.55 (m, 1H), 7.38-7.35 (m, 4H), 6.41 (d, J=9.8 Hz, 1H), 6.23 (t, 1H), 3.76 (s, 6H), 3.15 (s, 2H). HPLC (max plot) 100%; Rt 3.60 min. LC/MS: (ES+): 454.3, (ES−): 452.2.

Example 106

N-{3-[(3,5-dimethoxyphenyl)amino]quinoxalin-2-yl}-6-methylpyridine-3-sulfonamide (106)—potassium salt (Scheme 1)

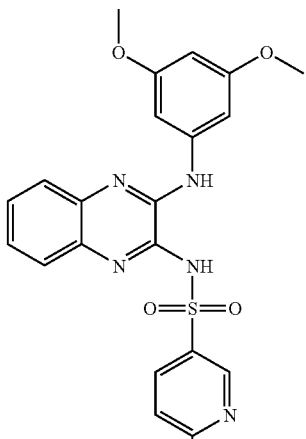

Following the protocol outlined in Procedure L, Example 106 is obtained from N-(3-chloroquinoxalin-2-yl)-6-methylpyridine-3-sulfonamide (150 mg; 0.45 mmol; 1 eq.) and 3,5-dimethoxyaniline (75.50 mg; 0.49 mmol; 1.10 eq.) in EtOH (2 ml) to afford 110 mg (54%) of the title compound as a parent (yellow powder). Treatment of the parent (108 mg; 0.24 mmol; 1 eq.) with an aqueous solution of potassium hydroxide (0.48 ml; 0.50 M; 0.24 mmol; 1 eq.) affords 121.6 mg (100%) of the title compound as a yellow powder. 1H NMR (DMSO-d6) δ 9.01 (d, J=1.9 Hz, 1H), 8.72 (s, 1H), 8.26-8.23 (m, 1H), 7.41-7.38 (m, 1H), 7.31-7.24 (m, 4H), 7.19-7.09 (m, 2H), 6.12 (t, J=2.3 Hz, 1H), 2.43 (s, 3H). HPLC (max plot) 98%; Rt 4.02 min. LC/MS: (ES+):452.0, (ES−): 450.2.

Example 107

N-{3-[(3,5-dimethoxyphenyl)amino]quinoxalin-2-yl}-4-fluoro-2-methylbenzenesulfonamide (107)—potassium salt (Scheme 1)

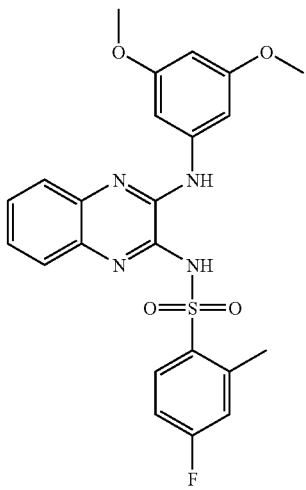

Following the protocol outlined in Procedure L, Example 107 is obtained from N-(3-chloroquinoxalin-2-yl)-4-fluoro-2-methylbenzenesulfonamide (100 mg; 0.28 mmol; 1 eq.) and 3,5-dimethoxyaniline (43.54 mg; 0.28 mmol; 1 eq.) in EtOH (2 ml) to afford 58 mg (43.5%) of the title compound as a parent (yellow powder). Treatment of the parent (58 mg; 0.12 mmol; 1 eq.) with an aqueous solution of potassium hydroxide (247.59 μl; 0.50 M; 0.12 mmol; 1 eq.) affords 58 mg (100%) of the title compound as a yellow powder. 1H NMR (DMSO-d6) δ 8.82 (s, 1H), 8.13 (dd, J=6.4, 8.4 Hz, 1H), 7.34-7.35 (m, 1H), 7.30 (d, J=2.3 Hz, 2H), 7.10-7.02 (m, 4H), 6.96-6.91 (m, 1H), 6.13 (t, J=2.3 Hz, 1H), 3.77 (s, 6H), 2.57 (s, 3H). HPLC (max plot) 99%; Rt 5.24 min. LC/MS: MS− (ES+):469.4, (ES−):467.3.

Example 108

N-{3-[(2,5-dimethoxyphenyl)amino]quinoxalin-2-yl}-6-methylpyridine-3-sulfonamide (108)—potassium salt (Scheme 1)

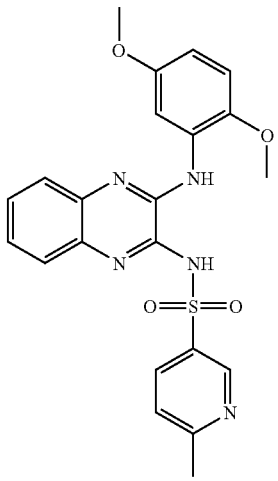

Following the protocol outlined in Procedure L, Example 108 is obtained from N-(3-chloroquinoxalin-2-yl)-6-methylpyridine-3-sulfonamide (150 mg; 0.45 mmol; 1 eq.) and 2,5-dimethoxyaniline (75.5 mg; 0.49 mmol; 1.1 eq.) in EtOH (2 ml) to afford 104 mg (51%) of the title compound as a parent (green powder). Treatment of the parent (104 mg; 0.23 mmol; 1 eq.) with an aqueous solution of potassium hydroxide (460.68 μl; 0.50 M; 0.23 mmol; 1 eq.) affords 114 mg (100%) of the title compound as a green powder. 1H NMR (DMSO-d6) δ 9.19 (s, 1H), 9.02 (s, 1H), 8.78 (br d, 1H), 8.25 (d, J=7.9 Hz, 1H), 7.43 (d, J=7.5 Hz, 1H), 7.27-7.12 (m, 4H), 6.95 (d, J=8.67 Hz, 1H), 6.49-6.47 (m, 1H), 3.88 (s, 3H), 3.75 (s, 3H), 2.44 (s, 3H). HPLC (max plot) 98%; Rt 4.20 min. LC/MS: (ES+): 452.3, (ES−): 450.6.

Example 109

4-cyano-N-{3-[(5-methoxy-2-methylphenyl)amino]quinoxalin-2-yl}benzenesulfonamide (109) (Scheme 1)

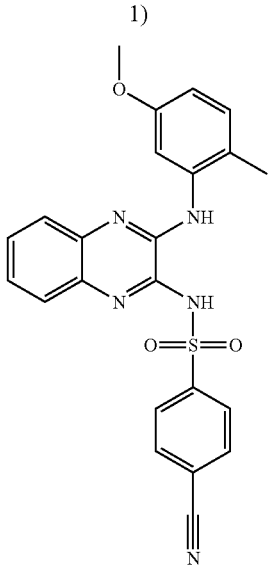

Following the protocol outlined in Procedure L, Example 109 is obtained from N-(3-chloroquinoxalin-2-yl)-4-cyanobenzenesulfonamide (536 mg; 1.55 mmol; 1 eq.) and 5-methoxy-2-methylaniline (234.59 mg; 1.71 mmol; 1.10 eq.) in EtOH (10 ml) to afford 417 mg (60%) of the title compound as a parent (yellow powder). 1H NMR (DMSO-d6) δ 2.04 (s, 3H), 3.75 (s, 3H), 6.64 (dd, J=2.6 Hz, J=8.3 Hz, 1H), 7.13 (d, J=8.3 Hz, 1H), 7.37 (m, 2H), 7.54 (m, 1H), 7.90 (m, 1H), 8.02 (m, 1H), 8.07 (d, J=8.3 Hz, 2H), 8.24 (d, J=8.3 Hz, 2H), 8.64 (br s, 1H), 12.70 (br s, 1H). HPLC (max plot) 99%; Rt 4.92 min. LC/MS: MS (ES+): 446.4, (ES−): 444.2.

Example 110

N-{3-[(5-methoxy-2-methylphenyl)amino]quinoxalin-2-yl}-6-methylpyridine-3-sulfonamide (110)—potassium salt (Scheme 1)

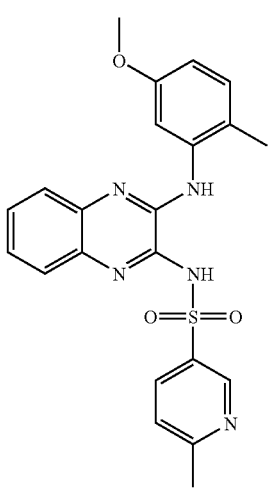

Following the protocol outlined in Procedure L, Example 110 is obtained from N-(3-chloroquinoxalin-2-yl)-6-methylpyridine-3-sulfonamide (531 mg; 1.59 mmol; 1 eq.) and 5-methoxy-2-methylaniline (326.37 mg; 2.38 mmol; 1.5 eq.) in EtOH (7 ml) to afford 557 mg (80%) of the title compound as a parent. Treatment of the parent (557 mg; 1.28 mmol; 1 eq.) with an aqueous solution of potassium hydroxide (2563.78 μl; 0.50 M; 1.28 mmol; 1 eq.) affords 598 mg (98%) of the title compound as a brown powder. 1H NMR (DMSO-d6) δ 9.02 (s, 1H), 8.88 (s, 1H), 8.60 (s, 1H), 8.25 (dd, J=9 et 3 Hz, 1H), 7.42 (dd, J=9 et 3 Hz, 1H), 7.30 (m, 2H), 7.15 (m, 3H), 6.50 (dd, J=9 et 3 Hz, 1H), 3.76 (s, 3H), 2.55 (s, 3H), 2.09 (s, 3H). HPLC (max plot) 99%; Rt 3.88 min. LC/MS: (ES+): 436.2, (ES−): 434.0.

Example 111

N-{3-[(2-chloro-5-methoxyphenyl)amino]quinoxalin-2-yl}-6-methylpyridine-3-sulfonamide (111)—potassium salt (Scheme 1)

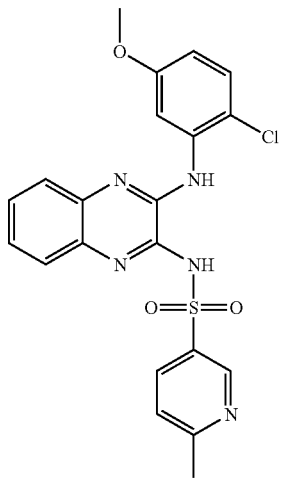

Following the protocol outlined in Procedure L, Example 111 is obtained from N-(3-chloroquinoxalin-2-yl)-6-methylpyridine-3-sulfonamide (474 mg; 1.42 mmol; 1 eq.) and 2-chloro-5-methoxyaniline (334.7 mg; 2.12 mmol; 1.5 eq.) in EtOH (7 ml) to afford 308 mg (47%) of the title compound as a parent. Treatment of the parent (308 mg; 0.678 mmol; 1 eq.) with an aqueous solution of potassium hydroxide (1358 μl; 0.5 M; 0.678 mmol; 1 eq.) affords 330 mg (98%) of the title compound as a yellow powder. 1H NMR (DMSO-d6) δ 9.40 (s, 1H), 9.03 (s, 1H), 8.92 (s, 1H), 8.25 (dd, J=9 et 3 Hz, 1H), 7.47 (dd, J=9 et 3 Hz, 1H), 7.40 (d, J=9 Hz, 1H), 7.23 (m, 3H), 6.59 (dd, J=9 et 3 Hz, 1H), 3.76 (s, 3H), 2.55 (s, 3H). HPLC (max plot) 99%; Rt 4.38 min. LC/MS: (ES+):456.2, (ES−): 454.1.

Example 112 methyl 5-[({3-[(3,5-dimethoxyphenyl)amino]quinoxalin-2-yl}amino)sulfonyl]pyridine-2-carboxylate (112) (Scheme 1)

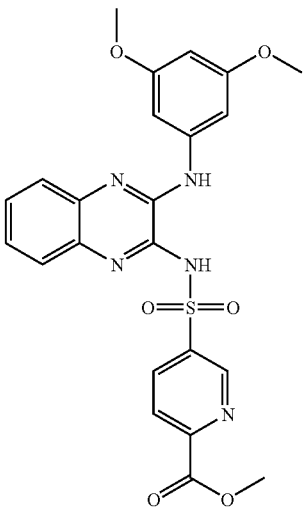

Following the protocol outlined in Procedure L, Example 112 is obtained from Methyl 5-{[(3-chloroquinoxalin-2-yl)amino]sulfonyl}pyridine-2-carboxylate (720 mg; 1.9 mmol; 1 eq.) and 3,5-dimethoxyaniline (727.9 mg; 4.75 mmol; 2.5 eq.) in EtOH (5 ml) to afford 650 mg (69%) of the title compound as a parent (yellow powder). 1H NMR (DMSO-d6) δ 9.37 (d, J=3 Hz, 1H), 8.98 (m, 1H), 8.63 (dd, J=9 and 3 Hz, 1H), 8.21 (d, J=9 Hz, 1H), 7.85 (m, 1H), 7.59 (m, 1H), 7.35 (m, 4H), 6.24 (m, 1H), 3.90 (s, 3H), 3.75 (s, 6H); HPLC (max plot) 86%; Rt 4.43 min. LC/MS: MS: (ES+): 496.2, (ES−): 494.2.

Example 113

N-{3-[(2-bromo-5-methoxyphenyl)amino]quinoxalin-2-yl}-1-methyl-1H-imidazole-4-sulfonamide (113) (Scheme 1)

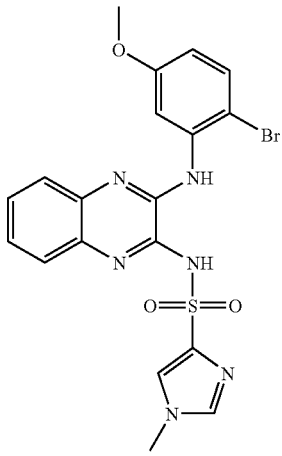

Following the protocol outlined in Procedure L, Example 113 is obtained from N-(3-chloroquinoxalin-2-yl)-1-methyl-1H-imidazole-4-sulfonamide (50 mg; 0.15 mmol; 1 eq.), 2-bromo-5-methoxyaniline (31.52 mg; 0.16 mmol; 1.01 eq.) and sodium hydroxyde (20 µl; 1 M; 0.02 mmol; 0.13 eq.) in water (1.50 ml) to afford 21.8 mg (29%) of the title compound as a parent (yellow powder). 1H NMR (DMSO-d6) δ 11.9 (s, 0.13H), 9.19 (s, 1H), 8.60 (s, 1H), 8.10-7.76 (m, 3H), 7.74-7.20 (m, 5H), 6.80-6.58 (m, 1H), 3.82 (s, 3H), 3.71 (s, 3H). HPLC (max plot) 99%; Rt 4.32 min. LC/MS: ES+491.2, ES−489.1.

Example 114

N-{3-[(3,5-dimethoxyphenyl)amino]quinoxalin-2-yl}-3-(morpholin-4-ylcarbonyl)benzenesulfonamide (114)—potassium salt (Scheme 1)

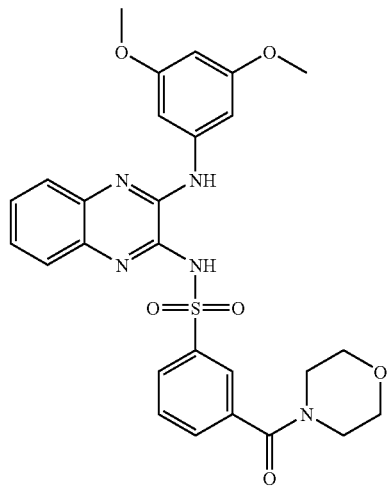

Following the protocol outlined in Procedure L, Example 114 is obtained from N-(3-chloroquinoxalin-2-yl)-3-(morpholin-4-ylcarbonyl)benzenesulfonamide (600 mg; 1.39 mmol; 1 eq.) and 3,5-dimethoxyaniline (212.31 mg; 1.39 mmol; 1 eq.) in EtOH (7 ml) to afford 237 mg(31%) of the title compound as a parent. Treatment of the parent (237 mg; 0.43 mmol; 1 eq.) with an aqueous solution of potassium hydroxide (862.43 µl; 0.50 M; 0.43 mmol; 1 eq.) affords 215 mg (85%) of the title compound as a yellow powder. 1H NMR (DMSO-d6) δ 8.78 (s, 1H), 8.05-8.02 (m, 2H), 7.49-7.38 (m, 3H), 7.31 (d, J=2.3 Hz, 2H), 7.20-7.08 (m, 3H), 6.14-6.12 (m, 1H), 3.77 (s, 6H), 3.65-3.10 (m, 8H). HPLC (max plot) 95%; Rt 4.25 min. LC/MS: LC/MS: (ES+): 550.1, (ES−): 548.2.

Procedure M

Example 115

3-[3-(2,5-Dimethoxy-phenylamino)-quinoxalin-2-ylsulfamoyl]-benzoic acid (115)

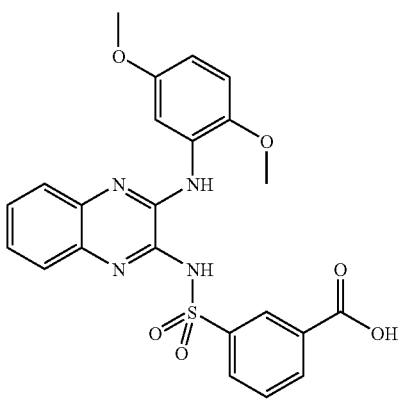

Methyl 3-[({3-[(2,5-dimethoxyphenyl)amino]quinoxalin-2-yl}amino)sulfonyl]benzoate (30 mg, 0.061 mmol), NaOH pellets (3.6 mg, 0.91 mmol) are dissolved in a 1 to 1 mixture of MeOH and $H_2O$ (4 ml) and the reaction mixture is stirred at rt overnight. When TLC confirms the total consumption of the starting ester, the reaction mixture was acidified with 1.5N HCl and precipitate was filtered and dried under vacuum to obtain example 6 as a white solid (26 mg, 89%). HPLC (max plot) 90%, rt. 4.15 min. LC/MS: (ES+): 481.1.

Example 116

3-[({3-[(3,5-Dimethoxyphenyl)amino]quinoxalin-2-yl}amino)sulfonyl]benzoic acid (116)

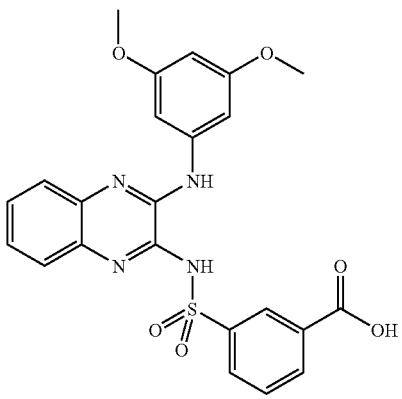

Following the general protocol outlined in Procedure M, Example 116 is obtained from methyl 3-[({3-[(3,5-dimethoxyphenyl)amino]quinoxalin-2-yl}amino)sulfonyl]benzoate in a 1 to 1 mixture of MeOH and $H_2O$ in the presence of NaOH (yellow solid, 10 mg, 15%). 1H NMR (DMSO-d6) δ 13.43 (s, 1H), 12.40 (s, 1H), 8.94 (s, 1H), 8.58 (s, 1H), 8.37 (d, J=7.9 Hz, 1H), 8.16 (d, J=7.5 Hz, 1H), 7.90 (s, 1H), 7.75-7.70 (m, 1H), 7.58-7.55 (m, 1H), 7.41-7.32 (m, 4H), 6.23-6.22 (m, 1H), 3.75 (s, 6H). HPLC (max plot) 93%, rt. 4.07 min. LC/MS: (ES+): 481.1.

Example 117

4-[({3-[(2,5-dimethoxyphenyl)amino]quinoxalin-2-yl}amino)sulfonyl]benzoic acid (117)

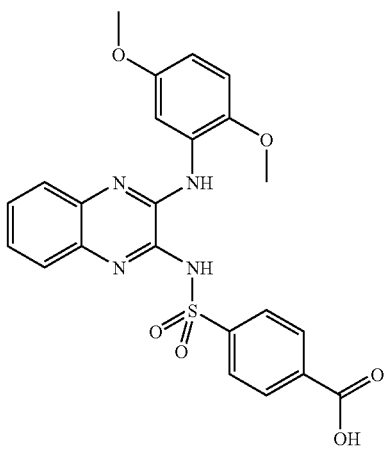

Following the general protocol outlined in Procedure M, Example 117 is obtained from methyl 4-[({3-[(2,5-dimethoxyphenyl)amino]quinoxalin-2-yl}amino)sulfonyl]benzoate in a 1 to 1 mixture of MeOH and $H_2O$ in the presence of NaOH (dark green solid, 10 mg, 23%). HPLC (max plot) 96%, rt. 4.17 min. LC/MS: (ES+): 481.5.

Example 118

4-[({3-[(3,5-dimethoxyphenyl)amino]quinoxalin-2-yl}amino)sulfonyl]benzoic acid (118)

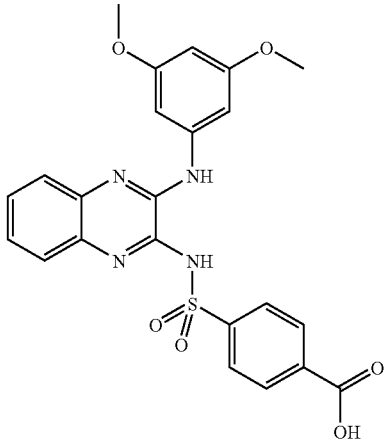

Following the general protocol outlined in Procedure M, Example 118 is obtained from methyl 4-[({3-[(3,5-dimethoxyphenyl)amino]quinoxalin-2-yl}amino)sulfonyl]benzoate in a 1 to 1 mixture of MeOH and $H_2O$ in the presence of NaOH (yellow solid, 10 mg, 15%). HPLC (max plot) 97%, rt. 4.06 min. LC/MS: (ES+): 481.5.

Example 119

4-[({3-[(2,5-dimethoxyphenyl)amino]quinoxalin-2-yl}amino)sulfonyl]butanoic acid (119)

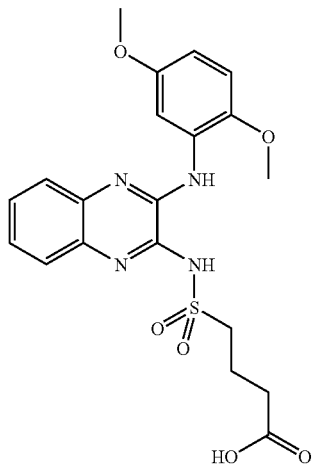

Following the general protocol outlined in Procedure M, Example 119 is obtained from methyl 4-[({3-[(2,5-dimethoxyphenyl)amino]quinoxalin-2-yl}amino)sulfonyl]butanoate in a 1 to 1 mixture of MeOH and H$_2$O in the presence of NaOH (dark green solid, 10 mg, 30%). HPLC (max plot) 99%, rt. 3.82 min. LC/MS: (ES+): 447.1.

Example 120

4-[({3-[(3,5-Dimethoxyphenyl)amino]quinoxalin-2-yl}amino)sulfonyl]butanoic acid (120)

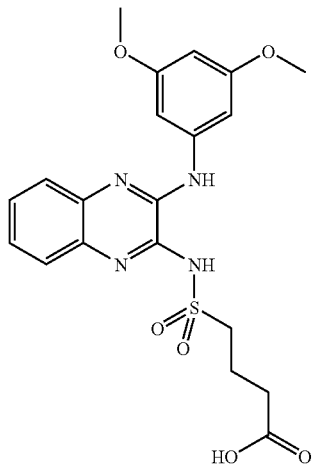

Following the general protocol outlined in Procedure M, Example 120 is obtained from methyl 4-[({3-[(3,5-dimethoxyphenyl)amino]quinoxalin-2-yl}amino)sulfonyl]butanoate in a 1 to 1 mixture of MeOH and H$_2$O in the presence of NaOH (yellow solid, 10 mg, 20%). HPLC (max plot) 99%, rt. 3.71 min. LC/MS: (ES+): 447.1.

Example 121

3-[({3-[(2,5-Dimethoxyphenyl)amino]quinoxalin-2-yl}amino)sulfonyl]thiophene-2-carboxylic acid (121)

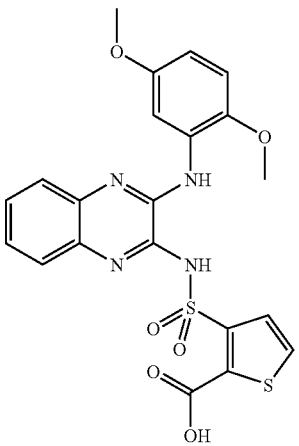

Following the general protocol outlined in Procedure M, Example 121 is obtained from methyl 3-[({3-[(2,5-dimethoxyphenyl)amino]quinoxalin-2-yl]amino)sulfonyl]thiophene-2-carboxylate in a 1 to 1 mixture of MeOH and H$_2$O in the presence of NaOH (yellow solid, 8 mg, 28%). HPLC (max plot) 97%, rt. 4.07 min. LC/MS: (ES+): 485.

Example 122

3-[({3-[(3,5-Dimethoxyphenyl)amino]quinoxalin-2-yl}amino)sulfonyl]thiophene-2-carboxylic acid (122)

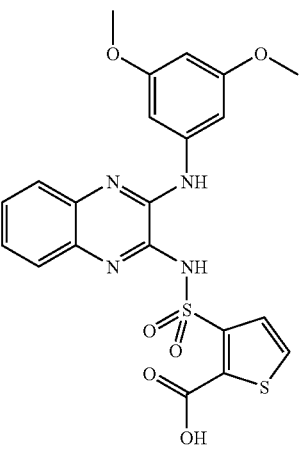

Following the general protocol outlined in Procedure M, Example 122 is obtained from methyl 3-[({3-[(3,5-dimethoxyphenyl)amino]quinoxalin-2-yl]amino)sulfonyl]thiophene-2-carboxylate in a 1 to 1 mixture of MeOH and H$_2$O in the presence of NaOH (yellow solid, 14 mg, 59%) HPLC (max plot) 94%, rt. 3.95 min. LC/MS: (ES+): 487.5.

Procedure N

Example 123

3-{4-[({3-[(3,5-dimethoxyphenyl)amino]quinoxalin-2-yl}amino)sulfonyl]phenyl}propanoic acid (123)

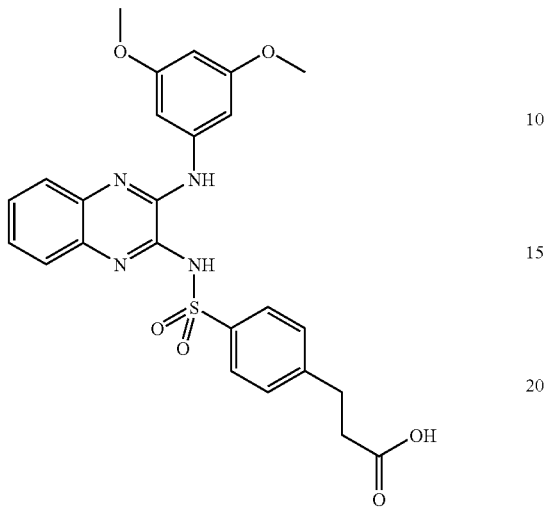

Methyl-3-{4-[({3-[(3,5-dimethoxyphenyl)amino]quinoxalin-2-yl}amino)sulfonyl]phenyl}propanoate (50 mg, 0.10 mmol, 1 eq.) and lithium hydroxide monohydrate (20.1 mg, 0.48 mmol, 5 eq.) are dissolved in THF (1 ml) and water (1 ml) and the yellow solution is heated up to 50° C. for 1 h. Aqueous HCl 1N is added until reaching acidic pH and the precipitate formed is filtered off then washed with water until neutral. The solid is dried under vacuum at 40° C. overnight, affording 38.1 mg (78%) of the title compound as a yellow powder. 1H NMR (DMSO-d6) δ 12.30-11.95 (m, 2H), 8.91 (s, 1H), 8.02 (d, J=8.2 Hz, 2H), 7-95-7.82 (br s, 1H), 7.60-7.50 (m, 1H), 7.48-7.23 (m, 6H), 6.23 (s, 1H), 3.75 (s, 6H), 2.88 (t, J=7.2 Hz, 2H), 2.56 (t, J=7.5 Hz, 2H). HPLC (max plot) 100%; Rt 4.10 min. LC/MS: (ES+): 509.4; (ES−): 507.4.

Example 124

5-[({3-[(2,5-dimethoxyphenyl)amino]quinoxalin-2-yl}amino)sulfonyl]-4-methylthiophene-2-carboxylic acid (124)

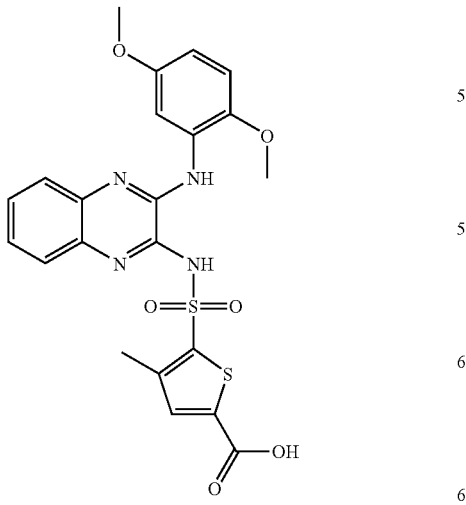

Following the protocol outlined in Procedure N, Example 124 is obtained from methyl 5-[({3-[(2,5-dimethoxyphenyl)amino]quinoxalin-2-yl}amino)sulfonyl]-4-methylthiophene-2-carboxylate (64 mg; 0.12 mmol; 1 eq) and lithium hydroxide monohydrate (26.1 mg; 0.62 mmol; 5 eq) in THF (1 ml) and water (1 ml) to afford 62.6 mg (100%) of the title compound as a yellow powder 1H NMR (DMSO-d6) δ 13.62 (brs, 1H), 12.76 (brs, 1H), 9.15 (s, 1H), 8.62 (d, J=2.7 Hz, 1H), 7.97 (d, J=7.5 Hz, 1H), 7.68 (s, 1H), 7.65 (m, 1H), 7.47-7.34 (m, 2H), 7.02 (d, J=8.7 Hz, 1H), 6.62 (dd, J=8.7, 2.7 Hz, 1H), 3.85 (s, 3H), 3.78 (s, 3H), 2.55 (s, 3H). HPLC (max plot) 99%; Rt 4.51 min. LC/MS: (ES+): 501.3, (ES−): 499.3.

Example 125

5-[({3-[(3,5-dimethoxyphenyl)amino]quinoxalin-2-yl}amino)sulfonyl]-4-methylthiophene-2-carboxylic acid (125)

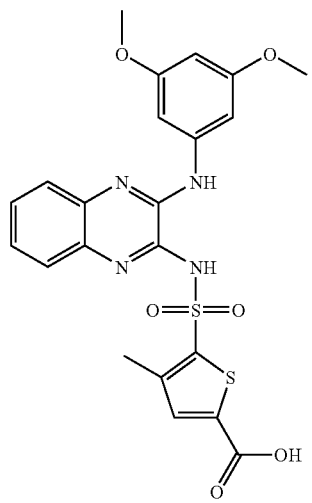

Following the protocol outlined in Procedure N, Example 125 is obtained from methyl 5-[({3-[(3,5-dimethoxyphenyl)amino]quinoxalin-2-yl}amino)sulfonyl]-4-methylthiophene-2-carboxylate (99.4 mg; 0.18 mmol; 1 eq) and lithium hydroxide monohydrate (37.74 mg; 0.90 mmol; 5 eq) in THF (1.5 ml) and water (1.5 ml) to afford 82.1 mg (91%) of the title compound as a yellow powder. 1H NMR (DMSO-d6) δ 13.56 (br s, 1H), 12.58 (br s, 1H), 8.90 (s, 1H), 7.89 (br s, 1H), 7.63-7.57 (m, 2H), 7.45-7.33 (m, 2H), 7.32 (d, J=2.2 Hz, 2H), 6.26 (t, J=2.2 Hz, 1H), 3.77 (s, 6H), 2.47 (s, 3H). HPLC (max plot) 98%; Rt 4.20 min. LC/MS: (ES+): 501.4, (ES−): 499.3.

Example 126

5-[({3-[(2,5-dimethoxyphenyl)amino]quinoxalin-2-yl}amino)sulfonyl]-1-methyl-1H-pyrrole-2-carboxylic acid (126)—di potassium salt

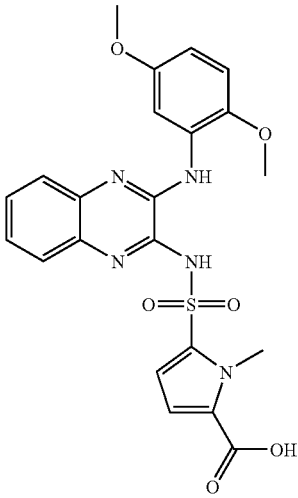

Following the protocol outlined in Procedure N, Example 126 is obtained from methyl 5-[({3-[(2,5-dimethoxyphenyl)amino]quinoxalin-2-yl}amino)sulfonyl]-1-methyl-1H-pyrrole-2-carboxylate (108.3 mg; 0.22 mmol; 1 eq) and lithium hydroxide monohydrate (45.67 mg; 1.09 mmol; 5 eq) in THF (2 ml) and water (1.5 ml) to afford 102.3 mg (97%) of the title compound as a green powder. Treatment of the parent (91.2 mg; 0.19 mmol; 1 eq) with an aqueous solution of potassium hydroxide (754.5 µl; 0.5 M; 0.38 mmol; 2 eq) affords 108.1 mg (100%) of the title compound as a green powder. 1H NMR (DMSO-d6) δ 9.31 (s, 1H), 8.83 (d, J=3.0 Hz, 1H), 7.43-7.35 (t, J=8.9 Hz, 2H), 7.20-7.05 (m, 3H), 6.93 (d, J=9.0 Hz, 1H), 6.65 (d, J=1.9 Hz, 1H), 6.46 (dd, J=8.7, 3.0 Hz, 1H), 3.89 (s, 3H), 3.81 (s, 3H), 3.77 (s, 3H). HPLC (max plot) 99%; Rt 3.96 min. LC/MS: (ES+): 484.4, (ES−): 482.4.

Example 127

5-[({3-[(3,5-dimethoxyphenyl)amino]quinoxalin-2-yl}amino)sulfonyl]-1-methyl-1H-pyrrole-2-carboxylic acid (127)—di potassium salt

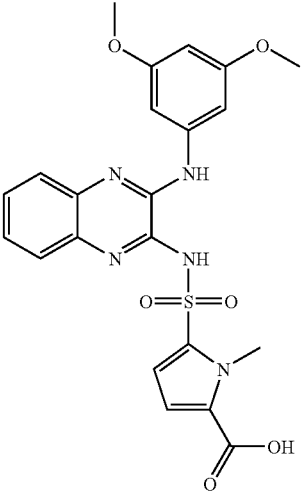

Following the protocol outlined in Procedure N, Example 127 is obtained from methyl 5-[({3-[(3,5-dimethoxyphenyl)amino]quinoxalin-2-yl}amino)sulfonyl]-1-methyl-1H-pyrrole-2-carboxylate (94.2 mg; 0.19 mmol; 1 eq) and lithium hydroxide monohydrate (39.72 mg; 0.95 mmol; 5 eq) in THF (2 ml) and water (1.5 ml) to afford 87.1 mg (95%) of the title compound as a yellow powder. Treatment of the parent (76.9 mg; 0.16 mmol; 1 eq) with an aqueous solution of potassium hydroxide (636.19 µl; 0.5 M; 0.32 mmol; 2 eq) affords 87.1 mg (98%) of the title compound as a yellow powder. 1H NMR (DMSO-d6) δ 8.85 (s, 1H), 7.40 (d, J=8.3 Hz, 2H), 7.28 (d, J=2.3 Hz, 2H), 7.21-7.13 (m, 2H), 7.09 (dt, J=7.5, 1.5 Hz, 1H), 6.62 (d, J=1.9 Hz, 1H), 6.11 (t, J=2.3 Hz, 1H), 3.79 (s, 3H), 3.78 (s, 6H). HPLC (max plot) 97%; Rt 3.88 min. LC/MS: (ES+): 484.5, (ES−): 482.5.

Example 128

5-[({3-[(3,5-dimethoxyphenyl)amino]quinoxalin-2-yl}amino)sulfonyl]pyridine-2-carboxylic acid (128)

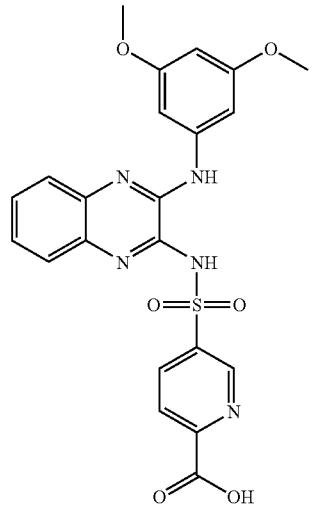

Following the protocol outlined in Procedure N, Example 128 is obtained from Methyl 5-[({3-[(3,5-dimethoxyphenyl)amino]quinoxalin-2-yl}amino)sulfonyl]pyridine-2-carboxylate (200 mg; 0.4 mmol; 1 eq.) and hydroxide monohydrate (84.68 mg; 2.02 mmol; 5 eq.) in THF (15 ml) and water (5 ml) to afford 185 mg (95%) of the title compound as a yellow powder. 1H NMR (DMSO-d6) δ 9.36 (d, J=3 Hz, 1H), 8.99 (m, 1H), 8.62 (dd, J=9 and 3 Hz, 1H), 8.20 (d, J=9 Hz, 1H), 7.87 (m, 1H), 7.59 (m, 1H), 7.35 (m, 4H), 6.24 (m, 1H), 3.76 (s, 6H). HPLC (max plot) 98.5%; Rt 4.04 min. LC/MS: (ES+): 482.2, (ES−): 480.2.

Procedure O
Example 129

N-{3-[(3,5-dimethoxyphenyl)amino]quinoxalin-2-yl}-3-(morpholin-4-ylmethyl)benzenesulfonamide (129)

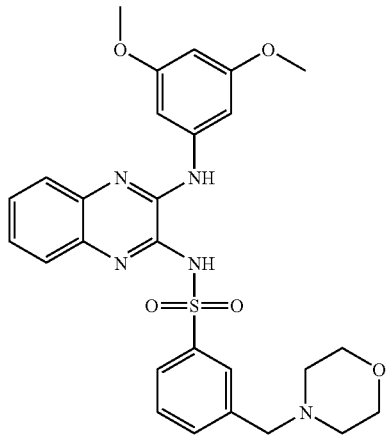

N-{3-[(3,5-dimethoxyphenyl)amino]quinoxalin-2-yl}-3-(morpholin-4-ylcarbonyl)benzenesulfonamide (184 mg; 0.33 mmol; 1 eq.) was suspended in THF (8 ml) and lithium aluminum hydride (669.57 µl; 1 M; 0.67 mmol; 2 eq.) was added dropwise. The solution was stirred at rt for 1 h 30. The reaction was quenched by addition of 25.4 µl of water, 25.4 µl of NaOH 1N then 3 times 25.4 µl of water and the precipitate formed was filtered through celite. The filtrate was evaporated then the oily residue was taken up in water and was neutralized with HCl 0.1N. After 1 h at 4° C. the precipitate formed was filtered and dried at 40° C. under vacuum overnight, affording 50 mg (28%) of the parent as a yellow solid. Treatment of the parent (50 mg; 0.09 mmol; 1 eq.) with HCl in MeOH (373.40 µl; 1.25 M; 0.47 mmol; 5 eq.) affords 38 mg (71%) of the title compound as a yellow powder. 1H NMR (DMSO-d6) δ 12.38 (br s, 1H), 10.66 (br s, 1H), 8.90 (s, 1H), 8.29 (s, 1H), 8.20-8.17 (m, 1H), 7.90 (s, 1H), 7.82-7.79 (m, 1H), 7.71-7.66 (m, 1H), 7.59-7.56 (m, 1H), 7.41-7.34 (m, 4H), 6.24-6.23 (m, 1H), 4.43 (s, 2H), 3.90-3.77 (m, 2H), 3.75 (s, 6H), 3.71-3.56 (m, 2H), 3.31-2.96 (m, 4H). HPLC (max plot) 98%; Rt 3.54 min. LC/MS: (ES+): 536.3, (ES-): 534.4.

Example 130

N-{3-[(3,5-dimethoxyphenyl)amino]quinoxalin-2-yl}-4-[(4-methylpiperazin-1-yl)methyl]benzenesulfonamide (130)—di HCl salt

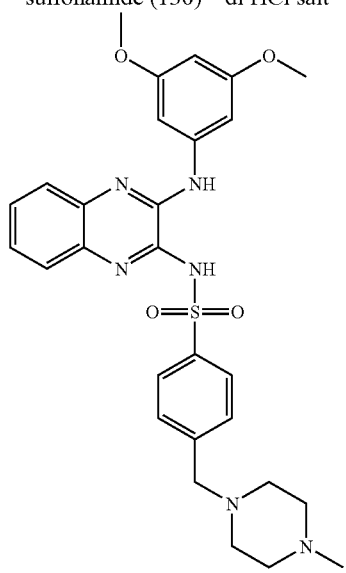

Following the protocol outlined in Procedure O, Example 130 is obtained from N-{3-[(3,5-dimethoxyphenyl)amino]quinoxalin-2-yl}-4-[(4-methylpiperazin-1-yl)carbonyl]benzenesulfonamide (171 mg; 0.3 mmol; 1 eq.) and lithium aluminum hydride (607.84 µl; 1 M; 0.61 mmol; 2 eq.) in THF (7 ml)) to afford 74 mg (44.38%) of the title compound as a parent. Treatment of the parent (74 mg; 0.13 mmol; 1 eq.) with HCl in MeOH (647.39 µl; 1.25 M; 0.81 mmol; 6 eq.) affords 72 mg (86%) of the title compound as a yellow powder. 1H NMR (DMSO-d6) δ 12.28 (br s, 1H), 10.02 (br s, 1H), 8.93 (s, 1H), 8.12 (d, J=7.9 Hz, 2H), 7.91 (s, 1H), 7.64-7.56 (m, 3H), 7.41-7.34 (m, 4H), 6.24-6.23 (m, 1H), 3.90-3.60 (m, 4H), 3.75 (s, 6H), 3.45-3.32 (m, 2H), 3.20-2.90 (m, 4H), 2.74 (s, 3H). HPLC (max plot) 99.5%; Rt 3.34 min. LC/MS: (ES+): 549.3, (ES-): 547.2. CHN analysis: [C28H32N6O4S-2.0 HCl-H20] Calculated: C52.58%, H5.67%, N13.14%; Found: C52.23%, H5.52%, N12.98%.

Example 131

4-(aminomethyl)-N-{3-[(2,5-dimethoxyphenyl)amino]quinoxalin-2-yl}benzenesulfonamide (131)—HCl salt

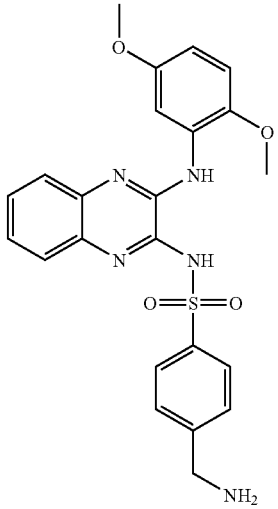

Following the protocol outlined in Procedure O, Example 131 is obtained from 4-cyano-N-{3-[(2,5-dimethoxyphenyl)amino]quinoxalin-2-yl}benzenesulfonamide (110 mg; 0.24 mmol; 1 eq) and lithium aluminum hydride (0.48 ml; 1 M; 0.48 mmol; 2 eq) in THF (3 ml)) to afford the title compound as a parent. Treatment of the parent with HCl in MeOH affords 75 mg (63%) of the title compound as a yellow powder. 1H NMR (DMSO-d6) δ 12.59 (br s, 1H), 9.15 (s, 1H), 8.63-8.48 (m, 1H), 8.40-8.15 (m, 1H), 8.10 (d, J=7.9 Hz, 2H), 7.94 (br s, 1H), 7.80-7.55 (m, 3H), 7.48-7.30 (m, 2H), 7 (d, J=8.7 Hz, 2H), 6.59 (dd, J=9.1, 2.6 Hz, 1H), 4.20-4.90 (m, 2H), 3.80 (s, 3H), 3.76 (s, 3H). 1H NMR (DMSO-d6) δ 5 exchangeable protons. HPLC (max plot) 98%; Rt 3.25 min. LC/MS: (ES+): 466.5, (ES-): 464.4; 1.48 min; 100%.

Example 132

N-{3-[(3,5-dimethoxyphenyl)amino]quinoxalin-2-yl}-3-(hydroxymethyl)benzenesulfonamide (132)

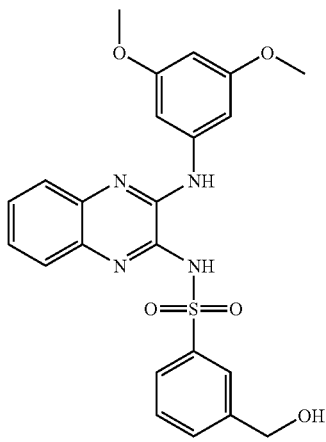

Following the protocol outlined in Procedure O, Example 132 is obtained from Methyl 3-[({3-[(3,5-dimethoxyphenyl)amino]quinoxalin-2-yl}amino)sulfonyl]benzoate (150 mg; 0.30 mmol; 1 eq) and lithium aluminum hydride (333.65 µl; 1 M; 0.33 mmol; 1.0 eq) in THF (8 ml) to afford 139 mg (98%) of the title compound as a parent (pale yellow powder). 1H NMR (DMSO-d6) δ 8.79 (s, 1H), 8.03 (s, 1H), 7.91 (dt, J=1.9, 7.2 Hz, 1H), 7.40-7.26 (m, 6H), 7.16-7.06 (m, 2H), 6.13-6.12 (m, 1H), 5.24 (t, J=5.7 Hz, 1H), 4.51 (d, J=5.7 Hz, 2H), 3.77 (s, 6H). HPLC (max plot) 98.5%; Rt 3.93 min. LC/MS: (ES+): 467.4, (ES−): 465.4.

Example 133

3-(aminomethyl)-N-{3-[(3,5-dimethoxyphenyl)amino]quinoxalin-2-yl}benzenesulfonamide (133)—HCl salt

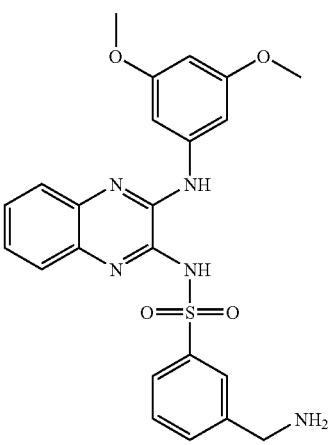

Following the protocol outlined in Procedure O, Example 133 is obtained from 3-cyano-N-{3-[(3,5-dimethoxyphenyl)amino]quinoxalin-2-yl}benzenesulfonamide (300 mg; 0.65 mmol; 1 eq) and lithium aluminum hydride (1300.11 µl; 1 M; 1.3 mmol; 2 eq in THF (8 ml) to afford 150 mg (50%) of the title compound as a parent. Treatment of the parent (150 mg; 0.32 mmol; 1 eq.) with HCl in MeOH (1.29 ml; 1.25 M; 1.61 mmol; 5 eq.) affords 64 mg (40%) of the title compound as a yellow powder. 1H NMR (DMSO-d6) δ 12.37 (br s, 1H), 8.85 (s, 1H), 8.27-8.12 (m, 4H), 7.91 (s, 1H), 7.70-7.56 (m, 3H), 7.37-7.32 (m, 4H), 6.23 (s, 1H), 4.17-4.11 (m, 2H), 3.75 (s, 6H). HPLC (max plot) 98.5%; Rt 3.12 min. LC/MS: (ES+): 466.4, (ES−): 464.4.

Example 134

N-{3-[(3,5-dimethoxyphenyl)amino]quinoxalin-2-yl}-4-(hydroxymethyl)benzenesulfonamide (134)

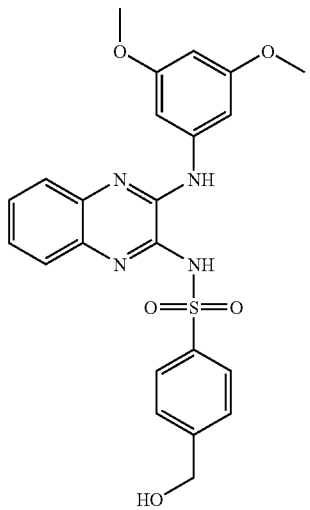

Following the protocol outlined in Procedure O, Example 134 is obtained from Methyl 4-[({3-[(3,5-dimethoxyphenyl)amino]quinoxalin-2-yl}amino)sulfonyl]benzoate (150 mg; 0.30 mmol; 1 eq.) and lithium aluminum hydride (333.65 µl; 1 M; 0.33 mmol; 1.1 eq.) in THF (8 ml) to afford 64 mg (45%) of the title compound as a parent (yellow powder). 1H NMR (DMSO-d6) δ 12.23 (s, 1H), 8.90 (s, 1H), 8.06 (d, J=8.3 Hz, 2H), 7.92 (s, 1H), 7.51-7.48 (m, 1H), 7.44 (d, J=8.3 Hz, 2H), 7.37-7.33 (m, 4H), 6.17-6.16 (m, 1H), 5.36 (s, 1H), 4.55 (s, 2H), 3.75 (s, 6H). HPLC (max plot) 100%; Rt 3.88 min. LC/MS: (ES+): 467.3, (ES−): 465.3.

Example 135

N-{3-[(3,5-dimethoxyphenyl)amino]quinoxalin-2-yl}-6-(hydroxymethyl)pyridine-3-sulfonamide (135)

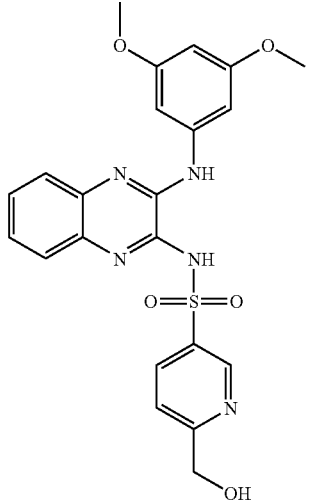

Following the protocol outlined in Procedure O, Example 135 is obtained from methyl 5-[({3-[(3,5-dimethoxyphenyl)

amino]quinoxalin-2-yl}amino)sulfonyl]pyridine-2-carboxylate (220 mg; 0.44 mmol; 1 eq.) and lithium aluminum hydride (0.49 ml; 1 M; 0.49 mmol; 1.1 eq.) in THF (8 ml) at −78° C. to afford 120 mg (58%) of the title compound as a parent (yellow powder). 1H NMR (DMSO-d6) δ 8.25 (m, 2H), 7.64 (d, J=3 Hz, 1H), 7.50 (m, 4H), 7.05 (s, 2H), 6.18 (s, 1H), 4.78 (s, 2H), 3.76 (s, 6H). HPLC (max plot) 71%; Rt 3.88 min. LC/MS: MS: (ES+): 468.5 and (ES−): 466.5.

Example 136

N-{3-[(3,5-dimethoxyphenyl)amino]quinoxalin-2-yl}-4-(morpholin-4-ylmethyl)benzenesulfonamide (136)—HCl salt

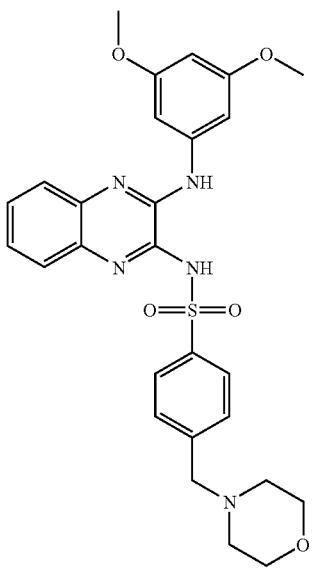

Following the protocol outlined in Procedure O, Example 136 is obtained from N-{3-[(3,5-dimethoxyphenyl)amino]quinoxalin-2-yl}-4-(morpholin-4-ylcarbonyl)benzenesulfonamide (165 mg; 0.3 mmol; 1 eq.) and lithium aluminum hydride (600.43 μl; 1 M; 0.6 mmol; 2 eq.) in THF (7 ml) to afford 98 mg (61%) of the title compound as a parent. Treatment of the parent benzenesulfonamide (97 mg; 0.18 mmol; 1 eq.) with HCl in MeOH (724.39 μl; 1.25 M; 0.91 mmol; 5 eq.) affords 96 mg (93%) of the title compound as a yellow powder. 1H NMR (DMSO-d6) δ 12.32 (br s, 1H), 10.54 (br s, 1H), 8.94 (s, 1H), 8.21 (d, J=7.9 Hz, 2H), 7.90 (s, 1H), 7.75 (d, J=7.9 Hz, 2H), 7.59-7.56 (m, 2H), 7.42-7.34 (m, 4H), 6.23 (t, J=2.3 Hz, 1H), 4.40 (s, 2H), 3.97-3.85 (m, 2H), 3.75 (s, 6H), 3.71-3.60 (m, 2H), 3.28-3.01 (m, 4H). HPLC (max plot) 99%; Rt 3.61 min. LC/MS: (ES+): 536.3, (ES−): 534.2.

Example 137

N-{3-[(3,5-dimethoxyphenyl)amino]quinoxalin-2-yl}-3-[(4-methylpiperazin-1-yl)methyl]benzenesulfonamide (137)—di HCl salt

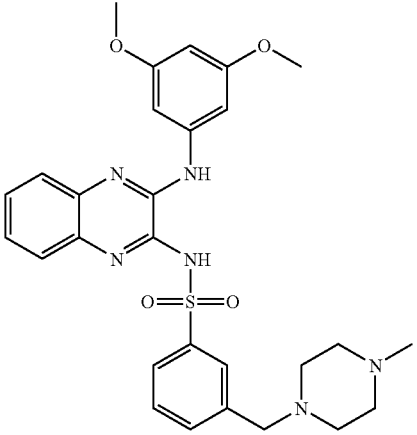

Following the protocol outlined in Procedure O, Example 137 is obtained from N-{3-[(3,5-dimethoxyphenyl)amino]quinoxalin-2-yl}-3-[(4-methylpiperazin-1-yl)carbonyl]benzenesulfonamide (267 mg; 0.47 mmol; 1 eq.) and lithium aluminum hydride (949.08 μl; 1 M; 0.95 mmol; 2 eq.) in THF (10 ml) to afford 211 mg (81%) of the title compound as a parent. Treatment of the parent benzenesulfonamide (211 mg; 0.38 mmol; 1 eq.) with HCl in MeOH (1845.93 μl; 1.25 M; 2.31 mmol; 6 eq.) affords 184 mg (77%) of the title compound as a yellow powder. 1H NMR (DMSO-d6) δ (, H), 12.31 (br s, 1H), 9.91 (br s, 1H), 8.91 (s, 1H), 8.12-8.05 (m, 2H), 7.91 (s, 1H), 7.61-7.56 (m, 3H), 7.42-7.33 (m, 4H), 6.25-6.23 (m, 1H), 3.75 (s, 6H), 3.75-3.25 (m, 6H), 3.10-2.85 (m, 4H), 2.71 (s, 3H). HPLC (max plot) 100%; Rt 3.33 min. LC/MS: (ES+): 549.4, (ES−): 547.3. CHN analysis: [C28H32N6O4S-2.0 HCl-0.8 H20] Calculated: C52.88%, H5.64%, N13.21%; Found: $C_{52.94}$%, H5.63%, N13.21%.

Example 138

N-{3-[(3,5-dimethoxyphenyl)amino]quinoxalin-2-yl}-4-[(dimethylamino)methyl]benzenesulfonamide (138)—HCl salt

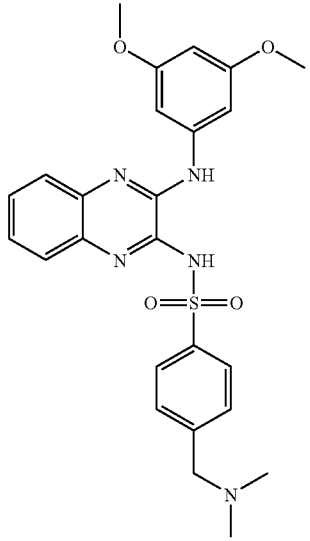

Following the protocol outlined in Procedure O, Example 138 is obtained from 4-[({3-[(3,5-dimethoxyphenyl)amino]

quinoxalin-2-yl}amino)sulfonyl]-N,N-dimethylbenzamide (155 mg; 0.31 mmol; 1 eq.) and lithium aluminum hydride (610.75 µl; 1 M; 0.61 mmol; 2 eq.) in THF (5 ml) to afford 84 mg (56%) of the title compound as a parent. Treatment of the parent benzenesulfonamide (84 mg; 0.17 mmol; 1 eq.) with HCl in MeOH (680.73 µl; 1.25 M; 0.85 mmol; 5 eq.) affords 93 mg (103%) of the title compound as a yellow powder. 1H NMR (DMSO-d6) δ 12.35 (s, 1H), 10.36 (s, 1H), 8.95 (s, 1H), 8.21 (d, J=8.3 Hz, 2H), 7.91 (s, 1H), 7.75 (d, J=8.3 Hz, 2H), 7.59-7.56 (m, 1H), 7.42-7.34 (m, 4H), 6.24-6.23 (m, 1H), 4.33 (d, J=5.3 Hz, 2H), 3.75 (s, 6H), 2.69 (d, J=4.9 Hz, 6H). HPLC (max plot) 98%; Rt 3.53 min. LC/MS: (ES+): 494.3, (ES−): 492.2.

Example 139

N-{3-[(3,5-dimethoxyphenyl)amino]quinoxalin-2-yl}-3-[(dimethylamino)methyl]benzenesulfonamide (139)—HCl salt

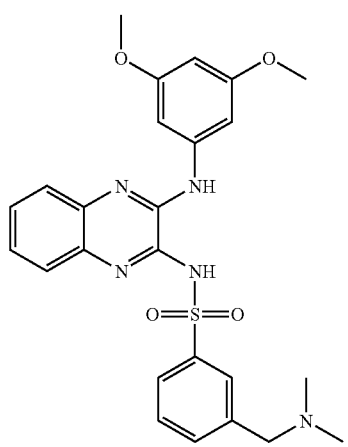

Following the protocol outlined in Procedure O Example 139 is obtained from 3-[({3-[(3,5-dimethoxyphenyl)amino]quinoxalin-2-yl}amino)sulfonyl]-N,N-dimethylbenzamide (102 mg; 0.2 mmol; 1 eq.) and lithium aluminum hydride (401.91 µl; 1 M; 0.4 mmol; 2 eq.) in THF (5 ml) to afford 56 mg (56.5%) of the title compound as a parent. Treatment of the parent benzenesulfonamide (56 mg; 0.11 mmol; 1 eq.) with HCl in MeOH (453.82 µl; 1.25 M; 0.57 mmol; 5 eq.) affords 52 mg (86.5%) of the title compound as a yellow powder. 1H NMR (DMSO-d6) δ 12.39 (s, 1H), 10.23 (s, 1H), 8.90 (s, 1H), 8.28 (s, 1H), 8.19 (d, J=8.3 Hz, 1H), 7.90 (s, 1H), 7.78 (d, J=7.9 Hz, 1H), 7.71-7.66 (m, 1H), 7.59-7.56 (m, 1H), 7.41-7.33 (m, 4H), 6.24-6.22 (m, 1H), 4.37 (br d, 2H), 3.75 (s, 6H), 2.70 (br d, 6H). HPLC (max plot) 98%; Rt 3.53 min. LC/MS: (ES+): 494.2, (ES−): 492.2.

Procedure P

Example 140

4-[({3-[(3,5-dimethoxyphenyl)amino]quinoxalin-2-yl}amino)sulfonyl]benzamide (140)—sodium salt

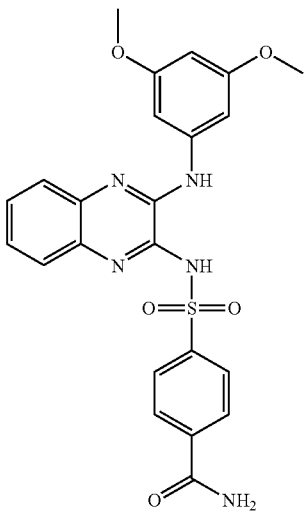

4-cyano-N-{3-[(3,5-dimethoxyphenyl)amino]quinoxalin-2-yl}benzenesulfonamide (101.2 mg; 0.22 mmol; 1 eq.) was dissolved in aqueous sodium hydroxide (0.5 ml) 5N and EtOH (0.5 ml) and the solution was heated up to 80° C. Over Night. The solution was cooled down and the solvent was removed. The solid residue was taken up in a small volume of EtOH and refluxed. After cooling at 4° C., the precipitate formed was filtered off, washed with EtOH and dried at 40° C. overnight. Recrystallization in ACN affords 45.4 mg (41%) of the title compound as a sodium salt (light yellow powder). 1H NMR (DMSO-d6) δ 8.80 (s, 1H), 7.90 (d, J=8.2 Hz, 2H), 7.78 (d, J=8.2 Hz, 2H), 7.37 (dd, J=7.5, 1.8 Hz, 1H), 7.29 (d, J=1.9 Hz, 2H), 7.23 (dd, J=7.9, 1.5 Hz, 1H), 7.17-7.01 (m, 2H), 6.12 (t, J=1.9 Hz, 1H), 3.77 (s, 6H). HPLC (max plot) 98.5%; Rt 4.06 min. LC/MS: (ES+): 481.2, (ES−): 479.2, 1.35 min, 99.5%.

Example 141

4-[({3-[(5-methoxy-2-methylphenyl)amino]quinoxalin-2-yl}amino)sulfonyl]benzamide (141)—sodium salt

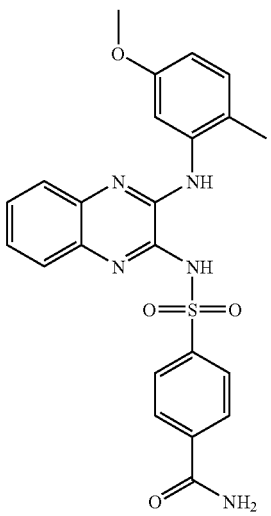

Following the protocol outlined in Procedure P, Example 141 is obtained from 4-cyano-N-{3-[(5-methoxy-2-methylphenyl)amino]quinoxalin-2-yl}benzenesulfonamide (113 mg; 0.25 mmol; 1 eq.) aqueous sodium hydroxide (0.5 ml) 5N in EtOH (1 ml) to afford 97 mg (79%) of the title compound as a yellow powder. 1H NMR (DMSO-d6) δ 8.75 (s, 1H), 8.43 (d, J=2.6 Hz, 1H), 7.70 (d, J=8.3 Hz, 2H), 7.60 (d, J=8.3 Hz, 2H), 7.19-7.16 (m, 1H), 7.07-7.04 (m, 1H), 6.95-6.86 (m, 3H), 6.29 (dd, J=2.6, 8.3 Hz, 1H), 3.56 (s, 3H), 2.03 (s, 3H). HPLC (max plot) 98%; Rt 4.39 min. LC/MS: (ES+): 465.3, (ES−): 463.1.

Procedure Q

Example 142

4-[({3-[(3,5-dimethoxyphenyl)amino]quinoxalin-2-yl}amino)sulfonyl]-N-(3-methoxypropyl)benzamide (142)

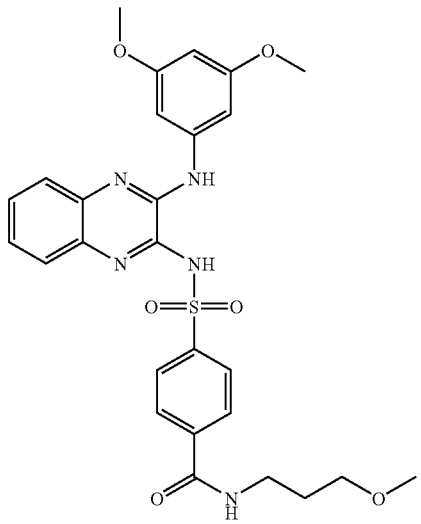

4-[({3-[(3,5-dimethoxyphenyl)amino]quinoxalin-2-yl}amino)sulfonyl]benzoic acid (100 mg; 0.21 mmol; 1 eq.), EDC-HCl (51.87 mg; 0.27 mmol; 1.3 eq.) and HOBT (36.56 mg; 0.27 mmol; 1.3 eq.) were taken up in DMA (5 ml) then DIEA(106.88 µl; 0.62 mmol; 3 eq.) and 3-methoxypropylamine (21.23 µl; 0.21 mmol; 1 eq.) were added. The solution was stirred at rt for 3 h. The DMA was evaporated and the residue was taken up in DCM. The organic phase was washed with a saturated solution of NaHCO₃ then a saturated solution of NH4Cl and brine. It was dried over MgSO₄ and concentrated to near dryness. The residue obtained was taken up in ACN and refluxed. After cooling at 4° C., the precipitate was filtered off then washed with ACN to afford 76 mg(66%) of the title compound as a parent. Treatment of the parent (74 mg; 0.13 mmol; 1 eq.) with an aqueous solution of potassium hydroxide (268.30 µl; 0.5 M; 0.13 mmol; 1 eq.) affords 76 mg (96%) of the title compound as a yellow powder. 1H NMR (DMSO-d6) δ 8.77 (s, 1H), 8.49-8.45 (m, 1H), 8.08 (d, J=8.3 Hz, 2H), 7.80 (d, J=8.3 Hz, 2H), 7.41-7.38 (m, 1H), 7.31 (d, J=2.3 Hz, 2H), 7.27-7.24 (m, 1H), 7.17-7.08 (m, 2H), 6.13-6.12 (m, 1H), 3.77 (s, 6H), 3.35-3.31 (m, 2H), 3.28-3.22 (m, 2H), 3.20 (s, 3H), 1.75-1.66 (m, 2H). HPLC (max plot) 97%; Rt 4.17 min. LC/MS: (ES+): 552.4, (ES−): 550.3.

Example 143

4-[({3-[(3,5-dimethoxyphenyl)amino]quinoxalin-2-yl}amino)sulfonyl]-N-[3-(dimethylamino)propyl] benzamide (143)—HCl salt

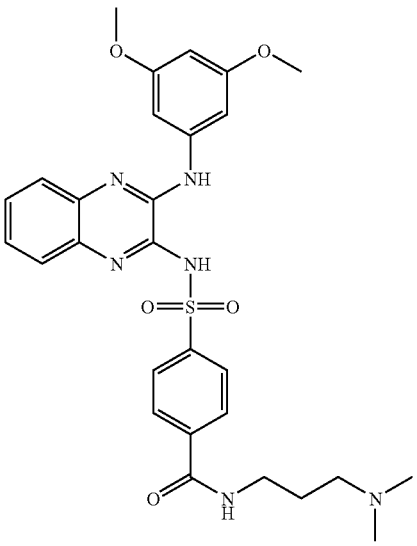

Following the protocol outlined in Procedure Q, Example 143 is obtained from 4-[({3-[(3,5-dimethoxyphenyl)amino] quinoxalin-2-yl}amino)sulfonyl]benzoic acid (100 mg; 0.21 mmol; 1 eq.), EDC-HCl (51.87 mg; 0.27 mmol; 1.3 eq.), HOBT (36.56 mg; 0.27 mmol; 1.3 eq.), DIEA (106.88 µl; 0.62 mmol; 3 eq.) and N,N-dimethyl-1,3-propanediamine (26.25 µl; 0.21 mmol; 1 eq.) in DMA (5 ml) to afford 81 mg (69%) of the title compound as a parent. Treatment of the parent (81 mg; 0.14 mmol; 1 eq.) with HCl in MeOH (0.5 ml; 1.25 M; 0.62 mmol; 4.36 eq.) affords 80 mg (93%) of the title compound as a dark yellow powder. 1H NMR (DMSO-d6) δ 9.90-9.50 (m, 1H), 9-8.60 (m, 2H), 8.25-8.10 (m, 2H), 8.05-7.80 (m, 2H), 7.55-7.10 (m, 6H), 6.25-6.10 (m, 1H), 3.80 (s, 6H), 3.45-3 (m, 4H), 2.76 (s, 6H), 2-1.80 (m, 2H). HPLC (max plot) 98%; Rt 3.24 min. LC/MS: (ES+): 565.4, (ES−): 563.4.

Example 144

3-[({3-[(3,5-dimethoxyphenyl)amino]quinoxalin-2-yl}amino)sulfonyl]-N-{3-(dimethylamino) propyl}benzamide (144)—HCl salt

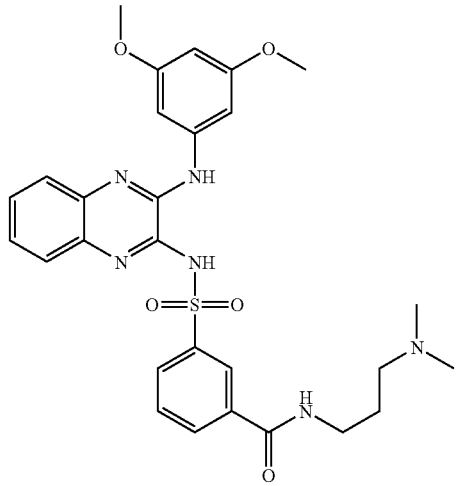

Following the protocol outlined in Procedure Q, Example 144 is obtained from 3-[({3-[(3,5-dimethoxyphenyl)amino]

quinoxalin-2-yl}amino)sulfonyl]benzoic acid (90 mg; 0.19 mmol; 1 eq.), EDC-HCl (46.68 mg; 0.24 mmol; 1.30 eq.), HOBT (32.90 mg; 0.24 mmol; 1.3 eq.), DIEA (96.19 μl; 0.56 mmol; 3 eq.) and N,N-dimethyl-1,3-propanediamine (23.63 μl; 0.19 mmol; 1 eq.) in DMA (5 ml) to afford the title compound as a parent. Treatment of the parent with HCl in MeOH affords 57 mg (54%) of the title compound as a yellow powder. 1H NMR (DMSO-d6) δ 12.39 (br s, 1H), 9.57 (br s, 1H), 8.90-8.88 (m, 2H), 8.55 (s, 1H), 8.28 (d, J=8.3 Hz, 1H), 8.10-8.08 (m, 1H), 7.91 (br s, 1H), 7.72-7.67 (m, 1H), 7.58-7.55 (m, 1H), 7.38-7.32 (m, 4H), 6.24-6.22 (m, 1H), 3.75 (s, 6H), 3.40-3.30 (m, 2H), 3.10-3.03 (m, 2H), 2.74 (s, 6H), 1.90-1.85 (m, 2H). HPLC (max plot) 98%; Rt 3.29 min. LC/MS: (ES+): 565.5. (ES−): 563.5.

Example 145

5-[({3-[(3,5-dimethoxyphenyl)amino]quinoxalin-2-yl}amino)sulfonyl]-N,N-dimethylpyridine-2-carboxamide (145)

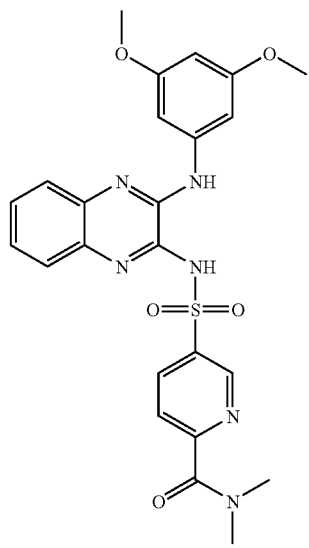

Following the protocol outlined in Procedure Q, Example 145 is obtained from 5-[({3-[(3,5-dimethoxyphenyl)amino] quinoxalin-2-yl}amino)sulfonyl]pyridine-2-carboxylic acid (100 mg; 0.21 mmol; 1 eq.), EDC-HCl (43.80 mg; 0.23 mmol; 1.1 eq.), HOBT (30.87 mg; 0.23 mmol; 1.1 eq.), DIEA (52.29 μl; 0.31 mmol; 1.5 eq.) and dimethylamine (103.84 μl; 2 M; 0.21 mmol; 1 eq.) in THF (4.5 ml) to afford 102 mg (96.5%) of the title compound as a parent (yellow powder). 1H NMR (DMSO-d6) δ 12.41 (br s, 1H), 9.21 (s, 1H), 8.94 (s, 1H), 8.56-8.53 (m, 1H), 7.85-7.53 (m, 3H), 7.35-7.30 (m, 4H), 6.21 (br t, 1H), 3.75 (s, 6H), 3.00 (s, 3H), 2.89 (s, 3H). HPLC (max plot) 99%; Rt 4.13 min. LC/MS: (ES+): 509.2, (ES−): 507.1.

Example 146

N-{3-[(3,5-dimethoxyphenyl)amino]quinoxalin-2-yl}-3-[(4-methylpiperazin-1-yl)carbonyl}benzenesulfonamide—potassium salt (146)

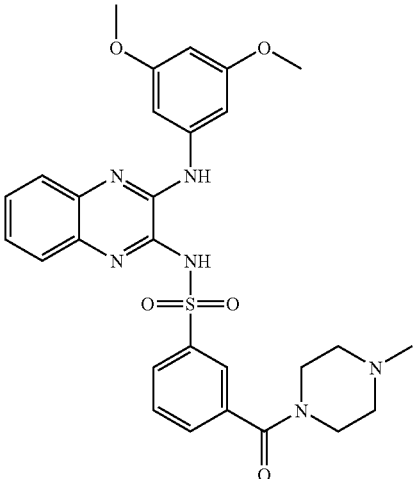

Following the protocol outlined in Procedure Q, Example 146 is obtained from 3-[({3-[(3,5-dimethoxyphenyl)amino] quinoxalin-2-yl}amino)sulfonyl]benzoic acid (300 mg; 0.62 mmol; 1 eq.), EDC-HCl (131.66 mg; 0.69 mmol; 1.1 eq.), HOBT (92.80 mg; 0.69 mmol; 1.1 eq.), DIEA (157.20 μl; 0.94 mmol; 1.5 eq.) and 1-methylpiperazine (69.49 μl; 0.62 mmol; 1 eq.) in DCM (12 ml) to afford 278 mg (79%) of the title compound as a parent. Treatment of the parent (275 mg; 0.49 mmol; 1 eq.) with and aqueous solution of potassium hydroxide (977.52 μl; 0.50 M; 0.49 mmol; 1 eq.) affords 301 mg (100%) of the title compound as a yellow powder. 1H NMR (DMSO-d6) δ 8.79 (s, 1H), 8.09-8.08 (m, 2H), 7.52-7.40 (m, 3H), 7.31 (d, J=2.3 Hz, 2H), 7.25 (br s, 1H), 7.16-7.14 (m, 2H), 6.14 (t, J=2.3 Hz, 1H), 3.77 (s, 6H), 3.52-3.25 (m, 4H), 3.05-2.30 (m, 7H). HPLC (max plot) 99%; Rt 3.45 min. LC/MS: (ES+): 563.6, (ES−): 561.1.

Example 147

N-{3-[(3,5-dimethoxyphenyl)amino]quinoxalin-2-yl}-6-(morpholin-4-ylcarbonyl)pyridine-3-sulfonamide (147)

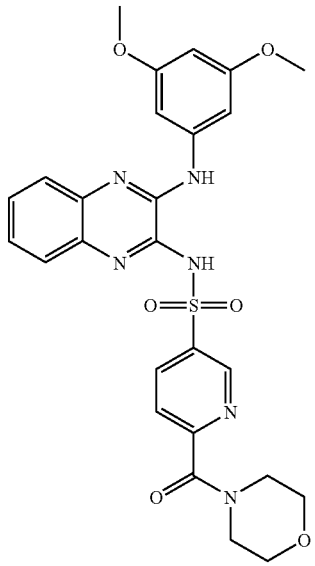

Following the protocol outlined in Procedure Q, Example 147 is obtained from 5-[({3-[(3,5-dimethoxyphenyl)amino]

quinoxalin-2-yl}amino)sulfonyl]pyridine-2-carboxylic acid (110 mg; 0.23 mmol; 1 eq.), EDC-HCl (55.43 mg; 0.28 mmol; 1.5 eq.), HOBT (39.07 mg; 0.28 mmol; 1.5 eq.), DIEA (118.52 μl; 0.69 mmol; 3 eq.) and morpholine (20.22 μl; 0.23 mmol; 1 eq.) in DCM (20 ml) to afford 140 mg (111.3%) of the title compound as a pale yellow oil. 1H NMR (DMSO-d6) δ 9.30 (d, J=3 Hz, 1H), 8.55 (m, 2H), 7.57 (d, J=9 Hz, 1H), 7.47 (m, 1H), 7.35 (m, 1H), 7.23 (d, J=3 Hz, 2H), 7.10 (m, 2H), 6.15 (m, 1H), 6.08 (m, 1H), 3.75 (s, 6H), 3.52 (m, 4H), 2.92 (m, 4H). HPLC (max plot) 91.5%; Rt 4.08 min. LC/MS: (ES+): 551.2, (ES−): 549.3.

Example 148

N-{3-[(3,5-dimethoxyphenyl)amino]pyrido[2,3-b]pyrazin-2-yl}ethane Sulfonamide (148)—potassium salt

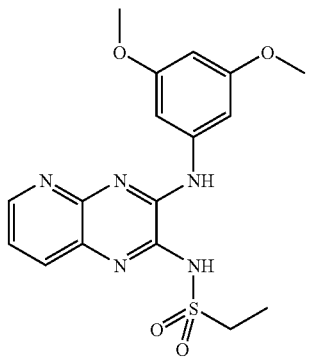

A suspension of 2,3-dichloro-pyrido[2,3-b]pyrazine (200 mg; 1 mmol; 1 eq), ethane sulfonamide (109.1 mg, 1 mmol, 1 eq.), 7-methyl-1,5,7-triazabicyclo[4.4.0]dec-5-ene on polystyrene.hl (862 mg, 2.5 mmol, 2.5 eq.) and NaI (149.87 mg, 1 mmol, 1 eq.) in DMA (5 ml) is heated at 100° C. in the microwave for 1 hour under high absorbance. HCl in dioxane (374.9 μl, 4M; 1.5 mmol, 1.5 eq.) then 3,5-dimethoxyaniline (765.8 mg, 5 mmol, 5 eq.) are added, and the resulting reaction mixture is heated at 170° C. in the microwave for 30 min. The polymer is filtered off, washed with DMA, and the solvent evaporated under reduced pressure. The product was extracted with EtOAc, the organic layer is washed with brine and dried under MgSO4 then concentrated to near dryness. The residue is purified by preparative HPLC to afford 69.4 mg (18%) of the title compound as a parent. The parent (58.6 mg, 0.15 mmol, 1 eq.) is suspended in water (2 ml) then potassium hydroxide (300.9 μl, 0.50 M, 0.15 mmol, 1 eq.) is added and the mixture is lyophilised to afford 64 mg (99%) of the title compound as a yellow powder. 1H NMR (DMSO-d6) δ 8.92 (s, 1H), 8.34 (dd, J=4.5, 1.7 Hz, 1H), 7.79 (dd, J=7.9, 1.7 Hz, 1H), 7.31 (d, J=2.3 Hz, 2H), 7.14 (dd, J=7.9, 4.5 Hz, 1H), 6.16 (t, J=2.3 Hz, 1H), 3.78 (s, 6H), 3.40 (q, J=7.5 Hz, 2H), 1.15 (t, J=7.5 Hz, 3H). HPLC (max plot) 99%; Rt 2.87 min. LC/MS: (ES+): 390.3, (ES−): 388.3.

Example 149

N-{3-[(3,5-dimethoxyphenyl)amino]quinoxalin-2-yl}-6-[(4-methylpiperazin-1-yl)methyl]pyridine-3-sulfonamide (149)

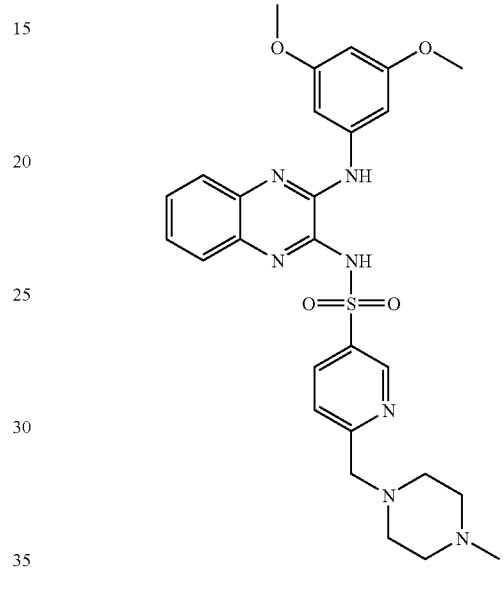

6-(chloromethyl)-N-{3-[(3,5-dimethoxyphenyl)amino]quinoxalin-2-yl}pyridine-3-sulfonamide (100 mg; 0.12 mmol; 1 eq.) and N-ethyl-N-isopropylpropan-2-amine (0.03 ml; 0.25 mmol; 2 eq.) are dissolved in ACN (25 ml) at room temperature then 1-methylpiperazine (0.06 ml; 0.62 mmol; 5 eq.) is added. The reaction mixture is stirred at room temperature for 2 hours. The reaction is quenched by addition of water and neutralized by addition of aqueous Na₂CO₃. The mixture is concentrated under reduced pressure. The residue obtained is taken up in DCM. The product is extracted with DCM, the organic phase is washed with citric acid 10% then dried over MgSO₄. After evaporation of the solvent, the crude residue obtained is purified by flash chromatography to afford 6 mg (9%) of the title compound as a white powder. 1H NMR (DMSO-d6) δ 9.17 (d, J=3 Hz, 1H), 8.30 (m, 1H), 8.24 (dd, J=9 and 3 Hz, 1H), 7.72 (dd, J=9 and 3 Hz, 1H), 7.63 (d, J=9 Hz, 1H), 7.44-7.38 (m, 3H), 7.15 (d, J=3 Hz, 2H), 6.27 (m, 1H), 3.85 (s, 6H), 3.75 (s, 2H), 2.57 (m, 8H), 2.52 (s, 3H). HPLC (max plot) 90%, Rt 3.34 min. LC/MS: MS: (ES+): 550.5, (ES−): 548.5.

Example 150

5-(aminomethyl)-N-{3-[(3,5-dimethoxyphenyl)amino]quinoxalin-2-yl}thiophene-2-sulfonamide (150)—HCl salt

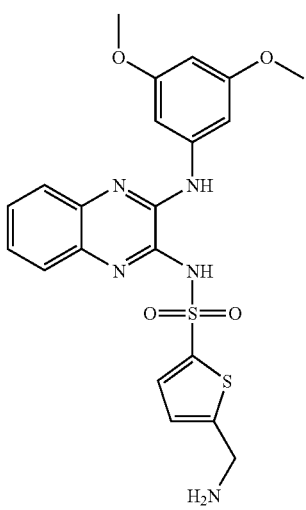

N-{3-[(3,5-dimethoxyphenyl)amino]quinoxalin-2-yl}-5-[(1,3-dioxo-1,3-dihydro-2H-isoindol-2-yl)methyl]thiophene-2-sulfonamide (584 mg; 0.97 mmol; 1 eq) is suspended in EtOH (10 ml) then hydrazine hydrate (0.14 ml; 2.91 mmol; 3 eq) is added. The reaction mixture is stirred at rt for 5 days. The mixture is filtered off and washed with ACN then recrystallized in EtOH to afford, after drying under vacuum, 184 mg (40%) of the title compound as a parent. Treatment of the parent (50 mg; 0.11 mmol; 1 eq) with HCl in MeOH (84.82 µl; 1.25 M; 0.11 mmol; 1 eq) affords 20 mg (37%) of the title compound as a yellow solid. 1H NMR (DMSO-d6) δ 12.28 (br s, 1H), 8.88 (s, 1H), 8.27 (br s, 2H), 7.94-7.85 (m, 1H), 7.84 (d, J=3.8 Hz, 1H), 7.54-7.51 (m, 1H), 7.37-7.28 (m, 4H), 7.19 (d, J=3.8 Hz, 1H), 6.18 (t, J=2.3 Hz, 1H), 4.23-4.16 (m, 2H), 3.70 (s, 6H). HPLC (max plot) 95.99%; Rt 3.16 min. LC/MS: (ES+): 472.5, (ES−): 470.4.

Example A

Biological Assays

The efficacy of compounds of the invention in inhibiting the PI3K induced-lipid phosphorylation may be tested in the following binding assay.

The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3$H, $^{125}$I, $^{33}$P). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin.

To a 96 wells MTP containing 10 µl of the test compound of Formula (I) (solubilized in 10% DMSO; to yield a concentration of 100, 25, 5.0, 1.25, 0.312, 0.078, 0.0195, 0.00488, 0.00122 and 0.0003 µM of the test compound), the following assay components are added: 1) 10 µl of lipid micelles 2) 20 µl of Kinase buffer ([$^{33}$P]γ-ATP 162 µM/300 nCi, MgCl$_2$ 2.5 mM, DTT 2.5 mM, Na$_3$VO$_4$ 25 µM in Hepes 40 mM, pH 7.4) and 3) 10 µl (10 ng) of Human recombinant GST-PI3δ (in Hepes 40 mM, pH 7.4, ethylenglycol 4%). After incubation at room temperature for 120 minutes, with gentle agitation, the reaction is stopped by addition of 200 µl of a solution containing 250 µg of neomycin-coated PVT SPA beads, ATP 60 mM and EDTA 6.2 mM in PBS. The assay is further incubated at room temperature for 60 minutes with gentle agitation to allow binding of phospholipids to neomycin-SPA beads. After precipitation of the neomycin-coated PVT SPA beads for 5 minutes at 1500×g, radioactive PtdIns(3)P is quantified by scintillation counting in a Wallac MicroBeta™ plate counter.

The values indicated in Table I below refer to the IC$_{50}$ (µM) with respect to PI3K, i.e. the amount necessary to achieve 50% inhibition of said target. Said values show a considerable inhibitory potency of pyrazine compounds with regard to PI3K.

Examples of inhibitory activities for compounds of the invention are set out in Table I below.

TABLE I

IC$_{50}$ values of pyrazine derivatives against PI3K.

| Example No | PI3K IC$_{50}$ (µM) |
|---|---|
| 29 | 0.240 |
| 13 | 0.080 |
| 11 | 0.430 |
| 86 | 0.073 |
| 65 | 0.056 |
| 144 | 0.030 |
| 138 | 0.027 |

Example B

SCF-Induced PKB/Akt Phosphorylation in Mast Cells

Protocol: Primary bone marrow cells were isolated from 4-8 weeks old wild type mice and derived to mast cells by incubation with medium containing 20 ng/nL of stem cell factor (SCF) (PeproTech, Switzerland) and 20 ng/mL of IL-3 (PeproTech, Switzerland) for at least 4 weeks. Confirmation of the expression of mast cell specific surface markers was done by FACS analysis using antibodies against c-kit (cKit-PE mouse antibody; Pharmingen). Cells were maintained in culture in the presence of SCF and IL-3. To induce PKB/Akt phosphorylation, mast cells were resuspended at 2.5×10$^6$ cells/mL and starved in medium containing no SCF or IL-3 for 24 h. After preincubation with compounds or 1% DMSO for 20 minutes, cells were activated with 20 ng/mL of SCF for 15 minutes at 37° C., fixed in 1.5% paraformaldehyde for 20 minutes and permeabilized with 0.2% Triton X-100 for 10 minutes, at room temperature. PKB/Akt phosphorylation was visualized using phospho-Ser-473 specific Akt antibodies (Cell Signaling) and standard FACS protocols.

Results: Inhibition of SCF-Induced Akt Phosphorylation

Examples of inhibitory activities for compounds of the invention are set out in Table II below.

TABLE II

| Example n° | IC50 μM |
|---|---|
| 150 | 0.09 |
| 130 | 0.13 |
| 131 | 0.15 |
| 138 | 0.18 |
| 134 | 0.21 |
| 139 | 0.27 |
| 39 | 0.35 |
| 149 | 0.39 |
| 137 | 0.40 |
| 20 | 0.41 |
| 135 | 0.54 |
| 132 | 0.68 |
| 109 | 0.82 |
| 65 | 1.19 |
| 106 | 1.22 |
| 136 | 1.22 |
| 95 | 1.60 |
| 38 | 1.89 |
| 56 | 2.42 |

TABLE III

| Example n° | IC50 μM |
|---|---|
| 150 | 0.007 |
| 39 | 0.011 |
| 131 | 0.013 |
| 138 | 0.016 |
| 65 | 0.021 |
| 20 | 0.024 |
| 15 | 0.026 |
| 111 | 0.026 |
| 139 | 0.027 |
| 13 | 0.03 |
| 14 | 0.034 |
| 137 | 0.04 |
| 38 | 0.04 |
| 130 | 0.06 |
| 42 | 0.11 |
| 110 | 0.14 |
| 101 | 0.15 |
| 129 | 0.29 |
| 136 | 0.37 |

Example C

IgM-Induced Akt Phosphorylation in B Cell

Protocol:
In Vitro Stimulation:

Human PBMC were prepared from a Buffy coat (Geneve Hospital) after a Ficoll gradient FICOLL-PAQUE Plus PHARMACIA ref: 17-1440-03).

Cell concentration was adjusted to $10^6$ cells per ml in RPMI (GIBCO Ref: 72400-21) without serum. Before stimulation, 90 μl of PBMC suspension was incubated with 10 μl of diluted compound in a 96 well round bottom plate for 20 minutes at 37° C.

For B cell activation, 30 μl of Fab'2 Goat anti IgM (Jackson Immuno-research) at 10 μg/ml was added to each well. After 5 minutes, cell activation was stopped with 4% paraformaldehyde (10 minutes at room temperature).

Fixed PBMC were then treated for 20 minutes with 0.15% Triton, washed twice with PBS and permeabilized with 50% methanol for 15 minutes.

Surface Staining:

PBMC were washed twice in PBS, resuspended in: PBS-4% FCS and incubated with anti P-Akt (1/100 dilution) for one hour at room temperature.

After one wash, PBMC were further stained for 30 minutes with a mixture of anti-CD19-PE (BD Biosciences), anti-IgM-FITC (BD Biosciences) and goat anti rabbit IgG-Alexa 647 (Molecular probe).

Flow Cytometry Analysis

After washing, PBMC (Peripheral Blood Mononuclear Cells) were analyzed on a FACSCalibur instrument (BD Biosciences) equipped with a 633 helium-neon laser, or stored at 4° C. for further analysis. $5 10^3$ B cells events were gathered per sample in the CD19 positive region.

For the analysis, a threshold was applied on P-Akt histogram of CD19+ IgM+ lymphocytes cells from the non stimulated samples and the percentage of cells above this threshold was determined for each sample.

Results: Inhibition of IgM-Induced Akt Phosphorylation.

Examples of inhibitory activities for compounds of the invention are set out in Table III below.

Example D

Passive Cutaneous Anaphylaxis (PCA)

Protocol:

Female Balb/c mice (Elevage Janvier) (8 week old) were intradermally injected by anti-DNP IgE (50 ng in 20 μl, id, 2 sites of injection) on their shaved backs. Twenty four hours later they received an intravenous injection of DNP-human serum albumin (50 μg/mouse) and Evans blue (25 mg/kg) by retroorbital injection. Thirty minutes later, the animals were sacrificed. The skin of the back was removed. The extravasated dye (punch diameter: 5 mm) was extracted from 2 punches by 0.4 ml of formamide and was quantified by fluorescence (E1: 585 nm, E2: 660 nm).

Inhibitors are administered by oral route at the dose of 30 mg/kg 2 hours before the challenge of DNP-human serum albumin and Evans blue.

Results:

Using this protocol, Example 65 exhibits 84% inhibition of vascular permeability at 30 mg/kg.

Example E

Preparation of a Pharmaceutical Formulation

Formulation 1—Tablets

A compound of Formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active pyrazine compound per tablet) in a tablet press.

Formulation 2—Capsules

A compound of Formula (I) is admixed as a dry powder with a starch diluent in an approximate 1:1 weight ratio. The mixture is filled into 250 mg capsules (125 mg of active pyrazine compound per capsule).

Formulation 3—Liquid

A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 ml.

Formulation 4—Tablets

A compound of Formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active pyrazine compound) in a tablet press.

Formulation 5—Injection

A compound of Formula (I) is dissolved in a buffered sterile saline injectable aqueous medium to a concentration of approximately 5 mg/ml.

The invention claimed is:

1. A compound according to Formula (I),

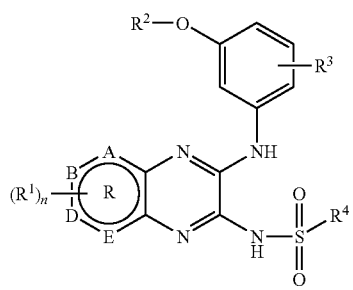

wherein:
A, B, D and E, each of which may be optionally substituted, are C, such that the ring R is an aromatic ring;
$R^1$ is selected from H, halogen, nitro, optionally substituted $C_1$-$C_6$-alkyl, optionally substituted $C_2$-$C_6$-alkenyl or optionally substituted $C_2$-$C_6$-alkynyl;
$R^2$ is selected from H, optionally substituted $C_1$-$C_6$-alkyl, optionally substituted $C_2$-$C_6$-alkenyl or optionally substituted $C_2$-$C_6$-alkynyl;
$R^3$ is selected from H, halo, optionally substituted $C_1$-$C_6$-alkyl, optionally substituted $C_2$-$C_6$-alkenyl, optionally substituted $C_2$-$C_6$-alkynyl, optionally substituted alkoxy, optionally substituted aryl or optionally substituted heteroaryl;
$R^4$ is selected from optionally substituted $C_1$-$C_6$-alkyl, optionally substituted $C_2$-$C_6$-alkenyl, optionally substituted $C_2$-$C_6$-alkynyl, optionally substituted aryl, optionally substituted heteroaryl, optionally substituted $C_3$-$C_8$ cycloalkyl, optionally substituted heterocycloalkyl, optionally substituted aryl $C_1$-$C_6$-alkyl, optionally substituted heteroaryl $C_1$-$C_6$-alkyl, optionally substituted $C_3$-$C_8$ cycloalkyl optionally substituted $C_1$-$C_6$-alkyl, optionally substituted heterocycloalkyl $C_1$-$C_6$-alkyl, optionally substituted aryl $C_2$-$C_6$-alkenyl or optionally substituted heteroaryl $C_2$-$C_6$-alkenyl;
n is an integer selected from 0, 1, 2, 3 and 4;
an optionally substituted group may be substituted with from 1 to 5 substituents selected from the group consisting of $C_1$-$C_6$-alkyl, $C_2$-$C_6$-alkenyl, $C_2$-$C_6$-alkynyl, cycloalkyl, heterocycloalkyl, $C_1$-$C_6$-alkyl aryl, $C_1$-$C_6$-alkyl heteroaryl, $C_1$-$C_6$-alkyl cycloalkyl, $C_1$-$C_6$-alkyl heterocycloalkyl, amino, ammonium, acyl, acyloxy, acylamino, aminocarbonyl, alkoxycarbonyl, ureido, aryl, carbamate, heteroaryl, sulfinyl, sulfonyl, alkoxy, sulfanyl, halogen, carboxy, trihalomethyl, cyano, hydroxy, mercapto and nitro;
with the first proviso that when $R^4$ is thiophenyl, it is not selected from group consisting of: unsubstituted thiophenyl, unsubstituted chloro-5-thiophenyl and unsubstituted bromo-5-thiophenyl;
with the second proviso that when $R^4$ is a phenyl, it is a mono-substituted phenyl that is not selected from the group consisting of: p-bromo phenyl; p-methoxy phenyl; p-ethoxy phenyl; o-, m- or p-chloro phenyl; m- or p-methyl phenyl; o- or p-fluoro phenyl; o-CF3-phenyl; p- or m-nitro phenyl; p-NHAc-phenyl and p-amino phenyl; or it is a multi-substituted phenyl, that is not an unsubstituted bi-substituted phenyl selected from the group consisting of: m-, p-dimethyl phenyl; m-, m-dimethyl phenyl; o-, p-dimethyl phenyl; o-, m-dimethyl phenyl; o-methyl p-fluoro phenyl; m-, m-dichloro phenyl; o-, m-dichloro phenyl; p-chloro m-nitro phenyl and o-ethoxy m-bromo phenyl;
with the final proviso that wherein $R^4$ is a 1,4 benzodioxin it is a substituted benzodioxin;
or an optically active form or a pharmaceutically acceptable salt thereof.

2. The compound according to claim 1, wherein $R^1$ is selected from H or halogen.

3. The compound according to claim 1, wherein $R^2$ is methyl, which may be optionally substituted.

4. The compound according to claim 1, wherein $R^3$ is selected from H or alkoxy, which may be optionally substituted.

5. The compound according to claim 1, wherein $R^3$ is selected from halo, optionally substituted aryl or optionally substituted heteroaryl.

6. The compound according to claim 1, wherein $R^4$ is selected from optionally substituted $C_1$-$C_6$-alkyl, optionally substituted $C_2$-$C_6$-alkenyl, optionally substituted $C_2$-$C_6$-alkynyl, optionally substituted aryl $C_1$-$C_6$-alkyl or optionally substituted heteroaryl $C_1$-$C_6$-alkyl.

7. The compound according to claim 1, wherein $R^1$ is selected from optionally substituted aryl or optionally substituted heteroaryl.

8. The compound according to claim 1, wherein $R^1$ is selected from H and halogen; $R^2$ is substituted methyl; and $R^3$ is selected from H or substituted alkoxy.

9. The compound according to claim 1, wherein $R^1$ is selected from H and halogen; $R^2$ is methyl; $R^3$ is selected from H or alkoxy.

10. The compound according to claim 1, wherein said compound is selected from:

4-cyano-N-{3-[(2,5-dimethoxyphenyl)amino]quinoxalin-2-yl}benzenesulfonamide;

N-{3-[(3,5-dimethoxyphenyl)amino]quinoxalin-2-yl}benzenesulfonamide;

3-[({3-[(3,5-dimethoxyphenyl)amino]quinoxalin-2-yl}amino)sulfonyl]benzoic acid;

N-{3-[(2,5-dimethoxyphenyl)amino]quinoxalin-2-yl}-1-methyl-1H-imidazole-4-sulfonamide;

N-{3-[(2,5-dimethoxyphenyl)amino]quinoxalin-2-yl}-4-methylbenzene sulfonamide;

N-{3-[(3,5-dimethoxyphenyl)amino]quinoxalin-2-yl}-3-methylbenzene sulfonamide;

N-{3-[(2,5-dimethoxyphenyl)amino]quinoxalin-2-yl}-3-methylbenzene sulfonamide;

N-{3-[(3,5-dimethoxyphenyl)amino]quinoxalin-2-yl}-4-methylbenzene sulfonamide;

5-bromo-N-{3-[(3,5-dimethoxyphenyl)amino]quinoxalin-2-yl}thiophene-2-sulfonamide;

N-{3-[(2,5-dimethoxyphenyl)amino]quinoxalin-2-yl}-1-pyridin-3-ylmethane sulfonamide;

Methyl 3-{4-[({3-[(3,5-dimethoxyphenyl)amino]quinoxalin-2-yl}amino)sulfonyl]phenyl}propanoate;

Methyl 4-[({3-[(3,5-dimethoxyphenyl)amino]quinoxalin-2-yl}amino)sulfonyl]benzoate;

N-{3-[(2,5-dimethoxyphenyl)amino]quinoxalin-2-yl}-3-fluorobenzene sulfonamide;
N-{3-[(3,5-dimethoxyphenyl)amino]quinoxalin-2-yl}-4-(methylsulfonyl)benzene sulfonamide;
N-{3-[(2,5-dimethoxyphenyl)amino]quinoxalin-2-yl}-2,3-dihydro-1,4-benzodioxine-6-sulfonamide;
N-{3-[(2,5-dimethoxyphenyl)amino]quinoxalin-2-yl}-4-(pyrrolidin-1-yl sulfonyl)benzenesulfonamide;
N-{3-[(2,5-dimethoxyphenyl)amino]quinoxalin-2-yl}-3-(methylsulfonyl)benzene sulfonamide;
N-{3-[(3,5-dimethoxyphenyl)amino]quinoxalin-2-yl}-3-(methylsulfonyl)benzene sulfonamide;
2-cyano-N-{3-[(3,5-dimethoxyphenyl)amino]quinoxalin-2-yl}benzene sulfonamide;
2-cyano-N-{3-[(2,5-dimethoxyphenyl)amino]quinoxalin-2-yl}benzene sulfonamide;
2-chloro-N-{3-[(3,5-dimethoxyphenyl)amino]quinoxalin-2-yl}benzene sulfonamide;
N-{3-[(2,5-dimethoxyphenyl)amino]quinoxalin-2-yl}pyridine-3-sulfonamide;
N-{3-[(3,5-dimethoxyphenyl)amino]quinoxalin-2-yl}-1-methyl-1H-imidazole-4-sulfonamide;
N-{3-[(2,5-dimethoxyphenyl)amino]quinoxalin-2-yl}-4-fluorobenzene sulfonamide;
N-{3-[(3,5-dimethoxyphenyl)amino]quinoxalin-2-yl}-4-fluorobenzene sulfonamide;
4-cyano-N-{3-[(3,5-dimethoxyphenyl)amino]quinoxalin-2-yl}benzene sulfonamide;
N-{3-[(2,5-dimethoxyphenyl)amino]quinoxalin-2-yl}benzenesulfonamide;
N-{3-[(2,5-dimethoxyphenyl)amino]quinoxalin-2-yl}methanesulfonamide;
N-{3-[(3,5-dimethoxyphenyl)amino]quinoxalin-2-yl}thiophene-3-sulfonamide;
N-{3-[(3,5-dimethoxyphenyl)amino]quinoxalin-2-yl}methanesulfonamide;
3-[({3-[(2,5-dimethoxyphenyl)amino]quinoxalin-2-yl}amino)sulfonyl]benzoic acid;
Methyl 4-[({3-[(2,5-dimethoxyphenyl)amino]quinoxalin-2-yl}amino)sulfonyl]benzoate;
Methyl 3-[({3-[(3,5-dimethoxyphenyl)amino]quinoxalin-2-yl}amino)sulfonyl]thiophene-2-carboxylate;
5-chloro-N-{3-[(2,5-dimethoxyphenyl)amino]quinoxalin-2-yl}-1,3-dimethyl-1H-pyrazole-4-sulfonamide;
4-chloro-N-{3-[(2,5-dimethoxyphenyl)amino]quinoxalin-2-yl}benzene sulfonamide;
3-[({3-[(2,5-dimethoxyphenyl)amino]quinoxalin-2-yl}amino)sulfonyl]thiophene-2-carboxylic acid;
3-{4-[({3-[(3,5-dimethoxyphenyl)amino]quinoxalin-2-yl}amino)sulfonyl]phenyl}propanoic acid;
N-{3-[(3,5-dimethoxyphenyl)amino]quinoxalin-2-yl}-3-methyl-2-oxo-2,3-dihydro-1,3-benzothiazole-6-sulfonamide;
N-{3-[(2,5-dimethoxyphenyl)amino]quinoxalin-2-yl}-2,1,3-benzothiadiazole-4-sulfonamide;
4-chloro-N-{3-[(3,5-dimethoxyphenyl)amino]quinoxalin-2-yl}benzene sulfonamide;
N-{3-[(2,5-dimethoxyphenyl)amino]quinoxalin-2-yl}-3-methyl-2-oxo-2,3-dihydro-1,3-benzothiazole-6-sulfonamide;
4-bromo-N-{3-[(2,5-dimethoxyphenyl)amino]quinoxalin-2-yl}benzene sulfonamide;
4-bromo-N-{3-[(3,5-dimethoxyphenyl)amino]quinoxalin-2-yl}benzene sulfonamide;
4-acetyl-N-{3-[(3,5-dimethoxyphenyl)amino]quinoxalin-2-yl}-benzene sulfonamide;
N-{3-[(3,5-dimethoxyphenyl)amino]quinoxalin-2-yl}propane-1-sulfonamide;
N-{3-[(2,5-dimethoxyphenyl)amino]quinoxalin-2-yl}thiophene-3-sulfonamide;
4-acetyl-N-{3-[(2,5-dimethoxyphenyl)amino]quinoxalin-2-yl}benzene sulfonamide;
N-{3-[(2,5-dimethoxyphenyl)amino]quinoxalin-2-yl}-1,2-dimethyl-1H-imidazole-5-sulfonamide;
N-{3-[(3,5-dimethoxyphenyl)amino]quinoxalin-2-yl}-2,1,3-benzoxadiazole-4-sulfonamide;
3-chloro-N-{3-[(3-dimethoxyphenyl)amino]quinoxalin-2-yl}benzene sulfonamide;
3-cyano-N-{3-[(2,5-dimethoxyphenyl)amino]quinoxalin-2-yl}benzene sulfonamide;
N-{3-[({3-[(3,5-dimethoxyphenyl)amino]quinoxalin-2-yl}amino)sulfonyl]phenyl}acetamide;
N-{3-[(2,5-dimethoxyphenyl)amino]quinoxalin-2-yl}propane-1-sulfonamide;
N-{3-[(2,5-dimethoxyphenyl)amino]quinoxalin-2-yl}-4-(trifluoromethyl)benzene sulfonamide;
4-[({3-[(3,5-dimethoxyphenyl)amino]quinoxalin-2-yl}amino)sulfonyl]butanoic acid;
3-chloro-N-{3-[(2,5-dimethoxyphenyl)amino]quinoxalin-2-yl}benzene sulfonamide;
N-{6-chloro-3-[(3,5-dimethoxyphenyl)amino]quinoxalin-2-yl}benzene sulfonamide;
N-{3-[(2,5-dimethoxyphenyl)amino]quinoxalin-2-yl}-1-pyridin-2-ylmethane sulfonamide;
N-{3-[(2,5-dimethoxyphenyl)amino]quinoxalin-2-yl}-4-methoxybenzene sulfonamide;
N-{3-[(3,5-dimethoxyphenyl)amino]pyrido[2,3-b]pyrazin-2-yl}ethane sulfonamide;
N-{3-[(3,5-dimethoxyphenyl)amino]quinoxalin-2-yl}-3-methoxybenzene sulfonamide;
N-{3-[(3,5-dimethoxyphenyl)amino]quinoxalin-2-yl}-1-pyridin-2-ylmethane sulfonamide;
N-{3-[(3,5-dimethoxyphenyl)amino]quinoxalin-2-yl}-1-pyridin-3-ylmethane sulfonamide;
Methyl 3-[({3-[(2,5-dimethoxyphenyl)amino]quinoxalin-2-yl}amino)sulfonyl]thiophene-2-carboxylate;
N-{3-[(3-methoxyphenyl)amino]quinoxalin-2-yl}benzenesulfonamide;
N-{3-[(3-methoxyphenyl)amino]quinoxalin-2-yl}benzenesulfonamide;
4-chloro-N-{3-[(3-methoxyphenyl)amino]quinoxalin-2-yl}benzenesulfonamide;
N-{3-[(2,5-dimethoxyphenyl)amino]quinoxalin-2-yl}-3-methoxybenzene sulfonamide;
4-[({3-[(2,5-dimethoxyphenyl)amino]quinoxalin-2-yl}amino)sulfonyl]butanoic acid;
N-{3-[(3-methoxyphenyl)amino]quinoxalin-2-yl}methanesulfonamide;
N-{3-[(2,5-dimethoxyphenyl)amino]quinoxalin-2-yl}-4-iodobenzene sulfonamide;
4-bromo-N-{3-[(3-methoxyphenyl)amino]quinoxalin-2-yl}benzene sulfonamide;
4-[({3-[(2,5-dimethoxyphenyl)amino]quinoxalin-2-yl}amino)sulfonyl]benzoic acid;
Methyl 4-[({3-[(2,5-dimethoxyphenyl)amino]quinoxalin-2-yl}amino)sulfonyl]butanoate;
4-[({3-[(3,5-dimethoxyphenyl)amino]quinoxalin-2-yl}amino)sulfonyl]benzoic acid;
N-{3-[(3,5-dimethoxyphenyl)amino]quinoxalin-2-yl}-2-fluorobenzene sulfonamide;
N-(3-{[5-methoxy-2-(1H-pyrrol-1-yl)phenyl]amino}quinoxalin-2-yl)benzene sulfonamide;

Methyl 3-[({3-[(2,5-dimethoxyphenyl)amino]quinoxalin-2-yl}amino)sulfonyl]benzoate;
N-{3-[(2,5-dimethoxyphenyl)amino]quinoxalin-2-yl}-6-morpholin-4-yl pyridine-3-sulfonamide;
4-methoxy-N-{3-[(3-methoxyphenyl)amino]quinoxalin-2-yl}benzene sulfonamide;
Methyl 3-[({3-[(3,5-dimethoxyphenyl)amino]quinoxalin-2-yl}amino)sulfonyl]benzoate;
3-[({3-[(3,5-dimethoxyphenyl)amino]quinoxalin-2-yl}amino)sulfonyl]thiophene-2-carboxylic acid;
N-{3-[(2-chloro-5-methoxyphenyl)amino]quinoxalin-2-yl}benzenesulfonamide;
N-{3-[(3,5-dimethoxyphenyl)amino]quinoxalin-2-yl}-2-(methylsulfonyl)benzene sulfonamide;
N-{3-[(2,5-dimethoxyphenyl)amino]quinoxalin-2-yl}-2-fluorobenzene sulfonamide;
4,5-dichloro-N-{3-[(2,5-dimethoxyphenyl)amino]quinoxalin-2-yl}thiophene-2-sulfonamide;
N-{3-[(5-methoxy-2-methylphenyl)amino]quinoxalin-2-yl}benzene sulfonamide;
N-{3-[(3,5-dimethoxyphenyl)amino]quinoxalin-2-yl}-3-fluorobenzene sulfonamide;
N-{3-[(2,5-dimethoxyphenyl)amino]quinoxalin-2-yl}-2-(methylsulfonyl)benzenesulfonamide;
N-{3-[(2,3-dihydro-1,4-benzodioxin-5-ylmethyl)amino]quinoxalin-2-yl}benzene sulfonamide;
N-{3-[(3,5-dimethoxyphenyl)amino]-6-nitroquinoxalin-2-yl}benzene sulfonamide;
N-{3-[(3,5-dimethoxyphenyl)amino]quinoxalin-2-yl}-4-(pyrrolidin-1-ylsulfonyl)benzene sulfonamide;
methyl 4-[({3-[(3,5-dimethoxyphenyl)amino]quinoxalin-2-yl}amino) sulfonyl]butanoate;
methyl 5-[({3-[(2,5-dimethoxyphenyl)amino]quinoxalin-2-yl}amino)sulfonyl]-4-methylthiophene-2-carboxylate;
methyl 5-[({3-[(2,5-dimethoxyphenyl)amino]quinoxalin-2-yl}amino)sulfonyl]-1-methyl-1H-pyrrole-2-carboxylate;
methyl5-[({3-[(3,5-dimethoxyphenyl)amino]quinoxalin-2-yl}amino)sulfonyl]-1-methyl-1H-pyrrole-2-carboxylate;
N-{3-[(2,5-dimethoxyphenyl)amino]quinoxalin-2-yl}thiophene-2-sulfonamide;
2-chloro-N-{3-[(2,5-dimethoxyphenyl)amino]quinoxalin-2-yl}-4-fluorobenzene sulfonamide;
2-chloro-N-{3-[(3,5-dimethoxyphenyl)amino]quinoxalin-2-yl}-4-fluorobenzene sulfonamide;
N-{3-[(3,5-dimethoxyphenyl)amino]quinoxalin-2-yl}pyridine-3-sulfonamide;
3-cyano-N-{3-[(3,5-dimethoxyphenyl)amino]quinoxalin-2-yl}-4-fluorobenzene sulfonamide;
3-cyano-N-{3-[(2,5-dimethoxyphenyl)amino]quinoxalin-2-yl}-4-fluorobenzene sulfonamide;
6-chloro-N-{3-[(3,5-dimethoxyphenyl)amino]quinoxalin-2-yl}pyridine-3-sulfonamide;
N-{3-[(3,5-dimethoxyphenyl)amino]quinoxalin-2-yl}-6-(dimethylamino)pyridine-3-sulfonamide;
N-{3-[(3,5-dimethoxyphenyl)amino]quinoxalin-2-yl}-6-[(3-methoxypropyl)amino]pyridine-3-sulfonamide;
N-{3-[(5-methoxy-2-methylphenyl)amino]quinoxalin-2-yl}pyridine-3-sulfonamide;
N-{3-[(2-chloro-5-methoxyphenyl)amino]quinoxalin-2-yl}-4-cyano benzene sulfonamide;
N-{3-[(2-chloro-5-methoxyphenyl)amino]quinoxalin-2-yl}pyridine-3-sulfonamide;
N-{3-[(3,5-dimethoxyphenyl)amino]quinoxalin-2-yl}-6-methoxypyridine-3-sulfonamide;
N-{3-[(3,5-dimethoxyphenyl)amino]quinoxalin-2-yl}-6-oxo-1,6-dihydropyridine-3-sulfonamide;
N-{3-[(3,5-dimethoxyphenyl)amino]quinoxalin-2-yl}-6-methylpyridine-3-sulfonamide;
N-{3-[(3,5-dimethoxyphenyl)amino]quinoxalin-2-yl}-4-fluoro-2-methylbenzene sulfonamide;
N-{3-[(2,5-dimethoxyphenyl)amino]quinoxalin-2-yl}-6-methylpyridine-3-sulfonamide;
4-cyano-N-{3-[(5-methoxy-2-methylphenyl)amino]quinoxalin-2-yl}benzene sulfonamide;
N-{3-[(5-methoxy-2-methylphenyl)amino]quinoxalin-2-yl}-6-methylpyridine-3-sulfonamide;
N-{3-[(2-chloro-5-methoxyphenyl)amino]quinoxalin-2-yl}-6-methylpyridine-3-sulfonamide;
methyl 5-[({3-[(3,5-dimethoxyphenyl)amino]quinoxalin-2-yl}amino)sulfonyl]pyridine-2-carboxylate;
N-[3-[(2-bromo-5-methoxyphenyl)amino]quinoxalin-2-yl]-1-methyl-1H-imidazole-4-sulfonamide;
N-3-[(3,5-dimethoxyphenyl)amino]quinoxalin-2-yl]-3-(morpholin-4-ylcarbonyl)benzenesulfonamide;
5-[({3-[(2,5-dimethoxyphenyl)amino]quinoxalin-2-yl}amino)sulfonyl]-4-methyl thiophene-2-carboxylic acid;
5-[({3-[(3,5-dimethoxyphenyl)amino]quinoxalin-2-yl}amino)sulfonyl]-4-methyl thiophene-2-carboxylic acid;
5-[({3-[(2,5-dimethoxyphenyl)amino]quinoxalin-2-yl}amino)sulfonyl]-1-methyl-1H-pyrrole-2-carboxylic acid;
5-[({3-[(3,5-dimethoxyphenyl)amino]quinoxalin-2-yl}amino)sulfonyl]-1-methyl-1H-pyrrole-2-carboxylic acid;
5-[({3-[(3,5-dimethoxyphenyl)amino]quinoxalin-2-yl}amino)sulfonyl]pyridine-2-carboxylic acid;
N-{3-[(3,5-dimethoxyphenyl)amino]quinoxalin-2-yl}-3-(morpholin-4-ylmethyl)benzene sulfonamide;
N-{3-[(3,5-dimethoxyphenyl)amino]quinoxalin-2-yl}-4-[(4-methylpiperazin-1-yl)methyl]benzenesulfonamide;
4-(aminomethyl)-N-{3-[(2,5-dimethoxyphenyl)amino]quinoxalin-2-yl}benzene sulfonamide;
N-{3-[(3,5-dimethoxyphenyl)amino]quinoxalin-2-yl}-3-(hydroxymethyl)benzenesulfonamide;
3-(aminomethyl)-N-[3-[(3,5-dimethoxyphenyl)amino]quinoxalin-2-yl]benzenesulfonamide;
N-{3-[(3,5-dimethoxyphenyl)amino]quinoxalin-2-yl}-4-(hydroxymethyl)benzenesulfonamide;
N-{3-[(3,5-dimethoxyphenyl)amino]quinoxalin-2-yl}-6-(hydroxymethyl)pyridine-3-sulfonamide;
N-{3-[(3,5-dimethoxyphenyl)amino]quinoxalin-2-yl}-4-(morpholin-4-ylmethyl)benzene sulfonamide;
N-{3-[(3,5-dimethoxyphenyl)amino]quinoxalin-2-yl}-3-[(4-methylpiperazin-1-yl)methyl]benzenesulfonamide;
N-{3-[(3,5-dimethoxyphenyl)amino]quinoxalin-2-yl}-4-[(dimethylamino)methyl]benzenesulfonamide;
N-{3-[(3,5-dimethoxyphenyl)amino]quinoxalin-2-yl}-3-[(dimethylamino)methyl]benzenesulfonamide;
4-[({3-[(3,5-dimethoxyphenyl)amino]quinoxalin-2-yl}amino)sulfonyl]benzamide;
4-[({3-[(5-methoxy-2-methylphenyl)amino]quinoxalin-2-yl}amino)sulfonyl]benzamide;
4-[({3-[(3,5-dimethoxyphenyl)amino]quinoxalin-2-yl}amino)sulfonyl]-N-(3-methoxypropyl)benzamide;
4-[({3-[(3,5-dimethoxyphenyl)amino]quinoxalin-2-yl}amino)sulfonyl]-N-[3-(dimethylamino)propyl]benzamide;

3-[({3-[(3,5-dimethoxyphenyl)amino]quinoxalin-2-yl}amino)sulfonyl]-N-[3-(dimethylamino)propyl]benzamide;

5-[({3-[(3,5-dimethoxyphenyl)amino]quinoxalin-2-yl}amino)sulfonyl]-N,N-dimethylpyridine-2-carboxamide;

N-{3-[(3,5-dimethoxyphenyl)amino]quinoxalin-2-yl}-3-[(4-methylpiperazin-1-yl)carbonyl]benzenesulfonamide;

N-{3-[(3,5-dimethoxyphenyl)amino]quinoxalin-2-yl}-6-(morpholin-4-ylcarbonyl)pyridine-3-sulfonamide;

N-{3-[(3,5-dimethoxyphenyl)amino]quinoxalin-2-yl}-6-[(4-methylpiperazin-1-yl)methyl]pyridine-3-sulfonamide; or 5-(aminomethyl)-N-{3-[(3,5-dimethoxyphenyl)amino]quinoxalin-2-yl}thiophene-2-sulfonamide.

11. The compound according to claim 1, wherein said compound is selected from:

4-cyano-N-{3-[(3,5-dimethoxyphenyl)amino]quinoxalin-2-yl}benzenesulfonamide;

2-chloro-N-{3-[(2,5-dimethoxyphenyl)amino]quinoxalin-2-yl}benzene sulfonamide;

5-chloro-N-[(3,5-dimethoxyphenyl)amino]quinoxalin-2-yl]-1,3-dimethyl-1H-pyrazole-4-sulfonamide;

N-{3-[({3-[(3,5-dimethoxyphenyl)amino]quinoxalin-2-yl}amino)sulfonyl]phenyl}acetamide;

3-cyano-N-{3-[(3,5-dimethoxyphenyl)amino]quinoxalin-2-yl}benzene sulfonamide;

N-{3-[(2,5-dimethoxyphenyl)amino]quinoxalin-2-yl}-4-(trifluoromethyl)benzene sulfonamide; or 4-fluoro-N-{[(3-methoxyphenyl)amino]quinoxalin-2-yl}benzenesulfonamide; and N-{3-[(3,5-dimethoxyphenyl)amino]quinoxalin-2-yl}-4-iodobenzene sulfonamide.

12. A pharmaceutical composition containing at least one pyrazine compound according to claim 1 and a pharmaceutically acceptable carrier, diluent or excipient thereof.

13. A process for the preparation of pyrazine compound according to claim 1, comprising reacting a compound of Formula (II) with an aniline of Formula (III) in absence of a base:

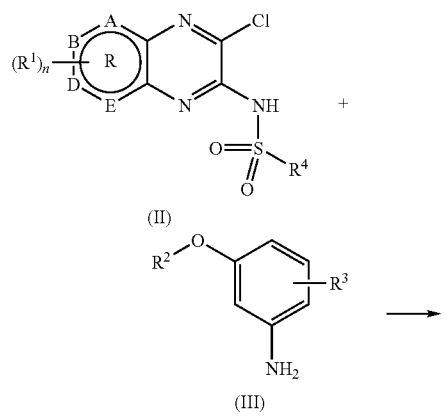

(II)

(III)

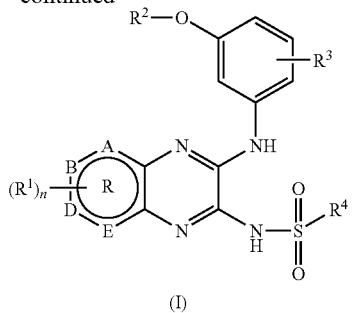

(I)

wherein n, A, B, D, E, R, $R^1$, $R^2$, $R^3$, $R^4$ are as defined in claim 1.

14. A process for the preparation of pyrazine compound according to claim 1, comprising reacting an amino compound of Formula (XI) and a sulfonylchloride of Formula (IX) in the presence of a base:

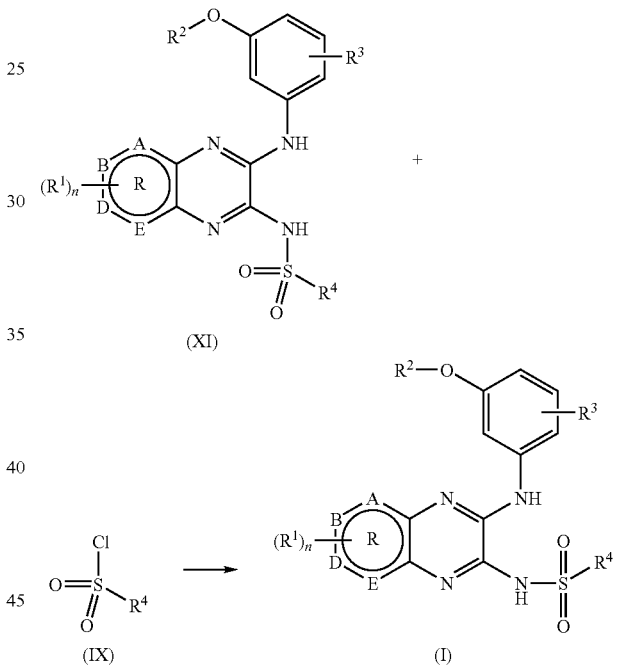

(XI)

(IX)

(I)

wherein n, A, B, D, E, R, $R^1$, $R^2$, $R^3$, $R^4$ are as defined in claim 1.

15. The process according to claim 14 wherein the base is pyridine.

16. The compound according to claim 1, wherein $R^1$ is H, $R^2$ is an optionally substituted $C_1$-$C_6$alkyl, $R^3$ is a $C_1$-$C_6$alkyl optionally substituted with hydroxyl and $R^4$ is an optionally substituted heteroaryl.

* * * * *

UNITED STATES PATENT AND TRADEMARK OFFICE
CERTIFICATE OF CORRECTION

PATENT NO. : 8,071,597 B2
APPLICATION NO. : 12/064284
DATED : December 6, 2011
INVENTOR(S) : Pascale Gaillard et al.

It is certified that error appears in the above-identified patent and that said Letters Patent is hereby corrected as shown below:

Column 4,
Line 32, "PI33Ks" should read --PI3Ks--.

Column 11,
Line 2, "cycloalkyl $C_1$-C6-alkyl" should read --cycloalkyl $C_1$-$C_6$-alkyl--.
Line 4, "$C_1$-C5-alkyl" should read --$C_1$-$C_5$-alkyl--.

Column 12,
Line 57, "(PI33Ks)" should read --(PI3Ks)--.
Line 58, "(PI33K)" should read --(PI3K)--.

Column 26,
Line 33, "erein" should read --wherein--.

Column 30,
Line 17, "E and $R^1$" should read --E and R, $R^1$--.
Line 66, "E and $R^1$" should read --E and R, $R^1$--.

Column 39,
Lines 65-66, "(100 0 mg;" should read --(1000 mg;--.

Column 43,
Line 7, "LCMS:" should read --LC/MS:--.

Column 44,
Line 36, "LCMS:" should read --LC/MS:--.

Signed and Sealed this
First Day of May, 2012

David J. Kappos
*Director of the United States Patent and Trademark Office*

CERTIFICATE OF CORRECTION (continued)
U.S. Pat. No. 8,071,597 B2

Column 46,
Line 25, "(Max polt) 98%, Rt, 4.09 min; LCMS" should read
--(Max plot) 98%, Rt, 4.09 min; LC/MS--.

Column 47,
Lines 64-65, "12.5-10-5" should read --12.5-10.5--.

Column 56,
Line 1, "8-30-8.10" should read --8.30-8.10--.

Column 70,
Line 3, "7.70-750" should read --7.70-7.50--.

Column 95,
Line 1, "1dimethoxyaniline" should read --dimethoxyaniline--.

Column 134,
Lines 63-64, "3-[({3-[(3,5-dimethoxyphenyl)amino]quinoxalin-2-yl]amino)sulfonyl]
thiophene-2-carboxylate" should read
--3-[({3-[(3,5-dimethoxyphenyl)amino]quinoxalin-2-yl}amino)sulfonyl]
thiophene-2-carboxylate--.

Column 144,
Line 37, "$C_{52.94}$%" should read --C52.94%--.

Column 154,
Line 3, "(10 ng)" should read --(100ng)--.

Column 158,
Lines 33, "wherein $R^1$" should read --wherein $R^4$--.

Column 162,
Lines 18-19, "N-[3-[(2-bromo-5-methoxyphenyl)amino]quinoxalin-2-yl]-1-methyl-1H-
imidazole-4-sulfonamide" should read
--N-{3-[(2-bromo-5-methoxyphenyl)amino]quinoxalin-2-yl}-1-methyl-1H-
imidazole-4-sulfonamide--.

Column 162,
Lines 20-21, "N-3-[(3,5-dimethoxyphenyl)amino]quinoxalin-2-yl]-3-(morpholin-4-
ylcarbonyl)benzenesulfonamide" should read
--N-{3-[(3,5-dimethoxyphenyl)amino]quinoxalin-2-yl}-3-(morpholin-4-
ylcarbonyl)benzenesulfonamide--.

CERTIFICATE OF CORRECTION (continued)
U.S. Pat. No. 8,071,597 B2

Lines 45-46, "3-(aminomethyl)-N-[3-[(3,5-dimethoxyphenyl)amino]quinoxalin-2-yl] benzenesulfonamide" should read
--3-(aminomethyl)-N-{3-[(3,5-dimethoxyphenyl)amino]quinoxalin-2-yl} benzenesulfonamide--.

Line 52, "benzene sulfonamide" should read --benzenesulfonamide--.

Column 163,
Lines 23-24, "5-chloro-N-[(3,5-dimethoxyphenyl)amino] quinoxalin-2-yl]-1,3-dimethyl-1H-pyrazole-4-sulfonamide" should read
--5-chloro-N-{3-[(3,5-dimethoxyphenyl)amino]quinoxalin-2-yl}-1,3-dimethyl-1H-pyrazole-4-sulfonamide--.

Lines 31 -32, "4-fluoro-N-{[(3-methoxyphenyl)amino]quinoxalin-2-yl} benzenesulfonamide" should read
--4-fluoro-N-{3-[(3-methoxyphenyl)amino]quinoxalin-2-yl} benzenesulfonamide--.

Column 164,
Lines 25-35,

" 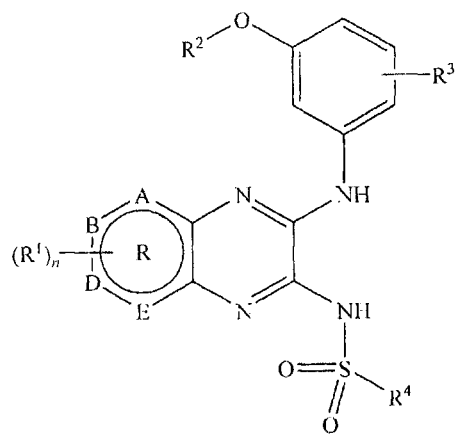 should read -- 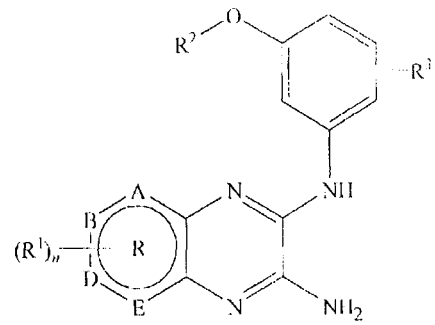 --.